United States Patent
Shen-Orr et al.

(10) Patent No.: US 11,262,358 B2
(45) Date of Patent: Mar. 1, 2022

(54) INFILTRATING IMMUNE CELL PROPORTIONS PREDICT ANTI-TNF RESPONSE IN COLON BIOPSIES

(71) Applicants: Technion Research & Development Foundation Limited, Haifa (IL); The Board of Trustees of the Leland Stanford Junior University, Stanford, CA (US)

(72) Inventors: Shai S. Shen-Orr, Karkur (IL); Elina Starovetsky, Yokneam Ilit (IL); Naama Maimon, Nir-Etzion (IL); Purvesh Khatri, Menlo Park, CA (US); Renaud Gaujoux, Cape Town (ZA); Francesco Vallania, San Fransisco, CA (US)

(73) Assignees: Technion Research & Development Foundation Limited, Haifa (IL); The Board of Trustees of the Leland Stanford Junior University, Stanford, CA (US)

( * ) Notice: Subject to any disclaimer, the term of this patent is extended or adjusted under 35 U.S.C. 154(b) by 387 days.

(21) Appl. No.: 16/091,988

(22) PCT Filed: Apr. 6, 2017

(86) PCT No.: PCT/IL2017/050419
§ 371 (c)(1),
(2) Date: Oct. 7, 2018

(87) PCT Pub. No.: WO2017/175228
PCT Pub. Date: Oct. 12, 2017

(65) Prior Publication Data
US 2019/0094223 A1 Mar. 28, 2019

Related U.S. Application Data

(60) Provisional application No. 62/318,971, filed on Apr. 6, 2016.

(51) Int. Cl.
*G01N 33/569* (2006.01)
*C12Q 1/6883* (2018.01)
*G01N 33/50* (2006.01)
*C40B 30/04* (2006.01)

(52) U.S. Cl.
CPC ..... *G01N 33/56972* (2013.01); *C12Q 1/6883* (2013.01); *C40B 30/04* (2013.01); *G01N 33/5047* (2013.01); *C12Q 2600/106* (2013.01); *C12Q 2600/158* (2013.01); *G01N 2800/065* (2013.01); *G01N 2800/52* (2013.01)

(58) Field of Classification Search
None
See application file for complete search history.

(56) References Cited

U.S. PATENT DOCUMENTS

2015/0050274 A1* 2/2015 Elenitoba-Johnson ............
C12Q 1/6886
424/133.1
2015/0232837 A1* 8/2015 Thibonnier ............ A61P 29/00
514/44 A

FOREIGN PATENT DOCUMENTS

WO WO 2013/080050 6/2013
WO WO 2017/175228 10/2017

OTHER PUBLICATIONS

Kambara et al. American J. Pathology 2015 185: 162-171 "In Vivo Depletion of CD206+ M2 macrophage Exaggerates Lung Injury in Endotoxemic Mice". (Year: 2015).*
Levin et al. J. Crohn's and Colitis 2016 p. 989-997 "Mechanism of Action of Anti-TNF Therapy in Inflammatory Bowel Disease". (Year: 2016).*
Magnusson et al. Aliment Pharmacol. Ther 2015 41:1149-1161 "Cultured Blood T-Cell responses predictanti-TNF therapy Response in Patients with Ulcerative Colitis". (Year: 2015).*
Vos et al. Inflamm. Bowel Dis 2012 18: 401-8 "Regulatory Macrophages Induced by Infliximab are Involved in Healing in Vivo and in Vitro". (Year: 2012).*
Li et al. (BMC Bioinformatics 2013 14:S11). (Year: 2013).*
International Preliminary Report on Patentability dated Oct. 9, 2018 from the International Searching Authority Re. Application No. PCT/IL2017/050419. (6 pages).
International Search Report and Written Opinion dated Jul. 9, 2017 from the International Searching Authority Re. Application No. PCT/IL2017/050419. (8 pages).
Arijs et al. "Predictive Value of Epithelial Gene Expression Profiles for Response to Infliximab in Crohn's Disease", Inflammatory Bowel Diseases 16.12 (2010): 2090-2098.
Li et al. "Circulating B Cell Subsets Correlate with Clinical Response to Anti-TNF Therapy in IBD". United European Gastroenterology Journal 1(Suppl. 1): A378-A379, 2013.
Wlodarczyk et al. "Neutrophil-Lymphocyte Ratio in Crohn's Disease Patients Predicts Sustained Response to Infliximab 52-Week Therapy". Journal of Gastrointestinal and Liver Diseases, 24(1) :127-128, Mar. 2015.
Office Action dated Feb. 18, 2020 From the Israel Patent Office Re. Application No. 262181 and Its Translation Into English. (7 Pages).
Supplementary European Search Report and the European Search Opinion dated Oct. 8, 2019 From the European Patent Office Re. Application No. 17778798.3. (11 Pages).

(Continued)

*Primary Examiner* — Changhwa J Cheu

(57) ABSTRACT

Provided are methods of predicting responsiveness of a subject having an inflammatory bowel disease (IBD) to a tumor necrosis factor (TNF)-alpha inhibitor, by analyzing a frequency of at least one subpopulation of immune cells in a tissue biopsy of the subject. Also provided are methods of selecting a treatment for a subject and kits for determining responsiveness of the subject to treatment with a TNF-alpha inhibitor.

12 Claims, 13 Drawing Sheets
(13 of 13 Drawing Sheet(s) Filed in Color)

Specification includes a Sequence Listing.

(56) References Cited

OTHER PUBLICATIONS

BioLegend "Purified Anti-Human CD 138 (Syndecan-1) Antibody", BioLegend, XP055626104, Version 3, 2 P., Sep. 6, 2014.

Frolova et al. "Expression of Toll-Like Receptor 2 (TLR2), TLR4, and CD14 in Biopsy Samples of Patients With Inflammatory Bowel Diseases: Upregulated Expression of TLR2 in Terminal Ileum of Patients With Ulcerative Colitis", Journal of Histochemistry & Cytochemistry. XP055625654, 56(3): 267-274, Published Online Nov. 26, 2007.

Gaujoux et al. "Cell-Centred Meta-Analysis Reveals Baseline Predictors of Anti-TNF Alpha Non-Response in Biopsy and Blood of Patients With IBD", Gut, XP055625670, 68(4): 604-614, Published Online Apr. 4, 2018.

Leiper et al. "Rituximab in Active Ulcerative Colitis", Gastroenterology, XP055626054, 142(1): 174-176, Published Online Nov. 21, 2011.

Scaldaferri el al. "Mucosal Biomarkers in Inflammatory Bowel Disease: Key Pathogenic Players or Disease Predictors?", World Journal of Gastroenterology, XP055090265, 16(21): 2616-2625, Jun. 7, 2010.

Office Action dated Jul. 9, 2019 From the Israel Patent Office Re. Application No. 262181 and Its Translation Into English. (4 Pages).

\* cited by examiner

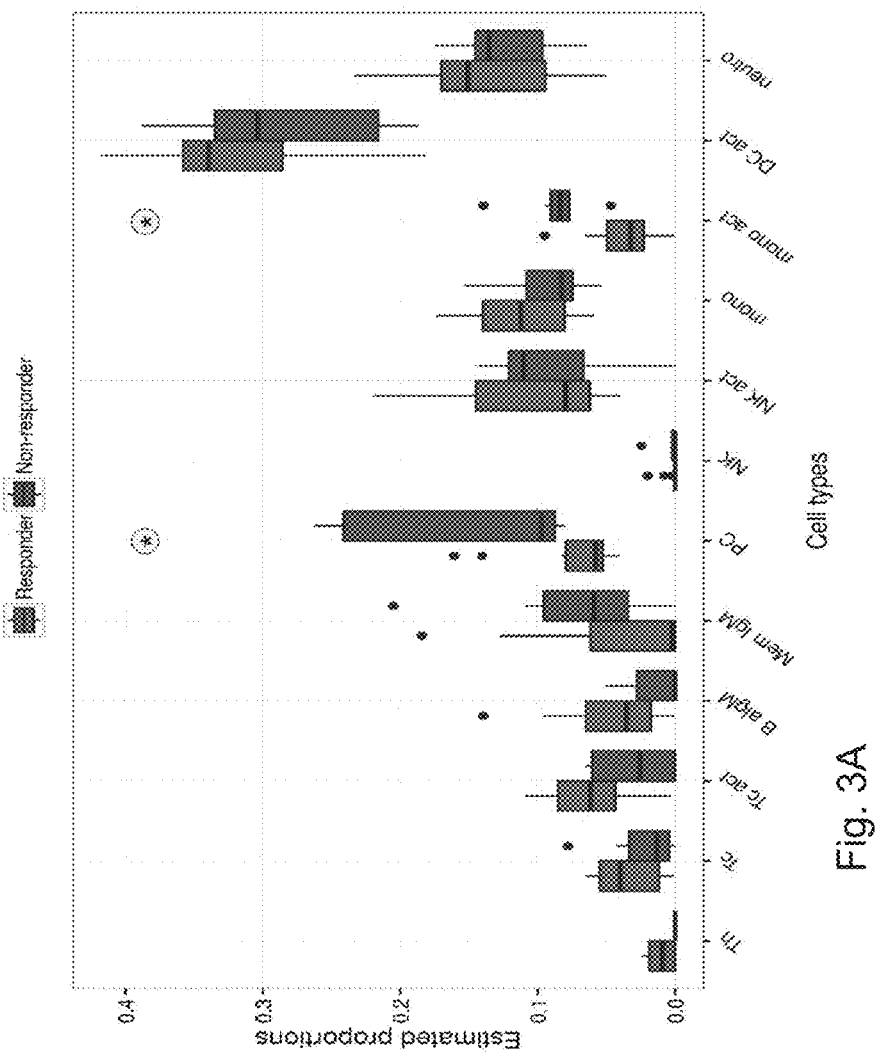
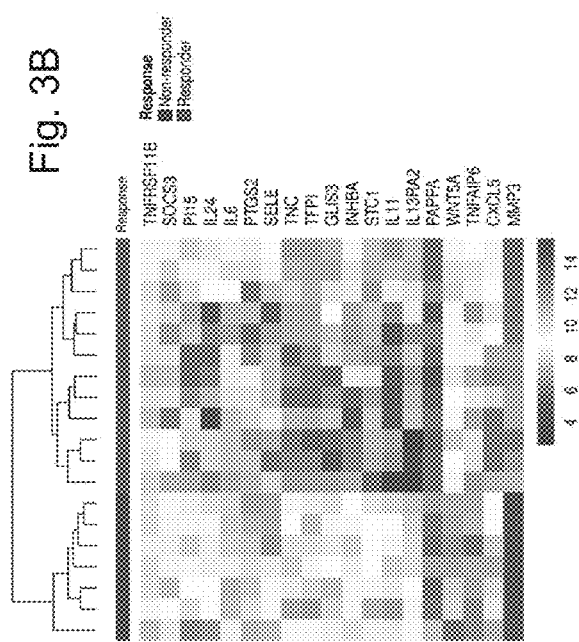
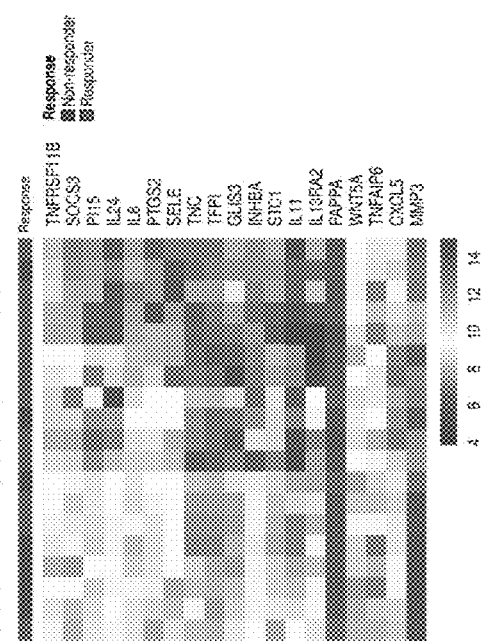

INFILTRATING IMMUNE CELL PROPORTIONS PREDICT ANTI-TNF RESPONSE IN COLON BIOPSIES

RELATED APPLICATIONS

This application is a National Phase of PCT Patent Application No. PCT/IL2017/050419 having International filing date of Apr. 6, 2017, which claims the benefit of priority under 35 USC § 119(e) of U.S. Provisional Patent Application No. 62/318,971, filed on Apr. 6, 2016. The contents of the above applications are all incorporated by reference as if fully set forth herein in their entirety.

STATEMENT REGARDING FEDERALLY SPONSORED RESEARCH OR DEVELOPMENT

This invention was made with Government support under contracts AI057229, AI109662, AI117925, and HL120001 awarded by the National Institutes of Health. The Government has certain rights in the invention.

SEQUENCE LISTING STATEMENT

The ASCII file, entitled 75557 SequenceListing.txt, created on 7 Oct., 2018, comprising 292,765 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods and kits for predicting responsiveness of a subject having an inflammatory bowel disease (IBD) to treatment with a tumor necrosis factor (TNF)-alpha inhibitor, more particularly, but not exclusively, to methods of selecting a treatment for a subject diagnosed with the inflammatory bowel disease (IBD).

Inflammatory Bowel Diseases (IBDs) comprises primarily from ulcerative colitis (UC) and Crohn's disease (CD) disease conditions, for which treatment with anti-TNF monoclonal antibodies such as Infliximab have shown an ability to treat inflammation and achieve mucosal healing (1, 2). However, response to such treatments is very heterogeneous, with overall only 60% of the patients showing clear primary phenotypic improvement (3). The remainder of patients do not respond at all, or lose response after a short period. Because of the high cost of the anti-TNF biologics combined with their systemic side effects and the uncertainty of response, these drugs are generally not used as a first line treatment. If anti-TNF is eventually prescribed, the patient's endoscopic and histologic state is monitored over 8 and 14 weeks to assess response. During this "trial" period, side effects such as infections, anaphylaxis-like reactions, induction of auto-antibodies, skin eruptions and injection site reactions have been reported or are common (1-5), which, for non-responder patients, adds up to the burden of their unresolved IBD condition.

Predictive gene signatures for response in IBD have previously been proposed based on microarray gene expression experiments. Two studies identified sets of genes that discriminate responders from non-responders in UC and CD colon biopsies respectively (4, 5). A core set of 5 genes (TNFRSF11B, STC1, PTGS2, IL13RA2 and IL11) defined from the UC cohort data could perfectly classify the independent CD samples, supporting a common mechanism of (non)-response to treatment in both conditions. These genes encode for proteins involved in signaling in the adaptive immune response, pathogenesis of inflammation and TNF pathways (6-8). Moreover, PTGS2, STC1 and IL13RA2, are also implicated in intestinal homeostasis and pathology (9-12). Yet, their forming role in the molecular mechanisms of infliximab is not well understood. Biomarkers from blood gene expression (13), and genetic susceptibility loci for disease or non-response to anti-TNF have also been proposed (14, 15), and, very recently, association with microbiome composition has been investigated (16). However, research has not yet translated into a clinical test that can predict response to anti-TNF prior to onset of treatment. Hence, finding a robust, clinically feasible predictive assay of response is of high value as it would provide a personalized patient care, and improve the benefit-cost ratio of anti-TNF therapies by enabling the early-on treatment of predicted responders while limiting the risk of failure to response.

Inflammation in IBD is driven by an exacerbated immune response, where infiltrating immune cells in colon tissue are key actors of the disease's etiology and progression, notably through the interface with intestinal commensal microbes (17). For example, the presence of macrophage-formed granulomas is a common flag for CD diagnostic, and plasmacytic or neutrophil infiltrates are common clinical indicators of tissue inflammation. Moreover, biological function analysis of gene-level differences associated with response displayed a clear enrichment in immune-related functional categories (4, 5). However, the link between response to anti-TNF response and the characteristics of the endothelial immune compartment has not yet been investigated.

US 20110059445 A1 to Paul Rutgeerts and Frans Schuit (Mucosal gene signatures) discloses in vitro methods of determining if a subject suffering from an inflammatory condition of the large intestine and/or small intestine will respond to anti-TNFα therapy, using the IL-13R(alpha)2 (in UC patients) and the IL-13R(alpha)2, TNFRSF11B, STC1, PTGS2 and IL-11 (in IBD patients).

US 20110045490 A1 to Zoltán Konthur, et al. discloses biomarkers such as RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2 for the prediction of responsiveness to an anti-tumour necrosis factor alpha (tnf) treatment.

U.S. 20100069256 to Frederic Baribaud et al. discloses a method of predicting the suitability of treatment with a target therapy for a gastrointestinal-related disorder with anti-TNFα antibody by assaying nucleic acids from a specimen obtained from the subject.

SUMMARY OF THE INVENTION

According to an aspect of some embodiments of the present invention there is provided a method of predicting responsiveness of a subject having an inflammatory bowel disease (IBD) to treatment with a tumor necrosis factor (TNF)-alpha inhibitor, comprising:

analyzing a frequency of at least one subpopulation of immune cells in a tissue biopsy of the subject, wherein a frequency above a predetermined threshold of immune cells of a subpopulation selected from the group consisting of activated monocytes M1 macrophages, memory B cells, and neutrophils is indicative of the subject being non-responder to the TNF-alpha inhibitor, and/or wherein a frequency below a predetermined threshold of immune cells of a subpopulation selected from the group consisting of activated monocytes M2 macrophages and CD8+ T cells is indicative of the subject being non-responder to the TNF-alpha inhibitor, thereby predicting the responsiveness of the subject having the inflammatory bowel disease (IBD) to the TNF-alpha inhibitor.

According to an aspect of some embodiments of the present invention there is provided a method of selecting treatment to inflammatory bowel disease (IBD) in a subject in need thereof, the method comprising:

(a) determining responsiveness to a TNF-alpha inhibitor according to the method of some embodiments of the invention; and (b) selecting treatment based on the responsiveness.

According to an aspect of some embodiments of the present invention there is provided a method of treating inflammatory bowel disease (IBD) in a subject in need thereof, the method comprising:

(a) determining responsiveness to a TNF-alpha inhibitor according to the method of some embodiments of the invention; and (b) treating the subject based on the responsiveness.

According to an aspect of some embodiments of the present invention there is provided a kit for predicting responsiveness of a subject to a tumor necrosis factor (TNF)-alpha inhibitor comprising an agent capable of analyzing a frequency of at least one subpopulation of immune cells in a tissue biopsy of the subject, and a reference expression data of the frequency of at least one subpopulation of immune cells of a tissue biopsy obtained from at least one TNF-alpha inhibitor responder subject and/or at least one TNF-alpha inhibitor non-responder subject, wherein the immune cells are of a subpopulation selected from the group consisting of: activated monocytes M1 macrophages, memory B cells, neutrophils, activated monocytes M2 macrophages and CD8+ T cells.

According to some embodiments of the invention, the tissue biopsy of the subject comprises an inflamed tissue.

According to some embodiments of the invention, the IBD comprises ulcerative colitis (UC).

According to some embodiments of the invention, the IBD comprises Crohn's disease (CD).

According to some embodiments of the invention, the tissue biopsy comprises a colon tissue.

According to some embodiments of the invention, the tissue biopsy comprises an ileum tissue.

According to some embodiments of the invention, the activated monocytes M1 macrophages are characterized by CD68+ expression signature.

According to some embodiments of the invention, the activated monocytes M1 macrophages are characterized by CD68+/CCR7+/CD86+/CD80+ expression signature.

According to some embodiments of the invention, the activated monocytes M1 macrophages are characterized by CD68+/CCR7+/CD86+/CD80+/CD11b+/CCR2+ expression signature.

According to some embodiments of the invention, the activated monocytes M2 macrophages are characterized by CD68+ expression signature.

According to some embodiments of the invention, the activated monocytes M2 macrophages are characterized by CD68+/CD163+/CD206+ expression signature.

According to some embodiments of the invention, the memory B cells are plasma cells, and wherein the plasma cells are characterized by positive expression of CD138.

According to some embodiments of the invention, the memory B cells are plasma cells, and wherein the plasma cells are characterized by CD138+/CD45+/BCMA+/CD38+/IgM+/IgG+/IgA+/IgE+.

According to some embodiments of the invention, the memory B cells are non-plasma cells, and wherein the non-plasma cells are characterized by CD20+/CD19+/CD45RA+ expression signature.

According to some embodiments of the invention, the memory B cells are non-plasma cells, and wherein the non-plasma cells are characterized by CD20+/CD 19+/CD45RA+/CD45+/MHC-Class II+/IgG+/IgA+/IgE+/IgD+ expression signature.

According to some embodiments of the invention, the neutrophils are characterized by CD45+, CD66b+ and/or CD16+ expression signature.

According to some embodiments of the invention, the CD8+ T cells are characterized by CD8+ expression signature.

According to some embodiments of the invention, the CD8+ T cells are characterized by CD8+/CD69+ expression signature.

According to some embodiments of the invention, the CD8+ T cells are characterized by CD8+/CD69+/CD3+/CD45+/CD45RA+ expression signature.

According to some embodiments of the invention, the subject is a naive subject who hasn't been treated with the TNF-alpha inhibitor.

According to some embodiments of the invention, the cells of the tissue biopsy are intact cells.

According to some embodiments of the invention, the analyzing the frequency of the at least one subpopulation of immune cells is performed by a morphometric analysis.

According to some embodiments of the invention, the analyzing the frequency of the at least one subpopulation of immune cells is performed using at least one histological stain.

According to some embodiments of the invention, the analyzing the frequency of the at least one subpopulation of immune cells is performed using at least one antibody.

According to some embodiments of the invention, the antibody is used in an immuno-histochemistry (IHC) or immuno-fluorescence method.

According to some embodiments of the invention, the antibody is used in flow cytometry or Fluorescence-activated cell sorting (FACS) analysis.

According to some embodiments of the invention, the analyzing the frequency of the at least one subpopulation of immune cells is performed by an RNA in-situ hybridization assay.

According to some embodiments of the invention, the analyzing the frequency of the at least one subpopulation of immune cells is performed by a single cell RNA sequencing (RNA SEQ) analysis.

According to some embodiments of the invention, the analyzing the frequency of the at least one subpopulation of immune cells is performed by exome sequencing.

According to some embodiments of the invention, the analyzing the frequency of the at least one subpopulation of immune cells is performed by RNA SEQ followed by deconvolution.

According to some embodiments of the invention, the analyzing the frequency of the at least one subpopulation of immune cells is performed by reverse-transcriptase polymerase chain reaction (RT-PCR) followed by deconvolution.

According to some embodiments of the invention, the analyzing the frequency of the at least one subpopulation of immune cells is performed by micro array followed by deconvolution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
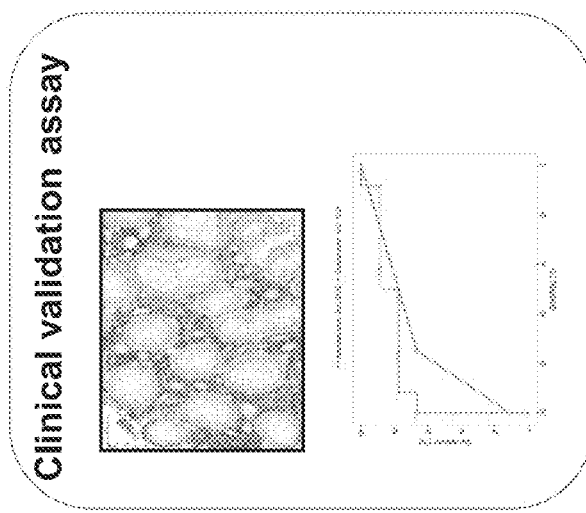
Figure 1A:
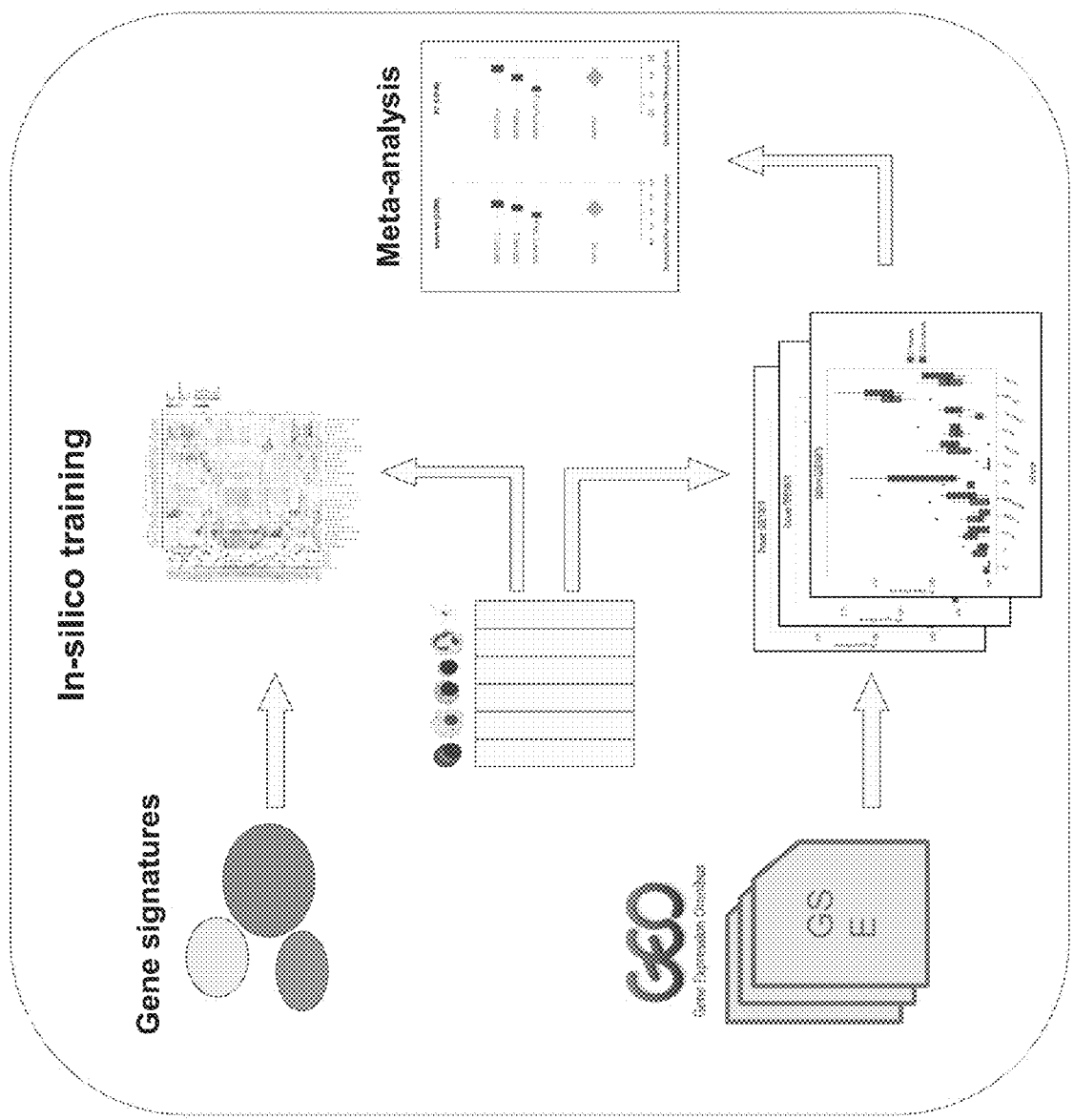

FIGS. 1A-B schematically illustrate the cell centered meta-analysis pipeline. Schematic view of the meta-analysis pipeline used to identify baseline cellular signature of response to anti-TNF. FIG. 1A—in-silico training. FIG. 1B—clinical validation assay.

Figure 2A:
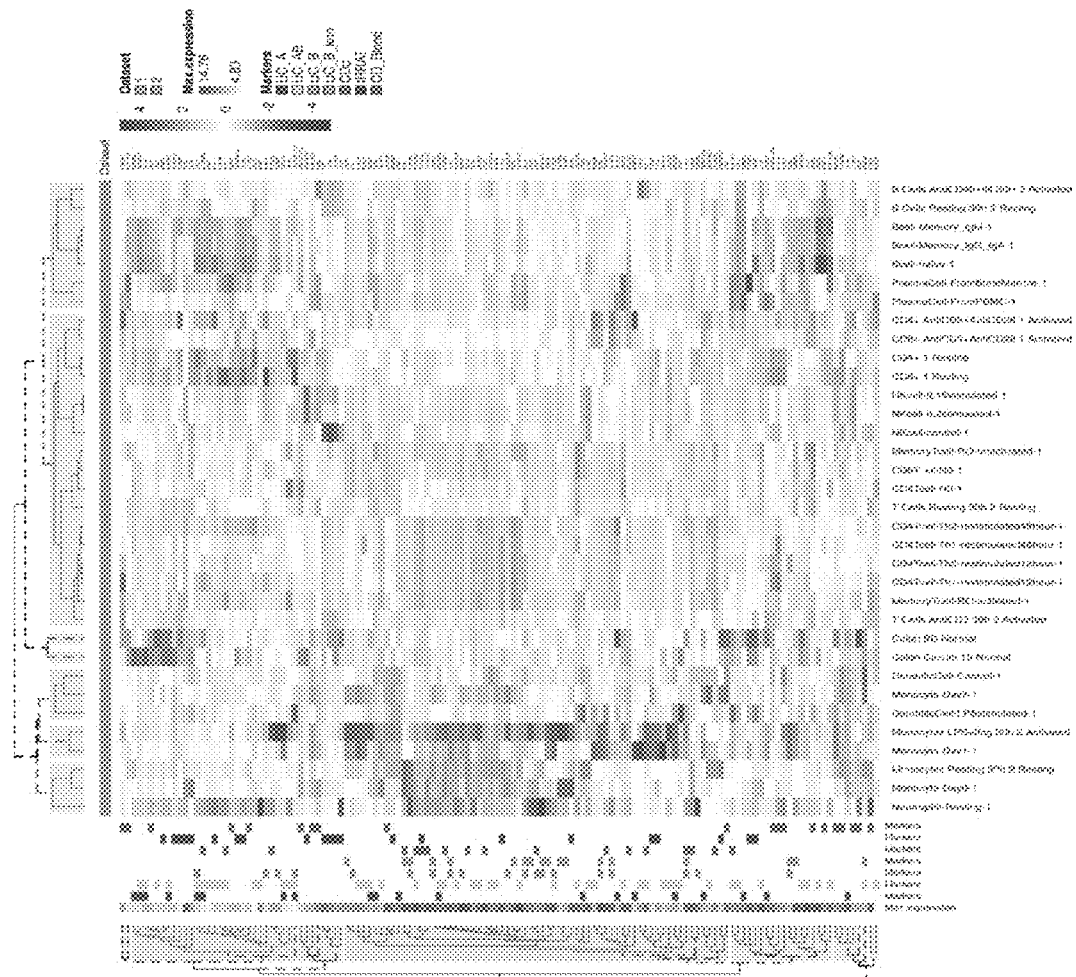
Figure 2B:
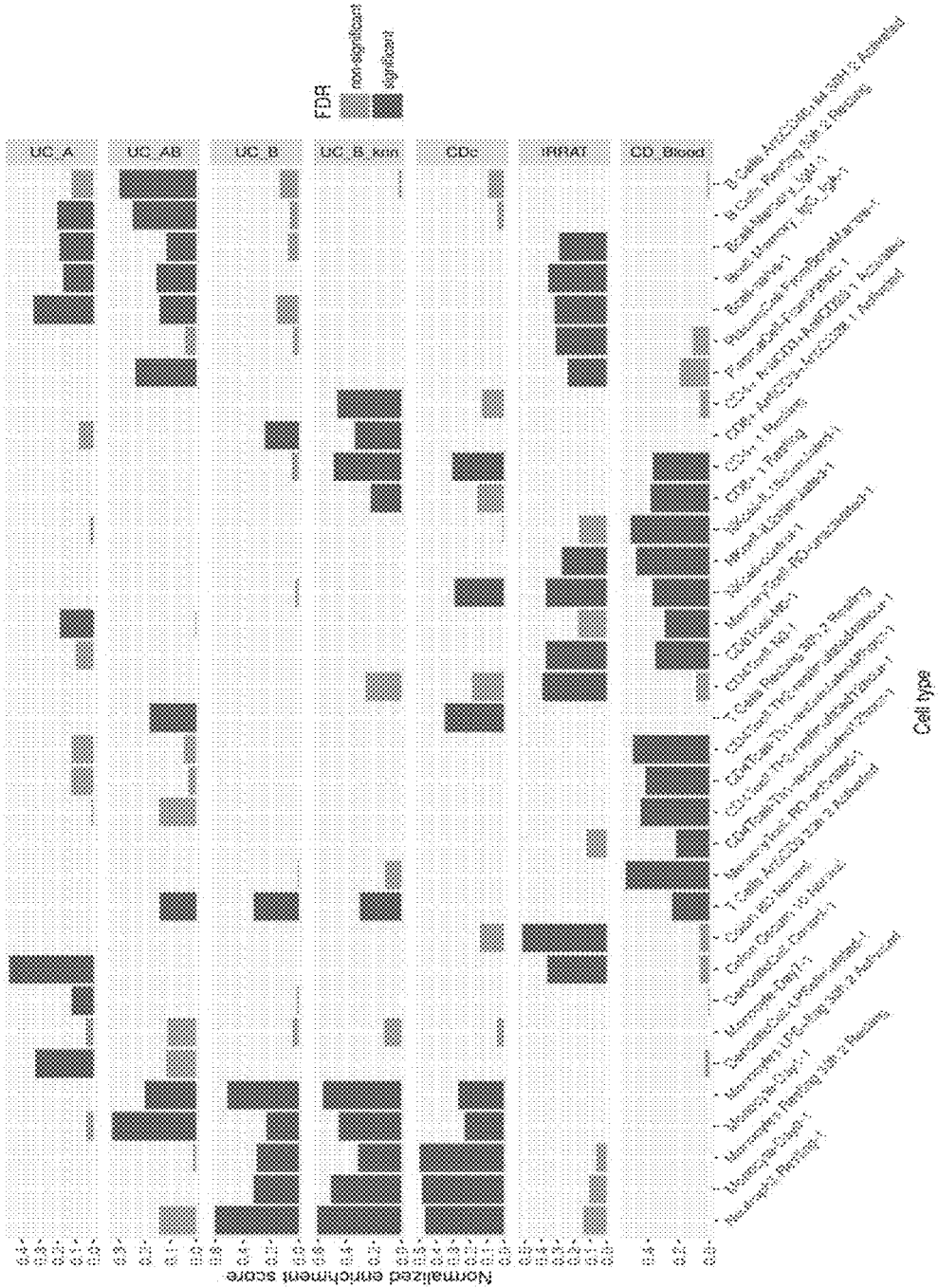

FIGS. 2A-B depict the cell type expression analysis of previously reported gene signature. FIG. 2A—Expression of gene signatures in immune cell subsets and colon tissue. Each row was standardized (z-score) separately to highlight gene expression cell type-specificity. Color scale range from blue/low to red/high, with white/zero representing average expression across all samples. Rows and columns were clustered using euclidean distance with average linkage. Row annotations indicates the absolute maximum log 2 expression of each gene (shades of green), and the membership(s) of each gene to a signature. Row dendrogram clades (8) are coloured to highlight genes that the present inventors associated with specific—group of—cell types. Column annotation indicates the GEO dataset from which each sample was obtained. Column dendrogram clades (7) are coloured to highlight cell types that belong to a common lineage. (B) Scores and p-values from single sample enrichment analysis using GSVA.

FIGS. 3A-C depict computational deconvolution of gene expression data. FIG. 3A—Boxplot of estimated proportions in cohort GSE16789 (baseline CD colon samples). Only cell types with non-zero proportions in more than 75% of the samples are shown. Group differences are highlighted by separate boxplots for responders (blue) and non-responders (red). Significant differences are indicated with circled stars (nominal p-value<=0.05, Wilcoxon rank sum test). The y-axis represents the estimated proportion of each cell type in each sample. "mono act"=M1 Macrophage. FIGS. 3B-C—Expression of the top 20-genes signature previously identified in UC patients, and shown to be able to predict response in CD patients (4) (FIG. 3B). After correction for estimated proportions of activated monocytes and plasma cells, the predictive power of this signature drops (FIG. 3C). The heatmap shows the log 2 expression of each gene. For better comparison, rows in the top panel were clustered using the same metric and linkage method as the columns (dendrogram not shown), and the resulting ordering was applied to the rows in the bottom panel.

Figure 4:
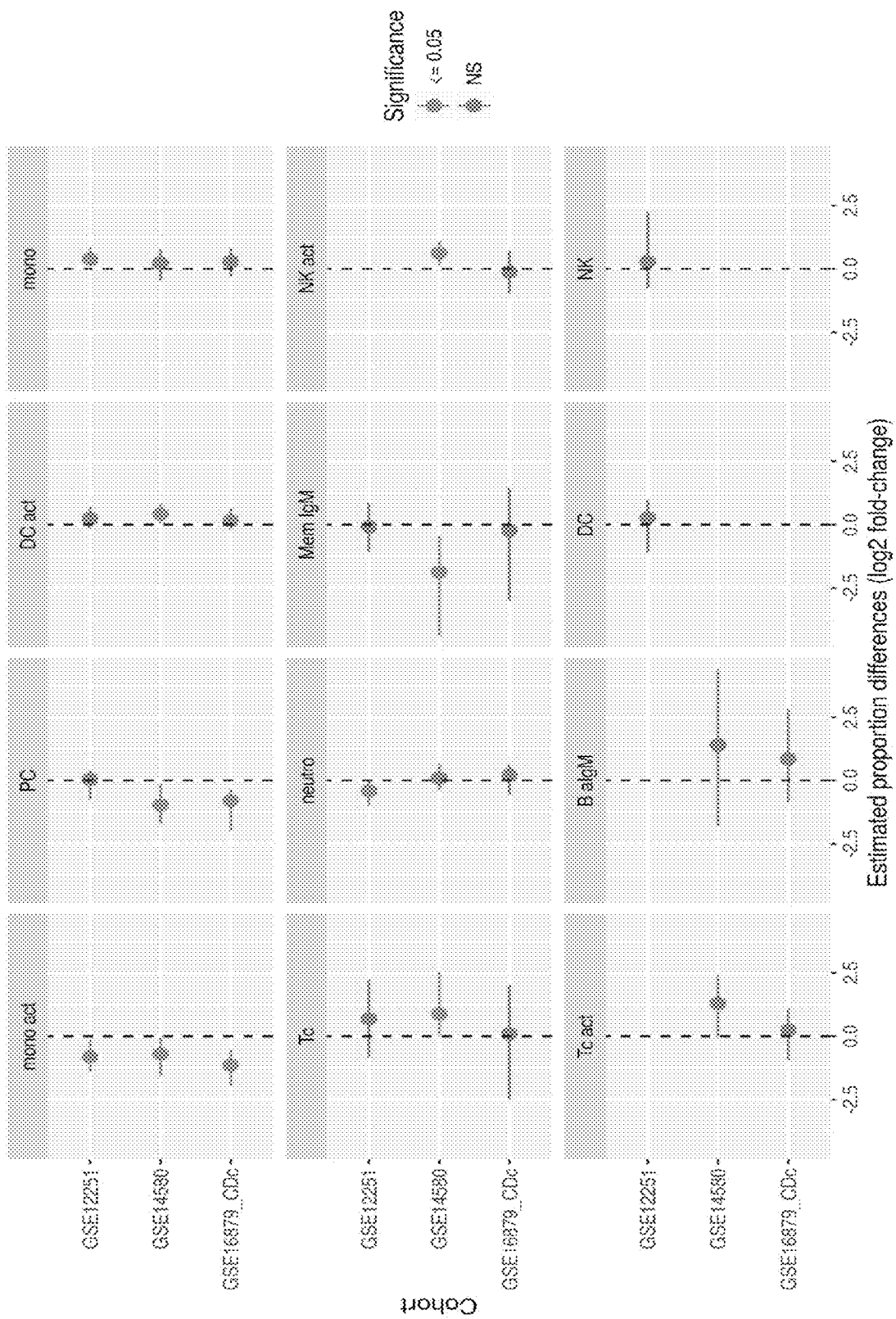

FIG. 4 depicts meta-analysis of cell subset proportion identified consistent immune cell subset different between responders and non-responder to infliximab. Each panel shows estimated group proportion differences (pseudo median) and 95% confidence interval for a given cell subset, across all discovery cohorts. Missing data comes from cell type/cohort pairs not included in the meta-analysis because of too many zero estimated proportions. The x-axis represents the log 2 proportion fold change (i.e. log 2(Responders/Non-Responders)). The y-axis indicates the discovery cohorts. Statistical significance was calculated using Wilcoxon rank sum test (nominal p-value<=0.05), and is shown in red (significant) and blue (non-significant). "mono act"=M1 Macrophage.

Figure 5B:
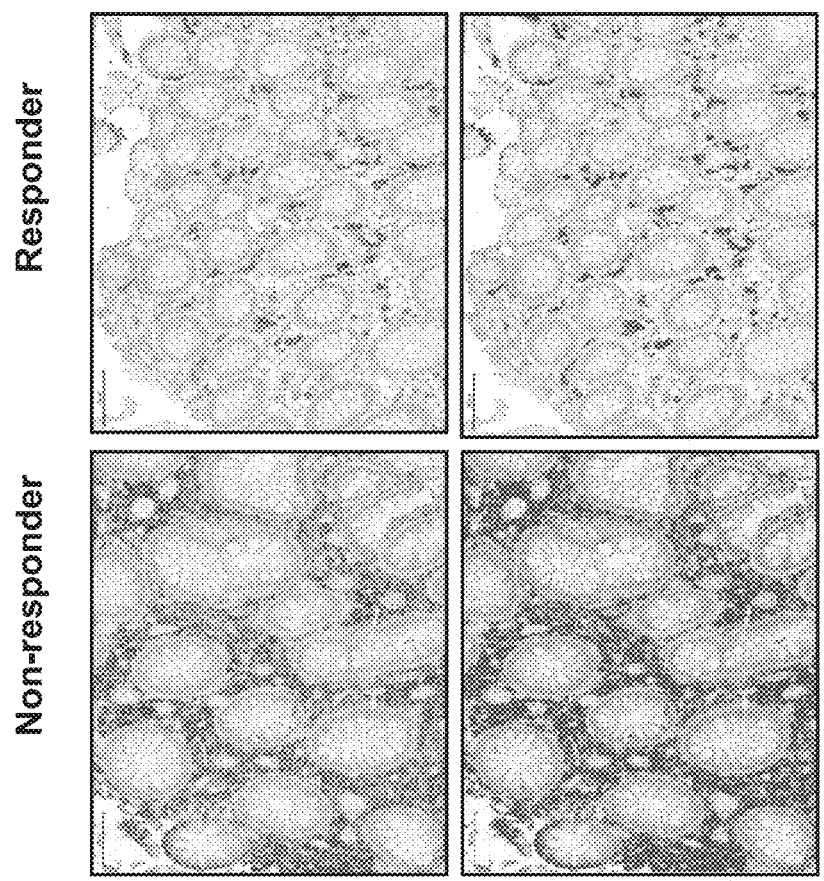
Figure 5A:
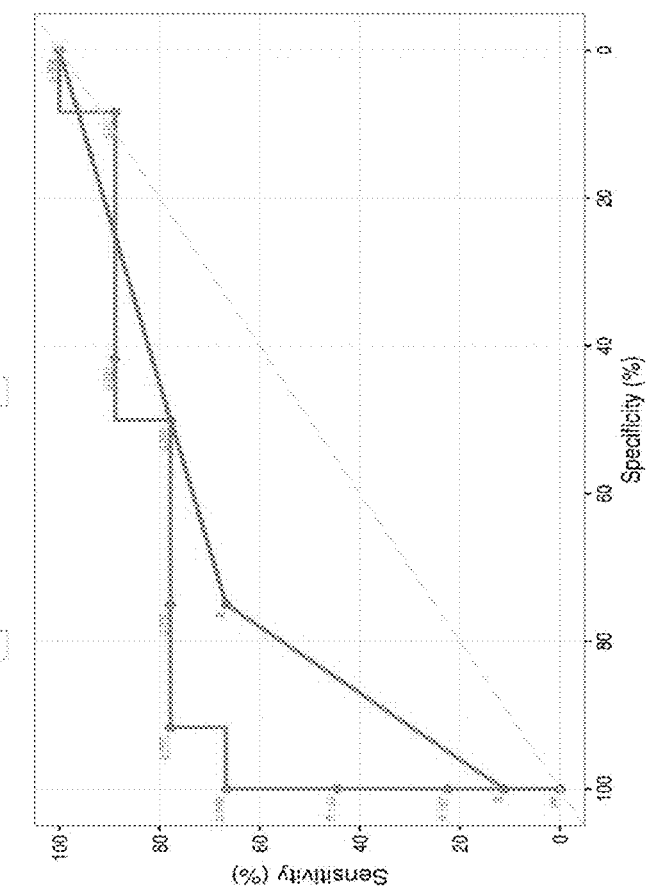

FIGS. 5A-B depict validation by staining of plasma cells in independent IBD biopsies. FIG. 5A—ROC curve showing the predictive power of plasma cell proportions from staining as quantified by two scoring methods: a clinician categorical score (blue) and automated pixel quantitation (red). The respective Area Under the Curve (AUC) achieved by each scoring method are indicated in the legend. FIG. 5B—Staining slides showing visual differences between responders and non-responders. CD138+ plasma cells are colored in brown, showing an increased staining in non-responsive patients. The blue staining indicates the brown regions detected by automated quantitation with ImagePro Plus software.

Figure 6:
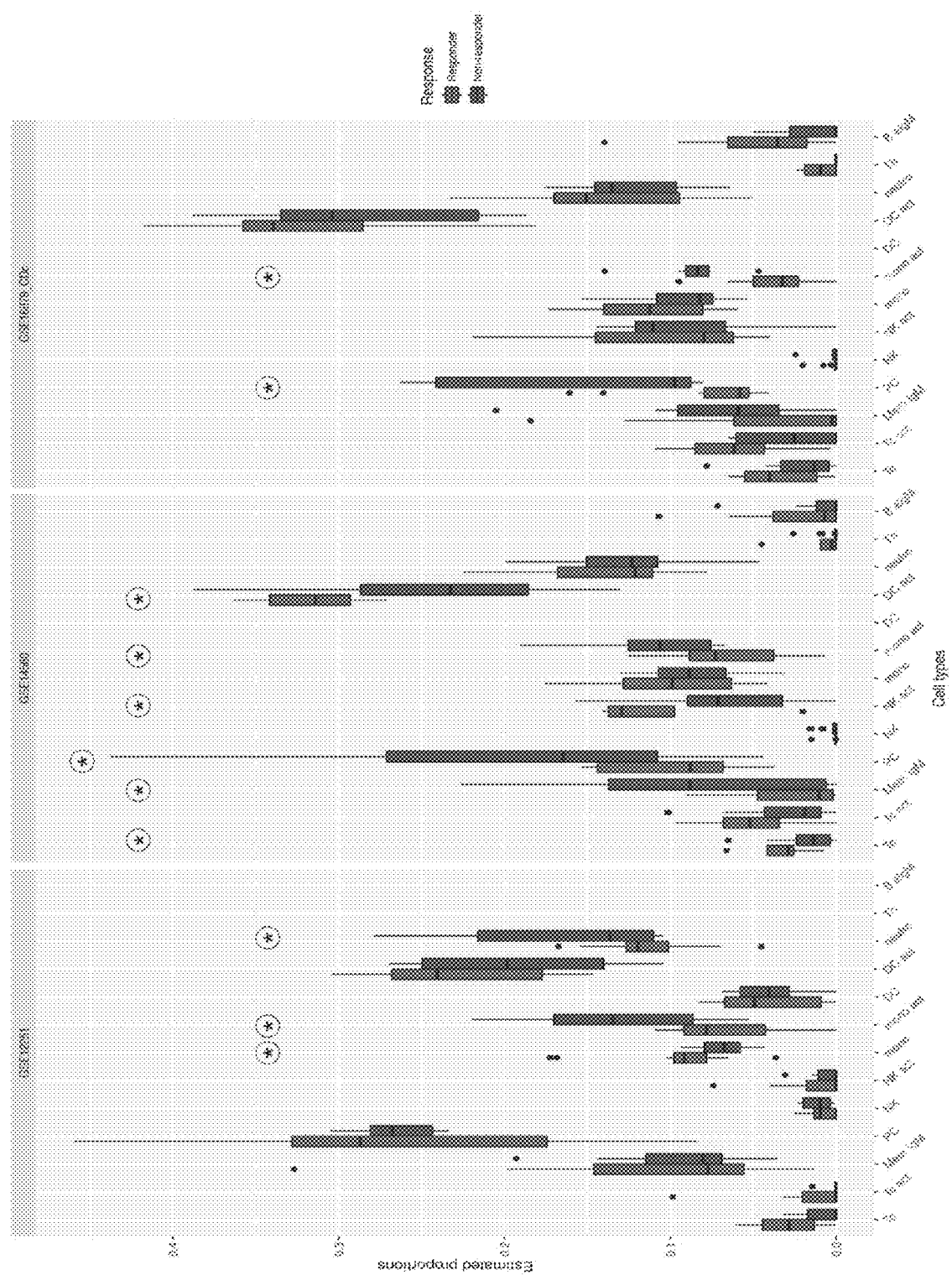

FIG. 6 depicts estimated cell type proportions in all discovery cohorts. Proportions were estimated in each sample separately and compared within each cohort between responders and non-responders. Only cell types with non-zero proportions in more than 75% of the samples are shown. Group differences are highlighted by separate boxplots for responders (blue) and non-responders (red). Significant differences are indicated with circled stars (nominal p-value<=0.05, wilcoxon rank sum test). "mono act"=M1 Macrophage.

Figures 7A, 7B:
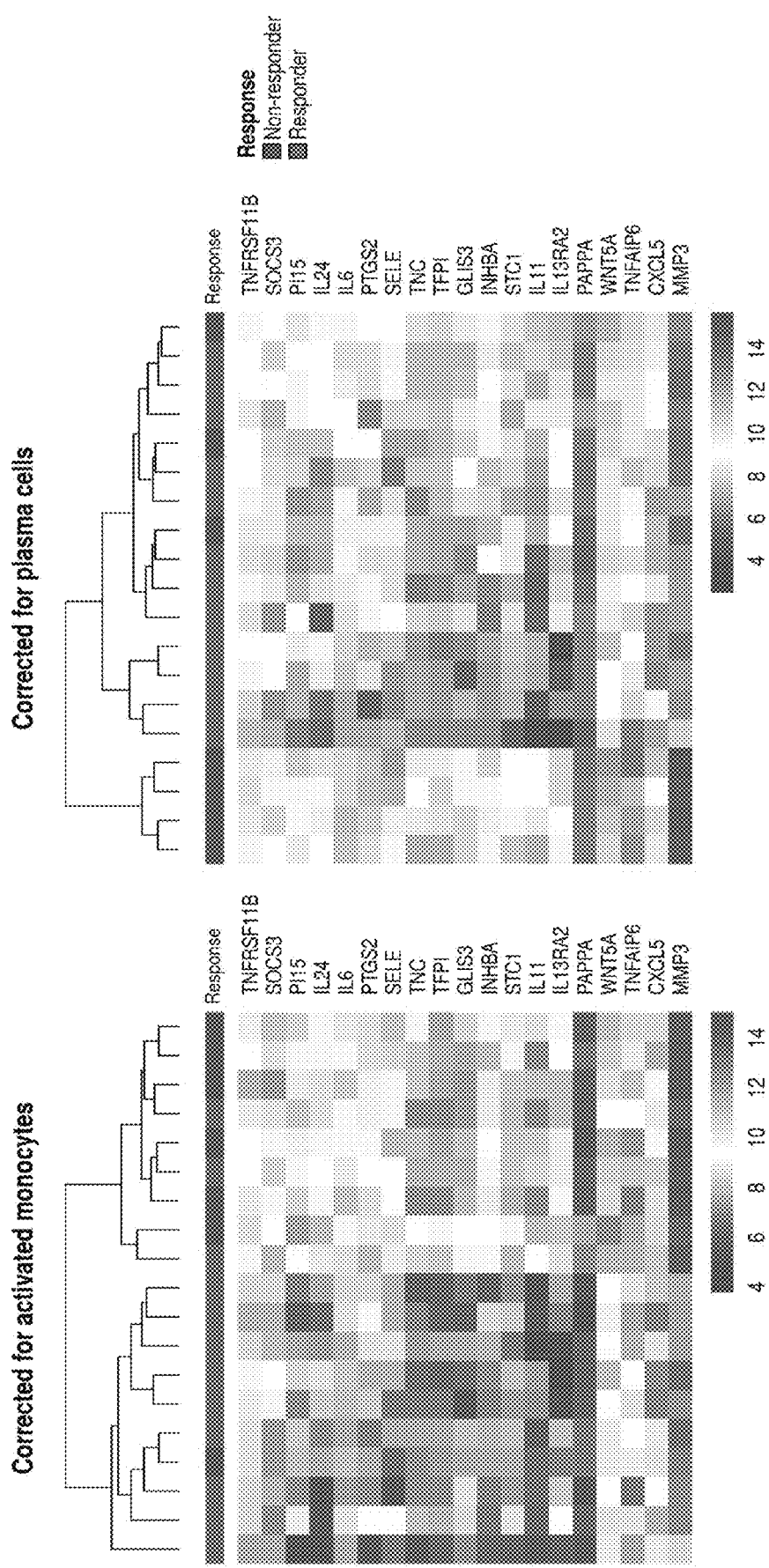

FIGS. 7A-B the predictive power of a 20-genes signatures after correction for cell type proportions. Expression of the 20-UC genes predictive signature in CDc samples, after correction for estimated proportions of activated monocytes (FIG. 7A) and plasma cells (FIG. 7B). After correction, the predictive power of this signature drops. The heatmap shows the log 2 expression of each gene. For better comparison, rows in both panels were ordered according to the clustering order in the original data (unadjusted for proportions) shown in FIG. 3B.

Figure 8:
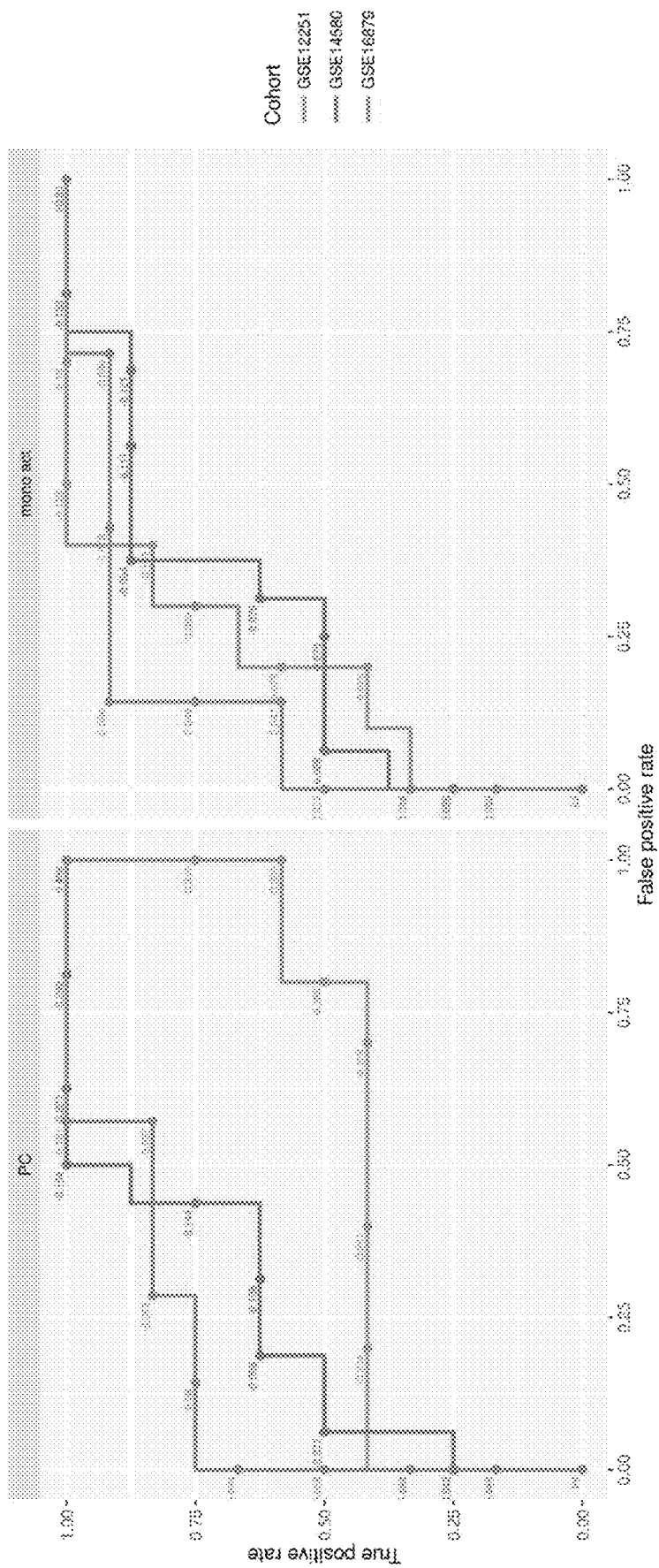

FIG. 8 depicts ROC curve analysis for the cell types selected in each of the discovery cohorts. Each panel shows the ROC curve computed from the estimated proportions of a given cell type [plasma cells (left) and activated monocytes (right)] in each discovery cohort: GSE12251 (red), GSE14580 (green) and GSE16879 (blue). The x and y axis represent the false positive rate (1-specificity) and true positive rate (sensitivity) respectively. "mono act"=M1 Macrophage.

Figure 9B:
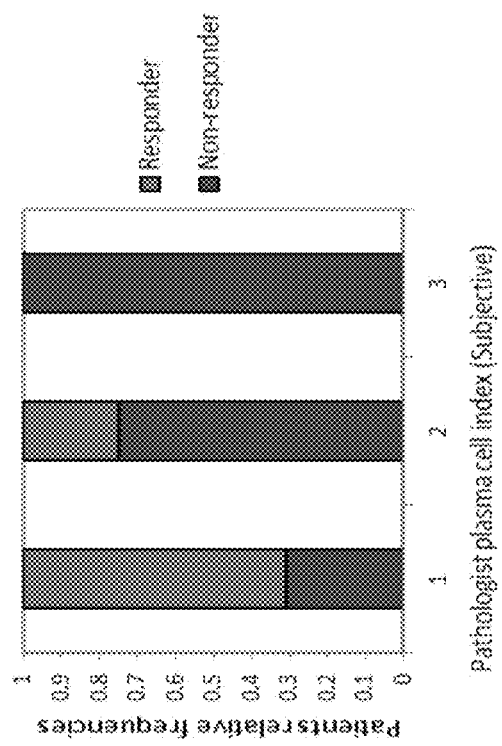
Figure 9A:
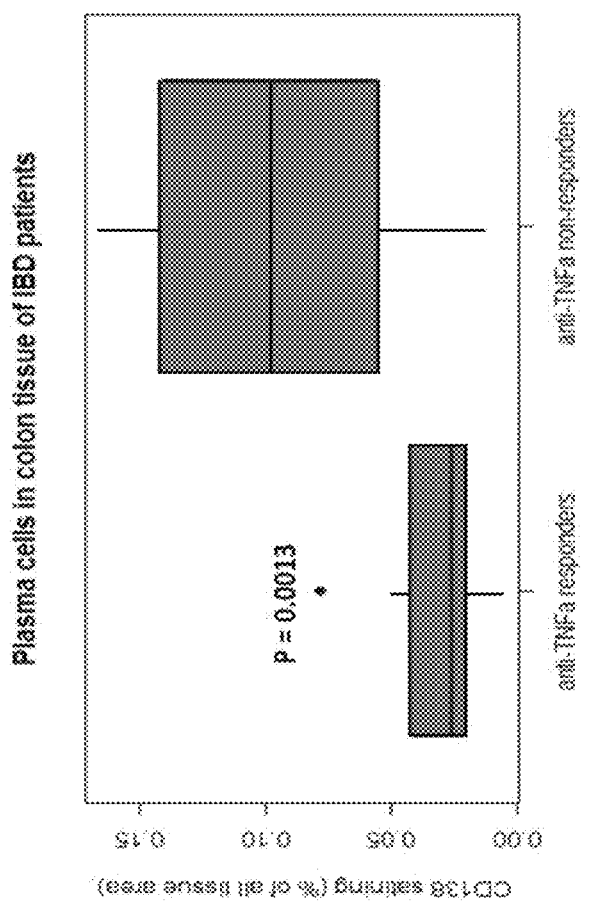

FIGS. 9A-B depict results from staining of plasma cells in the validation IBD biopsy samples. FIG. 9A—Automated quantitation. FIG. 9B—Pathologist blind score. The Y-axis gives the proportion of assessed biopsies achieving a given score (x-axis).

Figure 10:
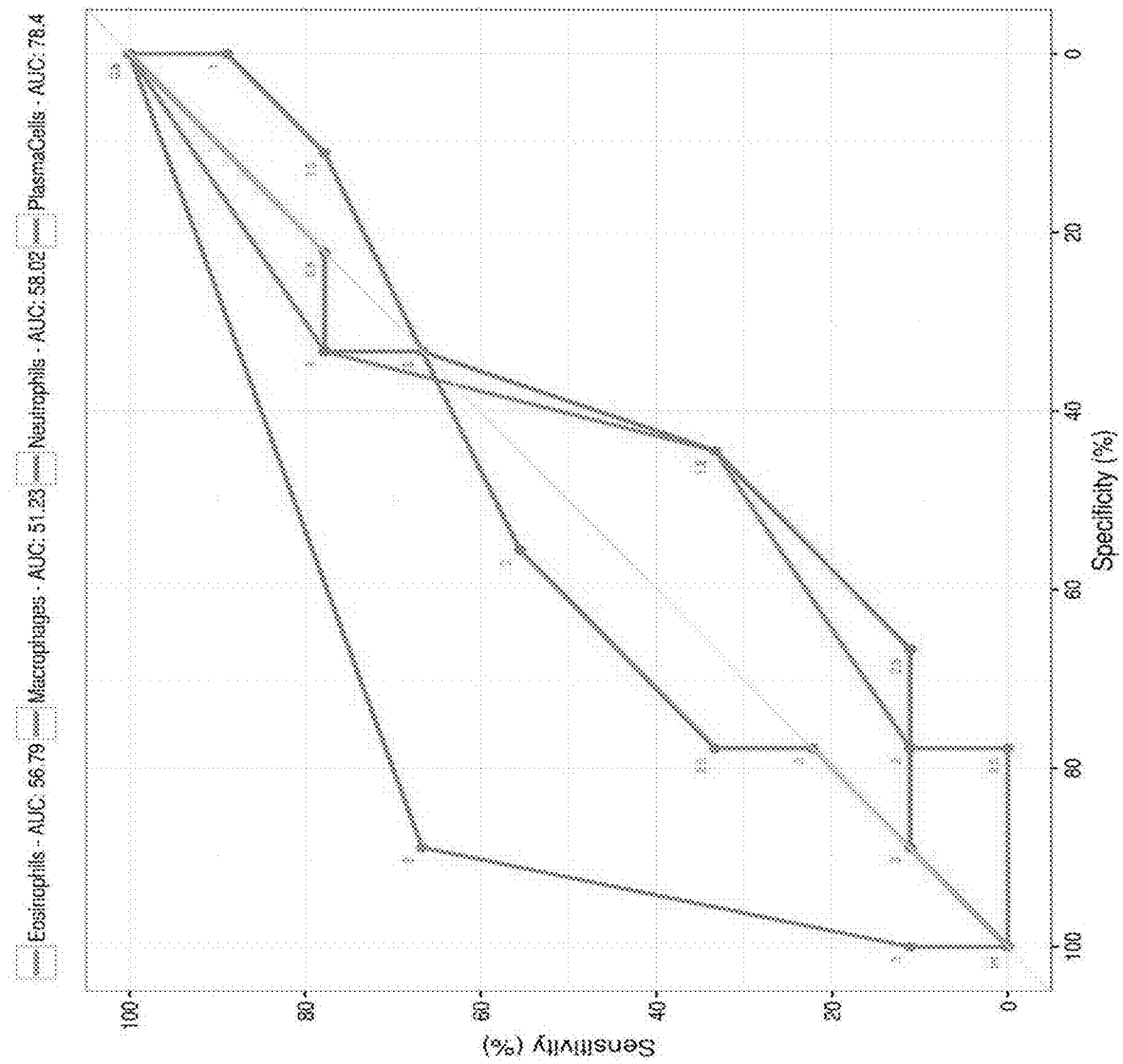

FIG. 10 depicts ROC curve analysis of pathologist validation of cell-types signatures highlights plasma cell differences between anti-TNF responders versus non-responders.

Figure 11A:
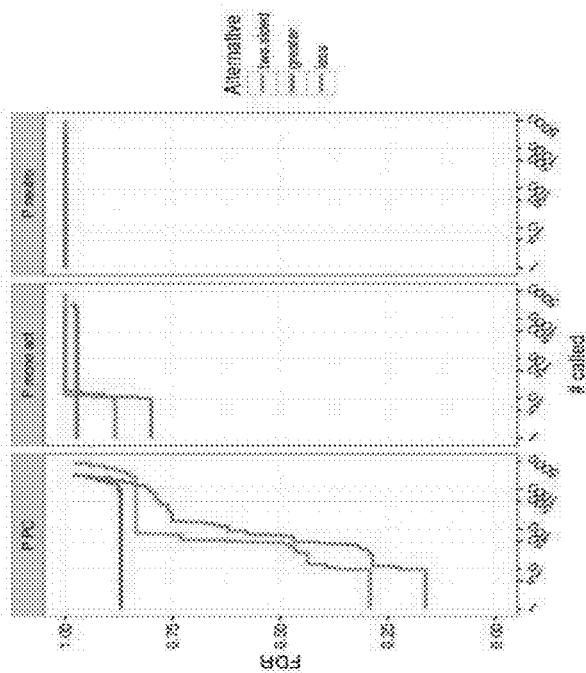
Figure 11B:
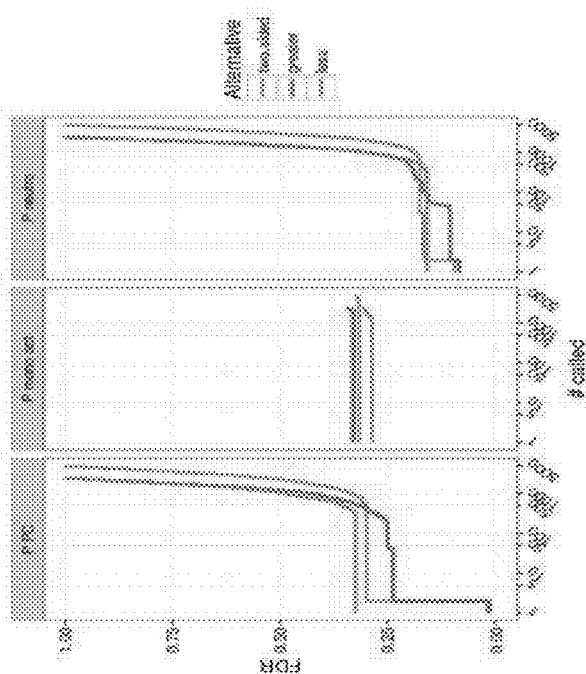
Figure 11C:
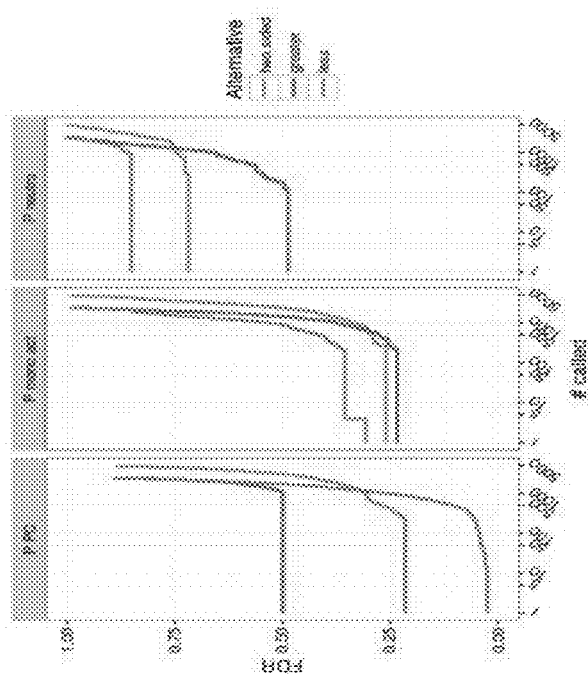

FIG. 11A-C depict cell type specific differential expression in all discovery cohorts. csSAM runs on the 3 discovery cohorts including plasma cells, activated monocytes and neutrophils identifies differentially expressed genes in plasma cells. "mono act"=M1 Macrophage.

Figure 12:
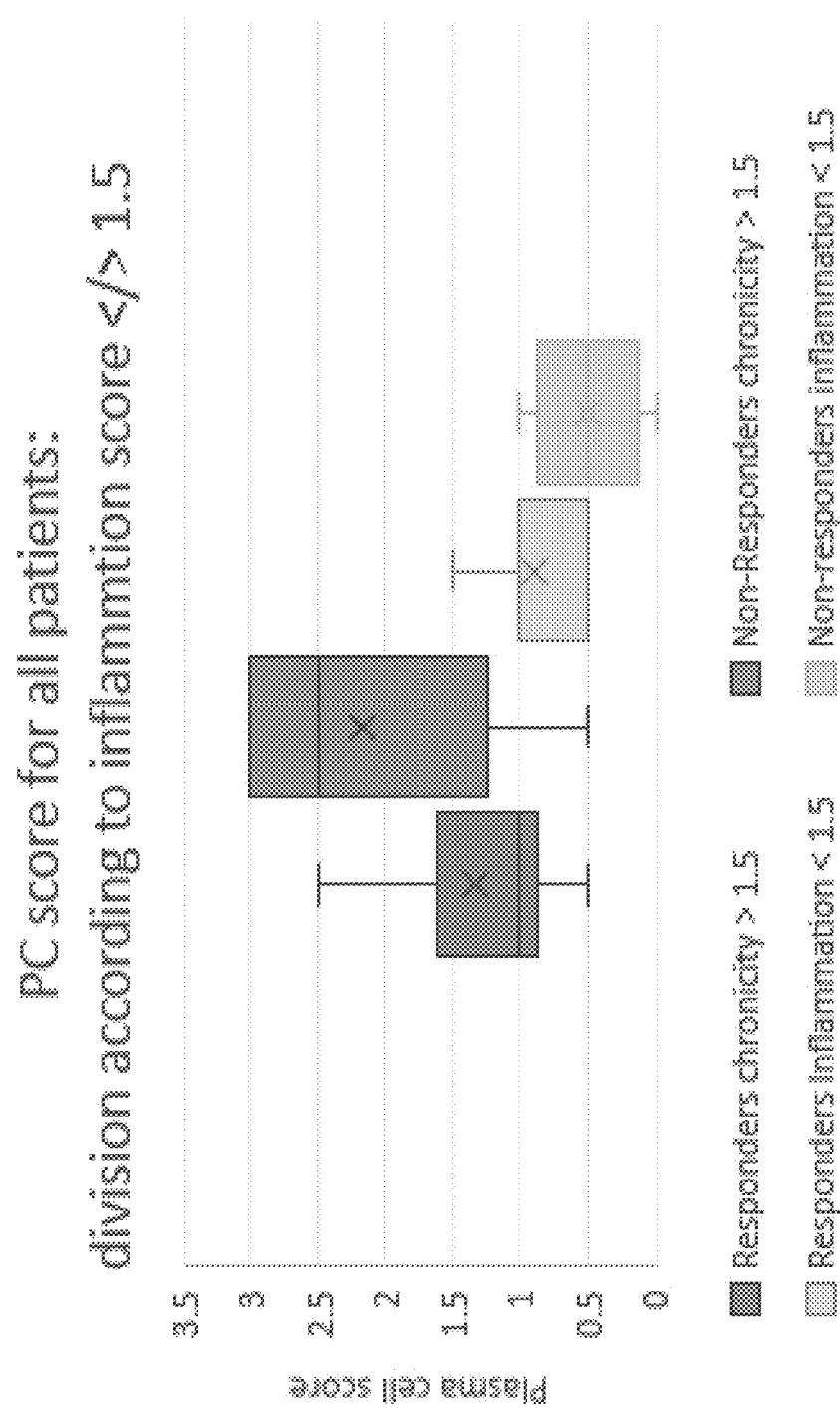

FIG. 12 is a histogram demonstrating that plasma cell proportions in inflamed colon tissue can predict response to infliximab (IFX) prior to treatment initiation. Formalin-fixed slides of paraffin-embedded colon tissues were immunostained with H&E to show the basic tissue morphology. All biopsies were collected prior to IFX therapy initiation. Slides were then coded and interpreted by a specialist pathologist. A specific cell abundance categorical index between 0 and 3 was determined by the pathologist for plasma cells proportion and for inflammation level. Chronic inflammation score was defined as a combined score that reflects tissue distortion and plasmacytosis. Minimal amount of cells or inflammation was scored as "0", whereas the highest cell abundance or inflammation stage detected across all slides was scored as "3". The tissues were scored one by one in a blinded manner. Nine non-responders and twenty responders were included in this 2nd cohort. Inflamed tissue sites (inflammation score>1.5) were scored from 7 responders and 5 non-responders.

DESCRIPTION OF SPECIFIC EMBODIMENTS OF THE INVENTION

The present invention, in some embodiments thereof, relates to methods and kits for predicting responsiveness of a subject having an inflammatory bowel disease (IBD) to treatment with a tumor necrosis factor (TNF)-alpha inhibitor, more particularly, but not exclusively, to methods of selecting a treatment for a subject diagnosed with the IBD.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

IBD conditions can be treated with a TNF-alpha inhibitor to treat inflammation and achieve mucosal healing. However, response to such treatments is very heterogeneous, with overall only 60% of the patients showing clear primary phenotypic improvement. The remainder of patients do not respond at all, or lose response after a short period. Because of the high cost of the anti-TNF biologics combined with their systemic side effects and the uncertainty of response, these drugs are generally not used as a first line treatment.

The present inventors have hypothesized that the relative proportions of the various immune cell subsets infiltrating the affected tissue does not only reflect disease state, but may also be predictive of a patient's potential to respond to anti-TNF treatment. Thus, as shown in the Examples section which follows, the present inventors analyzed public gene expression data using recent bioinformatics methodology developments that enable the computational deconvolution of mixture data such as blood or bulk tissue, i.e. the estimation of the proportions of constituting cell types directly from heterogeneous samples (18). By means of a meta-analysis framework, the present inventors integrated estimated immune cell subset proportions from multiple IBD cohorts, and identified consistent proportion differences between responders and non-responders in immune cells such as macrophages and plasma cells. The implication of plasma cells was further supported by a cell type-specific differential analysis. The present inventors validated these results on an independent set of samples, where plasma cells proportions assessed in immunostained biopsies could predict response to anti-TNF with high accuracy [Area Under the Curve (AUC) 80%]. Overall, these results propose a novel clinically feasible and efficient mean of predicting response to anti-TNF treatment in naive patients, which can be used to improve patient care through maximizing response rate. These results also provide novel insights on the immune target of TNF blockade in IBD.

Thus, according to an aspect of some embodiments of the invention there is provided a method of predicting responsiveness of a subject having an inflammatory bowel disease (IBD) to treatment with a tumor necrosis factor (TNF)-alpha inhibitor, the method comprising:

analyzing a frequency of at least one subpopulation of immune cells in a tissue biopsy of the subject, wherein a frequency above a predetermined threshold of immune cells of a subpopulation selected from the group consisting of activated monocytes M1 macrophages, memory B cells, and neutrophils is indicative of the subject being non-responder to the TNF-alpha inhibitor, and/or wherein a frequency below a predetermined threshold of immune cells of a subpopulation selected from the group consisting of activated monocytes M2 macrophages and CD8+ T cells is indicative of the subject being non-responder to the TNF-alpha inhibitor, thereby predicting the responsiveness of the subject having the inflammatory bowel disease (IBD) to the treatment with the TNF-alpha inhibitor.

According to some embodiments of the invention, the tissue biopsy of the subject comprises an inflamed tissue.

As used herein the term "inflammatory bowel disease (IBD)" refers to a pathology characterized by an inflammatory condition of the colon and the small intestine. Crohn's disease (CD) and ulcerative colitis (UC) are the principal types of inflammatory bowel disease.

According to some embodiments of the invention, the IBD comprises ulcerative colitis (UC).

Ulcerative colitis (UC) is a long-term condition that results in inflammation and ulcers of the colon and rectum. The primary symptom of active disease is abdominal pain and diarrhea mixed with blood. Other common symptoms include, weight loss, fever, anemia, which can be ranged from mild to severe. Symptoms typically occur intermittently with periods of no symptoms between flares; and complications may include megacolon, inflammation of the eye, joints, or liver, and colon cancer.

According to some embodiments of the invention, the IBD comprises Crohn's disease (CD).

Crohn's disease (CD) is a type of inflammatory bowel disease (IBD) that may affect any part of the gastrointestinal tract from mouth to anus. Signs and symptoms often include abdominal pain, diarrhea (which may be bloody if inflammation is severe), fever, and weight loss. Other complications may include anemia, skin rashes, arthritis, inflammation of the eye, and feeling tired.

As used herein, the term "subject" includes mammals, preferably human beings at any age which suffer from the pathology.

According to some embodiments of the invention, the subject is a naive subject who hasn't been treated with the TNF-alpha inhibitor.

According to some embodiments of the invention, the subject is refractory to corticosteroids and/or immunosuppression treatment. For example, the subject has been subjected to corticosteroids and/or immunosuppression treatment, yet without sufficient, or any therapeutic effect.

As used herein the phrase "TNF-alpha" or "tumor necrosis factor alpha", which is interchangeably used herein, refers to a multifunctional pro-inflammatory cytokine [also known as DIF; TNFA; TNFSF2; TNLG1F;] that belongs to the tumor necrosis factor (TNF) superfamily. TNF-alpha is mainly secreted by macrophages. It can bind to, and thus functions through its receptors TNFRSF1A/TNFR1 and TNFRSF1B/TNFBR. This cytokine is involved in the regulation of a wide spectrum of biological processes including cell proliferation, differentiation, apoptosis, lipid metabolism, and coagulation, and is being implicated in a variety of diseases, including autoimmune diseases, insulin resistance, and cancer.

It should be noted that the "responsiveness" of a subject to a TNF-alpha inhibitor refers to the success or failure of treatment of the subject with the TNF-alpha inhibitor.

A positive response to TNF-alpha inhibitor refers to an improvement following treatment with the TNF-alpha inhibitor in at least one relevant clinical parameter as compared to an untreated subject diagnosed with the same pathology (e.g., the same type, stage, degree and/or classification of the pathology), or as compared to the clinical parameters of the same subject prior to treatment with the TNF-alpha inhibitor. Hence, improvement of clinical symptom(s) following treatment implicates that the subject is a "responder" to the treatment.

On the other hand, a negative response to the treatment with the TNF-alpha inhibitor means that the subject has no sufficient improvement in clinical symptoms, or has a complete lack of improvement of clinical symptoms, or has a worsening of clinical symptoms characterizing the pathology (the IBD condition), with or without appearance of antibodies (e.g., antibody against infliximab) which neutralize the TNF-alpha inhibitor. Such a subject is a "non-responder" to the treatment.

According to some embodiments of the invention, a subject diagnosed with and/or suffering from Crohn's disease or ulcerative colitis is considered to be a responder to the treatment with the TNF-alpha inhibitor if his follow-up clinical data (a year after biopsy) point to remission by Physicians Global Assessment (PGA), laboratory parameters [haemoglobin (Hb), erythrocyte sedimentation rate (ESR), C-reactive protein (CRP), albumin] and used medicines (e.g., steroids, 5-ASA, thiopurines, methotrexate, biologics).

According to some embodiments of the invention, a subject diagnosed with and/or suffering from Crohn's disease or ulcerative colitis is considered to be a non-responder to the treatment with the TNF-alpha inhibitor if his follow-up clinical data (a year after biopsy) point to continuous flare/chronic disease by Physicians Global Assessment (PGA), laboratory parameters (Hb, ESR, CRP, albumin) and 25 used medicines (e.g., steroids, 5-ASA, thiopurines, methotrexate, biologics).

For example, a positive response to treatment with TNF-alpha inhibitor in a subject having an IBD such as ulcerative colitis (UC) or Crohn's disease (CD) disease is a mucosal healing.

Additional and/or alternative parameters which indicate a positive response to the treatment with the TNF-alpha inhibitor (thus indicating that the subject is responder to treatment) include, for example, reduction in the number of liquid or very soft stools; reduction in the abdominal pain; reduction in symptoms or findings presumed related to Crohn's disease: arthritis or arthralgia, iritis or uveitis, erythema nodosum, pyoderma gangrenosum, aphthous stomatitis, anal fissure, fistula or perirectal abscess, other bowel-related fistula, febrile (fever), episode over 100 degrees during past week; and/or reduction in abdominal mass.

The response (i.e., positive or negative) for treatment with the TNF-alpha inhibitor of some embodiments of the invention can be evaluated using known and accepted medical indexes and/or calculators.

For example, the Crohn's Disease Activity Index (CDAI) calculator gauges the progress or lack of progress for people with Crohn's disease. It is accepted that CDAI scores below 150 indicate a better prognosis than higher scores.

The CDAI calculator takes into consideration the following parameters:

(1). Number of liquid or very soft stools in one week;
(2). Sum of seven daily abdominal pain ratings: (0=none, 1=mild, 2=moderate, 3=severe);
(3). Sum of seven daily ratings of general well-being: (0=well, 1=slightly below par, 2=poor, 3=very poor, 4-=terrible);
(4). Symptoms or findings presumed related to Crohn's disease: arthritis or arthralgia, iritis or uveitis, erythema nodosum, pyoderma gangrenosum, aphthous stomatitis, anal fissure, fistula or perirectal abscess, other bowel-related fistula, febrile (fever) episode over 100 degrees during past week;
(5). Taking Lomotil or opiates for diarrhea;
(6). Abnormal mass: 0=none; 0.4=questionable; 1=present
(7). Hematocrit [(Typical−Current)×6] Normal average: For Male=47 For Female=42;
(8). 100× [(standard weight-actual body weight)/standard weight]

Additionally or alternatively, the clinical status of patients with CD following treatment with the TNF-alpha inhibitor can be evaluated using the Harvey-Bradshaw index (HBI) which was devised in 1980 as a simpler version of the Crohn's disease activity index (CDAI) for data collection purposes. It consists of only clinical parameters.

Following is a non-limiting an exemplary calculator for score using the HBI index.

TABLE 1

Table 1: Harvey-Bradshaw index (HBI).

| Parameter | Scoring |
|---|---|
| General well-being | very well +0 |
| | slightly below par +1 |
| | poor +2 |
| | very poor +3 |
| | terrible +4 |
| Abdominal pain | none +0 |
| | mild +1 |
| | moderate +2 |
| | severe +3 |
| Number of liquid stools per day | |
| Abdominal mass | none +0 |
| | dubious +1 |
| | definite +2 |
| | definite and tender +3 |

TABLE 1-continued

Table 1: Harvey-Bradshaw index (HBI).

| Parameter | Scoring |
| --- | --- |
| Complications | none +0 |
| | arthralgia +1 |
| | uveitis +1 |
| | erythema nodosum +1 |
| | aphthous ulcers +1 |
| | pyoderma gangrenosum +1 |
| | anal fissure +1 |
| | new fistula +1 |
| | abscess +1 |

Patients with Crohn's disease who scored 3 or less on the HBI are very likely to be in remission according to the CDAI. Patients with a score of 8 to 9 or higher are considered to have severe disease.

According to some embodiments of the invention, a subject diagnosed with and/or suffering from Crohn's disease is considered to be a responder to treatment with the TNF-alpha inhibitor if the Crohn's Disease Activity Index (CDAI) score is 150 or less.

According to some embodiments of the invention, a subject diagnosed with and/or suffering from Crohn's disease is considered to be a responder to treatment if following treatment with the TNF-alpha inhibitor the Crohn's Disease Activity Index (CDAI) score is reduced in at least 70 points as compared to the CDAI score prior to the treatment.

According to some embodiments of the invention, a subject diagnosed with and/or suffering from Crohn's disease is considered to be a responder to treatment if following treatment with the TNF-alpha inhibitor the Crohn's Disease Activity Index (CDAI) score is reduced in at least 70 points, e.g., by at least 71, 72, 73, 74, 75, 76, 77, 78, 79, 80, 81, 82, 83, 84, 85, 86, 87, 88, 89, 90, 95, 100, 105, 110, 115, 120, 125, 130, 135, 140, 145, or 150 points as compared to the CDAI score prior to the treatment.

According to some embodiments of the invention, a subject diagnosed with and/or suffering from Crohn's disease is considered to be a non-responder to the treatment with the TNF-alpha inhibitor if the Crohn's Disease Activity Index (CDAI) score is higher than 220.

According to some embodiments of the invention, a subject diagnosed with and/or suffering from Crohn's disease is considered to be a non-responder to the treatment if following treatment with the TNF-alpha inhibitor the Crohn's Disease Activity Index (CDAI) score remains the same or even increased as compared to the CDAI score prior to the treatment.

According to some embodiments of the invention, a subject diagnosed with and/or suffering from Crohn's disease is considered to be a non-responder to the treatment if following treatment with the TNF-alpha inhibitor the Crohn's Disease Activity Index (CDAI) score was reduced in a value lower than 69 as compared to the CDAI score prior to the treatment.

According to some embodiments of the invention, a subject diagnosed with and/or suffering from Crohn's disease is considered to be a non-responder to the treatment if following treatment with the TNF-alpha inhibitor the Crohn's Disease Activity Index (CDAI) score was reduced in a value lower than 69 points, e.g., the CDAI is lower than 68, 67, 66, 65, 64, 63, 62, 61, 60, 59, 58, 57, 56, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 point(s) as compared to the CDAI score prior to the treatment.

For patients having ulcerative colitis (UC) the Mayo Clinic scoring system (Rutgeerts P, Sandborn W J, Feagan B G, Reinisch W, et al. Infliximab for induction and maintenance therapy for ulcerative colitis. N Engl J Med. 2005 Dec. 8; 353(23):2462-76) can be used for assessments of UC activity before or following treatment with the TNF-alpha inhibitor. The Mayo score ranges from 0 to 12, with higher scores indicating more severe disease. This score can be used for both initial evaluation and monitoring treatment response.

Table 2 provides an exemplary calculator according to the Mayo Clinic scoring system.

TABLE 2

Table 2.

Stool Frequency
Normal number of stools for patient
1 to 2 stools per day more than normal
3 to 4 stools more than normal
>=5 stools more than normal
Rectal Bleeding
No blood seen.
Streaks of blood with stool less than half the time.
Obvious blood with stool most of the time.
Blood alone passes.
Endoscopic findings
Normal or inactive disease.
Mild Disease.
Moderate Disease.
Severe Disease.
Physician's Global Assessment
Normal
Mild disease
Moderate disease
Severe disease According to some embodiments of the invention, a subject diagnosed with and/or suffering from ulcerative colitis is considered to be a responder to treatment with the TNF-alpha inhibitor if the Mayo Clinic score is 2 or less.

According to some embodiments of the invention, a subject diagnosed with and/or suffering from ulcerative colitis is considered to be a responder to treatment if following treatment with the TNF-alpha inhibitor the Mayo Clinic score is reduced in at least 2 points as compared to the Mayo Clinic score prior to the treatment.

According to some embodiments of the invention, a subject diagnosed with and/or suffering from ulcerative colitis is considered to be a non-responder to the treatment if following treatment with the TNF-alpha inhibitor the Mayo Clinic score remains the same or even increased as compared to the Mayo Clinic score prior to the treatment.

Following is a non-limiting description of determining responsiveness of a subject to the anti-TNF treatment.

Clinical Evaluation of Patients:

The clinical state of the patients can be evaluated using the Harvey Bradshaw Index (HBI) at each visit in the Doctor's clinic. Clinical state was defined as either remission, mild disease, moderate disease, or severe disease based on the HBI score definition. Subjects can be defined as clinical responders if clinical state improved or remained at remission during all visits.

Biomarker response—evaluated biomarkers include, but are not limited to serum C-reactive protein (CRP) and fecal calprotectin. The determination of responders or non-responders can be performed using the following guidelines:

(1) Subjects having at least 2 fecal calprotectin samples taken at least 1 week apart are considered responders when at least a 50% reduction in levels is demonstrated in the second sample retrieved from the feces of the subject.

(2) Subjects who stably remain at normal levels of fecal calprotectin (≤50 mg/gram of feces) at all visits, regardless of serum CRP are considered responders.

(3) Subjects with less than 2 samples of fecal calprotectin are considered responders when demonstrated at least a 50% reduction in serum CRP levels in a second blood sample taken at least a week after the first blood sample.

(4) Subjects who exhibit normal levels of CRP (≤5 mg/dl) at all visits are considered responders.

Steroid dependence—The persistent need of concurrent steroid therapy is a valuable marker of disease state and of response to therapy. Subjects, who are receiving steroid therapy at the clinic visit at the 14$^{th}$ week of treatment ("14-week") are considered non-responders.

Immunogenic status—Subjects having measurable serum antibodies to Infliximab at their week 14-week visit are considered non-responders.

Study response algorithm—The present inventors have formulated a decision algorithm to conclude whether a subject is responsive or not to therapy. The algorithm is mainly based on the primary gastroenterologist following the subject. For each subject on the 14-week visit the physician, after reviewing the subjects' records, decides whether the subject responded to therapy, failed or if it is still indeterminate. For the latter (indeterminate), a decision tree is performed with the following steps: a definition of failure is set when steroid treatment is given at 14-week visit. If no steroids are given the next step is to test the biomarker dynamics. A substantial reduction in fecal calprotectin is defined as response. If fecal calprotectin is not available, a reduction in serum CRP (as defined previously) is considered a response to treatment. For subjects who are not steroid-dependent and show no substantial biomarker dynamics, a physician decision on week 26 is made to determine the response status.

As used herein the phrase a "TNF-alpha inhibitor" refers to an agent capable of inhibiting (e.g., downregulating) the expression level and/or activity of tumor necrosis factor alpha (TNFα) and/or capable of competing and/or antagonizing the TNFα activity.

For example, the anti TNFα inhibitor can inhibit the binding to TNFα to its TNFRSF1A/TNFR1 and/or TNFRSF1B/TNFBR receptors.

According to some embodiments of the invention, the TNF-alpha inhibitor is an antibody.

Non-limiting examples of anti-TNFα antibodies include, Infliximab, adalimumab, and certolizumab pegol.

Infliximab (e.g., marketed as REMICADE™, REMSIMA™, INFLECTRA™) is a chimeric IgG1κ monoclonal antibody (composed of human constant and murine variable regions) used as a biologic drug against tumor necrosis factor alpha (TNF-α) that is a key part of the autoimmune reaction. Infliximab neutralizes the biological activity of TNFα by binding with high affinity to the soluble and transmembrane forms of TNFα and inhibits binding of RNFα with its receptors. Infliximab has a molecular weight of approximately 149.1 kilodaltons, and is produced by a recombinant cell line cultured by continuous perfusion and is purified by a series of steps that includes measures to inactivate and remove viruses. Infliximab is used to treat autoimmune diseases such as Crohn's disease, ulcerative colitis, psoriasis, psoriatic arthritis, ankylosing spondylitis, and rheumatoid arthritis.

For example, treatment with Infliximab (IFX) can include, for example, intravenous infusion of 5 mg IFX per kg body weight. If additional treatment is needed, subsequent doses of IFX can be administered, e.g., after 2 and 6 weeks of the first dose of administration of IFX.

Adalimumab (e.g., marketed as HUMIRA™ and EXEMPTIA) is a medication used for rheumatoid arthritis, psoriatic arthritis, ankylosing spondylitis, Crohn's disease, ulcerative colitis, moderate to severe chronic psoriasis, moderate to severe hidradenitis suppurativa, and juvenile idiopathic arthritis. In rheumatoid arthritis, adalimumab has a response rate similar to methotrexate, and in combination nearly doubles the response rate of methotrexate alone. Like Infliximab, Adalimumab binds to TNFα and prevents it from activating TNF receptors.

Certolizumab pegol (e.g., CDP870, marketed as CIMZIA™) is a therapeutic monoclonal antibody to tumor necrosis factor alpha (TNF-α), for the treatment of Crohn's disease and rheumatoid arthritis.

Antibodies and methods of generating, isolating and/or using same are further described hereinunder.

According to some embodiments of the invention, the TNF-alpha inhibitor is an antagonist of TNFα such as a soluble TNF receptor.

Non-limiting examples of soluble TNF receptors which can be used according to some embodiments of the invention include ENBREL™ (Etanercept). Like Infliximab, Etanercept binds to TNFα, preventing it from activating TNF receptors.

Etanercept is a fusion protein produced by recombinant DNA. It fuses the TNF receptor to the constant end of the IgG1 antibody.

As described hereinabove, the method of some embodiments of the invention comprises analyzing a frequency of at least one subpopulation of immune cells in a tissue biopsy of the subject.

The tissue biopsy used by the method of some embodiments comprises a colon tissue.

The tissue biopsy used by the method of some embodiments comprises an ileum.

According to some embodiments of the invention, the cells of the tissue biopsy are intact cells.

According to some embodiments of the invention, a frequency above a predetermined threshold of immune cells of a subpopulation selected from the group consisting of activated monocytes M1 macrophages, memory B cells, and neutrophils is indicative of the subject being non-responder to the TNF-alpha inhibitor.

As used herein the phrase "frequency above a predetermined threshold" refers to a frequency of the subpopulation of immune cells which is at least 0.01%, 0.02%, 0.03%. 0.04%, 0.05%, 0.06%, 0.07%, 0.08%, 0.09%, 1%, 2%0, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 390/%, 40% or higher than a predetermined threshold.

The predetermined threshold can be determined by the frequency of the subpopulation of immune cells in the same tissue biopsy of a subject with a known outcome of TNF-alpha inhibitor treatment (i.e., responder or non-responder), yet, wherein the tissue biopsy of the subject is obtained prior to the first administration of the TNF-alpha inhibitor to the subject (i.e., when the subject is naive to the TNF-alpha treatment). Such a subject can be considered a reference subject. The reference subject can be a TNF-alpha responder or a TNF-alpha non-responder.

Non-limiting exemplary ranges of the subpopulations of immune cells in responders and non-responders patients can be found in Table 11 of the Examples section which follows.

According to some embodiments of the invention, a frequency of activated monocytes M1 macrophages which is above 10% (e.g., above 11%) indicates that the subject is predicted to be a non-responder to the treatment with the TNF-alpha inhibitor.

According to some embodiments of the invention, a frequency of plasma cells which is above 14% indicates that the subject is predicted to be a non-responder to the treatment with the TNF-alpha inhibitor.

According to some embodiments of the invention, a frequency of neutrophils which is above 13% (e.g., above 14%) indicates that the subject is predicted to be a non-responder to the treatment with the TNF-alpha inhibitor.

According to some embodiments of the invention, a ratio of M1/M2 macrophages which is higher than 1, e.g., higher than 1.1 is indicative of the subject being non-responder to treatment with the TNF-alpha inhibitor.

According to some embodiments of the invention, the method of predicting responsiveness of a subject having an inflammatory bowel disease (IBD) to a TNF-alpha inhibitor can be performed by:

(a) analyzing a frequency of at least one subpopulation of immune cells in a tissue biopsy of the subject, and;

(b) comparing the frequency of the at least one subpopulation of immune cells in the tissue biopsy of the subject to an expression data of the at least one subpopulation of immune cells in a corresponding tissue biopsy obtained from at least one TNF-alpha inhibitor responder subject and/or at least one TNF-alpha inhibitor non-responder subject, thereby predicting the responsiveness of the subject to the TNF-alpha inhibitor treatment.

As mentioned, the tissue biopsy can be from an inflamed region as determined by tissue distortion and plasmacytosis.

According to some embodiments of the invention, when the tissue biopsy comprises both an inflamed tissue and a non-inflamed tissue the method can sufficiently determine the responsiveness of the subject to (TNF)-alpha inhibitor therapy based on frequencies of macrophages or plasma cells.

According to some embodiments of the invention, when the tissue biopsy comprises mainly an inflamed tissue the method can sufficiently determine the responsiveness of the subject to (TNF)-alpha inhibitor therapy based on frequencies of plasma cells or macrophages According to some embodiments of the invention, the activated monocytes M1 macrophages are characterized by CD68+ and one of CCR7+, CD86+ or CD80+ or a combination of CCR7+, CD86+ and CD80+ as core expression signature.

It should be noted that the sign "+" as used herein refers to a positive expression (i.e., the cell expresses the indicated marker); and the sign "−" as used herein refers to a negative expression (i.e., the cell does not express the indicated marker).

According to some embodiments of the invention, the activated monocytes M1 macrophages are characterized by CD68+/CCR7+ expression signature.

According to some embodiments of the invention, the activated monocytes M1 macrophages are characterized by CD68+/CD86+ expression signature.

According to some embodiments of the invention, the activated monocytes M1 macrophages are characterized by CD68+/CD80+ expression signature.

According to some embodiments of the invention, the activated monocytes M1 macrophages are characterized by CD68+/CCR7+/CD86+ expression signature.

According to some embodiments of the invention, the activated monocytes M1 macrophages are characterized by CD68+/CCR7+/CD80+ expression signature.

According to some embodiments of the invention, the activated monocytes M1 macrophages are characterized by CD68+/CD86+/CD80+ expression signature.

According to some embodiments of the invention, the activated monocytes M1 macrophages are characterized by CD68+/CCR7+/CD86+/CD80+ expression signature.

Additionally or alternatively, the activated monocytes M1 macrophages are further characterized by CD11b+ and/or CCR2+ expression markers.

According to some embodiments of the invention, the activated monocytes M1 macrophages are characterized by CD68+/CCR7+/CD11b+/CCR2+ expression signature.

According to some embodiments of the invention, the activated monocytes M1 macrophages are characterized by CD68+/CCR7+/CD86+/CD80+/CD11b+ expression signature.

According to some embodiments of the invention, the activated monocytes M1 macrophages are characterized by CD68+/CCR7+/CD86+/CD80+/CCR2+ expression signature.

According to some embodiments of the invention, the activated monocytes M1 macrophages are characterized by CD68+/CCR7+/CD86+/CD80+/CD11b+/CCR2+ expression signature.

According to some embodiments of the invention, the memory B cells are plasma cells, and wherein the plasma cells are characterized by positive expression of a marker selected from the group consisting of: CD138 as a core signature, and optionally one or more of the markers selected from the group consisting of: CD45, BCMA, CD38, IgM, IgG, IgA and/or IgE.

According to some embodiments of the invention, the plasma cells are characterized by CD138+ expression signature.

According to some embodiments of the invention, the plasma cells are further characterized by a positive expression of one or more markers of the CD45, BCMA, CD38, IgM, IgG, IgA and/or IgE markers.

According to some embodiments of the invention, the plasma cells are characterized by CD138+/CD45+ expression signature.

According to some embodiments of the invention, the plasma cells are characterized by CD138+/BCMA+ expression signature.

According to some embodiments of the invention, the plasma cells are characterized by CD138+/CD38+ expression signature.

According to some embodiments of the invention, the plasma cells are characterized by CD138+/IgM+ expression signature.

According to some embodiments of the invention, the plasma cells are characterized by CD138+/IgG+ expression signature.

According to some embodiments of the invention, the plasma cells are characterized by CD138+/IgE+ expression signature.

According to some embodiments of the invention, the plasma cells are characterized by CD138+/CD45+/BCMA+/CD38+/IgM+/IgG+/IgA+/IgE+ expression signature.

According to some embodiments of the invention, the memory B cells are non-plasma cells, and wherein the non-plasma cells are characterized by positive expression of CD20, CD19, and CD45RA as a core signature.

According to some embodiments of the invention, the non-plasma cells are further characterized by an expression of at least one marker or a combination of markers selected from the group of CD45, MHC-Class II, IgG, IgA, IgE and/or IgD markers.

According to some embodiments of the invention, the neutrophils are characterized by CD45+, CD66b+ and/or CD16+ expression signature.

According to some embodiments of the invention, a frequency below a predetermined threshold of immune cells of a subpopulation selected from the group consisting of activated monocytes M2 macrophages and CD8+ T cells is indicative of the subject being non-responder to the TNF-alpha inhibitor, As used herein the phrase "frequency below a predetermined threshold" refers to a frequency of the subpopulation of immune cells which is lower than 50%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.08%, 0.07%, 0.06%, 0.05%, 0.04%, 0.03%, 0.02%, 0.01% of a predetermined threshold.

According to some embodiments of the invention, a frequency of CD8+ T cells which is lower than 2% indicates that the subject is predicted to be a non-responder to the treatment with the TNF-alpha inhibitor.

According to some embodiments of the invention, the activated monocytes M2 macrophages are characterized by CD68+ expression signature.

According to some embodiments of the invention, the activated monocytes M2 macrophages are further characterized by expression of one or more markers selected from the group consisting of CD163+ and CD206+.

According to some embodiments of the invention, the activated monocytes M2 macrophages are characterized by CD68+/CD163+ expression signature.

According to some embodiments of the invention, the activated monocytes M2 macrophages are characterized by CD68+/CD206+ expression signature.

According to some embodiments of the invention, the activated monocytes M2 macrophages are characterized by CD68+/CD163+/CD206+ expression signature.

According to some embodiments of the invention, the CD8+ T cells are characterized by CD8+ expression signature.

According to some embodiments of the invention, the CD8+ T cells are characterized by CD8+ and CD69+ expression signature.

According to some embodiments of the invention, the CD8+ T cells are characterized by CD8+/CD3+ expression signature.

According to some embodiments of the invention, the CD8+ T cells are characterized by CD8+/CD45+ expression signature.

According to some embodiments of the invention, the CD8+ T cells are characterized by CD8+/CD45RA+ expression signature.

According to some embodiments of the invention, the CD8+ T cells are characterized by CD8+/CD69+/CD3+ expression signature.

According to some embodiments of the invention, the CD8+ T cells are characterized by CD8+/CD69+/CD45+ expression signature.

According to some embodiments of the invention, the CD8+ T cells are characterized by CD8+/CD69+/CD45RA+ expression signature.

According to some embodiments of the invention, the CD8+ T cells are characterized by CD8+/CD69+/CD3+/CD45+/CD45RA+ expression signature.

Analysis of the frequency of at least one subpopulation of immune cells can be performed by determining the presence of the subpopulation of immune cells in the sample and calculating the frequencies thereof out of the total immune cells present in the sample. Methods of determining which subpopulations of immune cells are present in a sample include, for example, identification of cell types from the cells in the sample and calculating the frequencies of each subpopulation of immune cells.

According to some embodiments of the invention, the analyzing the frequency of the at least one subpopulation of immune cells is performed by a morphometric analysis.

According to some embodiments of the invention, the analyzing the frequency of the at least one subpopulation of immune cells is performed by using at least one histological stain.

According to some embodiments of the invention, the analyzing the frequency of the at least one subpopulation of immune cells is performed by using at least one antibody.

According to some embodiments of the invention, the antibody is used in an immuno-histochemistry (IHC) or immuno-fluorescence method.

According to some embodiments of the invention, the antibody is used in a flow cytometry or Fluorescence-activated cell sorting (FACS) analysis.

According to some embodiments of the invention, the analyzing the frequency of the at least one subpopulation of immune cells is performed by mass-cytometry.

According to some embodiments of the invention, the mass-cytometry is CyTOF (e.g., FLUIDIGM®).

According to some embodiments of the invention, the analyzing the frequency of the at least one subpopulation of immune cells is performed by an RNA in-situ hybridization assay.

According to some embodiments of the invention, the analyzing the frequency of the at least one subpopulation of immune cells is performed by a single cell RNA sequencing (RNA SEQ) analysis.

According to some embodiments of the invention, the analyzing the frequency of the at least one subpopulation of immune cells is performed by exome sequencing followed by computational deconvolution.

According to some embodiments of the invention, the analyzing the frequency of the at least one subpopulation of immune cells is performed by RNA SEQ followed by computational deconvolution.

According to some embodiments of the invention, the analyzing the frequency of the at least one subpopulation of immune cells is performed by reverse-transcriptase polymerase chain reaction (RT-PCR) followed by computational deconvolution.

According to some embodiments of the invention, the analyzing the frequency of the at least one subpopulation of immune cells is performed by microarray followed by computational deconvolution.

According to an aspect of some embodiments of the invention, there is provided a method of selecting treatment to inflammatory bowel disease (IBD) in a subject in need thereof, the method comprising:

(a) determining responsiveness to a treatment with a TNF-alpha inhibitor according to the method of some embodiments of the invention (e.g., any of the embodiments described hereinabove); and (b) selecting treatment based on the responsiveness.

According to an aspect of some embodiments of the invention, there is provided a method of treating to inflammatory bowel disease (IBD) in a subject in need thereof, the method comprising:

(a) determining responsiveness to a TNF-alpha inhibitor according to the method of some embodiments of the invention; and (b) treating the subject based on the responsiveness.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The treatment of the subject, e.g., the treatment plan or regimen, depends on the predicted responsiveness of the subject to the TNF-alpha inhibitor. For example, if the subject is predicted to response to the TNF-alpha inhibitor (a TNF-alpha inhibitor responder subject), then the treatment selected for treating such a responder subject can include administration of the TNF-alpha inhibitor. On the other hand, if the subject is predicted to not respond to the TNF-alpha inhibitor (a TNF-alpha non-responder subject), then the treatment selected for treating such as non-responder subject will not include the TNF-alpha inhibitor.

The agents of some embodiments of the invention which are described herein for predicting responsiveness of a subject to treatments with a tumor necrosis factor (TNF)-alpha inhibitor may be included in a diagnostic kit/article of manufacture preferably along with appropriate instructions for use and labels indicating FDA approval for use in diagnosing and/or assessing the prediction of responsiveness of a subject to treatment with a tumor necrosis factor (TNF)-alpha inhibitor.

Such a kit can include, for example, at least one container including at least one of the herein described diagnostic agents (e.g., an antibody which can specifically bind to a cell marker characteristic of the immune cell subpopulation; or a probe which can specifically hybridize to and/or elongate a nucleic acid sequence, e.g., an RNA sequence, characteristic of the immune cell subpopulation) and an imaging reagent packed in another container (e.g., enzymes, secondary antibodies, buffers, chromogenic substrates, fluorogenic material). The kit may also include appropriate buffers and preservatives for improving the shelf-life of the kit.

According to an aspect of some embodiments of the invention, there is provided a kit for predicting responsiveness of a subject to treatment with a tumor necrosis factor (TNF)-alpha inhibitor comprising an agent capable of analyzing a frequency of at least one subpopulation of immune cells in a tissue biopsy of the subject, and a reference expression data of the frequency of at least one subpopulation of immune cells of a tissue biopsy obtained from at least one TNF-alpha inhibitor responder subject and/or at least one TNF-alpha inhibitor non-responder subject, wherein the immune cells are of a subpopulation selected from the group consisting of: activated monocytes M1 macrophages, memory B cells, neutrophils, activated monocytes M2 macrophages and CD8+ T cells.

Table 3 hereinbelow, provides a non-limiting description of suitable agents (e.g., antibodies) for identifying subpopulations of immune cells from the tissue biopsy. It should be noted that the antibodies can be directly (e.g., by conjugation to a label) or indirectly labeled (e.g., by conjugation to an identifiable moiety) for visualization and further detection.

TABLE 3

| Population | Antibody | Catalogue number | Company |
|---|---|---|---|
| Plasma cells | Mouse anti human CD138 | MCA2459GA | AbD Serotec |
| Activated monocytes (M1) | Mouse anti Human CD68 | MCA5709 | AbD Serotec |
| | Mouse anti human CD80 | 305202 | BioLegend |
| | Goat anti Human CD86 | AF-141-NA | R&D Systems |
| | Mouse anti human CCR7 | MAB197 | R&D Systems |
| Activated monocytes (M2) | Mouse anti Human CD68 | MCA5709 | AbD Serotec |
| | Mouse anti human CD163 | MCA1853 | AbD Serotec |
| | Mouse anti human CD206 | MCA5552Z | AbD Serotec |
| CD8+ T cells | mouse anti human CD8 | MCA1817T | AbD Serotec |
| | mouse anti human CD69 | NBP2-25236 | Novus |
| Neutrophils | rabbit anti human CD16 | BS-6028R-A488 | BioSS |
| | mouse anti human C66b | NB100-77808 | Novus |
| Memory B cells | mouse anti human CD20 | MCA1915T | AbD Serotec |
| | mouse anti human CD19 | MCA2454 | AbD Serotec |
| | mouse anti human CD45RA | MCA88 | AbD Serotec |

Table 4 provides a non-limiting sequence information for the antigens (markers) which can be used to identify the various immune cells (e.g., subpopulation of cells) according to some embodiments of the invention. The Table provides the GenBank Accession numbers (and the respective sequence identifiers) for the polypeptides of the antigens (cell markers) and the polynucleotide encoding same. It should be noted that the polypeptides can be identified using various protein detection methods such as those described hereinunder; and that the polynucleotides can be identified using various RNA detection methods such as those described hereinunder.

TABLE 4

| Marker (presence "+"; absence "−" | Polypeptide GenBank Accession No. | Polypeptide SEQ ID NO: | Polynucleotide GenBank Accession No. | Polynucleotide SEQ ID NO: |
|---|---|---|---|---|
| CD68+ | NP_001035148 | 5 | NM_001040059.1 | 37 |
| CD68+ | NP_001242.2 | 6 | NM_001251.2 | 38 |
| CD86+ | NP_001193853.1 | 7 | NM_001206924.1 | 39 |
| CD86+ | NP_001193854.1 | 8 | NM_001206925.1 | 40 |

TABLE 4-continued

Table 4.

| Marker (presence "+"; absence "-" | Polypeptide GenBank Accession No. | Polypeptide SEQ ID NO: | Polynucleotide GenBank Accession No. | Polynucleotide SEQ ID NO: |
|---|---|---|---|---|
| CD86+ | NP_008820.3 | 9 | NM_006889.4 | 41 |
| CD86+ | NP_787058.4 | 10 | NM_175862.4 | 42 |
| CD86+ | NP_795711.1 | 11 | NM_176892.1 | 43 |
| CD64+ | NP_000557.1 | 12 | NM_000566.3 | 44 |
| CD20+ | NP_061883.1 | 13 | NM_019010.2 | 45 |
| CD19+ | NP_001761.3 | 14 | NM_001770.5 | 46 |
| CD19+ | NP_001171569.1 | 15 | NM_001178098.1 | 47 |
| IgD+ | — | | NG_001019.5 (977531 . . . 984804) | 48 |
| IgA+ | NP_067612.1 | 17 | NM_021601.3 | 49 |
| IgA+ | NP_001774.1 | 18 | NM_001783.3 | 50 |
| CD138+ | NP_001006947.1 | 19 | NM_001006946.1 | 51 |
| CD138+ | NP_002988.3 | 20 | NM_002997.4 | 52 |
| CD45+ | NP_001254727.1 | 21 | NM_001267798.1 | 53 |
| CD45+ | NP_002829.3 | 22 | NM_002838.4 | 54 |
| CD45+ | NP_563578.2 | 23 | NM_080921.3 | 55 |
| CD66b+ | NP_001807.2 | 24 | NM_001816.3 | 56 |
| CD16+ | NP_000560.5 | 25 | NM_000569.6 | 57 |
| CD16+ | NP_001121064.1 | 26 | NM_001127592.1 | 58 |
| CD16+ | NP_001121065.1 | 27 | NM_001127593.1 | 59 |
| CD16+ | NP_001121067.1 | 28 | NM_001127595.1 | 60 |
| CD16+ | NP_001121068.1 | 29 | NM_001127596.1 | 61 |
| CD163+ | NP_004235.4 | 30 | NM_004244.5 | 62 |
| CD163+ | NP_981961.2 | 31 | NM_203416.3 | 63 |
| CD206+ | NP_002429.1 | 32 | NM_002438.3 | 64 |
| CD8+ | NP_001139345.1 | 33 | NM_001145873.1 | 65 |
| CD8+ | NP_001759.3 | 34 | NM_001768.6 | 66 |
| CD8+ | NP_741969.1 | 35 | NM_171827.3 | 67 |
| CD69+ | NP_001772.1 | 36 | NM_001781.2 | 68 |

Following is a non-limiting description of methods of detecting RNA and/or protein sequences within cells of the tissue biopsy of some embodiments of the invention.

Methods of Detecting the Expression Level of RNA

The expression level of the RNA in the cells of some embodiments of the invention can be determined using methods known in the arts.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods.

For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide Microarray—

In this method oligonucleotide probes capable of specifically hybridizing with the polynucleotides of some embodiments of the invention are attached to a solid surface (e.g., a glass wafer). Each oligonucleotide probe is of approximately 20-25 nucleic acids in length. To detect the expression pattern of the polynucleotides of some embodiments of the invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA).

Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Exome sequencing (also known as Whole Exome Sequencing, WES or WXS) is a targeted sequencing approach that is restricted to the protein-coding regions of genomes (exome).

The exome is estimated to encompass approximately 1% of the genome, yet contains approximately 85% of disease-causing mutations. In the initial step, the subset of DNA encoding proteins (exons) are selected, followed by sequencing of the exons using a high throughput DNA sequencing technology. The exome sequencing enables a rapid, cost-effective identification of common single nucleotide variants (SNVs), copy number variations (CNVs), and small insertions or deletions (indels), as well as rare de novo mutations that may explain the heritability of Mendelian and complex disorders. Exome sequencing can be performed using, e.g., the Ion Torrent™ Next-Generation Sequencing (Available from ThermoFisher Scientific).

Strand Specific RNA-Sequencing Library Construction—

The following is a representative protocol for the preparation of sequencing libraries from purified RNAs. This protocol is optimized for very low amounts of input RNA, and uses an adapter-ligation strategy in order to map locations of crosslinks (e.g., for the AMT protocol). This RNA-sequencing protocol also includes several steps that remove contaminating ssDNA probes.

RNA can be extracted using the miRNeasy kit (Qiagen, 217004) and poly(A) RNA is further isolated using, for example, Oligo d (T25) beads (NEB, E7490L). The Poly(A) fraction is then fragmented (Invitrogen, AM8740), and fragments smaller than 200 bps are preferably eliminated (Zymo, R1016) and the remaining fraction is treated with FastAP Thermosensitive Alkaline Phosphatase (Thermo Scientific, EF0652) and T4 Polynucleotide Kinase (NEB, M0201L). RNA is then ligated to a RNA adaptor essentially as described in Engreitz, J. M. et al. *Science* 341: 1237973, (2013), which is fully incorporated herein by reference, using T4 RNA Ligase 1 (NEB, M0204L), which is then used to facilitate cDNA synthesis using Affinity Script Multiple Temperature Reverse Transcriptase (Agilent, 600105). More specifically, the following adaptors reported in Engreitz, J. M. et al. 2013 can be used:

```
RNA sequencing-RiL-19 3' RNA adaptor:
                                        (SEQ ID NO: 1)
Thosphate/rArGrArUrCrGrGrArArGrArGrCrGrUrCrGr
UrG/ddC;

RNA sequencing-AR17 RT primer:
                                        (SEQ ID NO: 2)
ACACGACGCTCTTCCGA;

RNA sequencing-3Tr3 5' DNA adaptor:
                                        (SEQ ID NO: 3)
/Phosphate/AGATCGGAAGAGCACACGTCTG/ddC;

RNA sequencing-PCR enrichment:
                                        (SEQ ID NO: 4)
AATGATACGGCGACCACCGAGATCTACACTCTTTCCCTACACGAC
GCTCTTCCGATCTCAAGCAGAAGACGGCATACGAGATNNNNNNNN
GTGACTGGAGTTCAGACGTGTGCTCTTCCGATCT.
```

RNA is then degraded and the cDNA is ligated to a DNA adaptor using T4 RNA Ligase 1 as described in Engreitz, J. M. et al. 2013. Final library amplification is completed using NEB Next High Fidelity 2×PCT Master Mix (M054L). To clean up the final PCR and removed adapter dimers, two subsequent 1× and 8×SPRI reactions ire completed to prepare the final library for sequencing.

Methods of Detecting the Expression Level of Protein

Non-limiting examples of protein detection methods include, flow cytometry (e.g., intra or extra-cellular flow cytometry), FACS, ELISA, Western Blot, RIA, immunohistochemistry, protein activity assays and Mass cytometry (e.g., CyTOF (FLUIDIGM®)).

Mass Cytometry:

Mass-cytometry uniquely combines time-of-flight mass spectrometry with Maxpar metal-labeling technology to enable breakthrough discovery and comprehensive functional profiling applications. Cellular targets are labeled with metal-tagged antibodies and detected and quantified by time-of-flight mass spectrometry. The high purity and choice of metal isotopes ensure minimal background noise from signal overlap or endogenous cellular components. For example, CyTOF (Fludigm) is a recently introduced mass-cytometer capable of detecting up to 40 markers conjugated to heavy metals simultaneously on single cells.

Enzyme Linked Immunosorbent Assay (ELISA):

This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabeled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

In Vitro Activity Assays:

In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis, the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

As mentioned above, the analysis of the subpopulations of immune cells can employ a method of detecting total RNA (e.g., RT-PCR, microarray, RNA SEQ, exome sequencing) or protein (e.g., ELISA, immunofluorescence, immunohistochemistry) or DNA methylation (e.g., Methylation microarray) in a biological sample, followed by a computational deconvolution.

Computational Deconvolution:

This method involves using computational algorithms to estimate the composition/proportion of constituting cell subpopulation in bulk samples assayed on a given technology. Often, but not necessarily, this makes use of prior knowledge in the form of cell subset markers or profiles from the same assay.

Deconvolution algorithms have been proposed for a variety of assays, including but not only, gene expression measured by microarray or RNA-seq, and methylation arrays essentially as described elsewhere (18), which is fully incorporated herein by reference.

As used herein, the term "antibody" refers to a substantially intact antibody molecule.

As used herein, the phrase "antibody fragment" refers to a functional fragment of an antibody (such as Fab, F(ab')2, Fv or single domain molecules such as VH and VL) that is capable of binding to an epitope of an antigen.

Suitable Antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) Fab, a fragment of an antibody molecule containing a monovalent antigen-binding portion of an antibody molecule which can be obtained by treating whole to antibody with the enzyme papain to yield the intact light chain and the Fd fragment of the heavy chain which consists of the variable and CH1 domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(v) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vi) Single domain antibodies are composed of a single VH or VL domains which exhibit sufficient affinity to the antigen.

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256: 495-497; Kozbor D. et al., 1985. J. Immunol. Methods 81:31-42; Cote R I. et al., 1983. Proc. Natl. Acad. Sci. U.S.A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumine (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed.

Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill.

The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to some embodiments of the invention can be prepared by proteolytic hydrolysis of the antibody or by expression in E. coli or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove the variable domains can be linked to generate a single chain Fv by an intermolecular disulfide bond, or alternately, such chains may be cross-linked by chemicals such as glutaraldehyde.

Preferably, the Fv is a single chain Fv.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Isolated complementarity determining region peptides can be obtained by constructing genes encoding the complementarity determining region of an antibody of interest. Such genes may be prepared, for example, by RT-PCR of mRNA of an antibody-producing cell. Ample guidance for practicing such methods is provided in the literature of the art (for example, refer to Larrick and Fry, 1991. Methods 2:106-10).

It will be appreciated that for human therapy or diagnostics, humanized antibodies are preferably used. Humanized forms of non human (e.g., murine) antibodies are genetically engineered chimeric antibodies or antibody fragments having-preferably minimal-portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues.

Humanized antibodies may also comprise residues which are found neither in the recipient antibody nor in the imported complementarity determining region or framework sequences.

In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence.

Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions.

Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147:86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368:812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

It will be appreciated that targeting of particular compartment within the cell can be achieved using intracellular antibodies (also known as "intrabodies"). These are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker [e.g., $(Gly_4Ser)_3$ and expressed as a single chain molecule. To inhibit marker activity in a cell, the expression vector encoding the intracellular antibody is introduced into the cell by standard transfection methods, as discussed hereinbefore.

Once antibodies are obtained, they may be tested for activity, for example via ELISA.

The antibody of some embodiments of the invention is used for therapeutic purposes, e.g., the antibody which is used as a TNF-alpha inhibitor.

Additionally or alternatively, several detection methods (e.g., protein detection methods) which are encompassed by some embodiments of the invention employ the use of antibodies (e.g., antibodies for diagnostic, identification and/or classification purposes).

According some embodiments of the invention, the antibody is conjugated to a functional moiety (also referred to as an "immunoconjugate") such as a detectable or a therapeutic moiety. The immunoconjugate molecule can be an isolated molecule such as a soluble and/or a synthetic molecule.

Various types of detectable or reporter moieties may be conjugated to the antibody of the invention. These include, but not are limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. el al., "Evaluating Receptor Stoichiometry by Fluorescence Resonance Energy Transfer," in "Receptors: A Practical Approach," 2nd ed., Stanford C. and Horton R. (eds.), Oxford University Press, U K. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody] or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532.

Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. el al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimmer or tetramer form of the antibody).

Table 5 provides non-limiting examples of identifiable moieties which can be conjugated to the antibody of the invention.

TABLE 5

Table 5.

| Identifiable Moiety | Amino Acid sequence (GenBank Accession No.) | SEQ ID NO: | Nucleic Acid sequence (GenBank Accession No.) | SEQ ID NO: |
| --- | --- | --- | --- | --- |
| Green Fluorescent protein | AAL33912 | 69 | AF435427 | 78 |
| Alkaline phosphatase | AAK73766 | 70 | AY042185 | 79 |
| Peroxidase | CAA00083 | 71 | A00740 | 80 |
| Histidine tag | Amino acids 264-269 of GenBank Accession No. AAK09208 | 72 | Nucleotides 790-807 of GenBank Accession No. AF329457 | 81 |
| Myc tag | Amino acids 273-283 of GenBank Accession No. AAK09208 | 73 | Nucleotides 817-849 of GenBank Accession No. AF329457 | 82 |
| Biotin lygase tag | LHHILDAQKMVWNHR/ | 74 | — | — |
| orange fluorescent protein | AAL33917 | 75 | AF435432 | 83 |
| Beta galactosidase | ACH42114 | 76 | EU626139 | 84 |
| Streptavidin | AAM49066 | 77 | AF283893 | 16 |

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 37 is expressed in a DNA sequence format (e.g., reciting T for thymine), but it can refer to either a DNA sequence that corresponds to a CD68 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

All analyses were performed in the R statistical software (www(dot)r-project(dot)org), using additional packages available from the Bioconductor project (www(dot)bioconductor(dot)org).

Cell Type Expression Pattern of Predictive Gene Signatures—

CEL files of sorted cell type samples from IRIS (GSE22886, (34)) and the Human body index (GSE7307) were downloaded from GEO, and normalized separately using frma. In GSE7307, the present inventors then extracted the profiles from all immune cells (10 profiles from monocyte, T cell and B cell lineages) and colon tissues (2 profiles). The present inventors then created a combined gene expression matrix, correcting for batch (dataset) effect using Combat. Previously reported gene signatures were collected as lists of gene symbols from their associated original publications or patent application as detailed in Table 6. Symbols were mapped to the genes assayed on platform HGU133A using Bioconductor symbol and alias mappings available in the hgu133plus2.db annotation package.

Gene Expression Datasets—

Normalized gene expression data for datasets GSE12251, GSE14580 and GSE16879 were downloaded from GEO using the GEOquery package. In each dataset the present inventors selected the relevant subset of baseline samples as described in Table 7, each forming a separate discovery cohort.

Deconvolution Analysis—

Given the total gene expression profile of a sample, gene expression deconvolution methods use prior knowledge obtained from sorted cells, e.g., as basis expression profiles or marker gene lists, to estimate the respective contribution of distinct cell types (18). In this work the present inventors used the basis signature and method developed in (26), which returns estimates for 17 immune cell types. The present inventors used the implementation available from the CellMix package (35).

Meta-Analysis of Cell Type Proportions—

Cell type proportion differences estimated in multiple cohorts were integrated in a meta-analysis. First cell type proportions were log 2-transformed and compared between responders and non-responders within each cohort using Wilcoxon rank sum test. Then nominal p-values were combined using Fisher combined probability test, which was corrected using Benjamini and Hochberg FDR correction. Cell types having nominal p-values<=0.05 in at least 2 cohorts and a combined FDR<=0.01 were selected for further analysis.

Patients in the Validation Cohort—

Archival slides from 23 patients with an established diagnosis of IBD (13 Crohn's Disease, 7 Ulcerative Colitis, 3 IBDU) from the gastroenterology department of Rambam Health Care Campus were included in this analysis. Responsiveness to anti-TNF treatment was assessed based on parameters such as: abdominal pain, bowel consistency and frequency, blood in stool, nausea/vomiting, constitutional symptoms, extracolonic manifestations, presence of abdominal mass, blood inflammatory markers, and colonic biopsy results. Patients were classified retrospectively as anti-TNF responders when they experienced clinical and/or mucosal improvement within 8 weeks after treatment initiation. Other data collected includes age, gender, disease state when biopsy was taken, disease-related surgery, co-morbidities and medications. A summary of these data is shown in Table 6.

Biopsy Collection in the Validation Cohort—

Colonic biopsies were collected from the patients during flexible sigmoidoscopy or full colonoscopy before their first anti-TNF treatment. Biopsies were taken from inflamed and/or uninflamed areas of the intestine ascending/transverse/descending colon and placed into formalin.

Immuno-Histochemistry Quantification—

Formalin-fixed slides of paraffin-embedded colon tissues, sectioned at 4 μm, were immunostained for the expression of plasma cells (CD138+). The slides were deparaffinized in Xylene (twice, 3 minutes each time) and rehydrated in gradually decreasing concentrations of EtOH (100% EtOH× 2, 95%, 85%, 70% and running water). 0.01 M sodium citrate buffer pH 6.0 was used to heat-induced epitope retrieval before incubation with antibody. Slides were immersed in the buffer and heated in a microwave for 20 minutes. The slides were rinsed in cool running water, washed in PBS with 0.1% Tween solution, and blocked in 10% goat serum. Then, they were incubated with CD138 primary monoclonal antibody in 4° C. overnight (obtained from Serotec, clone B-A38, dilution 1:250). For detection, the Polink-1 HRP Broad Spectrum DAB Detection Kit (GBI labs) was used.

Staining Data Analysis—

Two scoring methods were used for the analysis of stain biopsies: Slides were coded and interpreted blindly by a specialist pathologist. A "plasma cell abundance" subjective score between 0-3 was determined by the pathologist (minimal amount of plasma cells was scored as "0", the highest abundance which have seen within all slides was scored as "3"), and the tissues were scored one by one.

Slides were scanned in automatic digital slide scanner, and evaluated in Image-Pro Plus 6.0 software. 4 high stained fields were chosen randomly in each patient slide, and Brown color of DAB CD138+ cells was tested. Each field CD138+ staining value was divided by the same field whole tissue staining. Average of those 4 fields is presented.

Clinical Evaluation of Patients:

The clinical state of the patients was evaluated using the Harvey Bradshaw Index (HBI) at each visit. Clinical state was defined as either remission, mild disease, moderate disease, or severe disease based on the HBI score definition. Subjects were defined as clinical responders if clinical state improved or remained at remission during all visits.

Biomarker Response—

Evaluated biomarkers were serum C-reactive protein (CRP) and fecal calprotectin. Previous studies have shown that fecal calprotectin levels are highly correlated with disease severity. Due to low subject compliance with handling fecal material, the fecal calprotectin could not be obtained on all visits from all subjects. The determination of responders or non-responders was performed using the following guidelines:

(1) Subjects who had at least 2 fecal calprotectin samples taken at least 1 week apart were considered responders when at least a 50% reduction in levels was demonstrated in the second sample retrieved from the feces of the subject.

(2) Subjects who stably remained at normal levels of fecal calprotectin (≤50 mg/gram of feces) at all visits, regardless of serum CRP were considered responders.

(3) Subjects with less than 2 samples of fecal calprotectin were considered responders when demonstrated at least a 50% reduction in serum CRP levels in a second blood sample taken at least a week after the first blood sample.

(4) Subjects who exhibited normal levels of CRP (≤5 mg/dl) at all visits were considered responders.

Steroid Dependence—

The persistent need of concurrent steroid therapy is a valuable marker of disease state and of response to therapy. Subjects, who were receiving steroid therapy at the clinic visit at the $14^{th}$ week of treatment ("14-week") were considered non-responders.

Immunogenic Status—

Subjects who had measurable serum antibodies to Infliximab at their week 14-week visit were considered non-responders.

Study Response Algorithm—

The present inventors have formulated a decision algorithm to conclude whether a subject is responsive or not to therapy. The algorithm is mainly based on the primary gastroenterologist following the subject. For each subject on the 14-week visit the physician, after reviewing the subjects' records, decides whether the subject responded to therapy, failed or if it is still indeterminate. For the latter (indeterminate), a decision tree is performed with the following steps: a definition of failure is set when steroid treatment is given at 14-week visit. If no steroids are given the next step is to test the biomarker dynamics. A substantial reduction in fecal calprotectin is defined as response. If fecal calprotectin is not available, a reduction in serum CRP (as defined previously) is considered a response to treatment. For subjects who are not steroid-dependent and show no substantial biomarker dynamics, a physician decision on week 26 is made to determine the response status.

the above UC cohort (22); Signatures CDc and CD_blood were identified in CD patients from colon biopsies (5) and blood samples (PBMCs) respectively, the later using an iterative multivariate classification algorithm (13).

TABLE 6

Table 6: Previously proposed gene signatures of baseline response to anti-TNF.

| | N | Datasets | Disease/Tissue | Reference |
|---|---|---|---|---|
| UC_A | 20 | GSE14580 | UC/Colon | Arijs et al. (2009) Gut. 2009; 58(12): 1612-9. Pubmed: 19700435 |
| UC_B | 20 | GSE12251 | UC/Colon | Arijs et al. (2009) Gut. 2009; 58(12): 1612-9. Pubmed: 19700435 |
| UC_B_knn | 19 | GSE12251 | UC/Colon | www(dot)faqs(dot)org/patents/app/20100069256 |
| UC_AB | 53 | GSE12251, GSE14580 | UC/Colon | Arijs et al. (2009) Gut. 2009; 58(12): 1612-9. Pubmed: 19700435 |
| CDc | 20 | GSE16879 | CD/Colon | Arijs et al. Inflamm Bowel Dis. 2010; 16(12): 2090-8. Pubmed: 20848504 |
| IRRAT | 29 | GSE14580 | UC/Colon | Halloran et al. Inflamm Bowel Dis. 2014; 20(12): 2353-63 Pubmed: 25397893 |
| CD_Blood | 23 | IBD | Blood | Mesko et al. Genome Med. 2013; 5(6): 59 Pubmed: 23809696 |

N: number of genes in each signature.

Example 1

Previously Reported Gene Signatures Indicate Immune-Driven Signal

The present inventors have hypothesized that there is a baseline immune cellular signature of response to anti-TNF therapy, and accordingly, expected that at least part of previously predictive gene signatures detected by previous studies was indeed capturing an immune-driven signal, through genes that are more highly expressed by some immune cell subsets. To test this hypothesis, genes belonging to 7 gene signatures (i.e. gene sets) that were identified in studies of baseline response to anti-TNF in biopsies (6) or blood (1) (Table 6 below) have been considered. Most biopsy signatures (UC_A, UC_B, UC_AB, CDc and UC_B_knn) were originally defined based on the comparison of gene expression profiles between responders and non-responders to Infliximab treatment in UC and CD cohorts generated by two studies (4, 5). Signatures UC_A and UC_B were on two independent cohorts of UC patients (cohort A and B) from the top 20 differentially expressed genes; UC_AB was defined as the overlap between all differentially expressed genes in these two studies (53 genes) (4); Signature UC_B_knn was derived from UC cohort B using a different methodology based on k-nearest-neighbor classifier (20); The IRRAT signature (Injury-Repair Response Associated Transcripts) was defined in a kidney transplant study (21), but was subsequently found to correlate well with anti-TNF response at baseline in one of The present inventors looked at the expression of all signature genes across a variety of sorted immune cell subsets and bulk colon tissue samples obtained from two public datasets of sorted cell expression profiles (FIG. 2A, see Methods). Cell types from common hematopoietic lineage clustered together, mainly within B cells, T cells and Monocytes, while genes clustered in distinct blocks according to these lineages.

The association between each signature and each cell type was analyzed using a single sample enrichment analysis with GSVA (23) (FIG. 2B). Genes in the IRRAT signature were associated to subsets from the B cell lineage and neutrophils, while genes from CD_blood were associated to T cells. All other signatures were associated with monocytes. Hence overall most genes were more highly expressed by some immune cell subsets, rather than by colon tissues.

Very few genes were more highly expressed in colon tissues, and of those, most were also highly expressed in some other immune cell subset, mainly from the B cell lineage and neutrophils. This could indicate the presence of resident or infiltrating leukocyte populations within these tissues.

Example 2

Meta-Analysis Identifies Consistent Cell Type Proportion Differences

Meta-analysis of gene expression datasets has shown its ability to extract robust disease gene-based signatures by leveraging the biological and technical heterogeneity in data obtained from multiple sources to select genes that consistent and reproducible differences between two conditions (19, 24). This approach essentially consists of two steps: (1) a discovery phase that identifies features that are consistently different between two conditions in a set of discovery cohorts; and (2) a validation phase that assesses the ability of the selected features in classifying samples from an independent dataset. Here this methodology was applied in a novel way, by combining it with computational deconvolution techniques, to find robust cellular signatures that are predictive of anti-TNF response pre-treatment.

First the present inventors looked in the GEO database (25) for datasets of biopsies from IBD patients that were naive to anti-TNF therapy, and selected those for which both pre-treatment expression profiles and response status were available (GSE12251, GSE14580 and GSE16879).

Table 7 summarizes each dataset experimental design and relevant associated clinical data.

TABLE 7

Table 7. Summary of the datasets and biopsy samples used in the meta-analysis.
Discovery cohorts

| Dataset | Cohort | Samples* |
|---|---|---|
| GSE14580 | UC cohort A, colon biopsies, pre-treatment | 8 R /16 NR |
| GSE12251 | UC cohort B, colon biopsies, pre-treatment | 12 R/10 NR |
| GSE16879 | CD colon biopsies, pre-treatment | 12 R/7 NR |
| Validation | | |
| Rambam Hospital | UC/CD/IBDU colon and ileum biopsies | 9 R/11 NR |

*Responders (R)/Non-responders (NR).

These datasets contain biopsy gene expression profiles generated from 2 cohorts of UC patients (Cohort UC-A and UC-B in GSE14580 and GSE12251 respectively), and 1 cohort of CD (CD-C) patients (GSE16879). They were designed for the discovery of genes that can predict, at baseline, if a patient is likely to respond to an anti-TNF treatment (Infliximab), and, indeed, resulted in most of the previously proposed gene signatures analyzed hereinabove (4, 5). As a matter of fact, dataset GSE16879 contains profiles from other samples such as ileum CD biopsies, for which the response criterion was not as stringent as for the other samples, and consequently did not lead to any signature of response in the original study (5); it also includes pre-treatment UC samples that are part of dataset GSE14580, which were used therein, as well as post-treatment profiles from the same CD and UC patients (8 weeks after therapy initiation). In the baseline analysis, however, only the pre-treatment CD colon samples were used, all other samples were not used. Hence in the following, each cohort is referred using its corresponding GEO id.

Computational gene expression deconvolution methods can estimate the proportions of constituting cell types directly from heterogeneous samples (18). This is typically achieved using either sets of marker genes that are known to be expressed in a cell type-specific manner, or within a linear regression framework that jointly estimates all cell subset proportions—on each sample separately—from a reference compendium of sorted cell gene expression profiles (18). Using such a regression-based method (26), the present inventors estimated the proportion of 17 immune cell types in each sample, including most major cell subsets such as neutrophils, monocytes, B cell or T cell subpopulations in resting or activated state. Then, the estimated proportions of each cell type was compared between responders and non-responders, to identify candidate immune driver(s) of response. For robustness, the non-parametric Wilcoxon rank sum test was used, which is free of distributional assumption, and only cell types for which at least 75% of the samples had non-zero estimated proportions were considered. This analysis was performed initially in the CDc cohort (GSE16879), which revealed significant differences in activated monocytes and plasma cells, both showing higher proportions in non-responders (FIG. 2A). This same cohort was previously used to show that a predictive signature of 20 genes derived from UC patients was also able to perfectly discriminate responders and non-responders CD patients (5) (FIG. 3B). Having the estimated proportions of the two cell types that are the most associated with response enabled the present inventors to perform a second analysis to support the hypothesis of an immune based biomarkers of response. The total gene expression data was corrected for variation in activated monocytes and plasma cells, and the effect on the predictive power of the 20-genes signature was monitored. After correction, the classification accuracy dropped, suggesting that the gene signature indeed reflected, at least partially, a predictive variation in the proportions of these cell types (FIG. 3C). Notably, correcting for each cell type individually also lowered the signature's predictive power but not as much as when correcting for both (FIGS. 7A and 7B). Next, to strengthen the cell—based biomarker prediction, the present inventors repeated the analysis within each discovery cohort (FIG. 6). Significant differences were detected in activated monocytes which were lower in responders in all cohorts; plasma cells were lower in responders in 2 out 3 cohorts, including both UC and CD samples; finally, in either one of the cohorts, proportions of monocytes, activated dendritic cells, activated NK cells and CD8 T cells were higher in responders, while proportions of memory IgM B cells and neutrophils were higher in non-responders. Then, these differences were integrated across all cohorts in a meta-analysis, by combining p-values and selecting cell types that showed significant differences in at least 2 out of the 3 discovery cohorts (nominal p-value<=0.05) and a combined FDR≤0.01. This resulted in the selection of two cell subsets, activated monocytes and plasma cells, with responders having in both cases significantly lower proportions than non-responders (FIG. 4). In term of training set prediction power, separate ROC analysis within each cohort resulted in high mean accuracies of 90.3% and 77.8% Area Under the Curve (AUC) for activated monocytes and plasma cell proportions respectively (FIG. 8).

Validation of Cell Signatures by Staining in an Independent Set of Biopsies

In order to validate these findings, the present inventors looked at an independent set of 20 IBD patients (11 responders, 9 non-responders to anti-TNF) for which paraffin embedded biopsies had been stored prior anti-TNF treatment initiation, as part of common standard patient monitoring protocol in IBD. The present inventors defined cell type abundance scores from the examination of immunostained slides, and assessed how their proportion could predict response to treatment via ROC curve and Area Under the Curve (AUC). Since macrophages and plasma cells were the present inventors' top hits, the present inventors set out to define a macrophage and plasma cells morphological abundance score (low/medium/high) based on visual identification by a pathologist. For macrophages, this did not discriminate well responders from non-responders (FIG. 10), but plasma cells gave a clearly distinguishable differences. To test these findings, the present inventors stained for plasma cells (CD138+), and used two scoring strategies: first, a pathologist was asked to score the staining for low/medium/high abundance, while blind to the response status. Second, the present inventors used the proportions obtained by automated pixel quantitation averaged over multiple randomly chosen regions (see Methods). The pathologist and automated quantitation scores achieved 72.2% and 83.3% accuracy respectively (FIG. 5A). Visually, non-responsive patients showed very clear increased staining for plasma cells compared to non-responsive patients (FIG. 5B).

Tables 8A-B hereinbelow (Deconvolution basis signature), discloses raw data of the deconvolution estimation basis matrix. Table 9 herein below summarizes the results from the meta-analysis of the raw data.

TABLE 8A

Table 8A Deconvolution basis signature
5654 Adaptive immune cell subsets

| ENTREZ ID | Symbol | T CD4 | T CD4 activated | T CD8 | T CD8 activated | B cells |
|---|---|---|---|---|---|---|
|  |  | 5292.9 | 104.6 | 191.29 | 41.553 | 671.33 |
| 83481 | EPPK1 | 605.1 | 57.129 | 19.282 | 23.457 | 19.076 |
| 678 | ZFP36L2 | 5213.9 | 625.69 | 860.42 | 267.09 | 1040.9 |
|  |  | 1710.6 | 222.72 | 147.83 | 79.293 | 319.04 |
| 4929 | NR4A2 | 1407.8 | 247.46 | 19.61 | 143.09 | 50.766 |
|  |  | 1079.4 | 104.49 | 189.22 | 154.5 | 57.445 |
| 26289 | AK5 | 1379.6 | 330.29 | 203.27 | 52.567 | 50.005 |
| 3707 | ITPKB | 9321.4 | 1863.7 | 1799 | 613.54 | 1615.5 |
|  |  | 6951 | 389.67 | 369.9 | 408.86 | 1149.1 |
| 9241 | NOG | 1205.8 | 216.29 | 175.73 | 61.715 | 163.99 |
| 3337 | DNAJB1 | 4361.3 | 980.92 | 842.13 | 919.73 | 580.86 |
| 2935 | GSPT1 | 3343.6 | 1173.4 | 661.92 | 751.8 | 737.37 |
|  |  | 14624 | 2674.3 | 1387.4 | 3255.3 | 5202 |
| 4929 | NR4A2 | 1142.3 | 259.03 | 75.925 | 204.75 | 125.36 |
| 90139 | TSPAN18 | 1948.2 | 400.21 | 234 | 129.54 | 353.61 |
| 146330 | FBXL16 | 3811.3 | 1576.5 | 1403.5 | 697.89 | 732.34 |
| 678 | ZFP36L2 | 3793.8 | 620.67 | 771.55 | 219.34 | 1023.5 |
| 112744 | IL17F | 75.661 | 9648.6 | 96.514 | 126.73 | 146.75 |
| 3605 | IL17A | 7.194 | 809.34 | 3.396 | 10.259 | 7.24 |
| 1493 | CTLA4 | 1152.6 | 5171.8 | 644.65 | 1132.7 | 400.95 |
| 1493 | CTLA4 | 456.17 | 1826.6 | 170.64 | 539.95 | 77.447 |
| 940 | CD28 | 484.12 | 1102.4 | 350.46 | 347.35 | 148.4 |
| 51339 | DACT1 | 276.97 | 664.71 | 99.844 | 95.204 | 207.63 |
| 50616 | IL22 | 195.27 | 1621.9 | 140.2 | 272.41 | 182.77 |
| 143686 | SESN3 | 848.53 | 1665.6 | 388.3 | 162.9 | 305.6 |
| 128553 | TSHZ2 | 669.63 | 1663.3 | 288.41 | 312.36 | 171.51 |
| 145864 | HAPLN3 | 1946.6 | 8728.1 | 1101.6 | 2305.8 | 594.52 |
| 30812 | SOX8 | 298.04 | 1025 | 19.781 | 21.533 | 30.567 |
| 940 | CD28 | 424.1 | 927.04 | 284.99 | 249.87 | 32.017 |
| 1493 | CTLA4 | 829.63 | 2074.9 | 360.49 | 772.02 | 172.99 |
| 10320 | IKZF1 | 585.01 | 1251.5 | 289.46 | 343.31 | 289.61 |
| 29968 | PSAT1 | 346.27 | 2214.3 | 394.62 | 805.9 | 320.85 |
| 3578 | IL9 | 97.274 | 1343.5 | 49.426 | 410.4 | 83.163 |
| 128553 | TSHZ2 | 305.87 | 591.41 | 112.12 | 137.34 | 154.73 |
| 926 | CD8B | 41.855 | 32.983 | 1489.1 | 122.68 | 37.742 |
| 54674 | LRRN3 | 735.62 | 503.37 | 6792.8 | 1198.6 | 62.117 |
| 925 | CD8A | 310.06 | 405.99 | 9957.8 | 3315.8 | 611.63 |
| 926 | CD8B | 138.63 | 177.5 | 5811.1 | 2622.3 | 115.71 |
| 54674 | LRRN3 | 706.71 | 581.81 | 8644.5 | 2115.9 | 159.72 |
| 51676 | ASB2 | 79.337 | 112.51 | 2639.9 | 92.7.9 | 38.727 |
| 9666 | DZIP3 | 63.449 | 15.003 | 194.1 | 12.941 | 59.71 |
| 10730 | YME1L1 | 246.02 | 176.44 | 613.76 | 234.81 | 24.22 |
| 85315 | PAQR8 | 786.88 | 1044.9 | 2261.4 | 883.48 | 460.26 |
| 9402 | GRAP2 | 102.7 | 186.89 | 569.46 | 181.94 | 24.59 |
| 2833 | CXCR3 | 232.2 | 123.87 | 1592.3 | 282.94 | 73.401 |
| 3820 | KLRB1 | 237.41 | 181.43 | 750.95 | 276.46 | 270.68 |
| 4676 | NAP1L4 | 1095.9 | 1054.6 | 1961.3 | 1146 | 851.07 |
| 1731 | 1-Sep | 1853.2 | 1078 | 3456.8 | 1540.5 | 1236.1 |
| 814 | CAMK4 | 1278.2 | 978.5 | 2274.6 | 1265.9 | 238.29 |
| 57124 | CD248 | 366.65 | 216.83 | 1028.2 | 288.42 | 329.16 |
|  |  | 116.38 | 108.86 | 526.68 | 257.03 | 74.15 |
| 283869 | NPW | 5.177 | 5.275 | 4.551 | 539.25 | 6.061 |
| 199953 | TMEM201 | 192.86 | 235.07 | 220.53 | 3249.7 | 173.54 |
| 399694 | SHC4 | 59.433 | 60.769 | 40.265 | 570.24 | 33.133 |
| 3976 | LIF | 31.201 | 1084.5 | 36.214 | 5823.8 | 25.66 |
| 23176 | 8-Sep | 11.013 | 20.212 | 16.933 | 126.6 | 10.758 |
| 990 | CDC6 | 93.088 | 194.93 | 220.38 | 1223.1 | 107.62 |
| 51010 | EXOSC13 | 118.67 | 789.6 | 738.75 | 2638.3 | 174.02 |
| 1021 | CDK6 | 3018.2 | 4621.4 | 3289.6 | 19509 | 2481.6 |
| 51293 | CD320 | 144.21 | 273.65 | 232.18 | 1229.6 | 68.268 |
| 1503 | CTPS1 | 233.48 | 828.46 | 608.83 | 2722.2 | 268.05 |
| 84319 | CMSS1 | 844.34 | 1873.3 | 1306.2 | 6709.1 | 935.86 |
| 10622 | POLR3G | 111.28 | 129.25 | 80.188 | 499.74 | 110.15 |
| 199953 | TMEM201 | 169.99 | 261.11 | 249.09 | 1122.7 | 140.65 |
| 1021 | CDK6 | 1750.7 | 2549.3 | 1791.3 | 9645 | 1502.4 |
| 1841 | DTYMK | 108.09 | 195.01 | 278.64 | 1007.2 | 163.8 |
| 23464 | GCAT | 220.973 | 14.22 | 28.833 | 191.85 | 16.681 |

TABLE 8A-continued

Table 8A Deconvolution basis signature
5654 Adaptive immune cell subsets

| | | | | | | |
|---|---|---|---|---|---|---|
| 3336 | HSPE1 | 844.06 | 2476.6 | 1665.5 | 7532.5 | 669.89 |
| | | 59.386 | 43.757 | 62.947 | 48.205 | 1755 |
| 971 | CD72 | 58.037 | 36.506 | 120.52 | 81.1 | 2131.4 |
| 933 | CD22 | 15.819 | 9.314 | 10.67 | 9.456 | 4220.4 |
| | | 163.92 | 86.114 | 48.873 | 16.798 | 1334.1 |
| 6328 | SCN3A | 9.889 | 14.549 | 3.845 | 5.263 | 722.63 |
| 84518 | CNFN | 17.525 | 20.474 | 15.638 | 15.914 | 223.47 |
| 8115 | TCL1A | 413.37 | 244.87 | 53.831 | 83.168 | 11712 |
| 29802 | VPREB3 | 155.11 | 68.624 | 42.995 | 57.886 | 2850.9 |
| 79856 | SNX22 | 47.638 | 48.233 | 40.53 | 35.855 | 607.56 |
| 115123 | 3-Mar | 81.96 | 51.288 | 73.467 | 72.773 | 345.25 |
| 8115 | TCL1A | 641.02 | 399.85 | 114.45 | 76.966 | 13310 |
| | | 915.56 | 281.78 | 499.02 | 263.74 | 3325 |
| | | 221.07 | 128.11 | 19.172 | 32.89 | 1833 |
| 283663 | LINC00926 | 726.74 | 166.83 | 123 | 126.47 | 23022 |
| 283663 | LINC00926 | 692.64 | 453.05 | 520.19 | 392.15 | 13389 |
| 933 | CD22 | 390.89 | 254.78 | 175.49 | 153.74 | 5953.5 |
| 55278 | QRSL1 | 387.5 | 465.19 | 526.61 | 783.83 | 2643 |
| 94235 | GNG8 | 53.579 | 611.56 | 23.299 | 184.36 | 51.681 |
| 23089 | PEG10 | 46.498 | 31.167 | 66.482 | 18.336 | 253.9 |
| 7782 | SLC30A4 | 743.61 | 680.67 | 534.2 | 492.15 | 1318.3 |
| | | 72.247 | 269.15 | 243.03 | 479.83 | 451.44 |
| | | 121.46 | 90.123 | 93.263 | 76.315 | 493.97 |
| 148932 | MOB3C | 879.19 | 2018.4 | 1343.5 | 1029.6 | 825.81 |
| 80237 | ELL3 | 156.69 | 158.02 | 95.262 | 104.13 | 503.88 |
| 1184 | CLCN5 | 757.15 | 676.29 | 495.2 | 584.13 | 623.52 |
| 653121 | ZBTB8A | 163.85 | 107.16 | 57.552 | 97.531 | 219.78 |
| | | 53.024 | 126.27 | 68.75 | 269.56 | 451.93 |
| 1184 | CLCN5 | 155.94 | 162.89 | 109.18 | 181.57 | 159.9 |
| 94274 | PPP1R14A | 30.346 | 9.07 | 9.096 | 9.518 | 392.81 |
| 80237 | ELL3 | 159.7 | 130.7 | 92.114 | 118.93 | 420.44 |
| 1490 | CTGF | 22.249 | 22.905 | 6.739 | 3.515 | 43.341 |
| 148932 | MOB3C | 588.25 | 1078.3 | 640.07 | 622.65 | 514.18 |
| 140733 | MACROD2 | 210.22 | 110.16 | 58.043 | 68.735 | 3510.6 |
| 116449 | CLNK | 177.14 | 95.259 | 75.054 | 51.036 | 183.49 |
| 51237 | MZB1 | 768.21 | 1072 | 205.82 | 123.61 | 2046.6 |
| 3514 | IGKC | 17.024 | 12.551 | 9.378 | 10.146 | 26.928 |
| 3537 | IGLC1 | 27.368 | 28.913 | 16.45 | 26.404 | 135.1 |
| | | 476.89 | 528.5 | 108.54 | 42.032 | 957.48 |
| 81618 | ITM2C | 585.42 | 318.44 | 534.58 | 194.83 | 1031.8 |
| 51237 | MZB1 | 506.82 | 307.29 | 21.088 | 21.828 | 1374.2 |
| 608 | TNFRSF17 | 481.56 | 79.328 | 7.069 | 4.69 | 1187.8 |
| | | 669.73 | 445.68 | 99.639 | 82.5 | 1858 |
| 96610 | BMS1P20 | 1159.5 | 1240.9 | 243.81 | 144.13 | 4950.9 |
| | | 132.76 | 183.85 | 15.044 | 25.193 | 757.95 |
| 51303 | FKBP11 | 1010.8 | 1771.9 | 1287 | 1715.5 | 833.49 |
| | | 107.22 | 119.57 | 35.991 | 31.263 | 429.37 |
| | | 18.285 | 15.852 | 9.172 | 7.818 | 47.27 |
| | | 589.65 | 458.26 | 148.22 | 85.462 | 3392.6 |
| 79694 | MANEA | 87.389 | 192.19 | 113.36 | 190.16 | 109.12 |
| 28823 | IGLV1-44 | 316.7 | 249.63 | 21.981 | 8.441 | 1613 |
| 857 | CAV1 | 45.356 | 22.639 | 15.996 | 72.569 | 96.76 |
| 10316 | NMUR1 | 16.485 | 10.581 | 10.655 | 9.429 | 23.474 |
| 2043 | EPHA4 | 232.57 | 88.394 | 232.39 | 42.03 | 171.22 |
| 10079 | ATP9A | 11.562 | 14.731 | 6.817 | 9.387 | 12.617 |
| 9289 | ADGRG1 | 450.23 | 46.85 | 680.21 | 378.36 | 273.85 |
| 2043 | EPHA4 | 304.21 | 44.721 | 162.55 | 12.343 | 158.35 |
| 79901 | CYBRD1 | 7.287 | 5.64 | 5.593 | 5.551 | 9.848 |
| | | 56.285 | 18.537 | 102.77 | 15.889 | 50.579 |
| 151742 | PPM1L | 264.55 | 96.483 | 257.25 | 150.53 | 209.8 |
| 81563 | C1orf21 | 150.22 | 48.558 | 482.41 | 176.14 | 151.32 |
| 2619 | GAS1 | 12.055 | 10.149 | 9.647 | 9.038 | 20.012 |
| 59338 | PLEKHA1 | 2609.8 | 1355.1 | 1304.4 | 665.37 | 1768.9 |
| 2043 | EPHA4 | 900.99 | 422.48 | 455.53 | 254.47 | 417.9 |
| 4068 | SH2D1A | 390.85 | 464.3 | 737.65 | 455.64 | 77.492 |
| 2043 | EPHA4 | 634.35 | 162.79 | 615.75 | 128.7 | 195.17 |
| 2774 | GNAL | 85.932 | 63.9 | 41.075 | 28.466 | 74.428 |
| 5243 | ABCB1 | 281.26 | 147.7 | 424.3 | 150.74 | 410.31 |
| 11098 | PRSS23 | 337.78 | 158.02 | 147.29 | 189.44 | 245.58 |
| 127254 | ERICH3 | 53.192 | 88.232 | 19.387 | 54.307 | 43.526 |
| 57489 | ODF2L | 402.52 | 524.06 | 396.31 | 137.76 | 355.88 |
| 57489 | ODF2L | 361.13 | 401.41 | 336.7 | 142.21 | 219.51 |
| 257019 | FRMD3 | 304.9 | 315.32 | 121.07 | 156.3 | 292.62 |
| 10974 | ADIRF | 13.1 | 8.346 | 7.777 | 5.934 | 22.182 |
| 6672 | SP100 | 301.3 | 711.82 | 491.39 | 248.45 | 889.83 |
| 64108 | RTP4 | 156.03 | 1646.5 | 521.18 | 124.92 | 92.382 |
| 55603 | FAM46A | 209.46 | 254.63 | 56.082 | 30.957 | 262.27 |

TABLE 8A-continued

Table 8A Deconvolution basis signature
5654 Adaptive immune cell subsets

| | | | | | | |
|---|---|---|---|---|---|---|
| 54809 | SAMD9 | 878.92 | 5053.9 | 3029.7 | 540.35 | 1463 |
| 257019 | FRMD3 | 290.98 | 504.45 | 214.86 | 121.57 | 355.76 |
| 91624 | NEXN | 67.656 | 627 | 67.589 | 118.05 | 87.618 |
| | | 34.715 | 451.51 | 34.551 | 44.167 | 32.135 |
| 85363 | TRIM5 | 177.65 | 345.55 | 336.22 | 108.71 | 330.94 |
| 50650 | ARHGEF3 | 1839.8 | 2785.7 | 3143.2 | 928.31 | 802.1 |
| 100131733 | USP30-AS1 | 321.04 | 662.29 | 499.97 | 368.98 | 350.57 |
| | | 190.68 | 1376.2 | 626.48 | 604.37 | 248.31 |
| 2635 | GBP3 | 704.07 | 2327.8 | 2251.5 | 1177 | 507.74 |
| 5654 | HTRA1 | 298.66 | 211.29 | 129.67 | 158.13 | 244.18 |
| 2048 | EPHB2 | 18.128 | 14.747 | 13.441 | 10.721 | 22.435 |
| 10461 | MERTK | 170.5 | 109.41 | 114.19 | 123.07 | 217.36 |
| 4048 | LTA4H | 2762.8 | 3065.3 | 1893.5 | 2088.7 | 5716.5 |
| 2048 | EPHB2 | 30.863 | 44.763 | 17.499 | 32.405 | 59.756 |
| 10461 | MERTK | 190.69 | 107.8 | 58.619 | 53.798 | 117.56 |
| 340526 | RGAG4 | 78.208 | 111.4 | 61.529 | 63.163 | 103.33 |
| 284013 | VMO1 | 34.258 | 39.726 | 11.115 | 11.268 | 16.153 |
| 120939 | TMEM52B | 47.859 | 43.294 | 34.943 | 30.558 | 36.092 |
| 408 | ARRB1 | 34.25 | 29.224 | 38.111 | 72.62 | 31.272 |
| 2048 | EPHB2 | 197.37 | 142.57 | 136.13 | 141.82 | 204.37 |
| 2517 | FUCA1 | 242.55 | 302.08 | 495.6 | 216.27 | 440.56 |
| | | 170.59 | 108.76 | 126.74 | 100.47 | 271.42 |
| 2335 | FN1 | 26.448 | 27.259 | 17.197 | 26.945 | 30.48 |
| 11326 | VSIG4 | 233 | 137.81 | 120.47 | 81.189 | 213.86 |
| 2335 | FN1 | 70.789 | 23.169 | 29.882 | 44.304 | 59.421 |
| 51063 | CALHM2 | 314.56 | 124.06 | 776.91 | 70.875 | 230.96 |
| 55244 | SLC47A1 | 18.184 | 27.079 | 14.001 | 17.424 | 21.488 |
| 2162 | F13A1 | 289.19 | 154.99 | 124.88 | 105.2 | 313.25 |
| 10462 | CLEC10A | 117.66 | 77.553 | 54.795 | 58.318 | 113.97 |
| 246 | ALOX15 | 10.612 | 25.339 | 6.831 | 6.378 | 13.36 |
| 23475 | QPRT | 22.06 | 16.746 | 54.589 | 25.22 | 24.631 |
| 154092 | LINC01010 | 40.498 | 30.122 | 31.198 | 25.411 | 32.529 |
| 23017 | FAIM2 | 53.577 | 29.106 | 14.683 | 16.222 | 41.65 |
| 79839 | CCDC102B | 13.112 | 8.355 | 4.523 | 5.864 | 5.023 |
| 5445 | PON2 | 153.68 | 113.96 | 189.29 | 208.72 | 203.37 |
| 30835 | CD209 | 220.38 | 169.13 | 83.777 | 91.853 | 207.13 |
| 51477 | ISYNA1 | 285.49 | 212.26 | 179.91 | 183.44 | 292.53 |
| 30835 | CD209 | 106.67 | 65.52 | 19.824 | 18.065 | 59.958 |
| 2878 | GPX3 | 207.97 | 169.7 | 117.12 | 135.49 | 237.29 |
| 2878 | GPX3 | 202.77 | 174.29 | 157.95 | 111.93 | 261.65 |
| 5445 | PON2 | 142.99 | 90.515 | 112.25 | 122 | 90.488 |
| 56670 | SUCNR1 | 181.08 | 728.19 | 164.8 | 113.29 | 340.37 |
| 30850 | CDR2L | 14.937 | 10.283 | 11.864 | 17.984 | 14.459 |
| 11067 | C10orf10 | 37.582 | 61.905 | 18.124 | 17.372 | 28.084 |
| 6624 | FSCN1 | 21.011 | 314.03 | 33.576 | 161.6 | 16.286 |
| 54662 | TBC1D13 | 76.209 | 49.734 | 69.905 | 50.81 | 70.849 |
| 101930114 | LOC101930114 | 333.43 | 340.39 | 283.22 | 277.53 | 237.07 |
| 5157 | PDGFRL | 36.427 | 9.53 | 14.258 | 12.599 | 34.964 |
| 3429 | IFI27 | 162.25 | 912.04 | 119.25 | 65.958 | 75.112 |
| | | 78.773 | 668.53 | 20.265 | 24.835 | 25.86 |
| 80045 | GPR157 | 1127.6 | 936.33 | 442.69 | 373.89 | 792.28 |
| 80380 | PDCD1LG2 | 37.157 | 39.408 | 26.364 | 31.244 | 35.784 |
| 11067 | C10orf10 | 86.486 | 66.895 | 25.297 | 43.289 | 87.619 |
| 8820 | HESX1 | 15.962 | 20.309 | 9.002 | 16.894 | 20.791 |
| 6624 | FSCN1 | 20.332 | 566.4 | 33.336 | 168.56 | 71.603 |
| 11167 | FSTL1 | 192.12 | 120.83 | 113.92 | 109.45 | 195.78 |
| 54662 | TBC1D13 | 624.15 | 537.35 | 501.78 | 399.81 | 665.39 |
| 9175 | MAP3K13 | 6.504 | 4.804 | 3.886 | 3.113 | 5.906 |
| 3357 | HTR2B | 34.96 | 28.74 | 11.051 | 3.945 | 26.466 |
| 94015 | TTYH2 | 607.39 | 287.84 | 245.13 | 104.92 | 237.65 |
| 56300 | IL36G | 91.241 | 91.419 | 44.993 | 41.394 | 72.339 |
| 3036 | HAS1 | 83.836 | 49.02 | 39.758 | 51.693 | 82.304 |
| 7980 | TFPI2 | 15.299 | 25.449 | 6.514 | 7.562 | 15.212 |
| 11009 | IL24 | 85.352 | 83.076 | 38.318 | 38.162 | 251.23 |
| 4312 | MMP1 | 9.388 | 26.327 | 2.994 | 3.6 | 8.573 |
| 7980 | TFPI2 | 25.095 | 20.044 | 10.747 | 5.447 | 35.849 |
| 1440 | CSF3 | 18.01 | 24.088 | 13.039 | 11.862 | 29.41 |
| 3569 | IL6 | 207.34 | 440.66 | 94.669 | 75.292 | 320.72 |
| 4233 | MET | 11.918 | 12.065 | 5.665 | 56.352 | 11.912 |
| 169792 | GLIS3 | 51.725 | 42.231 | 9.847 | 76.931 | 13.202 |
| 51334 | PRR16 | 11.96 | 4.882 | 2.492 | 0.985 | 3.236 |
| 6374 | CXCL5 | 31.673 | 28.613 | 23.431 | 24.093 | 36.395 |
| 6660 | SOX5 | 9.836 | 7.861 | 7.661 | 6.475 | 29.154 |
| 79931 | TNIP3 | 30.483 | 496.06 | 87 | 200.55 | 28.186 |
| 8710 | SERPINB7 | 31.11 | 25.351 | 15.255 | 11.639 | 31.797 |
| 3690 | ITGB3 | 77.937 | 52.599 | 25.61 | 12.752 | 87.344 |
| 5743 | PTGS2 | 75.522 | 58.612 | 20.681 | 22.695 | 16.161 |

TABLE 8A-continued

Table 8A Deconvolution basis signature
5654 Adaptive immune cell subsets

| | | | | | | |
|---|---|---|---|---|---|---|
| 8794 | TNFRSF10C | 24.745 | 17.582 | 11.933 | 10.705 | 16.047 |
| 53829 | P2RY13 | 20.207 | 15.818 | 7.568 | 6.407 | 29.631 |
| 4311 | MME | 52.68 | 35.537 | 27.734 | 32.273 | 47.653 |
| 146225 | CMTM2 | 404.54 | 263.4 | 375.27 | 305.18 | 320.72 |
| 8794 | TNFRSF10C | 176.1 | 142.03 | 83.535 | 142.24 | 49.475 |
| 8794 | TNFRSF10C | 122.04 | 82.36 | 80.849 | 72.071 | 101.24 |
| 6286 | S100P | 341.03 | 96.34 | 29.987 | 26.748 | 230.68 |
| 3577 | CXCR1 | 55.571 | 34.928 | 30.255 | 30.118 | 51.796 |
| 60675 | PROK2 | 25.175 | 26.004 | 158.35 | 155.29 | 82.893 |
| 54682 | MANSC1 | 75.87 | 57.915 | 31.179 | 33.702 | 98.717 |
| 144423 | GLT1D1 | 48.013 | 28.57 | 27.015 | 34.934 | 109.92 |
| 3579 | CXCR2 | 48.606 | 7.934 | 13.365 | 4.607 | 34.921 |
| 25984 | KRT23 | 21.721 | 25.964 | 13.516 | 29.433 | 77.001 |
| 2215 | FCGR3B | 420.69 | 197.38 | 238.39 | 130.46 | 284.33 |
| 4311 | MME | 21.906 | 20.104 | 7.349 | 5.374 | 33.004 |
| 79908 | BTNL8 | 18.42 | 11.019 | 9.26 | 19.771 | 28.565 |
| | | 86.434 | 63.098 | 71.649 | 52.289 | 87.488 |
| | | 1854.5 | 61.454 | 48.362 | 44.29 | 999.91 |
| 80201 | HKDC1 | 442.35 | 35.677 | 47.464 | 21.902 | 45.899 |
| | | 297.62 | 19.749 | 6.99 | 17.411 | 66.318 |
| 3572 | IL6ST | 500.94 | 54.356 | 55.673 | 34.638 | 18.455 |
| 6711 | SPTBN1 | 1419.8 | 51.589 | 46.397 | 44.595 | 332.99 |
| 6920 | TCEA3 | 1084.5 | 225.21 | 238.7 | 62.339 | 68.575 |
| | | 1279.9 | 295.26 | 403.78 | 149.61 | 92.396 |
| 26119 | LDLRAP1 | 2504.4 | 344.2 | 835.09 | 62.217 | 197.35 |
| | | 2596.8 | 466.59 | 585.78 | 390.5 | 474.34 |
| 3562 | IL3 | 11.796 | 382.21 | 7.019 | 134.51 | 10.679 |
| 50616 | IL22 | 51.201 | 3661.6 | 26.909 | 880.39 | 42.27 |
| 64788 | LMF1 | 1219.7 | 1270.8 | 138.68 | 191.49 | 111.82 |
| | | 1125 | 2341.9 | 195.23 | 381.74 | 356.46 |
| 959 | CD40LG | 492.38 | 838.31 | 67.853 | 167.51 | 104.76 |
| 50943 | FOXP3 | 322.53 | 1418.7 | 167.46 | 635.89 | 89.541 |
| 54602 | NDFIP2 | 562.06 | 2564.1 | 486.91 | 2284.5 | 335.08 |
| 1493 | CTLA4 | 1240.2 | 4434.9 | 489.94 | 1618.8 | 53.729 |
| 55423 | SIRPG | 1279.7 | 344.58 | 1870.4 | 377.07 | 176.03 |
| 917 | CD3G | 2246.6 | 916.04 | 3622.2 | 876.21 | 201.71 |
| 10663 | CXCR6 | 147.04 | 969.58 | 1662.6 | 350.63 | 135.37 |
| 3090 | HIC1 | 37.26 | 320.67 | 1359.6 | 1251.4 | 43.644 |
| 27240 | SIT1 | 823.62 | 686.41 | 2063 | 786.65 | 1305.4 |
| 51676 | ASB2 | 380.33 | 402.91 | 2482.4 | 1135.9 | 242.59 |
| 91978 | TPGS1 | 147.3 | 83.667 | 652.05 | 427.54 | 76.829 |
| 28755 | TRAC | 9535.5 | 4889.7 | 11371 | 4324.1 | 989.81 |
| 3932 | LCK | 4328.6 | 1960.6 | 5769.7 | 2096.1 | 582.59 |
| 79413 | ZBED2 | 153.9 | 3485.5 | 158.99 | 5721.5 | 244.85 |
| 993 | CDC25A | 13.246 | 24.781 | 88.757 | 868.1 | 16.454 |
| 151230 | KLHL23 | 60.364 | 94.954 | 220.96 | 1774.3 | 72.694 |
| 29128 | UHRF1 | 236.33 | 1119.1 | 3816.9 | 11233 | 321.11 |
| | | 233.92 | 290.59 | 813.35 | 3551 | 308.18 |
| 29089 | UBE2T | 174.69 | 798.98 | 1705.3 | 6581 | 117.92 |
| 3070 | HELLS | 47.141 | 87.792 | 454.04 | 1303.1 | 93.846 |
| 8438 | RAD54L | 37.236 | 27.188 | 174 | 529.88 | 29.891 |
| 3070 | HELLS | 284.84 | 423.31 | 1327.9 | 3798.5 | 346.27 |
| 10563 | CXCL13 | 19.513 | 1354.7 | 29.476 | 1874.5 | 18.396 |
| 79075 | DSCC1 | 41.096 | 98.875 | 266.43 | 1054.4 | 34.983 |
| 4049 | LTA | 36.869 | 2186 | 19.704 | 2896.6 | 23.214 |
| 10328 | EMC8 | 27.346 | 73.761 | 32.207 | 695.77 | 25.677 |
| 84824 | FCRLA | 130.31 | 41.849 | 42.774 | 32.087 | 3782.4 |
| | | 668.07 | 294.22 | 50.476 | 56.156 | 21387 |
| 3899 | AFF3 | 533.25 | 92.106 | 343.14 | 118.34 | 9753.7 |
| 55024 | BANK1 | 131.67 | 62.309 | 17.332 | 13.043 | 5063.1 |
| 931 | MS4A1 | 756 | 462.64 | 129.79 | 55.3 | 13482 |
| | | 743.39 | 815.94 | 246.9 | 284.77 | 15139 |
| 931 | MS4A1 | 909.27 | 610.61 | 159.55 | 92.926 | 15292 |
| 199786 | FAM129C | 1149.9 | 781.16 | 583.52 | 548.37 | 15403 |
| 115350 | FCRL1 | 416.95 | 132.19 | 110.29 | 114.67 | 10113 |
| | | 415.85 | 176.56 | 284.27 | 153.54 | 7089.1 |
| 931 | MS4A1 | 291.55 | 183.21 | 166.4 | 186.99 | 8517.3 |
| 931 | MS4A1 | 1316.4 | 1018.6 | 104.4 | 58.217 | 33100 |
| 53335 | BCL11A | 338.58 | 370.66 | 69.794 | 59.023 | 13141 |
| 26040 | SETBP1 | 164.27 | 180.62 | 200.7 | 219.58 | 1157 |
| 53335 | BCL11A | 138.73 | 133.94 | 25.675 | 41.093 | 2742.6 |
| | | 41.785 | 67.193 | 9.726 | 5.421 | 163.95 |
| | | 13.19 | 15.156 | 7.21 | 7.64 | 141.74 |
| | | 968.69 | 815.12 | 23.298 | 23.718 | 5042.3 |
| 3514 | IGKC | 443.22 | 466.97 | 17.373 | 12.526 | 4208.7 |
| 857 | CAV1 | 78.802 | 62.756 | 35.597 | 78.088 | 88.197 |
| | | 677.66 | 476.06 | 157.64 | 134.86 | 2782.3 |

TABLE 8A-continued

Table 8A Deconvolution basis signature
5654 Adaptive immune cell subsets

| Entrez ID | Gene | | | | | |
|---|---|---|---|---|---|---|
| 100379345 | M1R181A2HG | 21.964 | 34.023 | 28.871 | 23.483 | 28.206 |
| 53637 | S1PR5 | 15.586 | 12.486 | 8.636 | 8.962 | 16.528 |
| 53637 | S1PR5 | 67.846 | 44.061 | 34.084 | 28.856 | 38.968 |
| 53637 | S1PR5 | 717.93 | 282.15 | 666.48 | 162.36 | 414.42 |
| 9231 | DLG5 | 48.54 | 24.378 | 25.433 | 19.693 | 44.627 |
| 90102 | PHLDB2 | 357.59 | 187.77 | 433.56 | 256.29 | 505.27 |
| 79899 | PRR5L | 180.15 | 197.03 | 170.88 | 145.01 | 166.91 |
| 7049 | TGFBR3 | 533.63 | 343.64 | 541.31 | 190.35 | 192.1 |
| 1524 | CX3CR1 | 1329.3 | 195.08 | 634.97 | 42.747 | 441.76 |
| 51348 | KLRF1 | 728.3 | 114.8 | 131.7 | 24.566 | 751.36 |
| 5775 | PTPN4 | 960.31 | 792.99 | 1209.5 | 415.43 | 695.24 |
| 5775 | PTPN4 | 424.84 | 365.3 | 571.27 | 223.34 | 289.89 |
| 7049 | TGFBR3 | 2940.3 | 2267.2 | 2912 | 1216.9 | 588.96 |
| 83888 | FGFBP2 | 2087.8 | 79.084 | 8123.5 | 2358.6 | 435.28 |
| 114879 | OSBPL5 | 301 | 127.76 | 248.21 | 171.33 | 202.29 |
| 219285 | SAMD9L | 768.39 | 9098.1 | 1581.8 | 440.99 | 1694.1 |
| 54877 | ZCCHC2 | 2470.2 | 5750.5 | 1562.2 | 2493.9 | 1912.9 |
| 356 | FASLG | 272.33 | 789.32 | 739.24 | 912.05 | 263.67 |
| 5920 | RARRES3 | 2719.8 | 2664.6 | 3060.1 | 235.33 | 849.11 |
| 388228 | SBK1 | 913.96 | 523.96 | 775.1 | 283.02 | 343.93 |
| 219285 | SAMD9L | 1329.8 | 9480.5 | 1860.7 | 712.66 | 1880.3 |
| 2219 | FCN1 | 467.99 | 60.392 | 78.933 | 58.575 | 284.26 |
| 9332 | CD163 | 101.82 | 119.76 | 79.024 | 61.356 | 118.4 |
| 23601 | CLEC5A | 119.11 | 95.737 | 92.389 | 84.429 | 228.91 |
| 9332 | CD163 | 71.858 | 85.886 | 38.251 | 24.845 | 68.466 |
| 51313 | FAM198B | 156.34 | 93.035 | 118.44 | 123.52 | 130.26 |
| 23166 | STAB1 | 128.66 | 107.3 | 93.651 | 72.915 | 83.267 |
| 10501 | SEMA6B | 33.318 | 21.347 | 24.505 | 33.317 | 76.208 |
| 7045 | TGFBI | 314.89 | 110.94 | 91.258 | 36.355 | 79.571 |
| 8536 | CAMK1 | 231.77 | 200.59 | 264.45 | 485.72 | 194.55 |
| 23166 | STAB1 | 161.92 | 111.78 | 150.14 | 170.8 | 190.98 |
| 206358 | SLC36A1 | 69.352 | 112.18 | 167.49 | 162.58 | 136.7 |
| 913 | CD1E | 23.446 | 31.112 | 24.51 | 19.626 | 10.493 |
| 713 | C1QB | 57.155 | 68.223 | 38.545 | 24.608 | 93.249 |
| 712 | C1QA | 62.558 | 24.101 | 23.867 | 20.628 | 32.379 |
| 910 | CD1B | 116.44 | 64.685 | 43.037 | 23.273 | 75.038 |
| 913 | CD1E | 76.574 | 73.689 | 34.628 | 34.141 | 101.33 |
| 714 | C1QC | 110.65 | 140.74 | 27.702 | 61.741 | 34.068 |
| 5480 | PPIC | 47.172 | 48.238 | 37.09 | 16.31 | 46.384 |
| 945 | CD33 | 23.86 | 26.068 | 11.41 | 9.258 | 25.716 |
| 909 | CD1A | 334.06 | 215.3 | 239.04 | 192.86 | 595.37 |
| 2 | A2M | 56.154 | 90.243 | 91.964 | 68.09 | 88.213 |
| 6357 | CCL13 | 103.8 | 102.11 | 70.412 | 68.673 | 165.5 |
| 1193 | CLIC2 | 19.734 | 13.509 | 4.991 | 7.239 | 27.693 |
| 5577 | PRKAR2B | 109.78 | 78.126 | 61.402 | 92.489 | 117.09 |
| 6614 | SIGLEC1 | 23.821 | 16.503 | 13.074 | 11.874 | 18.704 |
| 80380 | PDCD1LG2 | 16.213 | 14.334 | 24.966 | 7.891 | 14.958 |
| 942 | CD86 | 183.62 | 162.09 | 106.74 | 90.275 | 293.85 |
| 629 | CFB | 136.58 | 132.94 | 46.834 | 56.07 | 131.35 |
| 5055 | SERPINB2 | 104.82 | 108.06 | 56.517 | 32.963 | 71.147 |
| 55022 | PID1 | 68.932 | 25.883 | 27.311 | 36.14 | 27.062 |
| 2921 | CXCL3 | 24.788 | 25.074 | 21.049 | 26.677 | 53.966 |
| 6374 | CXCL5 | 32.322 | 5.255 | 14.219 | 3.561 | 33.529 |
| 2919 | CXCL1 | 102.29 | 72.235 | 49.323 | 38.146 | 109.13 |
| 3552 | IL1A | 88.623 | 145.24 | 90.422 | 35.318 | 155.24 |
| 718 | C3 | 59.883 | 26.757 | 34.401 | 17.188 | 28.973 |
| 6369 | CCL24 | 44.054 | 21.628 | 24.646 | 14.316 | 57.382 |
| 3624 | INHBA | 16.237 | 135.48 | 7.304 | 7.813 | 26.306 |
| 8875 | VNN2 | 269.9 | 77.17 | 513.82 | 12.6 | 355.24 |
| 1441 | CSF3R | 106.53 | 44.825 | 45.942 | 38.679 | 176.05 |
| 64407 | RGS18 | 348.74 | 282.09 | 132.72 | 112.99 | 257.38 |

| ENTREZ ID | B activated | B aIgM | B Mem IgG | B Mem IgM | Plasma cells |
|---|---|---|---|---|---|
|  | 125.9 | 78.485 | 1355.6 | 2167.6 | 575.7 |
| 83481 | 22.296 | 18.152 | 51.534 | 45.244 | 24.699 |
| 678 | 563.83 | 248.18 | 422.51 | 430.73 | 170.09 |
|  | 236.36 | 156.19 | 134.89 | 262.19 | 128.64 |
| 4929 | 112.38 | 322.4 | 202.34 | 365.71 | 42.58 |
|  | 81.581 | 162.01 | 48.368 | 116.49 | 31.034 |
| 26289 | 48.406 | 38.379 | 69.45 | 65.663 | 55.256 |
| 3707 | 2073.6 | 2786.8 | 231.11 | 151.04 | 294.67 |
|  | 388.4 | 630.63 | 1875.9 | 3071.5 | 448.05 |
| 9241 | 62.575 | 71.163 | 153.18 | 210.55 | 226.19 |
| 3337 | 779.84 | 629.17 | 342.02 | 318.99 | 888.9 |
| 2935 | 768.24 | 920.58 | 513.34 | 503.68 | 565.05 |
|  | 1429.3 | 2599.7 | 3060.4 | 3890.8 | 1513.1 |

TABLE 8A-continued

Table 8A Deconvolution basis signature
5654 Adaptive immune cell subsets

| | | | | | |
|---|---|---|---|---|---|
| 4929 | 209.68 | 312.83 | 502.61 | 820.81 | 97.28 |
| 90139 | 210.34 | 149.64 | 323.63 | 239.4 | 712.5 |
| 146330 | 672.19 | 494.3 | 833.77 | 550.58 | 1161 |
| 678 | 486.97 | 268.09 | 366.91 | 415.21 | 172.63 |
| 112744 | 99.437 | 125.95 | 181.58 | 145.47 | 169.89 |
| 3605 | 8.1 | 3.219 | 24.895 | 36.767 | 5.585 |
| 1493 | 331.91 | 319.33 | 599.21 | 486.96 | 540.88 |
| 1493 | 57.268 | 68.635 | 58.954 | 76.762 | 89.278 |
| 940 | 101.36 | 39.628 | 175.46 | 291.21 | 134.16 |
| 51339 | 228.89 | 116.55 | 212.18 | 274.44 | 115.61 |
| 50616 | 177 | 131.76 | 305.89 | 259.44 | 170.05 |
| 143686 | 519.98 | 590.79 | 135.39 | 151.2 | 120.16 |
| 128553 | 286.96 | 117.25 | 355.25 | 272.75 | 201.94 |
| 145864 | 1180.4 | 388.18 | 558.27 | 536.28 | 992.28 |
| 30812 | 26.109 | 23.557 | 28.412 | 27.116 | 41.972 |
| 940 | 33.209 | 17.453 | 61.339 | 66.092 | 45.075 |
| 1493 | 225.83 | 82.15 | 277.45 | 353.17 | 308.49 |
| 10320 | 355.95 | 186.75 | 251.73 | 257.34 | 202.66 |
| 29968 | 337.81 | 736.12 | 429.65 | 309.66 | 102.5.6 |
| 3578 | 57.007 | 22.289 | 145.32 | 101.28 | 54.427 |
| 128553 | 110.94 | 63.719 | 214.32 | 219.95 | 234.12 |
| 926 | 27.152 | 8.683 | 93.873 | 74.936 | 50.758 |
| 54674 | 40.136 | 28.776 | 157.23 | 118.26 | 33.943 |
| 925 | 460.91 | 106.98 | 363.04 | 243.73 | 125.54 |
| 926 | 130.58 | 54.383 | 281.08 | 335.21 | 118.48 |
| 54674 | 143.34 | 90.669 | 332.35 | 344.48 | 173.99 |
| 51676 | 46.681 | 31.775 | 53.498 | 43.509 | 219.16 |
| 9666 | 26.541 | 25.563 | 37.349 | 36.696 | 17.2 |
| 10730 | 30.823 | 24.564 | 39.521 | 42.166 | 31.209 |
| 85315 | 520.17 | 258.38 | 424.19 | 344.92 | 557.11 |
| 9402 | 16.219 | 12.373 | 19.32 | 20.428 | 13.39 |
| 2833 | 52.68 | 25.821 | 101.19 | 79.587 | 242.77 |
| 3820 | 110.13 | 115.56 | 162.12 | 76.456 | 206.92 |
| 4676 | 858.5 | 642.55 | 569.35 | 587.16 | 796.58 |
| 1731 | 1119.3 | 944.65 | 371.66 | 442.15 | 1079.7 |
| 814 | 296.08 | 68.922 | 188 | 231.35 | 301.28 |
| 57124 | 282.39 | 195.08 | 324.75 | 255.77 | 252.92 |
| | 61.25 | 39.666 | 104.62 | 117.43 | 122.23 |
| 283869 | 5.692 | 446.58 | 11.427 | 16.884 | 12.242 |
| 199953 | 170.17 | 95.56 | 141.98 | 147.22 | 290.42 |
| 399694 | 62.257 | 34.752 | 92.555 | 87.079 | 47.668 |
| 3976 | 21.031 | 19.177 | 49.072 | 46.371 | 25.724 |
| 23176 | 11.885 | 13.505 | 25.628 | 24.617 | 18.216 |
| 990 | 112.04 | 83.857 | 174.97 | 175.32 | 310.89 |
| 51010 | 567.47 | 822.37 | 48.067 | 79.427 | 299.82 |
| 1021 | 2276.6 | 1490.8 | 493.55 | 258.8 | 3295 |
| 51293 | 144.65 | 283.68 | 59.468 | 53.224 | 315.2 |
| 1503 | 532.91 | 994.27 | 373.66 | 397.97 | 386.96 |
| 84319 | 1139.8 | 3038.4 | 411.69 | 346.84 | 1622.2 |
| 10622 | 90.279 | 191.06 | 105.25 | 95.599 | 122.2 |
| 199953 | 160.81 | 171.54 | 123.62 | 129.9 | 114.47 |
| 1021 | 1408.9 | 897.3 | 752.27 | 632.6 | 2131.3 |
| 1841 | 160.07 | 273.64 | 133.27 | 153.84 | 292.14 |
| 23464 | 11.739 | 14.28 | 22.541 | 21.448 | 16.567 |
| 3336 | 1505.3 | 2903.3 | 846.93 | 783.39 | 1572.6 |
| | 162.4 | 482.29 | 413.11 | 121.42 | 128.14 |
| 971 | 429.63 | 938.19 | 245.96 | 573.81 | 17.596 |
| 933 | 899.99 | 1028.4 | 411.99 | 546.56 | 11.084 |
| | 244.78 | 244.54 | 171.12 | 212.56 | 22.94 |
| 6328 | 159.39 | 75.757 | 124.23 | 81.037 | 22.318 |
| 84518 | 42.35 | 25.314 | 47.823 | 161.18 | 31.814 |
| 8115 | 2673.8 | 2889.4 | 498.98 | 831.45 | 293.26 |
| 29802 | 755.75 | 264.61 | 1466.2 | 1287.6 | 178.78 |
| 79856 | 124.46 | 101.79 | 348.5 | 401.1 | 104.37 |
| 115123 | 86.994 | 110.34 | 75.808 | 75.208 | 61.51 |
| 8115 | 3401.9 | 2895.9 | 575.35 | 902.55 | 275.69 |
| | 798.08 | 831.82 | 778 | 802.7 | 432.14 |
| | 502.73 | 422.8 | 785.39 | 690.67 | 272.74 |
| 283663 | 6478.5 | 4462 | 6503.1 | 7265.8 | 226.35 |
| 283663 | 4016.6 | 2195.3 | 3613.9 | 4563.9 | 556.32 |
| 933 | 1829.8 | 1631.8 | 1793.3 | 2011 | 266.97 |
| 55278 | 875.1 | 727.76 | 1464.3 | 1714.3 | 621.96 |
| 94235 | 8705.2 | 681.42 | 43.5 | 64.063 | 57.214 |
| 23089 | 2036.6 | 121.93 | 81.024 | 103.77 | 73.413 |
| 7782 | 7943.9 | 326.7 | 1065.5 | 710.81 | 847.84 |
| | 3818.5 | 2789.4 | 150.52 | 188.22 | 240.7 |
| | 2956.6 | 774.48 | 232.44 | 167.55 | 182.61 |

TABLE 8A-continued

Table 8A Deconvolution basis signature
5654 Adaptive immune cell subsets

| | | | | | |
|---|---|---|---|---|---|
| 148932 | 13894 | 717.4 | 604.51 | 685.16 | 895.23 |
| 80237 | 2672.8 | 627.44 | 196.76 | 187.92 | 102 |
| 1184 | 4105.2 | 524.36 | 1044.6 | 1151.2 | 764.8 |
| 653121 | 2444 | 154.17 | 222.47 | 278.34 | 440.52 |
| | 3470.4 | 881.09 | 127.17 | 231.04 | 56.611 |
| 1184 | 1331.7 | 179.77 | 216.7 | 184.82 | 145.23 |
| 94274 | 2681.6 | 109.95 | 196.29 | 198.03 | 100.7 |
| 80237 | 1706 | 524.31 | 229.49 | 264.89 | 170.12 |
| 1490 | 265.32 | 34.172 | 29.803 | 13.406 | 12.285 |
| 148932 | 4626 | 496.97 | 611.27 | 530.52 | 453.65 |
| 140733 | 11697 | 5016.8 | 124.2 | 181.28 | 644.92 |
| 116449 | 657.76 | 44.223 | 102.93 | 129.5 | 188.89 |
| 51237 | 1716.7 | 785.93 | 740.4 | 838.1 | 37183 |
| 3514 | 11.946 | 14.494 | 23.924 | 21.578 | 677.99 |
| 3537 | 40.005 | 74.637 | 57.895 | 39.922 | 5202.1 |
| | 592.6 | 712.36 | 296.25 | 472.3 | 32592 |
| 81618 | 738.28 | 247.2 | 577.24 | 779.46 | 11437 |
| 51237 | 1319.5 | 490.69 | 260.48 | 239.29 | 17479 |
| 608 | 365.71 | 263.56 | 626.98 | 442.39 | 14375 |
| | 900.13 | 604.22 | 1247.4 | 2371.6 | 22774 |
| 96610 | 3547.4 | 1665.6 | 1460.3 | 1353.7 | 44647 |
| | 436.2 | 527.22 | 512.07 | 467.82 | 6583.2 |
| 51303 | 736.14 | 618.66 | 596.84 | 431.99 | 13740 |
| | 167.16 | 108.45 | 65.809 | 55.434 | 4308.9 |
| | 47.245 | 16.959 | 37.188 | 22.782 | 555.37 |
| | 2245 | 842.29 | 1265.4 | 1225.6 | 26624 |
| 79694 | 128.83 | 61.721 | 57.43 | 51.351 | 1510.6 |
| 28823 | 1120.6 | 591.59 | 697.15 | 670.13 | 13019 |
| 857 | 64.758 | 65.577 | 46.166 | 24.508 | 1889.2 |
| 10316 | 16.968 | 11.241 | 28.366 | 24.025 | 21.331 |
| 2043 | 92.377 | 36.349 | 140.79 | 81.496 | 54.073 |
| 10079 | 10.289 | 11.696 | 19.097 | 25.438 | 10.548 |
| 9289 | 146.6 | 17.949 | 47.686 | 42.818 | 31.702 |
| 2043 | 137.15 | 20.26 | 166.81 | 42.352 | 38.186 |
| 79901 | 8.445 | 7.804 | 19.536 | 17.719 | 8.519 |
| | 25.757 | 25.26 | 112.58 | 61.378 | 25.283 |
| 151742 | 240.56 | 152.7 | 259.38 | 192.84 | 210.88 |
| 81563 | 97.005 | 29.468 | 93.735 | 57.454 | 63.917 |
| 2619 | 12.016 | 8.361 | 24.734 | 25.129 | 12.794 |
| 59338 | 1304.9 | 762.61 | 848.99 | 955.81 | 356.19 |
| 2043 | 429.13 | 273.55 | 717.74 | 602.07 | 596.28 |
| 4068 | 72.491 | 74.097 | 47.594 | 46.695 | 20.921 |
| 2043 | 190.16 | 66.138 | 395.22 | 109.34 | 155.65 |
| 2774 | 43.235 | 33.021 | 90.869 | 85.197 | 79.187 |
| 5243 | 274.03 | 186.01 | 228.02 | 225.67 | 224.27 |
| 11098 | 359.39 | 132.8 | 330.03 | 377.04 | 351.5 |
| 127254 | 75.933 | 42.083 | 112.26 | 106.76 | 33.029 |
| 57489 | 155.38 | 159.46 | 183.49 | 113.26 | 312.66 |
| 57489 | 187.77 | 125.38 | 240.69 | 116.48 | 274.85 |
| 257019 | 214.85 | 117.87 | 312.93 | 474.35 | 213.8 |
| 10974 | 27.798 | 11.084 | 22.65 | 20.283 | 15.804 |
| 6672 | 574.84 | 396.32 | 225.06 | 197.43 | 120.03 |
| 64108 | 560.78 | 58.119 | 59.991 | 60.383 | 224.17 |
| 55603 | 338.22 | 140.46 | 70.072 | 70.491 | 96.183 |
| 54809 | 1883.7 | 500 | 389.29 | 544.59 | 1078.5 |
| 257019 | 267.45 | 226.52 | 846.65 | 811.22 | 387.72 |
| 91624 | 101.62 | 150.77 | 82.89 | 38.41 | 30.593 |
| | 29.07 | 32.918 | 52.246 | 56.176 | 76.157 |
| 85363 | 318.82 | 274.03 | 143.37 | 183.16 | 317.66 |
| 50650 | 999.06 | 266.06 | 374.46 | 472.91 | 440.33 |
| 100131733 | 250.69 | 163.87 | 200.3 | 148.86 | 637.26 |
| | 303.43 | 158.5 | 49.547 | 60.247 | 882.36 |
| 2635 | 597.15 | 260.27 | 260.49 | 282.58 | 680.29 |
| 5654 | 325.94 | 217.11 | 254.78 | 217.39 | 378.02 |
| 2048 | 19.212 | 13.813 | 41.378 | 38.509 | 19.184 |
| 10461 | 151.04 | 110.88 | 131.29 | 147.68 | 167.79 |
| 4048 | 5135.1 | 4152 | 2095.9 | 2279.2 | 3178.3 |
| 2048 | 19.794 | 14.376 | 68.248 | 49.623 | 86.171 |
| 10461 | 104.65 | 56.653 | 236.55 | 207.85 | 107.1 |
| 340526 | 94.134 | 75.628 | 96.029 | 94.257 | 95.477 |
| 284013 | 14.451 | 19.847 | 23.683 | 20.328 | 23.967 |
| 120939 | 85.694 | 45.534 | 69.956 | 54.285 | 134.15 |
| 408 | 19.392 | 15.134 | 37.238 | 34.008 | 20.44 |
| 2048 | 159.93 | 109.4 | 240.71 | 226.39 | 202.71 |
| 2517 | 450.22 | 469.94 | 416.64 | 325.97 | 713.2.1 |
| | 210.77 | 199.36 | 122.69 | 123.37 | 38.037 |
| 2335 | 25.495 | 42.183 | 81.327 | 103.35 | 16.885 |

TABLE 8A-continued

Table 8A Deconvolution basis signature
5654 Adaptive immune cell subsets

| | | | | | |
|---|---|---|---|---|---|
| 11326 | 154.35 | 61.94 | 352.53 | 358.35 | 198.53 |
| 2335 | 56.337 | 17.899 | 52.106 | 56.731 | 16.433 |
| 51063 | 151.41 | 104.78 | 139.07 | 174.98 | 129.8 |
| 55244 | 30.656 | 13.634 | 24.757 | 22.461 | 30.17 |
| 2162 | 233.58 | 115.91 | 479.91 | 402.89 | 247.61 |
| 10462 | 116.72 | 20.433 | 119.71 | 111.38 | 104.15 |
| 246 | 11.346 | 9.715 | 19.972 | 58.372 | 10.044 |
| 23475 | 16.766 | 31.21 | 87.88 | 56.88 | 141.4 |
| 154092 | 28.516 | 36.734 | 69.953 | 64.71 | 44.851 |
| 23017 | 21.3 | 18.821 | 28.089 | 25.181 | 28.634 |
| 79839 | 8.302 | 1.015 | 37.086 | 9.202 | 8.124 |
| 5445 | 121.68 | 97.311 | 120.96 | 128.04 | 130.15 |
| 30835 | 163.27 | 99.57 | 313.17 | 251 | 187.27 |
| 51477 | 198.33 | 85.288 | 65.867 | 135.68 | 52.564 |
| 30835 | 52.787 | 21.539 | 35.029 | 47.617 | 24.918 |
| 2878 | 182.73 | 161.49 | 414.11 | 438.13 | 229.3 |
| 2878 | 236.72 | 154.17 | 295.06 | 301.73 | 234.74 |
| 5445 | 64.661 | 62.882 | 113.24 | 149.34 | 50.288 |
| 56670 | 277.13 | 142.74 | 423.79 | 260.43 | 305.45 |
| 30850 | 8.9 | 13.077 | 13.102 | 13.026 | 10.069 |
| 11067 | 23.813 | 25.516 | 43.537 | 39.406 | 29.808 |
| 6624 | 63.516 | 55.39 | 54.472 | 29.717 | 24.173 |
| 54662 | 141.92 | 114.81 | 54.299 | 51.949 | 51.197 |
| 101930114 | 137.2 | 75.169 | 147.68 | 206.61 | 305.57 |
| 5157 | 16.96 | 44.181 | 40.21 | 22.475 | 13.408 |
| 3429 | 112.25 | 46.373 | 50.78 | 94.163 | 119.78 |
| | 39.337 | 23.056 | 114.36 | 60.898 | 40.013 |
| 80045 | 765.69 | 864.41 | 672.41 | 417.83 | 1021.2 |
| 80380 | 26.589 | 26.191 | 63.203 | 53.796 | 59.15 |
| 11067 | 102.61 | 23.724 | 58.954 | 61.644 | 63.256 |
| 8820 | 22.89 | 13.287 | 26.034 | 26.317 | 17.264 |
| 6624 | 102.41 | 67.491 | 10.366 | 6.506 | 7.758 |
| 11167 | 158.41 | 118.18 | 353.01 | 375.64 | 162.49 |
| 54662 | 730.1 | 446.29 | 528.19 | 571.03 | 405.15 |
| 9175 | 5.464 | 4.814 | 8.781 | 9.781 | 11.148 |
| 3357 | 10.004 | 15.287 | 25.989 | 17.253 | 29.89 |
| 94015 | 192.38 | 136.59 | 76.097 | 105.62 | 369.95 |
| 56300 | 78.498 | 53.339 | 171.73 | 175.77 | 85.443 |
| 3036 | 62.179 | 22.661 | 135.41 | 153.81 | 107.37 |
| 7980 | 135.04 | 88.061 | 22.203 | 21.938 | 12.314 |
| 11009 | 72.213 | 118.18 | 67.58 | 126.55 | 22.751 |
| 4312 | 16.557 | 7.346 | 33.165 | 45.886 | 6.634 |
| 7980 | 74.723 | 52.423 | 70.474 | 69.994 | 34.393 |
| 1440 | 19.209 | 19.475 | 26.511 | 26.774 | 20.875 |
| 3569 | 1588 | 284.03 | 341.25 | 435.91 | 145.62 |
| 4233 | 10.115 | 35.396 | 24.648 | 16.854 | 32.194 |
| 169792 | 16.12 | 14.462 | 83.659 | 111.02 | 64.578 |
| 51334 | 8.931 | 22.338 | 34.53 | 23.283 | 19.207 |
| 6374 | 9.425 | 17.418 | 54.262 | 77.543 | 38.061 |
| 6660 | 8.14 | 11.336 | 19.539 | 23.041 | 16.023 |
| 79931 | 19.561 | 27.081 | 64.546 | 62.118 | 37.863 |
| 8710 | 20.7 | 20.595 | 48.02 | 44.575 | 24.085 |
| 3690 | 100.16 | 79.679 | 27.204 | 28.815 | 13.054 |
| 5743 | 26.012 | 21.551 | 28.498 | 43.676 | 25.445 |
| 8794 | 12.525 | 12.11 | 37.874 | 17.543 | 9.775 |
| 53829 | 76.257 | 13.312 | 70.916 | 33.945 | 22.424 |
| 4311 | 44.56 | 32.565 | 106.81 | 102.32 | 68.168 |
| 146225 | 272.32 | 165.77 | 841.78 | 212.16 | 494.7 |
| 8794 | 43.257 | 26.589 | 45.615 | 59.935 | 125.79 |
| 8794 | 94.444 | 66.289 | 143.19 | 149.05 | 94.772 |
| 6286 | 299.56 | 120.18 | 69.519 | 41.807 | 30.985 |
| 3577 | 46.036 | 23.438 | 66.93 | 68.085 | 27.242 |
| 60675 | 49.74 | 28.545 | 24.378 | 16.613 | 53.691 |
| 54682 | 103.16 | 34.426 | 291.74 | 249.55 | 97.194 |
| 144423 | 33.965 | 25.369 | 54.365 | 48.216 | 45.415 |
| 3579 | 15.821 | 19.504 | 13.723 | 15.532 | 19.566 |
| 25984 | 62.235 | 52.891 | 151.99 | 138.74 | 106.63 |
| 2215 | 180.1 | 91.841 | 248.53 | 239.36 | 162.95 |
| 4311 | 64.683 | 12.237 | 32.656 | 30.344 | 18.396 |
| 79908 | 22.44 | 13.582 | 25.459 | 26.706 | 26.866 |
| | 50.563 | 44.979 | 99.362 | 61.429 | 110.7 |
| | 57.159 | 47.999 | 62.948 | 64.1 | 66.571 |
| 80201 | 34.716 | 31.414 | 65.151 | 73.108 | 71.596 |
| | 13.655 | 10.1 | 11.711 | 9.278 | 13.786 |
| 3572 | 33.371 | 45.084 | 127.48 | 253.1 | 93.452 |
| 6711 | 37.121 | 54.203 | 108.92 | 253.63 | 122.46 |

TABLE 8A-continued

Table 8A Deconvolution basis signature
5654 Adaptive immune cell subsets

| | | | | | |
|---|---|---|---|---|---|
| 6920 | 50.839 | 46.818 | 75.369 | 171.03 | 152.37 |
| | 109.06 | 137.22 | 125.98 | 246.18 | 43.598 |
| 26119 | 98.984 | 173 | 135.23 | 159.29 | 284.72 |
| | 448.8 | 270.5 | 136.42 | 258 | 408.3 |
| 3562 | 10.166 | 9.046 | 36.347 | 16.231 | 9.837 |
| 50616 | 53.862 | 16.571 | 102.85 | 70.52 | 146.28 |
| 64788 | 123.14 | 198.43 | 173.84 | 193.14 | 182.04 |
| | 283.78 | 174.75 | 205.37 | 190.32 | 240.26 |
| 959 | 46.611 | 20.655 | 64.876 | 58.402 | 42.182 |
| 50943 | 65.338 | 48.38 | 220.77 | 206.11 | 146.06 |
| 54602 | 441.29 | 350.3 | 661.08 | 704.09 | 614.13 |
| 1493 | 52.941 | 16.366 | 134.12 | 85.046 | 151.54 |
| 55423 | 122.11 | 36.387 | 183.64 | 157.75 | 97.431 |
| 917 | 87.324 | 19.905 | 53.472 | 55.177 | 32.644 |
| 10663 | 191.12 | 73.848 | 262.77 | 265.17 | 136.31 |
| 3090 | 62.872 | 53.679 | 62.066 | 56.536 | 43.042 |
| 27240 | 447.22 | 556.99 | 658.06 | 732.74 | 394.33 |
| 51676 | 289.52 | 203.62 | 242.59 | 200.29 | 612.31 |
| 91978 | 56.022 | 175.17 | 42.183 | 46.635 | 136.02 |
| 28755 | 734 | 297.26 | 509.97 | 406.85 | 471.19 |
| 3932 | 401.34 | 265.26 | 313.1 | 297.33 | 85.982 |
| 79413 | 328.8 | 549.38 | 314.44 | 244.52 | 123.05 |
| 993 | 12.278 | 11.699 | 27.212 | 27.494 | 47.288 |
| 151230 | 58.921 | 60.413 | 79.842 | 48.502 | 36.977 |
| 29128 | 227.75 | 796.15 | 223.23 | 171.58 | 1438.7 |
| | 279.31 | 439.72 | 282.41 | 256.85 | 363.93 |
| 29089 | 255.28 | 393.67 | 100.27 | 84.534 | 842.79 |
| 3070 | 106.47 | 136.72 | 41.992 | 43.732 | 61.13 |
| 8438 | 30.037 | 23.372 | 35.105 | 31.035 | 17.64 |
| 3070 | 421.1 | 591.66 | 309.23 | 325.53 | 424.17 |
| 10563 | 16.105 | 190.19 | 60.868 | 41.46 | 23.525 |
| 79075 | 45.943 | 45.53 | 38.164 | 54.297 | 115.2 |
| 4049 | 305.93 | 19.847 | 22.388 | 21.473 | 14.365 |
| 10328 | 34.441 | 63.591 | 60.775 | 60.12 | 98.738 |
| 84824 | 1105.1 | 2016.2 | 1131.8 | 1993.1 | 118.29 |
| | 11410 | 6419.6 | 332.54 | 1278.4 | 329.1 |
| 3899 | 6992 | 4487.8 | 1347.4 | 2163 | 17.917 |
| 55024 | 3369.7 | 1609 | 4849.6 | 4389 | 269.4 |
| 931 | 12327 | 7914.7 | 12484 | 14351 | 330.25 |
| | 11615 | 7550.3 | 4127.6 | 4829.9 | 1153.1 |
| 931 | 14082 | 8618.6 | 14009 | 16289 | 294.53 |
| 199786 | 7850.1 | 4753.7 | 3450 | 6123.6 | 822.34 |
| 115350 | 3156.3 | 1094.1 | 1986.9 | 2423.5 | 875.88 |
| | 3593 | 3206.7 | 1259.2 | 1392.3 | 207.42 |
| 931 | 10792 | 5230.7 | 3721.6 | 4253.6 | 312.53 |
| 931 | 35052 | 20987 | 23579 | 26239 | 395.68 |
| 53335 | 14169 | 6339.9 | 3436.7 | 3985.5 | 528.8 |
| 26040 | 3083.3 | 786.02 | 716.76 | 599.74 | 526.88 |
| 53335 | 3364.6 | 1258.2 | 1038.8 | 1261.6 | 187.64 |
| | 47.628 | 32.218 | 45.183 | 41.792 | 1278.4 |
| | 45.987 | 36.33 | 21.507 | 51.597 | 827.93 |
| | 2888.9 | 2118.1 | 2838.8 | 3291.2 | 34965 |
| 3514 | 2671.2 | 1577.3 | 1877 | 2561.6 | 34431 |
| 857 | 45.911 | 78.45 | 119.82 | 124.39 | 1721.2 |
| | 1358.7 | 976.07 | 737.17 | 1560.2 | 21772 |
| 100379345 | 39.402 | 43.26 | 60.684 | 63.493 | 39.157 |
| 53637 | 11.045 | 13.645 | 18.64 | 16.741 | 10.684 |
| 53637 | 48.293 | 33.393 | 82.363 | 80.263 | 80.665 |
| 53637 | 319.18 | 33.136 | 75.413 | 64.085 | 83.253 |
| 9231 | 16.9 | 23.514 | 39.08 | 38.174 | 37.877 |
| 90102 | 522.21 | 174.05 | 345.23 | 277.7 | 248.14 |
| 79899 | 153.61 | 34.386 | 135.85 | 178.07 | 56.217 |
| 7049 | 131.58 | 96.953 | 183.11 | 213.56 | 161.31 |
| 1524 | 79.278 | 23.436 | 156.29 | 157.04 | 89.718 |
| 51348 | 240.92 | 38.515 | 203.31 | 195.7 | 100.14 |
| 5775 | 526.92 | 334.2 | 378.6 | 407.28 | 491.97 |
| 5775 | 221.9 | 158.53 | 250.08 | 392.4 | 343.3 |
| 7049 | 522.78 | 231.16 | 741.98 | 630.24 | 599.46 |
| 83888 | 230.64 | 175.08 | 88.643 | 54.91 | 54.863 |
| 114879 | 110.69 | 69.018 | 132.79 | 113.05 | 114.13 |
| 219285 | 2391.7 | 104.07 | 157.76 | 419.91 | 2176.5 |
| 54877 | 2185.9 | 1046.7 | 922.62 | 816.44 | 599.11 |
| 356 | 181.14 | 81.324 | 227.78 | 206.89 | 174.67 |
| 5920 | 278.5 | 127.62 | 432.41 | 367.02 | 1801.9 |
| 388228 | 279.65 | 196.79 | 279.46 | 191.22 | 270.74 |
| 219285 | 2386.9 | 353.87 | 846.09 | 942.06 | 2698.5 |
| 2219 | 339.72 | 113.46 | 134.87 | 123.98 | 180.89 |

TABLE 8A-continued

Table 8A Deconvolution basis signature
5654 Adaptive immune cell subsets

| | | | | | |
|---|---|---|---|---|---|
| 9332 | 74.272 | 44.964 | 221.24 | 226.95 | 210.04 |
| 23601 | 150.82 | 73.627 | 226.83 | 219.5 | 159.9 |
| 9332 | 53.077 | 31.555 | 174.52 | 279.05 | 140.63 |
| 51313 | 140.87 | 68.801 | 294.18 | 302.38 | 218.98 |
| 23166 | 94.68 | 113.24 | 128.71 | 106.57 | 64 |
| 10501 | 44.16 | 22.369 | 63.408 | 40.779 | 118.86 |
| 7045 | 101.04 | 43.168 | 62.25 | 132.31 | 102.34 |
| 8536 | 167.43 | 176.85 | 157.92 | 185.87 | 191.37 |
| 23166 | 219.39 | 144.43 | 301.11 | 260.52 | 81.386 |
| 206358 | 242.86 | 134.87 | 81.805 | 73.633 | 100.04 |
| 913 | 18.039 | 17.494 | 38.018 | 79.575 | 21.279 |
| 713 | 62.42 | 33.698 | 50.778 | 36.277 | 18.398 |
| 712 | 49.396 | 11.998 | 83.199 | 44.593 | 74.948 |
| 910 | 76.53 | 60.891 | 184.23 | 121.28 | 202.85 |
| 913 | 67.955 | 48.996 | 74.338 | 72.827 | 86.424 |
| 714 | 71.675 | 33.642 | 118.86 | 56.562 | 125.48 |
| 5480 | 27.873 | 72.802 | 76.562 | 100.23 | 28.991 |
| 945 | 20.375 | 14.645 | 37.029 | 35.662 | 17.374 |
| 909 | 330.27 | 283.03 | 765.57 | 729.57 | 334.33 |
| 2 | 61.413 | 70.048 | 110.28 | 217.55 | 116.79 |
| 6357 | 111.1 | 53.946 | 134.15 | 164.72 | 100.83 |
| 1193 | 27.378 | 16.056 | 17.633 | 17.894 | 9.958 |
| 5577 | 64.795 | 78.53 | 96.114 | 111.03 | 96.123 |
| 6614 | 14.555 | 17.02 | 27.273 | 27.555 | 13.05 |
| 80380 | 12.758 | 13.968 | 20.981 | 22.152 | 13.788 |
| 942 | 267.82 | 183.33 | 618.49 | 400.78 | 281.29 |
| 629 | 83.048 | 43.087 | 129.28 | 79.264 | 59.938 |
| 5055 | 96.217 | 41.219 | 113.71 | 115.17 | 71.027 |
| 55022 | 43.915 | 33.14 | 85.735 | 108.6 | 45.643 |
| 2921 | 18.063 | 38.137 | 56.646 | 50.331 | 87.434 |
| 6374 | 12.421 | 21.868 | 49.028 | 37.239 | 15.912 |
| 2919 | 94.808 | 78.084 | 156.84 | 130.59 | 91.55 |
| 3552 | 63.8 | 81.281 | 287.8 | 220.03 | 111.54 |
| 718 | 26.25 | 17.639 | 27.042 | 25.763 | 39.066 |
| 6369 | 49.296 | 26.492 | 25.721 | 26.113 | 19.318 |
| 3624 | 14.216 | 20.578 | 20.333 | 18.133 | 8.488 |
| 8875 | 189.21 | 167.27 | 287.16 | 314.52 | 168.83 |
| 1441 | 82.909 | 41.943 | 74.399 | 38.012 | 29.283 |
| 64407 | 151.54 | 93.752 | 264.46 | 229.04 | 186.15 |

TABLE 8B

Table 8B Deconvolution basis signature
Adaptive immune cell subsets

| ENTREZ ID | Symbol | NK | NK activated | Monocyte | Activated monocytes | mDC | mDC activated | Neutrophil |
|---|---|---|---|---|---|---|---|---|
| | | 234.22 | 193.38 | 60.43 | 94.563 | 44.379 | 42.333 | 528.59 |
| 83481 | EPPK1 | 22.594 | 25.374 | 15.907 | 23.304 | 17.794 | 14.671 | 49.81 |
| 678 | ZFP36L2 | 944.54 | 829.88 | 947.23 | 303.25 | 768 | 224.49 | 685.29 |
| | | 118.91 | 74.872 | 49.12 | 36.745 | 26.144 | 19.642 | 24.981 |
| 4929 | NR4A2 | 16.994 | 108.1 | 62.992 | 220.11 | 49.329 | 100.96 | 106.7 |
| | | 102.67 | 116.49 | 189.11 | 128.72 | 103 | 82.624 | 72.219 |
| 26289 | AK5 | 199.32 | 175.49 | 27.348 | 33.242 | 26.782 | 42.736 | 114.44 |
| 3707 | ITPKB | 2300 | 12.48 | 134.46 | 135.6 | 290.04 | 94.781 | 610.74 |
| | | 192.38 | 340.33 | 209.66 | 263.31 | 151.63 | 182.99 | 1779.9 |
| 9241 | NOG | 108.3 | 65.022 | 67.638 | 107.4 | 66.928 | 68.087 | 245.57 |
| 3337 | DNAJB1 | 913.3 | 898.93 | 1674.3 | 1546.3 | 1153.8 | 890.5 | 815.13 |
| 2935 | GSPT1 | 460.41 | 371.28 | 148.31 | 138.81 | 121.14 | 117.47 | 234.13 |
| | | 773.73 | 774.08 | 460.05 | 327.9 | 234.19 | 363.43 | 1545.7 |
| 4929 | NR4A2 | 167.22 | 211.2 | 153.38 | 325.82 | 153.57 | 127.94 | 217.77 |
| 90139 | TSPAN18 | 93.089 | 110.13 | 83.97 | 121.68 | 134.12 | 124.52 | 230.54 |
| 146330 | FBXL16 | 311.67 | 323.29 | 224.19 | 245.56 | 351.13 | 401.22 | 1170.8 |
| 678 | ZFP36L2 | 893.78 | 701.58 | 1109.2 | 276.4 | 869.58 | 278.41 | 706.3 |
| 112744 | IL17F | 132.08 | 57.788 | 66.779 | 62.439 | 48.914 | 67.21 | 192.07 |
| 3605 | IL17A | 6.173 | 21.649 | 12.938 | 15.326 | 13.615 | 19.02 | 18.389 |
| 1493 | CTLA4 | 280.2 | 272.35 | 127.25 | 202.8 | 219.86 | 213.03 | 546.89 |
| 1493 | CTLA4 | 105.53 | 117.46 | 74.196 | 74.198 | 166.69 | 144.29 | 185.74 |
| 940 | CD28 | 54.782 | 99.024 | 69.36 | 108.31 | 103.85 | 99.261 | 313.67 |
| 51339 | DACT1 | 56.953 | 114.38 | 164.18 | 108.19 | 238.82 | 129.36 | 226.99 |
| 50616 | IL22 | 130.08 | 140.77 | 160.41 | 208.94 | 195.76 | 176.95 | 458.47 |
| 143686 | SESN3 | 479.75 | 251.81 | 70.653 | 94.283 | 209.79 | 790.54 | 79.465 |
| 128553 | TSHZ2 | 169.31 | 130.05 | 81.735 | 121.52 | 97.362 | 109.71 | 253.85 |

TABLE 8B-continued

Table 8B Deconvolution basis signature
Adaptive immune cell subsets

| ENTREZ ID | Symbol | NK | NK activated | Monocyte | Activated monocytes | mDC | mDC activated | Neutrophil |
|---|---|---|---|---|---|---|---|---|
| 145864 | HAPLN3 | 563.5 | 2809.2 | 254.6 | 430.41 | 267.09 | 1769.6 | 644.6 |
| 30812 | SOX8 | 39.268 | 45.119 | 15.518 | 25.178 | 50.898 | 22.052 | 25.256 |
| 940 | CD28 | 65.611 | 35.191 | 29.141 | 49.231 | 19.951 | 27.802 | 37.221 |
| 1493 | CTLA4 | 124.66 | 116.43 | 92.171 | 92.422 | 121.75 | 109.83 | 501.04 |
| 10320 | IKZF1 | 571.49 | 213.94 | 254.88 | 233.08 | 271.55 | 439.89 | 210.19 |
| 29968 | PSAT1 | 199.65 | 207.83 | 202.32 | 287.5 | 581.74 | 510.86 | 477.33 |
| 3578 | IL9 | 95.923 | 63.72 | 52.85 | 60.811 | 68.764 | 52.046 | 88.46 |
| 128553 | TSHZ2 | 102.72 | 72.86 | 28.29 | 63.443 | 42.089 | 40.373 | 163.89 |
| 926 | CD8B | 66.688 | 29.283 | 42.361 | 57.728 | 46.062 | 30.886 | 58.733 |
| 54674 | LRRN3 | 46.41 | 34.332 | 99.24 | 152.85 | 121.16 | 87.014 | 107.64 |
| 925 | CD8A | 1747.3 | 1021.5 | 176.49 | 358.05 | 191.57 | 212.95 | 659.97 |
| 926 | CD8B | 239.29 | 169.83 | 138.51 | 232.77 | 128.76 | 116.27 | 422.64 |
| 54674 | LRRN3 | 111.6 | 105.81 | 175.1 | 267.95 | 204.2.3 | 201.49 | 495.58 |
| 51676 | ASB2 | 31.89 | 23.954 | 18.171 | 22.51 | 23.759 | 68.321 | 32.828 |
| 9666 | DZIP3 | 35.794 | 21.865 | 21.678 | 28.81 | 39.256 | 44.789 | 30.134 |
| 10730 | YME1L1 | 23.72 | 13.456 | 19.854 | 21.666 | 14.435 | 20.995 | 53.299 |
| 85315 | PAQR8 | 945.21 | 671.94 | 472.6 | 224.57 | 882.61 | 233.68 | 556.69 |
| 9402 | GRAP2 | 189.79 | 247.42 | 18.973 | 24.599 | 22.105 | 22.97 | 27.632 |
| 2833 | CXCR3 | 602.71 | 345.71 | 49.709 | 78.357 | 64.907 | 28.424 | 62.056 |
| 3820 | KLRB1 | 278.26 | 253.8 | 41.45 | 39.372 | 63.174 | 30.798 | 241.79 |
| 4676 | NAP1L4 | 1028.9 | 774.41 | 1198.6 | 1045.5 | 896.23 | 1096.3 | 451.85 |
| 1731 | 1-Sep | 1159.2 | 975.22 | 21.243 | 61.854 | 26.316 | 69.847 | 148.47 |
| 814 | CAMK4 | 139.73 | 101.14 | 25.46 | 75.621 | 50.817 | 142.6 | 204.37 |
| 57124 | CD248 | 213.8 | 213.93 | 317.03 | 255.8 | 371.85 | 289.84 | 453.31 |
|  |  | 49.748 | 27.014 | 31.759 | 55.044 | 32.022 | 36.939 | 217.53 |
| 283869 | NPW | 4.098 | 4.461 | 7.843 | 11.752 | 8.392 | 9.127 | 7.039 |
| 199953 | TMEM201 | 134.75 | 135.83 | 100.88 | 112.42 | 107.51 | 102.01 | 213.66 |
| 399694 | SHC4 | 21.764 | 31.468 | 18.077 | 29.599 | 26.114 | 25.334 | 60.573 |
| 3976 | LIF | 20.468 | 84.797 | 104.49 | 625.31 | 55.962 | 48.533 | 66.225 |
| 23176 | 8-Sep | 13.231 | 10.118 | 20.444 | 23.372 | 23.637 | 21.66 | 24.944 |
| 990 | CDC6 | 80.572 | 41.998 | 52.73 | 66.45 | 58.133 | 41.306 | 272.02 |
| 51010 | EXOSC3 | 499.31 | 691.75 | 285.35 | 269.96 | 183.8 | 226.82 | 93.13 |
| 1021 | CDK6 | 1248.6 | 830.99 | 475.77 | 235.09 | 1131.8 | 1444.6 | 318.97 |
| 51293 | CD320 | 113.03 | 29.97 | 59.036 | 145.06 | 75.737 | 63.493 | 39.181 |
| 1503 | CTPS1 | 223.21 | 303.98 | 430.55 | 239.9 | 573.47 | 332.52 | 293.59 |
| 84319 | CMSS1 | 427.68 | 588.48 | 366.89 | 183.34 | 348.61 | 236.71 | 368.07 |
| 10622 | POLR3G | 65.923 | 66.872 | 62.421 | 96.927 | 95.214 | 73.507 | 98.346 |
| 199953 | TMEM201 | 115.85 | 116.68 | 56.981 | 51.74 | 109.25 | 33.679 | 89.197 |
| 1021 | CDK6 | 830.37 | 552.98 | 397.79 | 296.18 | 766.85 | 720.85 | 518.97 |
| 1841 | DTYMK | 178.37 | 112.05 | 210.83 | 157.6 | 223.51 | 179.2 | 45.123 |
| 23464 | GCAT | 17.535 | 9.065 | 24.936 | 33.227 | 23.741 | 24.881 | 37.288 |
| 3336 | HSPE1 | 605.63 | 767.69 | 1753.7 | 1231 | 2327 | 1763.6 | 188.67 |
|  |  | 60.648 | 39.065 | 34.083 | 55.897 | 28.843 | 37.901 | 114.38 |
| 971 | CD72 | 140.01 | 70.636 | 86.43 | 25.64 | 98.175 | 38.692 | 20.212 |
| 933 | CD22 | 17.766 | 12.93 | 105.23 | 68.891 | 59.415 | 28.518 | 31.877 |
|  |  | 70.721 | 45.52 | 19.657 | 34.482 | 25.068 | 27.183 | 27.135 |
| 6328 | SCN3A | 9.035 | 16.917 | 20.771 | 16.759 | 15.008 | 14.52 | 30.192 |
| 84518 | CNFN | 13.975 | 11.258 | 14.451 | 23.411 | 16.705 | 19.943 | 27.996 |
| 8115 | TCL1A | 180.04 | 170.35 | 119.83 | 297.68 | 185.86 | 228.53 | 348.28 |
| 29802 | VPREB3 | 61.713 | 94.775 | 90.293 | 96.477 | 78.715 | 97.26 | 123.4 |
| 79856 | SNX22 | 44.03 | 51.925 | 27.59 | 49.441 | 36.764 | 35.319 | 111.72 |
| 115123 | 3-Mar | 39.875 | 54.774 | 28.204 | 37.371 | 32.484 | 30.718 | 88.844 |
| 8115 | TCL1A | 286.46 | 251.84 | 247 | 312.07 | 191.15 | 185.85 | 392.58 |
|  |  | 407.7 | 331.35 | 113.97 | 184.05 | 84.152 | 122.42 | 456.53 |
|  |  | 31.909 | 47.045 | 11.475 | 22.142 | 16.219 | 13.423 | 120.6 |
| 283663 | LINC00926 | 265.95 | 221.32 | 914.55 | 1401.3 | 239.32 | 423.65 | 219.41 |
| 283663 | LINC00926 | 476.24 | 428.56 | 669.75 | 1095.6 | 309.15 | 406.34 | 897.64 |
| 933 | CD22 | 243.9 | 251.42 | 697.13 | 618.3 | 649.58 | 454.74 | 714.06 |
| 55278 | QRSL1 | 354.9 | 363.68 | 464.82 | 337.89 | 791.38 | 630.87 | 176.49 |
| 94235 | GNG8 | 16.072 | 16.477 | 17.853 | 61.13 | 14.916 | 18.059 | 41.406 |
| 23089 | PEG10 | 54.027 | 25.162 | 34.173 | 64.445 | 37.859 | 21.48 | 90.119 |
| 7782 | SLC30A4 | 805.39 | 1089.5 | 85.611 | 279.09 | 740.4 | 422.82 | 497.14 |
|  |  | 122.51 | 111.59 | 513.67 | 723.39 | 598.57 | 235.17 | 29.861 |
|  |  | 91.025 | 91.24 | 45.43 | 58.428 | 42.262 | 45.095 | 185.27 |
| 148932 | MOB3C | 1533.5 | 3005.6 | 1422 | 1492.7 | 1051.1 | 937.14 | 980.55 |
| 80237 | ELL3 | 132.33 | 109.34 | 241.61 | 198.86 | 252.73 | 569.53 | 256.98 |
| 1184 | CLCN5 | 628.32 | 554.57 | 767.28 | 555.77 | 891.8 | 452.43 | 1058.2 |
| 653121 | ZBTB8A | 133.21 | 138.24 | 97.11 | 73.722 | 383.62 | 117.5 | 352.18 |
|  |  | 98.693 | 36.689 | 294.02 | 279.9 | 911.37 | 208.28 | 38.002 |
| 1184 | CLCN5 | 123.85 | 106.44 | 244.96 | 215.04 | 243.33 | 146.17 | 260.36 |
| 94274 | PPP1R14A | 11.632 | 11.142 | 9.568 | 26.704 | 96.818 | 610.68 | 22.289 |
| 80237 | ELL3 | 146.24 | 169.55 | 197.8 | 185.91 | 202.84 | 505.74 | 244.67 |
| 1490 | CTGF | 15.781 | 21.534 | 11.813 | 18.578 | 17.114 | 41.291 | 35.862 |
| 148932 | MOB3C | 829.5 | 1255.6 | 710.25 | 607.66 | 533.21 | 447.56 | 630.08 |

TABLE 8B-continued

Table 8B Deconvolution basis signature
Adaptive immune cell subsets

| ENTREZ ID | Symbol | NK | NK activated | Monocyte | Activated monocytes | mDC | mDC activated | Neutrophil |
|---|---|---|---|---|---|---|---|---|
| 140733 | MACROD2 | 79.989 | 66.195 | 42.426 | 76.844 | 58.566 | 40.426 | 140.71 |
| 116449 | CLNK | 144.92 | 97.92 | 42.783 | 47.617 | 43.627 | 37.469 | 164 |
| 51237 | MZB1 | 52.632 | 104.09 | 19.182 | 52.139 | 32.979 | 18.784 | 67.427 |
| 3514 | IGKC | 15.836 | 17.732 | 23.55 | 32.221 | 33.423 | 26.31 | 32.073 |
| 3537 | IGLC1 | 22.518 | 18.29 | 18.087 | 22.137 | 20.973 | 43.664 | 43.749 |
| | | 92.062 | 77.439 | 21.719 | 38.212 | 25.846 | 35.352 | 64.939 |
| 81618 | ITM2C | 542.99 | 323.12 | 33.527 | 83.342 | 50.067 | 43.392 | 129.57 |
| 51237 | MZB1 | 16.949 | 17.981 | 29.661 | 37.977 | 33.723 | 31.289 | 40.291 |
| 608 | TNFRSF17 | 25.957 | 9.114 | 21.037 | 21.426 | 26.508 | 35.455 | 32.888 |
| | | 146.08 | 117.63 | 154.76 | 164.45 | 135.49 | 142.59 | 353.57 |
| 96610 | BMS1P20 | 76.908 | 111.4 | 74.646 | 119.1 | 83.672 | 98.779 | 225.79 |
| | | 44.886 | 41.648 | 29.585 | 73.693 | 31.832 | 47.005 | 75.732 |
| 51303 | FKBP11 | 951.93 | 1748.7 | 153.69 | 225.52 | 152.68 | 102.36 | 170.24 |
| | | 28.589 | 30.469 | 25.767 | 36.928 | 23.977 | 25.044 | 43.659 |
| | | 14.155 | 11.369 | 21.694 | 31.114 | 22.223 | 19.143 | 23.746 |
| | | 43.581 | 136.18 | 116.63 | 117.3 | 107.23 | 160.4 | 243.01 |
| 79694 | MANEA | 85.751 | 124.28 | 111.99 | 82.277 | 196.15 | 182.86 | 5.879 |
| 28823 | 1GLV1-44 | 31.014 | 20.293 | 21.717 | 30.131 | 21.158 | 20.484 | 70.638 |
| 857 | CAV1 | 14.734 | 23.886 | 23.042 | 136.1 | 51.28 | 156.41 | 46.812 |
| 10316 | NMUR1 | 172.26 | 28.295 | 24.576 | 43.296 | 32.587 | 28.674 | 25.14 |
| 2043 | EPHA4 | 2761.4 | 735.14 | 25.869 | 40.016 | 27.074 | 27.474 | 82.083 |
| 10079 | ATP9A | 948.85 | 203.48 | 40.959 | 55.259 | 160.09 | 41.003 | 27.762 |
| 9289 | ADGRG1 | 5945.4 | 1929.6 | 50.639 | 140.34 | 46.329 | 72.247 | 180.88 |
| 2043 | EPHA4 | 1388.8 | 396.3 | 25.82 | 30.08 | 30.872 | 25.258 | 53.499 |
| 79901 | CYBRD1 | 121.89 | 7.789 | 21.734 | 21.921 | 33.831 | 21.927 | 19.441 |
| | | 535.44 | 147.87 | 18.017 | 23.31 | 13.838 | 26.439 | 28.242 |
| 151742 | PPM1L | 1220.4 | 304.67 | 157.85 | 96.387 | 413.32 | 116.43 | 274.48 |
| 81563 | C1orf21 | 2150.6 | 903.11 | 84.932 | 390.11 | 31.397 | 23.844 | 159.08 |
| 2619 | GAS1 | 178.7 | 35.304 | 17.643 | 34.257 | 42.159 | 26.652 | 44.204 |
| 59338 | PLEKHA1 | 7208.2 | 2925.4 | 617.2 | 652.31 | 909.71 | 1482.1 | 442.03 |
| 2043 | EPHA4 | 2364.5 | 967.61 | 145.92 | 239.82 | 138.98 | 172.69 | 440 |
| 4068 | SH2D1A | 1693 | 746.65 | 51.221 | 51.22 | 39.309 | 41.259 | 66.209 |
| 2043 | EPHA4 | 3974.9 | 1121.7 | 19.352 | 28.697 | 24.173 | 24.334 | 157.95 |
| 2774 | GNAL | 193.61 | 90.085 | 39.564 | 54.834 | 62.992 | 63.343 | 84.722 |
| 5243 | ABCB1 | 1488.5 | 773.91 | 78.088 | 55.655 | 48.71 | 46.583 | 298.63 |
| 11098 | PRSS23 | 2740.9 | 775.99 | 92.684 | 108.22 | 107.02 | 101.46 | 407.85 |
| 127254 | ERICH3 | 96.537 | 5221.1 | 20.035 | 16.235 | 31.973 | 19.899 | 76.112 |
| 57489 | ODF2L | 469.39 | 2852.3 | 29.954 | 88.016 | 51.95 | 64.323 | 111.68 |
| 57489 | ODF2L | 401.76 | 2054.4 | 33.763 | 61.725 | 39.819 | 107.49 | 86.458 |
| 257019 | FRMD3 | 284.1 | 1797.8 | 76.125 | 133.01 | 202.21 | 294.68 | |
| 10974 | ADIRF | 11.696 | 225.5 | 19.308 | 40.143 | 28.946 | 25.319 | 23.581 |
| 6672 | SP100 | 990.02 | 3884 | 572.42 | 755.13 | 276.02 | 661.01 | 630.04 |
| 64108 | RTP4 | 836.07 | 6115.6 | 346.26 | 438.55 | 577.13 | 1663.7 | 64.385 |
| 55603 | FAM46A | 750.31 | 2775.4 | 406.81 | 129.68 | 401.53 | 597.47 | 211.98 |
| 54809 | SAMD9 | 4316.6 | 19829 | 471.56 | 584.64 | 274.6 | 2650.4 | 1593.1 |
| 257019 | FRMD3 | 223.91 | 3689.8 | 94.875 | 77.308 | 140.16 | 266.24 | 748.24 |
| 91624 | NEXN | 115.11 | 2299.9 | 17.823 | 28.107 | 16.964 | 51.955 | 64.69 |
| | | 21.641 | 2082.2 | 39.556 | 27.231 | 22.498 | 96.451 | 70.775 |
| 85363 | TRIM5 | 431.34 | 1212.8 | 328.47 | 236.23 | 326.44 | 417.5 | 213.38 |
| 50650 | ARHGEF3 | 4649.5 | 10693 | 808.73 | 521.37 | 1982.5 | 1260 | 265.32 |
| 100131733 | USP30-AS1 | 430.83 | 2257.5 | 109.55 | 72.205 | 85.077 | 413.35 | 267.85 |
| | | 259.52 | 4757.8 | 25.85 | 56.1 | 24.379 | 190.18 | 128.97 |
| 2635 | GBP3 | 3614.4 | 9689.2 | 235.89 | 408.95 | 477.37 | 1973.1 | 442.26 |
| 5654 | HTRA1 | 182.02 | 100.41 | 4524.5 | 721.17 | 344.37 | 393.46 | 408.27 |
| 2048 | EPHB2 | 36.082 | 33.919 | 750 | 37.251 | 66.137 | 111.51 | 40.488 |
| 10461 | MERTK | 155.64 | 143.83 | 2057.5 | 444.14 | 347.38 | 196.23 | 221.36 |
| 4048 | LTA4H | 2278 | 832.7 | 21704 | 2697.3 | 4330.1 | 1290.8 | 1902.3 |
| 2048 | EPHB2 | 54.592 | 51.961 | 1348.1 | 30.996 | 332.32 | 326.9 | 110.81 |
| 10461 | MERTK | 126.88 | 50.745 | 3131.1 | 768.85 | 422.35 | 132.67 | 247.23 |
| 340526 | RGAG4 | 112.3 | 123.43 | 933.54 | 233.76 | 297.81 | 126.5 | 147.74 |
| 284013 | VMO1 | 362.26 | 11.41 | 2665.1 | 396.29 | 97.002 | 261.12 | 21.038 |
| 120939 | TMEM52B | 72.249 | 101.61 | 821.29 | 191.39 | 106.19 | 115.88 | 143.71 |
| 408 | ARRB1 | 144 | 87.986 | 591.46 | 169.9 | 179.32 | 77.117 | 79.13 |
| 2048 | EPHB2 | 117.7 | 98.776 | 1139.8 | 190.47 | 393.61 | 362.3 | 378.24 |
| 2517 | FUCA1 | 2269 | 1457.2 | 23621 | 1428.6 | 7804.2 | 2832.3 | 348.69 |
| | | 149.94 | 79.806 | 2508.8 | 1320.1 | 1363.3 | 601.22 | 135.64 |
| 2335 | FN1 | 366.11 | 53.143 | 16242 | 58.443 | 2883.5 | 2906 | 165.13 |
| 11326 | VSIG4 | 205.15 | 68.283 | 3604.2 | 370.12 | 157.55 | 209.64 | 455.5 |
| 2335 | FN1 | 698.9 | 104.41 | 19697 | 64.194 | 4322.9 | 4511 | 73.793 |
| 51063 | CALHM2 | 874.44 | 374.83 | 2336.4 | 451.57 | 899.63 | 218.93 | 379.34 |
| 55244 | SLC47A1 | 18.268 | 31.408 | 34.706 | 31.818 | 1294.5 | 62.187 | 37.893 |
| 2162 | F13A1 | 199.86 | 162.12 | 301.41 | 267.62 | 9213.4 | 463.63 | 663.21 |
| 10462 | CLEC10A | 242.18 | 51.339 | 666.23 | 247.07 | 10346 | 234.87 | 219.09 |
| 246 | ALOX15 | 27.642 | 27.956 | 26.953 | 29.212 | 4539.9 | 72.346 | 182.96 |

TABLE 8B-continued

Table 8B Deconvolution basis signature
Adaptive immune cell subsets

| ENTREZ ID | Symbol | NK | NK activated | Monocyte | Activated monocytes | mDC | mDC activated | Neutrophil |
|---|---|---|---|---|---|---|---|---|
| 23475 | QPRT | 27.911 | 18.443 | 39.471 | 38.229 | 3854.3 | 108.41 | 77.585 |
| 154092 | LINC01010 | 23.433 | 33.679 | 57.564 | 49.195 | 1113.4 | 122.32 | 43.176 |
| 23017 | FAIM2 | 18.124 | 15.246 | 38.708 | 44.951 | 1986 | 47.632 | 35.496 |
| 79839 | CCDC102B | 16.601 | 9.295 | 16.732 | 22.858 | 224.25 | 24.244 | 10.698 |
| 5445 | PON2 | 434.92 | 340.34 | 276.18 | 103.43 | 5310.8 | 766.1 | 141.11 |
| 30835 | CD209 | 118.57 | 188.32 | 365.69 | 835.46 | 7460.1 | 742.95 | 370.95 |
| 51477 | ISYNA1 | 172.47 | 121.04 | 178.53 | 181.87 | 2664.7 | 426.65 | 120.38 |
| 30835 | CD209 | 40.149 | 53.679 | 90.689 | 154.74 | 1321.4 | 166.3 | 140.49 |
| 2878 | GPX3 | 289.86 | 166.4 | 2820.8 | 773.89 | 17689 | 2021.5 | 666.64 |
| 2878 | GPX3 | 290.97 | 235.63 | 1813.8 | 724.23 | 10819 | 1542.4 | 612.69 |
| 5445 | PON2 | 188.76 | 161.04 | 168.75 | 41.48 | 3833.2 | 579.46 | 69.345 |
| 56670 | SUCNR1 | 166.02 | 133.08 | 158.29 | 517.6 | 4885.7 | 822.66 | 343.58 |
| 30850 | CDR2L | 15.938 | 20.626 | 54.75 | 40.053 | 904.74 | 77.118 | 39.601 |
| 11067 | C10orf10 | 24.176 | 45.143 | 33.926 | 63.693 | 95.817 | 2692.8 | 36.858 |
| 6624 | FSCN1 | 81.53 | 523.84 | 136.01 | 184.31 | 670.32 | 17366 | 98.237 |
| 54662 | TBC1D13 | 98.944 | 262.08 | 96.11 | 188.52 | 289.66 | 5087.5 | 56.742 |
| 101930114 | LOC101930114 | 150.12 | 378.01 | 86.24 | 121.02 | 294.11 | 15782 | 284.28 |
| 5157 | PDGFRL | 28.375 | 53.462 | 47.721 | 49.514 | 53.746 | 1387.7 | 20.595 |
| 3429 | IFI27 | 134.04 | 1488.9 | 210.18 | 325.75 | 138.05 | 17765 | 151.87 |
|  |  | 74.727 | 153.21 | 53.552 | 33.817 | 95.649 | 8820.3 | 107.24 |
| 80045 | GPR157 | 990.63 | 1117.5 | 941.2 | 500.12 | 390.29 | 9736.3 | 730.17 |
| 80380 | PDCD1LG2 | 21.387 | 27.365 | 24.291 | 29.793 | 122.17 | 1974.3 | 53.788 |
| 11067 | C10orf10 | 76.594 | 37.144 | 76.86 | 55.657 | 65.272 | 1186.5 | 89.081 |
| 8820 | HESX1 | 13.973 | 59.359 | 33.421 | 25.657 | 40.231 | 1691.5 | 22.801 |
| 6624 | FSCN1 | 126.4 | 620.29 | 171.77 | 344.98 | 1454.9 | 16899 | 52.809 |
| 11167 | FSTL1 | 93.606 | 105.83 | 192.63 | 274.55 | 188.9 | 4875.7 | 381.91 |
| 54662 | TBC1D13 | 582 | 689.43 | 770.72 | 899.75 | 1147.7 | 7639.7 | 681.05 |
| 9175 | MAP3K13 | 9.844 | 6.678 | 11.997 | 17.73 | 14.728 | 173.95 | 11.757 |
| 3357 | HTR2B | 44.103 | 23.668 | 20.289 | 20.805 | 23.311 | 815.72 | 23.146 |
| 94015 | TTYH2 | 403.48 | 548.11 | 194.02 | 123.57 | 283.43 | 7052.4 | 203.15 |
| 56300 | IL36G | 75.673 | 95.566 | 193.5 | 13364 | 96.662 | 140.58 | 158.08 |
| 3036 | HAS1 | 52.122 | 23.743 | 85.531 | 6520.7 | 125.32 | 73.135 | 144.91 |
| 7980 | TFPI2 | 14.302 | 264.75 | 228.32 | 10802 | 22.39 | 274.11 | 37.116 |
| 11009 | IL24 | 89.089 | 27.311 | 98.807 | 7265 | 37.723 | 43.914 | 230.31 |
| 4312 | MMP1 | 14.214 | 3.569 | 15.962 | 2464.7 | 22.158 | 26.477 | 38.896 |
| 7980 | TFPI2 | 31.933 | 59.772 | 146.36 | 3886.6 | 28.623 | 142.85 | 22.053 |
| 1440 | CSF3 | 47.925 | 24.496 | 27.293 | 2163.5 | 30.881 | 31.705 | 36.188 |
| 3569 | IL6 | 97.655 | 1336.6 | 1632.4 | 34971 | 204.43 | 2510.5 | 240.88 |
| 4233 | MET | 15.715 | 16.009 | 360.15 | 4883.1 | 27.917 | 148.52 | 23.036 |
| 169792 | GLIS3 | 13.486 | 37.029 | 185.27 | 1833 | 46.519 | 15.028 | 127.91 |
| 51334 | PRR16 | 19.619 | 10.144 | 72.589 | 812.71 | 19.002 | 17.112 | 43.945 |
| 6374 | CXCL5 | 9.621 | 15.056 | 175.25 | 1677.9 | 40.346 | 43.681 | 99.159 |
| 6660 | SOX5 | 9.393 | 10.435 | 26.932 | 296.21 | 30.578 | 32.724 | 14.187 |
| 79931 | TNIP3 | 13.75 | 34.176 | 660.08 | 8318.5 | 49.416 | 180.07 | 35.132 |
| 8710 | SERPINB7 | 26.193 | 269.05 | 48.317 | 8770.5 | 32.96 | 803.26 | 45.827 |
| 3690 | ITGB3 | 82.961 | 102.15 | 50.385 | 2003.3 | 53.605 | 172.65 | 112.65 |
| 5743 | PTGS2 | 22.052 | 57.425 | 434.21 | 23846 | 79.633 | 293.33 | 2414 |
| 8794 | TNFRSF10C | 23.394 | 13.984 | 40.419 | 75.161 | 46.084 | 27.389 | 7494 |
| 53829 | P2RY13 | 15.617 | 12.05 | 22.463 | 29.8 | 106.12 | 24.156 | 7096 |
| 4311 | MME | 45.207 | 25.599 | 56.171 | 108.62 | 66.398 | 51.768 | 5834.4 |
| 146225 | CMTM2 | 260.95 | 291.93 | 161.55 | 189.59 | 204.06 | 184.9 | 41610 |
| 8794 | TNFRSF10C | 95.751 | 43.935 | 27.844 | 33.083 | 31.309 | 39.868 | 11321 |
| 8794 | TNFRSF10C | 69.516 | 66.842 | 124.52 | 98.004 | 132 | 127.39 | 7001.1 |
| 6286 | S100P | 35.679 | 40.597 | 196.07 | 287.74 | 71.192 | 50.918 | 21441 |
| 3577 | CXCR1 | 150.19 | 36.452 | 38.777 | 47.861 | 34.59 | 34.741 | 6702.9 |
| 60675 | PROK2 | 27.394 | 7.688 | 94.419 | 58.926 | 11.755 | 29.657 | 13698 |
| 54682 | MANSC1 | 32.466 | 53.104 | 75.79 | 54.837 | 60.247 | 61.276 | 2613.4 |
| 144423 | GLT1D1 | 97.688 | 90.763 | 406.39 | 290.12 | 29.735 | 19.451 | 12243 |
| 3579 | CXCR2 | 392.19 | 100.84 | 111.39 | 20.749 | 453.51 | 83.791 | 12028 |
| 25984 | KRT23 | 36.835 | 49.514 | 68.24 | 67.635 | 90.373 | 68.849 | 3796.8 |
| 2215 | FCGR3B | 901.02 | 693.72 | 1388 | 330.29 | 466.68 | 231.55 | 32749 |
| 4311 | MME | 18.525 | 13.907 | 21.308 | 93.096 | 27.296 | 25.716 | 2580 |
| 79908 | BTNL8 | 19.269 | 15.886 | 38.278 | 55.531 | 50.442 | 42.432 | 1195.4 |
|  |  | 56.534 | 90.265 | 162.63 | 125.69 | 139.7 | 144.21 | 2915.3 |
|  |  | 43.711 | 36.304 | 28.181 | 36.962 | 26.687 | 31.636 | 101.33 |
| 80201 | HKDC1 | 26.961 | 45.619 | 23.442 | 29.542 | 32.629 | 24.274 | 58.015 |
|  |  | 10.559 | 20.107 | 16.677 | 28.563 | 25.355 | 25.463 | 33.51 |
| 3572 | IL6ST | 18.648 | 75.83 | 17.295 | 19.91 | 12.723 | 20.567 | 66.204 |
| 6711 | SPTBN1 | 40.456 | 30.066 | 29.822 | 33.681 | 25.029 | 28.475 | 88.178 |
| 6920 | TCEA3 | 116.74 | 24.173 | 42.689 | 80.724 | 58.11 | 61.04 | 198.9 |
|  |  | 125.04 | 63.024 | 38.942 | 29.201 | 84.617 | 132.45 | 136.94 |
| 26119 | LDLRAP1 | 512.32 | 232.72 | 316.47 | 283.63 | 570.71 | 174.09 | 140.7 |
|  |  | 1183.6 | 722.03 | 174.49 | 97.182 | 94.599 | 65.5 | 229.94 |
| 3562 | IL3 | 9.531 | 7.443 | 16.465 | 22.998 | 20.151 | 21.977 | 18.31 |

TABLE 8B-continued

Table 8B Deconvolution basis signature
Adaptive immune cell subsets

| ENTREZ ID | Symbol | NK | NK activated | Monocyte | Activated monocytes | mDC | mDC activated | Neutrophil |
|---|---|---|---|---|---|---|---|---|
| 50616 | IL22 | 86.691 | 40.447 | 29.994 | 57.904 | 25.763 | 21.935 | 91.888 |
| 64788 | LMF1 | 146.1 | 153.11 | 42.787 | 41.659 | 142.33 | 46.938 | 114.22 |
|  |  | 149.76 | 123.63 | 72.559 | 162.63 | 116.99 | 71.606 | 208.72 |
| 959 | CD40LG | 40.464 | 49.649 | 34.919 | 30.912 | 38.454 | 28.851 | 88.189 |
| 50943 | FOXP3 | 127.15 | 81.559 | 32.344 | 77.866 | 46.594 | 46.038 | 122.99 |
| 54602 | NDFIP2 | 370.94 | 370.3 | 183.16 | 259.95 | 348.39 | 267.85 | 711.33 |
| 1493 | CTLA4 | 9.094 | 48.237 | 37.288 | 50.691 | 101.61 | 64.781 | 132.91 |
| 55423 | SIRPG | 105.48 | 80.092 | 107.77 | 138.53 | 127.52 | 151.82 | 220.38 |
| 917 | CD3G | 477.55 | 288.48 | 44.127 | 84.826 | 45.794 | 46.494 | 83.39 |
| 10663 | CXCR6 | 406.47 | 375.57 | 152.71 | 177.96 | 163.36 | 154.32 | 292.65 |
| 3090 | HIC1 | 190.21 | 119.43 | 47.963 | 42.613 | 46.522 | 177.53 | 73.215 |
| 27240 | SIT1 | 199.48 | 132.05 | 101.21 | 123.34 | 407.85 | 119.45 | 174.4 |
| 51676 | ASB2 | 274.66 | 272.28 | 135.17 | 143.8 | 94.268 | 172.17 | 376.9 |
| 91978 | TPGS1 | 53.805 | 54.227 | 136.66 | 121.66 | 142.86 | 168.85 | 43.394 |
| 28755 | TRAC | 786.27 | 699.43 | 305.97 | 565.94 | 236.82 | 296.6 | 844.63 |
| 3932 | LCK | 2360.8 | 993.94 | 268.64 | 389.46 | 154.42 | 148.7 | 415.79 |
| 79413 | ZBED2 | 130.91 | 87.84 | 77.241 | 139.93 | 117.45 | 87.879 | 257.46 |
| 993 | CDC25A | 12.808 | 8.661 | 21.27 | 35.54 | 28.316 | 18.804 | 23.371 |
| 151230 | KLHL23 | 86.999 | 91.376 | 27.185 | 36.326 | 19.515 | 22.162 | 51.824 |
| 29128 | UHRF1 | 184.73 | 95.148 | 68.223 | 51.556 | 36.754 | 33.832 | 223.99 |
|  |  | 137.58 | 95.521 | 32.602 | 48.19 | 34.163 | 57.902 | 99.755 |
| 29089 | UBE2T | 137.04 | 110.9 | 41.216 | 64.275 | 62.825 | 50.933 | 53.295 |
| 3070 | HELLS | 6.926 | 6.673 | 16.983 | 29.67 | 25.008 | 24.039 | 28.993 |
| 8438 | RAD54L | 55.063 | 35.177 | 56.263 | 47.656 | 48.391 | 46.296 | 57.866 |
| 3070 | HELLS | 176.76 | 154 | 34.591 | 65.708 | 34.752 | 50.621 | 298.73 |
| 10563 | CXCL13 | 28.792 | 94.868 | 25.984 | 158.1 | 27.05 | 242.1 | 41.323 |
| 79075 | DSCC1 | 61.206 | 23.793 | 101.91 | 136.67 | 98.441 | 95.428 | 61.939 |
| 4049 | LTA | 18.138 | 118.74 | 20.557 | 29.577 | 27.044 | 28.376 | 32.132 |
| 10328 | EMC8 | 29.093 | 23.251 | 36.363 | 39.324 | 34.294 | 22.123 | 37.046 |
| 84824 | FCRLA | 45.306 | 35.399 | 33.046 | 52.991 | 28.414 | 16.273 | 85.514 |
|  |  | 45.323 | 42.148 | 14.306 | 59.328 | 16.55 | 23.564 | 65.166 |
| 3899 | AFF3 | 278.65 | 183.3 | 30.892 | 227.31 | 28.426 | 22.836 | 36.823 |
| 55024 | BANK1 | 87.887 | 93.53 | 35.155 | 98.414 | 81.002 | 42.046 | 96.465 |
| 931 | MS4A1 | 161.02 | 229.51 | 115.45 | 406.1 | 130.5 | 190.71 | 468.78 |
|  |  | 188.29 | 83.886 | 44.602 | 109.46 | 38.954 | 42.475 | 172.67 |
| 931 | MS4A1 | 225.68 | 328.16 | 265.38 | 525.55 | 198.48 | 283.11 | 571.83 |
| 199786 | FAM129C | 702.73 | 706.12 | 256.69 | 301.58 | 217.31 | 334.95 | 1098.2 |
| 115350 | FCRL1 | 108.17 | 132.07 | 64.362 | 69.389 | 74.8 | 93.924 | 289.88 |
|  |  | 191.43 | 156.86 | 97.122 | 121.18 | 138.05 | 110.89 | 567.87 |
| 931 | MS4A1 | 80.829 | 114.15 | 101.59 | 113.37 | 101.97 | 103.15 | 253.83 |
| 931 | MS4A1 | 326.13 | 440.54 | 128.31 | 417.2 | 81.803 | 158.62 | 326.6 |
| 53335 | BCL11A | 278.77 | 344.03 | 188.3 | 1126.3 | 142.9 | 935.66 | 524.55 |
| 26040 | SETBP1 | 182.44 | 205.55 | 75.283 | 105.32 | 347.1 | 146.98 | 127.52 |
| 53335 | BCL11A | 51.388 | 86.743 | 146.78 | 603.73 | 84.55 | 594.52 | 212.77 |
|  |  | 6.244 | 13.577 | 15.288 | 17.852 | 17.773 | 16.565 | 14.048 |
|  |  | 8.998 | 9.784 | 20.519 | 27.983 | 23.596 | 15.285 | 39.095 |
|  |  | 22.09 | 30.102 | 44.255 | 58.244 | 47.213 | 46.657 | 53.954 |
| 3514 | IGKC | 25.025 | 27.54 | 26.512 | 58.57 | 29.03 | 25.412 | 43.521 |
| 857 | CAV1 | 32.745 | 47.461 | 43.329 | 83.562 | 51.181 | 114.21 | 120.86 |
|  |  | 156.03 | 222.68 | 145.78 | 228.12 | 167.6 | 153.98 | 378.45 |
| 100379345 | MIR181A2HG | 1357.6 | 1006 | 18.416 | 25.441 | 20.915 | 20.658 | 43.551 |
| 53637 | S1PR5 | 636.77 | 472.14 | 16.048 | 20.791 | 17.434 | 18.811 | 19.978 |
| 53637 | S1PR5 | 1050.1 | 856.24 | 18.334 | 27.73 | 21.672 | 26.124 | 41.053 |
| 53637 | S1PR5 | 10394 | 9089.6 | 32.645 | 56.232 | 50.011 | 38.707 | 78.204 |
| 9231 | DLG5 | 593.45 | 203.75 | 22.159 | 47.671 | 29.067 | 22.446 | 35.15 |
| 90102 | PHLDB2 | 3883.5 | 2824.8 | 57.803 | 75.66 | 44.914 | 112.46 | 259.01 |
| 79899 | PRR5L | 1486.1 | 742.55 | 54.253 | 57.897 | 48.31 | 112.77 | 211.31 |
| 7049 | TGFBR3 | 4462.7 | 3660.1 | 148.41 | 166.84 | 82.078 | 112.41 | 324.45 |
| 1524 | CX3CR1 | 11626 | 7080.3 | 846.43 | 55.954 | 46.831 | 65.088 | 703.38 |
| 51348 | KLRF1 | 7620.2 | 5981.3 | 75.985 | 74.24 | 100.25 | 97.755 | 204.09 |
| 5775 | PTPN4 | 6757.7 | 6224.2 | 130.69 | 179.31 | 485.75 | 147.81 | 541.49 |
| 5775 | PTPN4 | 3242.9 | 2902.9 | 90.022 | 88.882 | 109.14 | 78.403 | 328.46 |
| 7049 | TGFBR3 | 14704 | 12273 | 167.22 | 280.79 | 134 | 140.35 | 1264.7 |
| 83888 | FGFBP2 | 37240 | 11588 | 30.563 | 76.403 | 31.688 | 27.257 | 521.22 |
| 114879 | OSBPL5 | 2031.1 | 2266.5 | 101.74 | 59.833 | 139.28 | 77.974 | 127.23 |
| 219285 | SAMD9L | 2468.3 | 25077 | 389.99 | 535.76 | 573.04 | 4217.1 | 849.73 |
| 54877 | ZCCHC2 | 2777.4 | 13364 | 2181.8 | 2110.6 | 3070.1 | 2447.8 | 1979.3 |
| 356 | FASLG | 1767.8 | 4539.7 | 170.68 | 255.05 | 115.16 | 146.5 | 379.82 |
| 5920 | RARRES3 | 7967.4 | 15536 | 142.96 | 272 | 114.99 | 681.38 | 388.82 |
| 388228 | SBK1 | 1362.5 | 3717.5 | 45.33 | 75.229 | 66.294 | 84.376 | 443.53 |
| 219285 | SAMD9L | 2070.9 | 15246 | 608.57 | 541.2 | 934.09 | 3897.5 | 1137.3 |
| 2219 | FCN1 | 671.24 | 314.21 | 12909 | 835.39 | 177.32 | 267.64 | 5507.7 |
| 9332 | CD163 | 263.89 | 77.313 | 9682.4 | 8620.1 | 827.99 | 239.35 | 265.16 |
| 23601 | CLEC5A | 1117.4 | 316.18 | 19857 | 11344 | 2299.7 | 896.82 | 347.84 |

TABLE 8B-continued

Table 8B Deconvolution basis signature
Adaptive immune cell subsets

| ENTREZ ID | Symbol | NK | NK activated | Monocyte | Activated monocytes | mDC | mDC activated | Neutrophil |
|---|---|---|---|---|---|---|---|---|
| 9332 | CD163 | 241.85 | 36.597 | 8883.9 | 7051.5 | 908.66 | 212.78 | 175.95 |
| 51313 | FAM198B | 437.88 | 202.42 | 4948.7 | 822.28 | 4023.9 | 569.82 | 309.26 |
| 23166 | STAB1 | 600.3 | 293.96 | 10839 | 1936.2 | 8595.5 | 1317.1 | 174.1 |
| 10501 | SEMA6B | 107.53 | 73.612 | 1094.7 | 910.27 | 52.127 | 143.82 | 30.585 |
| 7045 | TGFBI | 3343 | 793.16 | 31162 | 3217 | 25407 | 5132.9 | 103.22 |
| 8536 | CAMK1 | 336.18 | 168.74 | 4099.8 | 349.29 | 3162 | 432.58 | 573.02 |
| 23166 | STAB1 | 705.38 | 383.12 | 13007 | 3057.7 | 9961.8 | 2083.4 | 329.11 |
| 206358 | SLC36A1 | 249.87 | 161.79 | 2534.6 | 715.27 | 1603.8 | 653.16 | 330.92 |
| 913 | CD1E | 40.886 | 10.775 | 97.286 | 121.26 | 16075 | 5709.7 | 69.112 |
| 713 | C1QB | 77.011 | 102.19 | 182.48 | 146.48 | 10592 | 7856.7 | 41.177 |
| 712 | C1QA | 50.142 | 86.203 | 184.27 | 108.09 | 7282.4 | 2928.5 | 76.151 |
| 910 | CD1B | 106.28 | 55.634 | 90.609 | 383.87 | 17114 | 4264.6 | 170.68 |
| 913 | CD1E | 115.69 | 80.099 | 81.505 | 94.16 | 6752.7 | 1417.6 | 118.17 |
| 714 | C1QC | 139.21 | 130.21 | 495.99 | 88.076 | 12507 | 11043 | 156.99 |
| 5480 | PPIC | 26.824 | 12.981 | 32.336 | 55.873 | 707.73 | 310.34 | 39.174 |
| 945 | CD33 | 19.578 | 19.477 | 679.76 | 121.04 | 1593.4 | 133.38 | 60.619 |
| 909 | CD1A | 236.08 | 255.17 | 374.32 | 400.57 | 17758 | 3408.6 | 715.59 |
| 2 | A2M | 212.65 | 114.82 | 533.47 | 194.51 | 14937 | 15010 | 110.11 |
| 6357 | CCL13 | 157.64 | 289.58 | 242.42 | 455.08 | 6434.5 | 11487 | 174.82 |
| 1193 | CLIC2 | 115.54 | 209.36 | 190.72 | 234.49 | 3590.7 | 8375.9 | 22.283 |
| 5577 | PRKAR2B | 108.68 | 84.149 | 166.4 | 144.73 | 669.88 | 3171.9 | 167.26 |
| 6614 | SIGLEC1 | 29.371 | 89.235 | 275.86 | 294.87 | 710.24 | 6005.1 | 49.332 |
| 80380 | PDCD1LG2 | 33.651 | 23.536 | 50.538 | 60.569 | 174.05 | 1520.5 | 26.35 |
| 942 | CD86 | 137.07 | 318.48 | 630.29 | 242.14 | 2070.3 | 8560 | 203.25 |
| 629 | CFB | 110.84 | 127.86 | 139.77 | 1128.5 | 252.42 | 4969.9 | 187.81 |
| 5055 | SERPINB2 | 83.1 | 95.581 | 4287.5 | 24461 | 98.613 | 352.89 | 181.87 |
| 55022 | PID1 | 154.69 | 54.538 | 7487.2 | 11205 | 34.221 | 105.68 | 78.269 |
| 2921 | CXCL3 | 63.616 | 22.828 | 3914.7 | 27356 | 131.59 | 522.63 | 73.882 |
| 6374 | CXCL5 | 20.307 | 12.939 | 4063.1 | 33167 | 20.269 | 445.88 | 102.86 |
| 2919 | CXCL1 | 86.887 | 118.64 | 6214.2 | 35585 | 100.46 | 1191.3 | 1368.5 |
| 3552 | IL1A | 112.61 | 77.232 | 2599.8 | 22595 | 213.69 | 660.82 | 323.06 |
| 718 | C3 | 62.908 | 45.944 | 5647.8 | 8096.8 | 246.51 | 282.92 | 49.628 |
| 6369 | CCL24 | 235.72 | 198.21 | 9587.6 | 13839 | 113.99 | 365.61 | 68.75 |
| 3624 | INHBA | 20.287 | 104.69 | 536.09 | 11449 | 171.22 | 4927.5 | 19.921 |
| 8875 | VNN2 | 499.61 | 320.66 | 223.25 | 4735.8 | 44.71 | 72.248 | 19069 |
| 1441 | CSF3R | 24.289 | 44.759 | 819.72 | 100.75 | 190.43 | 109.83 | 10132 |
| 64407 | RGS18 | 315.04 | 200.03 | 374.78 | 94.765 | 1421.8 | 103.53 | 10444 |

Tables 8A-B describe the data of the deconvolution basis signature matrix from (26) that was used by the present inventors to estimate immune cell subset proportions in all discovery cohorts. The present inventors used the version provided by the CellMix package (35). Rows are Affymetrix HG-U133plusV2 probesets, with the first 4 columns providing the probeset ID and the corresponding ENTREZ gene ID, gene symbol and description (if available), as mapped using Bioconductor annotation package hgu133plus2.db. The remaining 17 columns contain the reference expression profiles for each cell subset, which are detailed in Table 10 herein below.

Table 9 herein below, describes the results of the meta-analysis performed on the 3 discovery cohorts. Each row contains the results of testing differences in the proportions of a given cell type in a given cohort between responders and non-responders to the treatment with the Infliximab TNF-alpha inhibitor. The quantity tested was the log 2 fold change log 2 (Responder/Non-responder). The columns provide the following information:

Cohort: cohort ID; Cell type: cell type name; Cl. low: lower bound of the 95% confidence interval of the estimated proportion difference; Cl. up: upper bound of the 95% confidence interval of the estimated proportion difference; estimate: estimated (pseudo-)median proportion difference; p. value: nominal p-value for Wilcoxon rank sum test; Fstat: Fisher combined probability statistic; Fpvalue: nominal p-value for Fisher combined probability test; Ffdr: false discovery rate obtained by adjusting Fpvalue with Benjamini and Hochberg procedure; Significance: significance flag for the nominal Wilcoxon p-values as used in FIG. 4.

TABLE 9

Table 9.

| Cohort | Cell type | Cl. low | Cl. up | estimate | p. value | Fstat | Fpvalue | Ffdr | Significance |
|---|---|---|---|---|---|---|---|---|---|
| GSE16879 | PC | -2.008935664 | -0.334124253 | -0.802445899 | 0.005239343 | 18.70073489 | 0.000899793 | 0.004349001 | ≤0.05 |
| GSE16879 | mono act | -1.921136072 | -0.555524195 | -1.138916477 | 0.005907491 | 25.07777803 | 4.85303E-05 | 0.000469126 | ≤0.05 |
| GSE12251 | mono act | -1.40090001 | -0.146123505 | -0.801394223 | 0.015871126 | 25.07777803 | 4.85303E-05 | 0.000469126 | ≤0.05 |
| GSE12251 | mono | 0.083431836 | 0.834009379 | 0.387433072 | 0.020580039 | 11.72217689 | 0.019541354 | 0.047224938 | ≤0.05 |
| GSE14580 | PC | -1.711129042 | -0.110985781 | -0.969678819 | 0.022970314 | 18.70073489 | 0.000899793 | 0.004349001 | ≤0.05 |
| GSE14580 | DC act | 0.070788646 | 0.848562982 | 0.428528154 | 0.022970314 | 13.38778995 | 0.009528501 | 0.030702949 | ≤0.05 |
| GSE14580 | Mem IgM | -4.410775103 | -0.443741036 | -1.876461659 | 0.024455936 | 8.217074503 | 0.083942424 | 0.115920491 | ≤0.05 |

TABLE 9-continued

Table 9.

| Cohort | Cell type | CI. low | CI. up | estimate | p. value | Fstat | Fpvalue | Ffdr | Significance |
|---|---|---|---|---|---|---|---|---|---|
| GSE14580 | NK act | 0.158764344 | 1.114754472 | 0.614506832 | 0.029177221 | 7.643379983 | 0.105550528 | 0.133085448 | ≤0.05 |
| GSE14580 | Tc | 0.022416538 | 2.518080552 | 0.891074973 | 0.036817534 | 9.070169168 | 0.059369317 | 0.114780679 | ≤0.05 |
| GSE14580 | mono act | −1.562598302 | −0.071899857 | −0.685699358 | 0.038231283 | 25.07777803 | 4.85303E-05 | 0.000469126 | ≤0.05 |
| GSE12251 | neutro | −1.006490965 | −0.005595542 | −0.409687906 | 0.042570433 | 8.368643695 | 0.078970351 | 0.115920491 | ≤0.05 |
| GSE14580 | Tc act | −0.049689147 | 2.400520526 | 1.304423587 | 0.079325765 | 6.093702195 | 0.192258968 | 0.223020403 | NS |
| GSE12251 | DC act | −0.150356751 | 0.693861677 | 0.242245285 | 0.140237472 | 13.38778995 | 0.009528501 | 0.030702949 | NS |
| GSE16879 | mono | −0.315416999 | 0.833763874 | 0.307548902 | 0.226839724 | 11.72217689 | 0.019541354 | 0.047224938 | NS |
| GSE12251 | Tc | −0.836041001 | 2.245527305 | 0.689010828 | 0.303696304 | 9.070169168 | 0.059369317 | 0.114780679 | NS |
| GSE16879 | B aIgM | −0.847957179 | 2.815656569 | 0.850008944 | 0.372727273 | 3.653317908 | 0.454951927 | 0.488652069 | NS |
| GSE16879 | DC act | −0.189549359 | 0.648479142 | 0.160272986 | 0.384456617 | 13.38778995 | 0.009528501 | 0.030702949 | NS |
| GSE14580 | B aIgM | −1.77844547 | 4.402900973 | 1.401951715 | 0.431818182 | 3.653317908 | 0.454951927 | 0.488652069 | NS |
| GSE16879 | neutro | −0.557117307 | 0.627022737 | 0.21094443 | 0.482416448 | 8.368643695 | 0.078970351 | 0.115920491 | NS |
| GSE12251 | DC | −1.099228501 | 0.972877023 | 0.273246793 | 0.548961874 | 1.199452572 | 0.87818874 | 0.891865528 | NS |
| GSE12251 | NK | −0.757662222 | 2.273034201 | 0.285909939 | 0.572603867 | 1.115122267 | 0.891865528 | 0.891865528 | NS |
| GSE16879 | Tc act | −0.959908605 | 1.106714795 | 0.239515529 | 0.598901099 | 6.093702195 | 0.192258968 | 0.223020403 | NS |
| GSE14580 | mono | −0.451452948 | 0.77132921 | 0.23122276 | 0.610093396 | 11.72217689 | 0.019541354 | 0.047224938 | NS |
| GSE12251 | PC | −0.767490557 | 0.396927657 | 0.044086237 | 0.722342673 | 18.70073489 | 0.000899793 | 0.004349001 | NS |
| GSE14580 | neutro | −0.351036164 | 0.636440896 | 0.094296973 | 0.741723331 | 8.368643695 | 0.078970351 | 0.115920491 | NS |
| GSE16879 | NK act | −0.980713316 | 0.729732326 | −0.112269758 | 0.750269339 | 7.643379983 | 0.105550528 | 0.133085448 | NS |
| GSE16879 | Mem IgM | −2.998462888 | 1.445422883 | −0.231855628 | 0.818181818 | 8.217074503 | 0.083942424 | 0.115920491 | NS |
| GSE12251 | Mem IgM | −1.08237294 | 0.875547513 | −0.086327202 | 0.821203564 | 8.217074503 | 0.083942424 | 0.115920491 | NS |
| GSE16879 | Tc | −2.490998581 | 2.028537181 | 0.099652984 | 0.959276018 | 9.070169168 | 0.059369317 | 0.114780679 | NS |

"mono act" = M1 Macrophage.

Example 3

Immune Cell Types Analyzed

Table 10 herein below provides the cell type of each subpopulation which can be analyzed (short name or symbol, and cell description), the cell separation method, and the characteristics markers.

TABLE 10

Table 10.

| Symbol | Cell Type Description | Cell Separation Method | Markers |
|---|---|---|---|
| Th | Resting helper T cells | RosetteSep CD4+ T-cell enrichment cocktail | CD45RA-high; CD4+; CD45RO− |
| Th act | Activated helper T cells | Plate-bound anti-CD3 and anti-CD28 | |
| Tc | Resting cytotoxic T cells | RosetteSep CD8+ T-cell enrichment cocktail | CD45RA+; CD8+; CD45RO− |
| Tc act | Activated cytotoxic T cells | Plate-bound anti-CD3 and anti-CD28 | |
| B | Resting B cells | MACS CD138 microbeads and CD19 microbeads | CD19+; CD27−; IgG/A− |
| B act | Activated B cells | Anti-CD40 and IL4, 23 hours | |
| B aIgM | BCR-ligated B cells | Anti-IgM, 24 hours | |
| Mem IgG | IgA/IgG memory B cells | sorted C19+/CD27+/IgM− | CD19+; CD27+; IgM− |
| Mem IgM | IgM memory B cells | sorted C19+/CD27+/IgG/A− | CD19+; CD27+; IgG/A− |
| PC | Plasma cells | MACS CD138 microbeads and FACS | CD20 FITC, CD138 PE and CD19 APC |
| NK | Resting NK cells | RosetteSep NK-cell enrichment cocktail plus CD2 microbeads | |
| NK act | Activated NK cells | IL2, 16 hours | |
| mono | Monocytes | MACS CD14 microbeads | |
| mono act M1 macrophages | Activated Monocytes/Macrophages differentiated from monocytes | LPS, 24 hours | M1: CD68, CD86, CCR7; |
| M2 macrophages | | | M2: CD68, CD 163, CD206 (MR); |

TABLE 10-continued

Table 10.

| Symbol | Cell Type Description | Cell Separation Method | Markers |
|---|---|---|---|
| DC | Resting dendritic cells | Differentiated from monocytes with IL4 and GMCSF | |
| DC act | Activated dendritic cells | LPS, 24 hours | |
| neutro | Neutrophils | Ficoll gradient centrifugation of heparanized blood | |

Table 11 describes the frequencies of the subpopulation of cells in TNF-alpha inhibitor responders versus non-responders.

TABLE 11

Table 11. Confidence intervals (95% CI) and non-overlapping exemplary ranges [representative (Repr.) range] of proportions estimated by computational deconvolution for cell types that showed significant differences in at least one of the discovery cohorts, and optimal cutoff for the plasma cell clinician index (PC-index) and automated quantitation quantitative score (PC-score) from immunostaining in the validation cohort.

| Cohort | Cell type | Non-responders 95% CI | Responders 95% CI | Non-responders Repr. range | Responders Repr. range |
|---|---|---|---|---|---|
| GSE16879 | PC | 0.082-0.261 | 0.052-0.105 | 0.105-0.261 | 0.052-0.082 |
| GSE16879 | mono act M1 | 0.062-0.113 | 0.024-0.059 | 0.062-0.113 | 0.024-0.059 |
| GSE12251 | mono act M1 | 0.089-0.171 | 0.052-0.094 | 0.094-0.171 | 0.052-0.089 |
| GSE12251 | mono | 0.057-0.079 | 0.073-0.129 | 0.057-0.073 | 0.079-0.129 |
| GSE14580 | PC | 0.123-0.264 | 0.057-0.145 | 0.145-0.264 | 0.057-0.123 |
| GSE14580 | DC act | 0.193-0.292 | 0.282-0.350 | 0.193-0.282 | 0.292-0.350 |
| GSE14580 | Mem IgM | 0.059-0.165 | 0.002-0.091 | 0.091-0.165 | 0.002-0.059 |
| GSE14580 | NK act | 0.052-0.095 | 0.073-0.139 | 0.052-0.073 | 0.095-0.139 |
| GSE14580 | Tc | 0.011-0.031 | 0.017-0.050 | 0.011-0.017 | 0.031-0.050 |
| GSE14580 | mono act M1 | 0.088-0.130 | 0.026-0.101 | 0.101-0.130 | 0.026-0.088 |
| GSE12251 | neutro | 0.115-0.212 | 0.089-0.135 | 0.135-0.212 | 0.089-0.115 |
| Validation | PC-Index | ≥2 | ≤1 | | |
| Validation | PC-Score | ≥0.056 | <0.056 | | |

Example 4

The present inventors have surprisingly uncovered that the predictive power of the gene signatures of some embodiments of the invention is much higher when the inflammation status of the tissue is accounted for. The present inventors have assessed the training set predictive power as single cellular biomarkers by ROC analysis in each GEO cohort separately. Activated monocyte proportions achieved high AUC values in all cohorts (AUC=77%, 82% and 890/% in the *UC-A*, *UC-B* and *CDc* cohorts respectively). Plasma cell proportions performed similarly well in cohorts *UC-A* and *CDc* (AUC=79% and 88% respectively), but gave a weaker signal in cohort *UC-B* (AUC=45%), which was expected since proportion differences were not found significant in this cohort in first place. In exploratory cohorts UC-A and CDc the collected tissues were all from inflamed mucosa sites, as opposed to cohort UC-B wherein the tissue samples included both normal and inflamed biopsies. Hence, the ROC curves for UC-A and CDc have a much higher % AUC than the UC-B cohort.

The present inventors have carried out an additional validation, whereby the present inventors included a cohort of normal and inflamed biopsy samples from IBD patients. Plasma cell numbers from non inflamed biopsies of 9 non responders and 20 responders were collected, and from inflamed tissue sites of 7 responders and 5 non-responders prior to anti-TNF therapy initiation. Thus, as shown in FIG. 12, the plasma cell proportions in inflamed colon tissue can predict response to infliximab (IFX) prior to treatment initiation with high and unprecedented accuracy.

It should be noted that a mixed tissue biopsy (i.e., having inflamed and non-inflamed cells) is sufficient for determining the responsiveness of the subject to anti-TNF therapy based on frequencies of macrophages and plasma cells in some cohorts.

In addition, it should be noted that a tissue biopsy from an inflamed area, e.g., which includes mainly inflamed cells, is sufficient for determining the responsiveness of the subject to anti-TNF therapy based on frequencies of plasma cells and macrophages.

Analysis and Discussion

The treatment of IBDs using monoclonal antibodies against TNF-alpha has shown to be very effective in achieving complete mucosal remission, however only in 60% of patients (3). This high failure rate, together with the unavailability of a reliable test to predict response, the high cost of anti-TNF biologics and many major side effects on the patients' immune system greatly undermine the benefit/cost ratio of such an otherwise effective therapy. In this work, the present inventors used a cell-centered approach based on computational methods to elucidate cell subsets whose proportions can predict response to anti-TNF therapy in IBD patients, prior starting treatment. By validating the present inventors' findings in paraffin embedded stained biopsies the present inventors show that such prediction is easily possible in a clinical setting.

Previous attempts to find predictive biomarkers used gene expression assays on bulk colon biopsies (4, 5). Traditional analysis of gene expression data look for genes that show differential expression patterns between conditions. However, due to both technical and biological variability, gene-based signatures are commonly difficult to reproduce. In this context, looking at functionally coordinated modules such as pathways or co-expression network is known to greatly improve robustness of findings. In a similar way, cells can be considered as the fundamental functional units whose coordinated gene expression programs are regulated according to conditions and stimuli. In disease conditions, in particular, immune cell subsets home to target tissues where they may turn to fight the cause of disease or in the worst scenario exacerbate the existing pathology if their actions are dis-regulated. This is all the more the case for inflammatory diseases such as IBD where immune activity has a role in pathogenesis. This inflammatory process involves interaction between different subsets of immune cells as well as cross talk with cells of the gut tissue through cytokine signaling, overall forming a complex dynamic system (17). The present inventors' approach identified immune cells as major contributors to gene signatures of colon tissue in IBD. Thus, the present inventors focused efforts on looking for biomarkers within the main actors of this system, i.e. the variety of immune cell subsets. For this reason, the present inventors expect these predictions to be more robust and reproducible than gene/pathway based biomarkers. An additional advantage of this cell-centered approach lays in the interpretability of the results, because they directly point to specific cell subsets, from which it is easier to derive immunological and mechanistic hypotheses. Last but not least, cell subset proportions are easily and accurately assayed in clinical settings, for example in the routinely stored biopsies in the case of IBD. In an in-silico discovery phase, the present inventors used computational deconvolution techniques to estimate the proportions of infiltrating immune cell subsets in colon tissues directly from public gene expression data of bulk tissue. While batch effects, tissue or disease heterogeneity makes proportion estimates from separate cohorts not directly comparable, group differences in proportions (fold change) within each cohort are comparable and indicative of differential immune compartment (27). By formally integrating these observed differences across multiple cohorts, the present inventors were able to capture the most consistent signal within a heterogeneous technical and biological background, in a similar way as gene-based meta-analysis are performed (19, 24). The present inventors' approach detected that non-responders have consistently greater proportions of activated monocytes and plasma cells than responders. When validating these finding, the present inventors found that macrophage proportions were not predictive of response, although showing the most consistent differences across all discovery cohorts. This may be due to a discrepancy between the resolution of their in-silico estimates and their assessment in the stained biopsies. Indeed, the reference gene expression profile used to estimate the proportion of activated monocytes was generated from monocytes 24 hours after in-vitro stimulation with LPS (26), which would qualify them as classically activated macrophages (M1). These are also known as inflammatory macrophages, due to their secretion of pro-inflammatory cytokines such as TNFα, IL-1β, IL-6 and IL-12 (36). The present inventors are currently investigating if M1 or M2 macrophages proportions could indeed provide accurate response prediction. However, these two cell subsets are thought to be the two extreme of a continuum phenotype, with their respective markers being rather quantitative than binary. This may prevent their distinction by staining, and require more advanced technology like flow-cytometry which are not directly implementable in routine clinical protocols. Nonetheless, the predictive power of plasma cells is remarkable. Moreover, immunostaining for CD138+ cells can be done using antibodies that are known to be very specific and efficient on this cell population, which presents the additional characteristics of being also distinguishable by morphology. Overall, this promises to provide a robust and accurate prediction clinical assay.

Infliximab has been shown to induce monocyte apoptosis in patients with chronic active CD, which could explain its strong anti-inflammatory effect (28). Basal plasmacytosis, defined as a dense infiltration of plasma cells in the lower one third of the mucosa (29), is considered to be an early feature of IBD (30). The presence of basal plasmacytosis in colon biopsies of UC patients has notably been identified as an independent predictor of shorter time to clinical relapse (29).

It is well known that dysregulation of various immune cell populations can be seen in the gut of patients with IBD. Their inflamed gut may become massively infiltrated with B cells alongside with IgA+ and IgG+ plasma cells, depending on the severity of inflammation, though the mechanisms of this recruitment are not fully clear (31-33). In this context, it is believed that the intestinal microbiota plays a key role in driving inflammatory responses during disease development and progression. Palm et al investigated the involvement of mucosal IgA (secreted by plasma cells) in IBD gut barrier function, and have shown that bacteria taxa-specific levels of IgA might distinguish between members of the microbiota that impact disease susceptibility and/or severity, and the remaining members of the microbiota (37) emphasizing the role of IgA+ mucosal plasma cells in gut homeostasis and disease. In UC, plasma cells also produce non-specific Antibodies, such as perinuclear anti-cytoplasmic neutrophil (pANCA) (38). Absence of this antibody was strongly associated with better response to Infliximab (39, 40).

IgG antibodies are the most abundant serum immunoglobulins, involved in the secondary immune response, and their numbers increase in response to infection, chronic inflammation, and autoimmune diseases (41,42). IgG-producing plasma cells heavily infiltrate the inflamed mucosa of patients with IBD. It was suggested that IgG plasma cells create immune complexes (IC) with their specific antigens. This IgG-IC activates intestinal macrophages via their FcγRs, and exacerbating intestinal inflammation, demonstrating plasma cell-macrophage cooperation as another potent inducer of intestinal inflammation besides commensal bacteria. Recently, FcγRIIA was also identified as a susceptible gene of UC in Japanese and European descent populations (43,44). In vitro IgG-IC stimulation caused increasing number of macrophages in the inflamed mucosa of UC patients, and induced the extensive production of pro-inflammatory cytokines such as TNF, IL-1β and IL-6. In addition, neutrophil expression of FcγRI is upregulated in adult patients with clinically active IBD (45). The high numbers of plasma cells together with activated monocytes in the present inventors' predictive signature can point to involvement of this signaling pathway by lamina propria mononuclear cells (LPMCs) (46).

The present inventors validated these results for plasma cells in a completely independent set of 20 IBD samples (UC, CD, IBDU) by staining biopsy slides for CD138 positive cells. Proportions obtained by automated quantitation achieved very high accuracy (AUC 82.4%).

Taken together, the present inventors' predictive assay is easily applicable in clinical settings and can dramatically improve the cost/benefit of anti-TNF therapy prescription for IBD patients. In future, a similar approach will be tested to achieve a higher resolution insight into the nature of macrophage subsetting in IBD biopsies, to derive an additional predictive value from biopsies obtained routinely prior to anti-TNF therapy initiation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. S. B. Hanauer, B. G. Feagan, G. R. Lichtenstein, L. F. Mayer, S. Schreiber, J. F. Colombel, D. Rachmilewitz, D. C. Wolf, A. Olson, W. Bao, P. Rutgeerts, Maintenance infliximab for Crohn's disease: The ACCENT I randomised trial, *Lancet* 359, 1541-1549 (2002).
2. G. R. Lichtenstein, S. Yan, M. Bala, M. Blank, B. E. Sands, Infliximab maintenance treatment reduces hospitalizations, surgeries, and procedures in fistulizing Crohn's disease, *Gastroenterology* 128, 862-869 (2005).
3. S. Ben-Horin, U. Kopylov, Y. Chowers, Optimizing anti-TNF treatments in inflammatory bowel disease, *Autoimmunity Reviews* 13, 24-30 (2014).
4. I. Arijs, K. Li, G. Toedter, R. Quintens, L. Van Lommel, K. Van Steen, P. Leemans, G. De Hertogh, K. Lemaire, M. Ferrante, F. Schnitzler, L. Thorrez, K. Ma, X-Y. R. Song, C. Marano, G. Van Assche, S. Vermeire, K. Geboes, F. Schuit, F. Baribaud, P. Rutgeerts, Mucosal gene signatures to predict response to infliximab in patients with ulcerative colitis., *Gut* 58, 1612-9 (2009).
5. I. Arijs, R. Quintens, L. Van Lommel, K. Van Steen, G. De Hertogh, K. Lemaire, A. Schraenen, C. Perrier, G. Van Assche, S. Vermeire, K. Geboes, F. Schuit, P. Rutgeerts, Predictive value of epithelial gene expression profiles for response to infliximab in Crohn's disease, *Inflammatory bowel diseases* 16, 2090-8 (2010).
6. Q. Chen, L. Rabach, P. Noble, T. Zheng, C. G. Lee, R. J. Homer, J. A. Elias, IL-11 receptor alpha in the pathogenesis of IL-13-induced inflammation and remodeling, *Journal of immunology* (Baltimore, Md.: 1950) 174, 2305-13 (2005).
7. A. J. Ashcroft, S. M. Cruickshank, P. I. Croucher, M. J. Perry, S. Rollinson, J. M. Lippitt, J. A. Child, C. Dunstan, P. J. Felsburg, G. J. Morgan, S. R. Carding, Colonic dendritic cells, intestinal inflammation, and T cell-mediated bone destruction are modulated by recombinant osteoprotegerin, *Immunity* 19, 849-61 (2003).
8. A. J. Ashcroft, S. R. Carding, RANK ligand and osteoprotegerin: emerging roles in mucosal inflammation, *Gut* 54, 1345-6 (2005).
9. P. Mannon, W. Reinisch, Interleukin 13 and its role in gut defence and inflammation, *Gut* 61, 1765-73 (2012).
10. H. Kefalakes, T. J. Stylianides, G. Amanakis, G. Kolios, Exacerbation of inflammatory bowel diseases associated with the use of nonsteroidal anti-inflammatory drugs: myth or reality?, *European journal of clinical pharmacology* 65, 963-70 (2009).
11. J. L. Wallace, Prostaglandin biology in inflammatory bowel disease, *Gastroenterology clinics of North America* 30, 971-80 (2001).
12. C. Chen, M. S. Jamaluddin, S. Yan, D. Sheikh-Hamad, Q. Yao, Human stanniocalcin-1 blocks TNF-alpha-induced monolayer permeability in human coronary artery endothelial cells, *Arteriosclerosis, thrombosis, and vascular biology* 28, 906-12 (2008).
13. B. Mesko, S. Poliska, A. Vnmcsa, Z. Szekanecz, K. Palatka, Z. Hollo, A. Horvath, L. Steiner, G. Zahuczky, J. Podani, A. Nagy, Peripheral blood derived gene panels predict response to infliximab in rheumatoid arthritis and Crohn's disease, *Genome Medicine* 5, 59 (2013).
14. B. Khor, A. Gardet, R. J. Xavier, Genetics and pathogenesis of inflammatory bowel disease, *Nature* 474, 307-317 (2011).
15. M. C. Dubinsky, L. Mei, M. Friedman, T. Dhere, T. Haritunians, H. Hakonarson, C. Kim, J. Glessner, S. R. Targan, D. P. McGovern, K. D. Taylor, J. I. Rotter, Genome wide association (GWA) predictors of anti-TNFalpha therapeutic responsiveness in pediatric inflammatory bowel disease, *Inflammatory bowel diseases* 16, 1357-66 (2010).
16. M. K. Magnusson, H. Strid, M. Sapnara, A. Lasson, A. Bajor, K.-A. Ung, L. Öhman, Anti-TNF therapy response in patients with ulcerative colitis is associated with colonic anti-microbial peptide expression and microbiota composition, *Journal of Crohn's and Colitis*, jjw051 (2016).
17. C. Abraham, R. Medzhitov, Interactions between the host innate immune system and microbes in inflammatory bowel disease, *Gastroenterology* 140, 1729-1737 (2011).
18. S. S. Shen-Orr, R. Gaujoux, Computational deconvolution: extracting cell type-specific information from heterogeneous samples, *Current opinion in immunology* 25, 571-8 (2013).
19. R. Chen, P. Khatri, P. K. Mazur, M. Polin, Y. Zheng, D. Vaka, C. D. Hoang, J. Shrager, Y. Xu, S. Vicent, A. J. Butte, E. A. Sweet-Cordero, A meta-Analysis of lung cancer gene expression identifies PTK7 as a survival gene in lung adenocarcinoma, *Cancer Research* 74, 2892-2902 (2014).
20. F. Baribaud, X. K. Li, Markers and Methods for Assessing and Treating Ulcerative Colitis and Related Disorders Using a 20 Gene Panel (available at www(dot)faqs(dot) org/patents/app/20100069256).
21. T. F. Mueller, G. Einecke, J. Reeve, B. Sis, M. Mengel, G. S. Jhangri, S. Bunnag, J. Cruz, D. Wishart, C. Meng, G. Broderick, B. Kaplan, P. F. Halloran, Microarray analysis of rejection in human kidney transplants using pathogenesis-based transcript sets, *American Journal of Transplantation* 7, 2712-2722 (2007).
22. B. Halloran, J. Chang, D. Q. Shih, D. McGovern, K. Famulski, C. Evaschesen, R. N. Fedorak, A. Thiesen, S. Targan, P. F. Halloran, Molecular patterns in human ulcerative colitis and correlation with response to infliximab. *Inflammatory bowel diseases* 20, 2353-63 (2014).
23. S. Hanzelmann, R. Castelo, J. Guinney, GSVA: gene set variation analysis for microarray and RNA-seq data. *BMC bioinformatics* 14, 7 (2013).
24. T. E. Sweeney, A. Shidham, H. R. Wong, P. Khatri, A comprehensive time-course—based multicohort analysis of sepsis and sterile inflammation reveals a robust diagnostic gene set, *Science Translational Medicine* 7, 1-16 (2015).
25. T. Barrett, D. B. Troup, S. E. Wilhite, P. Ledoux, C. Evangelista, I. F. Kim, M. Tomashevsky, K. a Marshall, K. H. Phillippy, P. M. Sherman, R. N. Muertter, M. Holko, O. Ayanbule, A. Yefanov, A. Soboleva, NCBI GEO: archive for functional genomics data sets-10 years on. *Nucleic acids research* 39, D1005-10 (2011).
26. A. R. Abbas, K. Wolslegel, D. Seshasayee, Z. Modrusan, H. F. Clark, Deconvolution of blood microarray data identifies cellular activation patterns in systemic lupus erythematosus. *PloS one* 4, e6098 (2009).
27. P. Karpiński, D. Frydecka, M. M. Sasiadek, B. Misiak, Reduced number of peripheral natural killer cells in schizophrenia but not in bipolar disorder, *Brain, Behavior, and Immunity* (2016), doi: 10.1016/j.bbi.2016.02.005.
28. A. Lügering, M. Schmidt, N. Luigering, H. G. Pauels, W. Domschke, T. Kucharzik, Infliximab induces apoptosis in monocytes from patients with chronic active Crohn's disease by using a caspase-dependent pathway. *Gastroenterology* 121, 1145-57 (2001).
29. a Bitton, M. a Peppercorn, D. a Antonioli, J. L. Niles, S. Shah, a Bousvaros, B. Ransil, G. Wild, a Cohen, M. D. Edwardes, a C. Stevens, Clinical, biological, and histologic parameters as predictors of relapse in ulcerative colitis. *Gastroenterology* 120, 13-20 (2001).
30. V. Villanacci, E. Antonelli, G. Reboldi, M. Salemme, G. Casella, G. Bassotti, Endoscopic biopsy samples of naïve "colitides" patients: role of basal plasmacytosis, *Journal of Crohn's & colitis* 8, 1438-43 (2014).
31. F. Schnitzler, H. Fidder, M. Ferrante, M. Noman, I. Arijs, G. Van Assche, I. Hoffman, K. Van Steen, S. Vermeire, P. Rutgeerts, Long-term outcome of treatment with infliximab in 614 patients with Crohn's disease: results from a single-centre cohort, *Gut* 58, 492-500 (2009).
32. D. Reijasse, C. Le Pendeven, J. Cosnes, A. Dehee, J.-P. Gendre, J.-C. Nicolas, L. Beaugerie, Epstein-Barr virus viral load in Crohn's disease: effect of immunosuppressive therapy, *Inflammatory bowel diseases* 10, 85-90 (2004).
33. R. S. Wallis, M. S. Broder, J. Y. Wong, M. E. Hanson, D. O. Beenhouwer, Granulomatous Infectious Diseases Associated with Tumor Necrosis Factor Antagonists, *Clinical Infectious Diseases* 38, 1261-1265 (2004).
34. A. R. Abbas, D. Baldwin, Y. Ma, W. Ouyang, A. Gurney, F. Martin, S. Fong, M. van Lookeren Campagne, P. Godowski, P. M. Williams, a C. Chan, H. F. Clark, Immune response in silico (IRIS): immune-specific genes identified from a compendium of microarray expression data. *Genes and immunity* 6, 319-31 (2005).
35. R. Gaujoux, C. Seoighe, CellMix: A Comprehensive Toolbox for Gene Expression Deconvolution. *Bioinformatics* (Oxford, England), 1-2 (2013).
36. F. O. Martinez, S. Gordon, M. Locati, A. Mantovani, Transcriptional profiling of the human monocyte-to-macrophage differentiation and polarization: new molecules and patterns of gene expression. *Journal of immunology* (Baltimore, Md.: 1950) 177, 7303-11 (2006).
37. N. W. Palm, M. R. De Zoete, T. W. Cullen, N. A. Barry, J. Stefanowski, L. Hao, P. H. Degnan, J. Hu, I. Peter, W. Zhang, E. Ruggiero, J. H. Cho, A. L. Goodman, R. A. Flavell, Immunoglobulin A coating identifies colitogenic bacteria in inflammatory bowel disease, *Cell* 158, 1000-1010 (2014).
38. J. A. Rump, J. Schölmerich, V. Gross, M. Roth, R. Helfesrieder, A. Rautmann, J. Lüdemann, W. L. Gross, H. H. Peter, A new type of perinuclear anti-neutrophil cytoplasmic antibody (p-ANCA) in active ulcerative colitis but not in Crohn's disease. *Immunobiology* 181, 406-13 (1990).
39. M. Ferrante, S. Vermeire, K. H. Katsanos, M. Noman, G. Van Assche, F. Schnitzler, I. Arijs, G. De Hertogh, I. Hoffman, J. K. Geboes, P. Rutgeerts, Predictors of early response to infliximab in patients with ulcerative colitis. *Inflammatory bowel diseases* 13, 123-8 (2007).
40. M. Jürgens, R. P. Laubender, F. Hartl, M. Weidinger, J. Seiderer, J. Wagner, M. Wetzke, F. Beigel, S. Pfennig, J. Stallhofer, F. Schnitzler, C. Tillack, P. Lohse, B. Göke, J. Glas, T. Ochsenkühn, S. Brand, Disease activity, ANCA, and IL23R genotype status determine early response to infliximab in patients with ulcerative colitis. *The American journal of gastroenterology* 105, 1811-9 (2010).
41. S. E. Plevy, C. J. Landers, J. Prehn, N. M. Carramanzana, R. L. Deem, D. Shealy, S. R. Targan, A role for TNF-alpha and mucosal T helper-1 cytokines in the pathogenesis of Crohn's disease. *Journal of immunology* (Baltimore, Md.: 1950) 159, 6276-82 (1997).
42. F. Hiepe, T. DOrner, A. E. Hauser, B. F. Hoyer, H. Mei, A. Radbruch, Long-lived autoreactive plasma cells drive persistent autoimmune inflammation, *Nature reviews. Rheumatology* 7, 170-8 (2011).
43. D. P. B. McGovern, A. Gardet, L. Torkvist, P. Goyette, J. Essers, K. D. Taylor, B. M. Neale, R. T. H. Ong, C. Lagace, C. Li, T. Green, C. R. Stevens, C. Beauchamp, P. R. Fleshner, M. Carlson, M. D'Amato, J. Halfvarson, M. L. Hibberd, M. Lordal, L. Padyukov, A. Andriulli, E. Colombo, A. Latiano, O. Palmieri, E.-J. Bernard, C. Deslandres, D. W. Hommes, D. J. de Jong, P. C. Stokkers, R. K. Weersma, Y. Sharma, M. S. Silverberg, J. H. Cho, J. Wu, K. Roeder, S. R. Brant, L. P. Schumm, R. H. Duerr, M. C. Dubinsky, N. L. Glazer, T. Haritunians, A. Ippoliti, G. Y. Melmed, D. S. Siscovick, E. A. Vasiliauskas, S. R. Targan, V. Annese, C. Wijmenga, S. Pettersson, J. I. Rotter, R. J. Xavier, M. J. Daly, J. D. Rioux, M. Seielstad, Genome-wide association identifies multiple ulcerative colitis susceptibility loci. *Nature genetics* 42, 332-7 (2010).
44. K. Asano, T. Matsushita, J. Umeno, N. Hosono, A. Takahashi, T. Kawaguchi, T. Matsumoto, T. Matsui, Y. Kakuta, Y. Kinouchi, T. Shimosegawa, M. Hosokawa, Y. Arimura, Y. Shinomura, Y. Kiyohara, T. Tsunoda, N. Kamatani, M. Iida, Y. Nakamura, M. Kubo, A genome-wide association study identifies three new susceptibility loci for ulcerative colitis in the Japanese population. *Nature genetics* 41, 1325-9 (2009).
45. P. Minar, Y. Haberman, I. Jurickova, T. Wen, M. E. Rothenberg, M.-O. Kim, S. A. Saeed, R. N. Baldassano, M. Stephens, J. Markowitz, J. Rosh, W. V. Crandall, M. B. Heyman, D. R. Mack, A. M. Griffiths, S. S. Baker, J. S. Hyams, S. Kugathasan, L. A. Denson, Utility of neutrophil Fcγ receptor I (CD64) index as a biomarker for mucosal inflammation in pediatric Crohn's disease. *Inflammatory bowel diseases* 20, 1037-48 (2014).

46. M. Uo, T. Hisamatsu, J. Miyoshi, D. Kaito, K. Yoneno, M. T. Kitazume, M. Mori, A. Sugita, K. Koganei, K. Matsuoka, T. Kanai, T. Hibi, Mucosal CXCR4+ IgG plasma cells contribute to the pathogenesis of human ulcerative colitis through FcγR-mediated CD14 macrophage activation. *Gut* 62, 1734-44 (2013).

What is claimed is:

1. A method of treating inflammatory bowel disease (IBD) in a subject in need thereof, the method comprising:
   (a) determining responsiveness to a TNF-alpha inhibitor by:
   analyzing a frequency of at least one subpopulation of immune cells in a tissue biopsy of the subject,
   wherein a frequency above a predetermined threshold of immune cells of a subpopulation selected from the group consisting of memory B cells, and neutrophils is indicative of the subject being non-responder to the TNF-alpha inhibitor, and/or
   wherein a frequency below a predetermined threshold of immune cells of a subpopulation of CD8+ T cells is indicative of the subject being non-responder to the TNF-alpha inhibitor,
   wherein said memory B cells are plasma cells, and wherein said plasma cells are characterized by positive expression of CD138;
   or wherein said memory B cells are non-plasma cells, and wherein said non-plasma cells are characterized by CD20+, CD19+ and CD45RA+ expression signature;
   wherein said neutrophils are characterized by CD45+, CD66b+ and CD16+ expression signature; and
   wherein said CD8+ T cells are characterized by CD8+ and CD69+ expression signature,
   thereby predicting the responsiveness of the subject having the inflammatory bowel disease (IBD) to the TNF-alpha inhibitor; and
   (b) treating said subject with the TNF-alpha inhibitor when the subject is a responder to the TNF-alpha inhibitor based on said responsiveness or with a steroid, 5-ASA, thiopurines and/or methotrexate, when the subject is a non-responder to the TNF-alpha inhibitor based on said responsiveness.

2. The method of claim 1, wherein said subject is a naive subject who hasn't been treated with said TNF-alpha inhibitor.

3. The method of claim 1, wherein said cells of said tissue biopsy are intact cells.

4. The method of claim 1, wherein said analyzing said frequency of said at least one subpopulation of immune cells is performed by a morphometric analysis.

5. The method of claim 1, wherein said analyzing said frequency of said at least one subpopulation of immune cells is performed using at least one histological stain.

6. The method of claim 1, wherein said analyzing said frequency of said at least one subpopulation of immune cells is performed using at least one antibody.

7. The method of claim 1, wherein said analyzing said frequency of said at least one subpopulation of immune cells is performed by an RNA in-situ hybridization assay.

8. The method of claim 1, wherein said analyzing said frequency of said at least one subpopulation of immune cells is performed by a single cell RNA sequencing (RNA SEQ) analysis.

9. The method of claim 1, wherein said analyzing said frequency of said at least one subpopulation of immune cells is performed by exome sequencing.

10. The method of claim 1, wherein said analyzing said frequency of said at least one subpopulation of immune cells is performed by RNA SEQ followed by deconvolution.

11. The method of claim 1, wherein said analyzing said frequency of said at least one subpopulation of immune cells is performed by reverse-transcriptase polymerase chain reaction (RT-PCR) followed by deconvolution.

12. The method of claim 1, wherein said analyzing said frequency of said at least one subpopulation of immune cells is performed by micro array followed by deconvolution.

* * * * *

SEQUENCE LISTING

```
<160> NUMBER OF SEQ ID NOS: 84

<210> SEQ ID NO 1
<211> LENGTH: 20
<212> TYPE: RNA
<213> ORGANISM: Artificial sequence
<220> FEATURE:
<223> OTHER INFORMATION: Single strand RNA oligonucleotide
<220> FEATURE:
<221> NAME/KEY: misc_feature
<222> LOCATION: (1)..(1)
<223> OTHER INFORMATION: 5 phosphate
<220> FEATURE:
<221> NAME/KEY: misc_feature
<222> LOCATION: (20)..(20)
<223> OTHER INFORMATION: 3 dideoxycytosine to block self-ligation

<400> SEQUENCE: 1
agaucggaag agcgucgugc                                                  20

<210> SEQ ID NO 2
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 2
acacgacgct cttccga                                                     17

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5 phosphate
<220> FEATURE:
<221> NAME/KEY: misc_feature
<222> LOCATION: (23)..(23)
<223> OTHER INFORMATION: 3 dideoxycytosine to block self-ligation

<400> SEQUENCE: 3
agatcggaag agcacacgtc tgc                                              23

<210> SEQ ID NO 4
<211> LENGTH: 124
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (83)..(90)
<223> OTHER INFORMATION: n is a, c, g, or t

<400> SEQUENCE: 4
aatgatacgg cgaccaccga gatctacact ctttccctac acgacgctct tccgatctca      60
agcagaagac ggcatacgag atnnnnnnnn gtgactggag ttcagacgtg tgctcttccg     120
atct                                                                  124
```

```
<210> SEQ ID NO 5
<211> LENGTH: 327
<212> TYPE: PRT
<213> ORGANISM: homo sapiens

<400> SEQUENCE: 5

Met Arg Leu Ala Val Leu Phe Ser Gly Ala Leu Leu Gly Leu Leu Ala
1               5                   10                  15

Glu Ser Thr Gly Thr Thr Ser His Arg Thr Thr Lys Ser His Lys Thr
            20                  25                  30

Thr Thr His Arg Thr Thr Thr Thr Gly Thr Thr Ser His Gly Pro Thr
        35                  40                  45

Thr Ala Thr His Asn Pro Thr Thr Ser His Gly Asn Val Thr Val
    50                  55                  60

His Pro Thr Ser Asn Ser Thr Ala Thr Ser Gln Gly Pro Ser Thr Ala
65                  70                  75                  80

Thr His Ser Pro Ala Thr Thr Ser His Gly Asn Ala Thr Val His Pro
                85                  90                  95

Thr Ser Asn Ser Thr Ala Thr Ser Pro Gly Phe Thr Ser Ala His
            100                 105                 110

Pro Glu Pro Pro Pro Ser Pro Ser Pro Ser Pro Thr Ser Lys Glu
        115                 120                 125

Thr Ile Gly Asp Tyr Thr Trp Thr Asn Gly Ser Gln Pro Cys Val His
    130                 135                 140

Leu Gln Ala Gln Ile Gln Ile Arg Val Met Tyr Thr Thr Gln Gly Gly
145                 150                 155                 160

Gly Glu Ala Trp Gly Ile Ser Val Leu Asn Pro Asn Lys Thr Lys Val
                165                 170                 175

Gln Gly Ser Cys Glu Gly Ala His Pro His Leu Leu Ser Phe Pro
            180                 185                 190

Tyr Gly His Leu Ser Phe Gly Phe Met Gln Asp Leu Gln Gln Lys Val
        195                 200                 205

Val Tyr Leu Ser Tyr Met Ala Val Glu Tyr Asn Val Ser Phe Pro His
    210                 215                 220

Ala Ala Gln Trp Thr Phe Ser Ala Gln Asn Ala Ser Leu Arg Asp Leu
225                 230                 235                 240

Gln Ala Pro Leu Gly Gln Ser Phe Ser Cys Ser Asn Ser Ser Ile Ile
                245                 250                 255

Leu Ser Pro Ala Val His Leu Asp Leu Leu Ser Leu Arg Leu Gln Ala
            260                 265                 270

Ala Gln Leu Pro His Thr Gly Val Phe Gly Gln Ser Phe Ser Cys Pro
        275                 280                 285

Ser Asp Arg Ser Ile Leu Leu Pro Leu Ile Ile Gly Leu Ile Leu Leu
    290                 295                 300

Gly Leu Leu Ala Leu Val Leu Ile Ala Phe Cys Ile Ile Arg Arg Arg
305                 310                 315                 320

Pro Ser Ala Tyr Gln Ala Leu
                325

<210> SEQ ID NO 6
<211> LENGTH: 354
<212> TYPE: PRT
<213> ORGANISM: homo sapiens
```

```
<400> SEQUENCE: 6

Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro Pro
    130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Lys Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu

<210> SEQ ID NO 7
<211> LENGTH: 217
<212> TYPE: PRT
<213> ORGANISM: homo sapiens
```

<400> SEQUENCE: 7

```
Met Asp Pro Gln Cys Thr Met Gly Leu Ser Asn Ile Leu Phe Val Met
1               5                   10                  15
Ala Phe Leu Leu Ser Ala Asn Phe Ser Gln Pro Glu Ile Val Pro Ile
                20                  25                  30
Ser Asn Ile Thr Glu Asn Val Tyr Ile Asn Leu Thr Cys Ser Ser Ile
                35                  40                  45
His Gly Tyr Pro Glu Pro Lys Lys Met Ser Val Leu Leu Arg Thr Lys
        50                  55                  60
Asn Ser Thr Ile Glu Tyr Asp Gly Ile Met Gln Lys Ser Gln Asp Asn
65                  70                  75                  80
Val Thr Glu Leu Tyr Asp Val Ser Ile Ser Leu Ser Val Ser Phe Pro
                85                  90                  95
Asp Val Thr Ser Asn Met Thr Ile Phe Cys Ile Leu Glu Thr Asp Lys
                100                 105                 110
Thr Arg Leu Leu Ser Ser Pro Phe Ser Ile Glu Leu Glu Asp Pro Gln
            115                 120                 125
Pro Pro Pro Asp His Ile Pro Trp Ile Thr Ala Val Leu Pro Thr Val
        130                 135                 140
Ile Ile Cys Val Met Val Phe Cys Leu Ile Leu Trp Lys Trp Lys Lys
145                 150                 155                 160
Lys Lys Arg Pro Arg Asn Ser Tyr Lys Cys Gly Thr Asn Thr Met Glu
                165                 170                 175
Arg Glu Glu Ser Glu Gln Thr Lys Lys Arg Glu Lys Ile His Ile Pro
            180                 185                 190
Glu Arg Ser Asp Glu Ala Gln Arg Val Phe Lys Ser Ser Lys Thr Ser
        195                 200                 205
Ser Cys Asp Lys Ser Asp Thr Cys Phe
    210                 215
```

<210> SEQ ID NO 8
<211> LENGTH: 247
<212> TYPE: PRT
<213> ORGANISM: homo sapiens

<400> SEQUENCE: 8

```
Met Gly Arg Thr Ser Phe Asp Ser Asp Ser Trp Thr Leu Arg Leu His
1               5                   10                  15
Asn Leu Gln Ile Lys Asp Lys Gly Leu Tyr Gln Cys Ile Ile His His
                20                  25                  30
Lys Lys Pro Thr Gly Met Ile Arg Ile His Gln Met Asn Ser Glu Leu
            35                  40                  45
Ser Val Leu Ala Asn Phe Ser Gln Pro Glu Ile Val Pro Ile Ser Asn
        50                  55                  60
Ile Thr Glu Asn Val Tyr Ile Asn Leu Thr Cys Ser Ser Ile His Gly
65                  70                  75                  80
Tyr Pro Glu Pro Lys Lys Met Ser Val Leu Leu Arg Thr Lys Asn Ser
                85                  90                  95
Thr Ile Glu Tyr Asp Gly Ile Met Gln Lys Ser Gln Asp Asn Val Thr
                100                 105                 110
Glu Leu Tyr Asp Val Ser Ile Ser Leu Ser Val Ser Phe Pro Asp Val
            115                 120                 125
Thr Ser Asn Met Thr Ile Phe Cys Ile Leu Glu Thr Asp Lys Thr Arg
        130                 135                 140
```

```
Leu Leu Ser Ser Pro Phe Ser Ile Glu Leu Glu Asp Pro Gln Pro Pro
145                 150                 155                 160

Pro Asp His Ile Pro Trp Ile Thr Ala Val Leu Pro Thr Val Ile Ile
                165                 170                 175

Cys Val Met Val Phe Cys Leu Ile Leu Trp Lys Trp Lys Lys Lys Lys
            180                 185                 190

Arg Pro Arg Asn Ser Tyr Lys Cys Gly Thr Asn Thr Met Glu Arg Glu
        195                 200                 205

Glu Ser Glu Gln Thr Lys Lys Arg Glu Lys Ile His Ile Pro Glu Arg
    210                 215                 220

Ser Asp Glu Ala Gln Arg Val Phe Lys Ser Ser Lys Thr Ser Ser Cys
225                 230                 235                 240

Asp Lys Ser Asp Thr Cys Phe
                245

<210> SEQ ID NO 9
<211> LENGTH: 323
<212> TYPE: PRT
<213> ORGANISM: homo sapiens

<400> SEQUENCE: 9

Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Lys Arg Pro Arg Asn
            260                 265                 270
```

Ser Tyr Lys Cys Gly Thr Asn Thr Met Glu Arg Glu Glu Ser Glu Gln
            275                 280                 285

Thr Lys Lys Arg Glu Lys Ile His Ile Pro Glu Arg Ser Asp Glu Ala
        290                 295                 300

Gln Arg Val Phe Lys Ser Ser Lys Thr Ser Ser Cys Asp Lys Ser Asp
305                 310                 315                 320

Thr Cys Phe

<210> SEQ ID NO 10
<211> LENGTH: 329
<212> TYPE: PRT
<213> ORGANISM: homo sapiens

<400> SEQUENCE: 10

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
290                 295                 300

-continued

Glu Arg Ser Asp Glu Ala Gln Arg Val Phe Lys Ser Ser Lys Thr Ser
305                 310                 315                 320

Ser Cys Asp Lys Ser Asp Thr Cys Phe
            325

<210> SEQ ID NO 11
<211> LENGTH: 275
<212> TYPE: PRT
<213> ORGANISM: homo sapiens

<400> SEQUENCE: 11

Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
210                 215                 220

Pro Phe Ser Ile Gly Thr Asn Thr Met Glu Arg Glu Glu Ser Glu Gln
225                 230                 235                 240

Thr Lys Lys Arg Glu Lys Ile His Ile Pro Glu Arg Ser Asp Glu Ala
                245                 250                 255

Gln Arg Val Phe Lys Ser Ser Lys Thr Ser Ser Cys Asp Lys Ser Asp
            260                 265                 270

Thr Cys Phe
        275

<210> SEQ ID NO 12
<211> LENGTH: 374
<212> TYPE: PRT
<213> ORGANISM: homo sapiens

<400> SEQUENCE: 12

```
Met Trp Phe Leu Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
        130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370
```

<210> SEQ ID NO 13
<211> LENGTH: 424
<212> TYPE: PRT
<213> ORGANISM: homo sapiens

```
<400> SEQUENCE: 13

Met Asp Phe Ser Arg Arg Ser Phe His Arg Ser Leu Ser Ser Ser Leu
1               5                   10                  15

Gln Ala Pro Val Val Ser Thr Val Gly Met Gln Arg Leu Gly Thr Thr
            20                  25                  30

Pro Ser Val Tyr Gly Gly Ala Gly Gly Arg Gly Ile Arg Ile Ser Asn
        35                  40                  45

Ser Arg His Thr Val Asn Tyr Gly Ser Asp Leu Thr Gly Gly Gly Asp
    50                  55                  60

Leu Phe Val Gly Asn Glu Lys Met Ala Met Gln Asn Leu Asn Asp Arg
65                  70                  75                  80

Leu Ala Ser Tyr Leu Glu Lys Val Arg Thr Leu Glu Gln Ser Asn Ser
                85                  90                  95

Lys Leu Glu Val Gln Ile Lys Gln Trp Tyr Glu Thr Asn Ala Pro Arg
            100                 105                 110

Ala Gly Arg Asp Tyr Ser Ala Tyr Tyr Arg Gln Ile Glu Glu Leu Arg
        115                 120                 125

Ser Gln Ile Lys Asp Ala Gln Leu Gln Asn Ala Arg Cys Val Leu Gln
    130                 135                 140

Ile Asp Asn Ala Lys Leu Ala Ala Glu Asp Phe Arg Leu Lys Tyr Glu
145                 150                 155                 160

Thr Glu Arg Gly Ile Arg Leu Thr Val Glu Ala Asp Leu Gln Gly Leu
                165                 170                 175

Asn Lys Val Phe Asp Asp Leu Thr Leu His Lys Thr Asp Leu Glu Ile
            180                 185                 190

Gln Ile Glu Glu Leu Asn Lys Asp Leu Ala Leu Leu Lys Lys Glu His
        195                 200                 205

Gln Glu Glu Val Asp Gly Leu His Lys His Leu Gly Asn Thr Val Asn
    210                 215                 220

Val Glu Val Asp Ala Ala Pro Gly Leu Asn Leu Gly Val Ile Met Asn
225                 230                 235                 240

Glu Met Arg Gln Lys Tyr Glu Val Met Ala Gln Lys Asn Leu Gln Glu
                245                 250                 255

Ala Lys Glu Gln Phe Glu Arg Gln Thr Ala Val Leu Gln Gln Gln Val
            260                 265                 270

Thr Val Asn Thr Glu Glu Leu Lys Gly Thr Glu Val Gln Leu Thr Glu
    275                 280                 285

Leu Arg Arg Thr Ser Gln Ser Leu Glu Ile Glu Leu Gln Ser His Leu
290                 295                 300

Ser Met Lys Glu Ser Leu Glu His Thr Leu Glu Glu Thr Lys Ala Arg
305                 310                 315                 320

Tyr Ser Ser Gln Leu Ala Asn Leu Gln Ser Leu Leu Ser Ser Leu Glu
                325                 330                 335

Ala Gln Leu Met Gln Ile Arg Ser Asn Met Glu Arg Gln Asn Asn Glu
            340                 345                 350

Tyr His Ile Leu Leu Asp Ile Lys Thr Arg Leu Glu Gln Glu Ile Ala
    355                 360                 365

Thr Tyr Arg Arg Leu Leu Glu Gly Glu Asp Val Lys Thr Thr Glu Tyr
370                 375                 380

Gln Leu Ser Thr Leu Glu Glu Arg Asp Ile Lys Lys Thr Arg Lys Ile
385                 390                 395                 400
```

Lys Thr Val Val Gln Glu Val Asp Gly Lys Val Val Ser Ser Glu
                405                 410                 415

Val Lys Glu Val Glu Glu Asn Ile
            420

<210> SEQ ID NO 14
<211> LENGTH: 556
<212> TYPE: PRT
<213> ORGANISM: homo sapiens

<400> SEQUENCE: 14

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

```
Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Gly Gly Tyr Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 15
<211> LENGTH: 557
<212> TYPE: PRT
<213> ORGANISM: homo sapiens

<400> SEQUENCE: 15

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175
```

```
Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
                485                 490                 495

Gly Ser Gln Ser Tyr Glu Asp Met Arg Gly Ile Leu Tyr Ala Ala Pro
            500                 505                 510

Gln Leu Arg Ser Ile Arg Gly Gln Pro Gly Pro Asn His Glu Glu Asp
        515                 520                 525

Ala Asp Ser Tyr Glu Asn Met Asp Asn Pro Asp Gly Pro Asp Pro Ala
    530                 535                 540

Trp Gly Gly Gly Gly Arg Met Gly Thr Trp Ser Thr Arg
545                 550                 555

<210> SEQ ID NO 16
<211> LENGTH: 483
<212> TYPE: DNA
<213> ORGANISM: Artificial sequence
<220> FEATURE:
<223> OTHER INFORMATION: Streptavidin nucleic acid sequence
```

<400> SEQUENCE: 16

```
gacccgagca aagattctaa agcacaagta tctgctgcag aagcaggaat tacaggcaca      60
tggtataatc agctgggatc tacatttatt gttacagccg gcgcagatgg agctcttaca    120
ggaacatatg aatctgctgt tggaaatgca gaatctagat acgtgcttac aggaagatat    180
gattctgcac ctgcaacaga tggatccgga acagcacttg gatggacagt tgcatggaaa    240
aacaattata gaaacgcaca tagcgctaca acatggtctg ccaatatgt gggaggtgca      300
gaagcaagaa ttaacacaca atggctttta acatctggaa caacagaagc aaatgcatgg    360
aaaagtactc ttgttggaca tgatacattt acaaaagtta aacctagcgc agcatctatc    420
gatgcagcga aaaagcagg agttaacaat ggcaatcctt tagatgcagt tcaacaataa      480
tga                                                                   483
```

<210> SEQ ID NO 17
<211> LENGTH: 188
<212> TYPE: PRT
<213> ORGANISM: homo sapiens

<400> SEQUENCE: 17

```
Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Glu Pro Pro Arg Pro Phe Leu
                85                  90                  95

Asp Met Gly Glu Gly Thr Lys Asn Arg Ile Ile Thr Ala Glu Gly Ile
            100                 105                 110

Ile Leu Leu Phe Cys Ala Val Val Pro Gly Thr Leu Leu Leu Phe Arg
        115                 120                 125

Lys Arg Trp Gln Asn Glu Lys Leu Gly Leu Asp Ala Gly Asp Glu Tyr
    130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185
```

<210> SEQ ID NO 18
<211> LENGTH: 226
<212> TYPE: PRT
<213> ORGANISM: homo sapiens

<400> SEQUENCE: 18

```
Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30
```

```
Leu Trp Met His Lys Val Pro Ala Ser Leu Met Val Ser Leu Gly Glu
             35                  40                  45

Asp Ala His Phe Gln Cys Pro His Asn Ser Ser Asn Asn Ala Asn Val
 50                  55                  60

Thr Trp Trp Arg Val Leu His Gly Asn Tyr Thr Trp Pro Pro Glu Phe
 65                  70                  75                  80

Leu Gly Pro Gly Glu Asp Pro Asn Gly Thr Leu Ile Ile Gln Asn Val
                 85                  90                  95

Asn Lys Ser His Gly Gly Ile Tyr Val Cys Arg Val Gln Glu Gly Asn
                100                 105                 110

Glu Ser Tyr Gln Gln Ser Cys Gly Thr Tyr Leu Arg Val Arg Gln Pro
            115                 120                 125

Pro Pro Arg Pro Phe Leu Asp Met Gly Glu Gly Thr Lys Asn Arg Ile
        130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
210                 215                 220

Lys Pro
225

<210> SEQ ID NO 19
<211> LENGTH: 310
<212> TYPE: PRT
<213> ORGANISM: homo sapiens

<400> SEQUENCE: 19

Met Arg Arg Ala Ala Leu Trp Leu Trp Leu Cys Ala Leu Ala Leu Ser
 1               5                  10                  15

Leu Gln Pro Ala Leu Pro Gln Ile Val Ala Thr Asn Leu Pro Pro Glu
             20                  25                  30

Asp Gln Asp Gly Ser Gly Asp Asp Ser Asp Asn Phe Ser Gly Ser Gly
             35                  40                  45

Ala Gly Ala Leu Gln Asp Ile Thr Leu Ser Gln Gln Thr Pro Ser Thr
 50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
                100                 105                 110

Gly Leu Thr Ala Arg Glu Gln Glu Ala Thr Pro Arg Pro Arg Glu Thr
            115                 120                 125

Thr Gln Leu Pro Thr Thr His Gln Ala Ser Thr Thr Ala Thr Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175
```

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 20
<211> LENGTH: 310
<212> TYPE: PRT
<213> ORGANISM: homo sapiens

<400> SEQUENCE: 20

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

```
Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Asp Glu Gly Ser Tyr Ser Leu
        275                 280                 285

Glu Glu Pro Lys Gln Ala Asn Gly Gly Ala Tyr Gln Lys Pro Thr Lys
        290                 295                 300

Gln Glu Glu Phe Tyr Ala
305                 310

<210> SEQ ID NO 21
<211> LENGTH: 87
<212> TYPE: PRT
<213> ORGANISM: homo sapiens

<400> SEQUENCE: 21

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly His Leu Gln Ala Glu Gln Gly Ser Gln Ser Lys Ser Pro
        35                  40                  45

Asn Leu Lys Ser Arg Glu Ala Asp Ser Ser Ala Phe Ser Trp Trp Pro
50                  55                  60

Lys Ala Arg Glu Pro Leu Thr Asn His Trp Ser Lys Ser Lys Ser Pro
65                  70                  75                  80

Lys Ala Glu Glu Leu Gly Val
                85

<210> SEQ ID NO 22
<211> LENGTH: 1306
<212> TYPE: PRT
<213> ORGANISM: homo sapiens

<400> SEQUENCE: 22

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
    130                 135                 140

Ile Ser Asp Val Pro Gly Glu Arg Ser Thr Ala Ser Thr Phe Pro Thr
145                 150                 155                 160
```

-continued

Asp Pro Val Ser Pro Leu Thr Thr Thr Leu Ser Leu Ala His His Ser
                165                 170                 175

Ser Ala Ala Leu Pro Ala Arg Thr Ser Asn Thr Thr Ile Thr Ala Asn
            180                 185                 190

Thr Ser Asp Ala Tyr Leu Asn Ala Ser Glu Thr Thr Thr Leu Ser Pro
        195                 200                 205

Ser Gly Ser Ala Val Ile Ser Thr Thr Thr Ile Ala Thr Thr Pro Ser
    210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
            260                 265                 270

Leu Thr Glu Cys Lys Asn Ala Ser Val Ser Ile Ser His Asn Ser Cys
        275                 280                 285

Thr Ala Pro Asp Lys Thr Leu Ile Leu Asp Val Pro Pro Gly Val Glu
    290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
            340                 345                 350

Glu Ile Lys Leu Glu Asn Leu Glu Pro Glu His Glu Tyr Lys Cys Asp
        355                 360                 365

Ser Glu Ile Leu Tyr Asn Asn His Lys Phe Thr Asn Ala Ser Lys Ile
    370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
                405                 410                 415

Arg Ser Phe His Asn Phe Thr Leu Cys Tyr Ile Lys Glu Thr Glu Lys
            420                 425                 430

Asp Cys Leu Asn Leu Asp Lys Asn Leu Ile Lys Tyr Asp Leu Gln Asn
        435                 440                 445

Leu Lys Pro Tyr Thr Lys Tyr Val Leu Ser Leu His Ala Tyr Ile Ile
    450                 455                 460

Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
                485                 490                 495

Ser Asp Asn Ser Met His Val Lys Cys Arg Pro Pro Arg Asp Arg Asn
            500                 505                 510

Gly Pro His Glu Arg Tyr His Leu Glu Val Glu Ala Gly Asn Thr Leu
        515                 520                 525

Val Arg Asn Glu Ser His Lys Asn Cys Asp Phe Arg Val Lys Asp Leu
    530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
                565                 570                 575

```
Lys Ala Leu Ile Ala Phe Leu Ala Phe Leu Ile Ile Val Thr Ser Ile
                580                 585                 590

Ala Leu Leu Val Val Leu Tyr Lys Ile Tyr Asp Leu His Lys Lys Arg
        595                 600                 605

Ser Cys Asn Leu Asp Glu Gln Gln Glu Leu Val Glu Arg Asp Asp Glu
        610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655

Phe Gln Ser Ile Pro Arg Val Phe Ser Lys Phe Pro Ile Lys Glu Ala
                660                 665                 670

Arg Lys Pro Phe Asn Gln Asn Lys Asn Arg Tyr Val Asp Ile Leu Pro
                675                 680                 685

Tyr Asp Tyr Asn Arg Val Glu Leu Ser Glu Ile Asn Gly Asp Ala Gly
                690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
                740                 745                 750

Arg Cys Glu Glu Gly Asn Arg Asn Lys Cys Ala Glu Tyr Trp Pro Ser
                755                 760                 765

Met Glu Glu Gly Thr Arg Ala Phe Gly Asp Val Val Val Lys Ile Asn
        770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
                820                 825                 830

Lys Leu Arg Arg Arg Val Asn Ala Phe Ser Asn Phe Phe Ser Gly Pro
                835                 840                 845

Ile Val Val His Cys Ser Ala Gly Val Gly Arg Thr Gly Thr Tyr Ile
        850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
                900                 905                 910

Asn Gln Phe Gly Glu Thr Glu Val Asn Leu Ser Glu Leu His Pro Tyr
                915                 920                 925

Leu His Asn Met Lys Lys Arg Asp Pro Pro Ser Glu Pro Ser Pro Leu
        930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975

Val Ile Pro Tyr Asp Tyr Asn Arg Val Pro Leu Lys His Glu Leu Glu
                980                 985                 990
```

Met Ser Lys Glu Ser Glu His Asp  Ser Asp Glu Ser Ser  Asp Asp Asp
            995                 1000                 1005

Ser Asp Ser Glu Glu Pro Ser  Lys Tyr Ile Asn Ala  Ser Phe Ile
    1010                1015                 1020

Met Ser Tyr Trp Lys Pro Glu  Val Met Ile Ala Ala  Gln Gly Pro
    1025                1030                 1035

Leu Lys Glu Thr Ile Gly Asp  Phe Trp Gln Met Ile  Phe Gln Arg
    1040                1045                 1050

Lys Val Lys Val Ile Val Met  Leu Thr Glu Leu Lys  His Gly Asp
    1055                1060                 1065

Gln Glu Ile Cys Ala Gln Tyr  Trp Gly Glu Gly Lys  Gln Thr Tyr
    1070                1075                 1080

Gly Asp Ile Glu Val Asp Leu  Lys Asp Thr Asp Lys  Ser Ser Thr
    1085                1090                 1095

Tyr Thr Leu Arg Val Phe Glu  Leu Arg His Ser Lys  Arg Lys Asp
    1100                1105                 1110

Ser Arg Thr Val Tyr Gln Tyr  Gln Tyr Thr Asn Trp  Ser Val Glu
    1115                1120                 1125

Gln Leu Pro Ala Glu Pro Lys  Glu Leu Ile Ser Met  Ile Gln Val
    1130                1135                 1140

Val Lys Gln Lys Leu Pro Gln  Lys Asn Ser Ser Glu  Gly Asn Lys
    1145                1150                 1155

His His Lys Ser Thr Pro Leu  Leu Ile His Cys Arg  Asp Gly Ser
    1160                1165                 1170

Gln Gln Thr Gly Ile Phe Cys  Ala Leu Leu Asn Leu  Leu Glu Ser
    1175                1180                 1185

Ala Glu Thr Glu Glu Val Val  Asp Ile Phe Gln Val  Val Lys Ala
    1190                1195                 1200

Leu Arg Lys Ala Arg Pro Gly  Met Val Ser Thr Phe  Glu Gln Tyr
    1205                1210                 1215

Gln Phe Leu Tyr Asp Val Ile  Ala Ser Thr Tyr Pro  Ala Gln Asn
    1220                1225                 1230

Gly Gln Val Lys Lys Asn Asn  His Gln Glu Asp Lys  Ile Glu Phe
    1235                1240                 1245

Asp Asn Glu Val Asp Lys Val  Lys Gln Asp Ala Asn  Cys Val Asn
    1250                1255                 1260

Pro Leu Gly Ala Pro Glu Lys  Leu Pro Glu Ala Lys  Glu Gln Ala
    1265                1270                 1275

Glu Gly Ser Glu Pro Thr Ser  Gly Thr Glu Gly Pro  Glu His Ser
    1280                1285                 1290

Val Asn Gly Pro Ala Ser Pro  Ala Leu Asn Gln Gly  Ser
    1295                1300                 1305

<210> SEQ ID NO 23
<211> LENGTH: 1145
<212> TYPE: PRT
<213> ORGANISM: homo sapiens

<400> SEQUENCE: 23

Met Thr Met Tyr Leu Trp Leu  Lys Leu Leu Ala Phe  Gly Phe Ala Phe
1               5                    10                   15

Leu Asp Thr Glu Val Phe Val  Thr Gly Gln Ser Pro  Thr Pro Ser Pro
            20                   25                   30

Thr Asp Ala Tyr Leu Asn Ala  Ser Glu Thr Thr Thr  Leu Ser Pro Ser
        35                   40                   45

```
Gly Ser Ala Val Ile Ser Thr Thr Ile Ala Thr Thr Pro Ser Lys
 50                  55                  60

Pro Thr Cys Asp Glu Lys Tyr Ala Asn Ile Thr Val Asp Tyr Leu Tyr
 65                  70                  75                  80

Asn Lys Glu Thr Lys Leu Phe Thr Ala Lys Leu Asn Val Asn Glu Asn
                 85                  90                  95

Val Glu Cys Gly Asn Asn Thr Cys Thr Asn Asn Glu Val His Asn Leu
            100                 105                 110

Thr Glu Cys Lys Asn Ala Ser Val Ser Ile Ser His Asn Ser Cys Thr
        115                 120                 125

Ala Pro Asp Lys Thr Leu Ile Leu Asp Val Pro Pro Gly Val Glu Lys
130                 135                 140

Phe Gln Leu His Asp Cys Thr Gln Val Glu Lys Ala Asp Thr Thr Ile
145                 150                 155                 160

Cys Leu Lys Trp Lys Asn Ile Glu Thr Phe Thr Cys Asp Thr Gln Asn
                165                 170                 175

Ile Thr Tyr Arg Phe Gln Cys Gly Asn Met Ile Phe Asp Asn Lys Glu
            180                 185                 190

Ile Lys Leu Glu Asn Leu Glu Pro Glu His Glu Tyr Lys Cys Asp Ser
        195                 200                 205

Glu Ile Leu Tyr Asn Asn His Lys Phe Thr Asn Ala Ser Lys Ile Ile
210                 215                 220

Lys Thr Asp Phe Gly Ser Pro Gly Glu Pro Gln Ile Ile Phe Cys Arg
225                 230                 235                 240

Ser Glu Ala Ala His Gln Gly Val Ile Thr Trp Asn Pro Pro Gln Arg
                245                 250                 255

Ser Phe His Asn Phe Thr Leu Cys Tyr Ile Lys Glu Thr Glu Lys Asp
            260                 265                 270

Cys Leu Asn Leu Asp Lys Asn Leu Ile Lys Tyr Asp Leu Gln Asn Leu
        275                 280                 285

Lys Pro Tyr Thr Lys Tyr Val Leu Ser Leu His Ala Tyr Ile Ile Ala
290                 295                 300

Lys Val Gln Arg Asn Gly Ser Ala Ala Met Cys His Phe Thr Thr Lys
305                 310                 315                 320

Ser Ala Pro Pro Ser Gln Val Trp Asn Met Thr Val Ser Met Thr Ser
                325                 330                 335

Asp Asn Ser Met His Val Lys Cys Arg Pro Pro Arg Asp Arg Asn Gly
            340                 345                 350

Pro His Glu Arg Tyr His Leu Glu Val Glu Ala Gly Asn Thr Leu Val
        355                 360                 365

Arg Asn Glu Ser His Lys Asn Cys Asp Phe Arg Val Lys Asp Leu Gln
370                 375                 380

Tyr Ser Thr Asp Tyr Thr Phe Lys Ala Tyr Phe His Asn Gly Asp Tyr
385                 390                 395                 400

Pro Gly Glu Pro Phe Ile Leu His His Ser Thr Ser Tyr Asn Ser Lys
                405                 410                 415

Ala Leu Ile Ala Phe Leu Ala Phe Leu Ile Ile Val Thr Ser Ile Ala
            420                 425                 430

Leu Leu Val Val Leu Tyr Lys Ile Tyr Asp Leu His Lys Lys Arg Ser
        435                 440                 445

Cys Asn Leu Asp Glu Gln Gln Glu Leu Val Glu Arg Asp Asp Glu Lys
450                 455                 460
```

```
Gln Leu Met Asn Val Glu Pro Ile His Ala Asp Ile Leu Leu Glu Thr
465                 470                 475                 480

Tyr Lys Arg Lys Ile Ala Asp Glu Gly Arg Leu Phe Leu Ala Glu Phe
                485                 490                 495

Gln Ser Ile Pro Arg Val Phe Ser Lys Phe Pro Ile Lys Glu Ala Arg
            500                 505                 510

Lys Pro Phe Asn Gln Asn Lys Asn Arg Tyr Val Asp Ile Leu Pro Tyr
        515                 520                 525

Asp Tyr Asn Arg Val Glu Leu Ser Glu Ile Asn Gly Asp Ala Gly Ser
    530                 535                 540

Asn Tyr Ile Asn Ala Ser Tyr Ile Asp Gly Phe Lys Glu Pro Arg Lys
545                 550                 555                 560

Tyr Ile Ala Ala Gln Gly Pro Arg Asp Glu Thr Val Asp Asp Phe Trp
                565                 570                 575

Arg Met Ile Trp Glu Gln Lys Ala Thr Val Ile Val Met Val Thr Arg
            580                 585                 590

Cys Glu Glu Gly Asn Arg Asn Lys Cys Ala Glu Tyr Trp Pro Ser Met
        595                 600                 605

Glu Glu Gly Thr Arg Ala Phe Gly Asp Val Val Lys Ile Asn Gln
    610                 615                 620

His Lys Arg Cys Pro Asp Tyr Ile Ile Gln Lys Leu Asn Ile Val Asn
625                 630                 635                 640

Lys Lys Glu Lys Ala Thr Gly Arg Glu Val Thr His Ile Gln Phe Thr
                645                 650                 655

Ser Trp Pro Asp His Gly Val Pro Glu Asp Pro His Leu Leu Leu Lys
            660                 665                 670

Leu Arg Arg Arg Val Asn Ala Phe Ser Asn Phe Phe Ser Gly Pro Ile
        675                 680                 685

Val Val His Cys Ser Ala Gly Val Gly Arg Thr Gly Thr Tyr Ile Gly
    690                 695                 700

Ile Asp Ala Met Leu Glu Gly Leu Glu Ala Glu Asn Lys Val Asp Val
705                 710                 715                 720

Tyr Gly Tyr Val Val Lys Leu Arg Arg Gln Arg Cys Leu Met Val Gln
                725                 730                 735

Val Glu Ala Gln Tyr Ile Leu Ile His Gln Ala Leu Val Glu Tyr Asn
            740                 745                 750

Gln Phe Gly Glu Thr Glu Val Asn Leu Ser Glu Leu His Pro Tyr Leu
        755                 760                 765

His Asn Met Lys Lys Arg Asp Pro Pro Ser Glu Pro Ser Pro Leu Glu
    770                 775                 780

Ala Glu Phe Gln Arg Leu Pro Ser Tyr Arg Ser Trp Arg Thr Gln His
785                 790                 795                 800

Ile Gly Asn Gln Glu Glu Asn Lys Ser Lys Asn Arg Asn Ser Asn Val
                805                 810                 815

Ile Pro Tyr Asp Tyr Asn Arg Val Pro Leu Lys His Glu Leu Glu Met
            820                 825                 830

Ser Lys Glu Ser Glu His Asp Ser Asp Glu Ser Ser Asp Asp Asp Ser
        835                 840                 845

Asp Ser Glu Glu Pro Ser Lys Tyr Ile Asn Ala Ser Phe Ile Met Ser
    850                 855                 860

Tyr Trp Lys Pro Glu Val Met Ile Ala Ala Gln Gly Pro Leu Lys Glu
865                 870                 875                 880
```

Thr Ile Gly Asp Phe Trp Gln Met Ile Phe Gln Arg Lys Val Lys Val
                885                 890                 895

Ile Val Met Leu Thr Glu Leu Lys His Gly Asp Gln Glu Ile Cys Ala
            900                 905                 910

Gln Tyr Trp Gly Glu Gly Lys Gln Thr Tyr Gly Asp Ile Glu Val Asp
        915                 920                 925

Leu Lys Asp Thr Asp Lys Ser Ser Thr Tyr Thr Leu Arg Val Phe Glu
930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
                965                 970                 975

Ile Ser Met Ile Gln Val Val Lys Gln Lys Leu Pro Gln Lys Asn Ser
            980                 985                 990

Ser Glu Gly Asn Lys His His Lys Ser Thr Pro Leu Leu Ile His Cys
        995                 1000                1005

Arg Asp Gly Ser Gln Gln Thr Gly Ile Phe Cys Ala Leu Leu Asn
    1010                1015                1020

Leu Leu Glu Ser Ala Glu Thr Glu Glu Val Val Asp Ile Phe Gln
    1025                1030                1035

Val Val Lys Ala Leu Arg Lys Ala Arg Pro Gly Met Val Ser Thr
    1040                1045                1050

Phe Glu Gln Tyr Gln Phe Leu Tyr Asp Val Ile Ala Ser Thr Tyr
    1055                1060                1065

Pro Ala Gln Asn Gly Gln Val Lys Lys Asn Asn His Gln Glu Asp
    1070                1075                1080

Lys Ile Glu Phe Asp Asn Glu Val Asp Lys Val Lys Gln Asp Ala
    1085                1090                1095

Asn Cys Val Asn Pro Leu Gly Ala Pro Glu Lys Leu Pro Glu Ala
    1100                1105                1110

Lys Glu Gln Ala Glu Gly Ser Glu Pro Thr Ser Gly Thr Glu Gly
    1115                1120                1125

Pro Glu His Ser Val Asn Gly Pro Ala Ser Pro Ala Leu Asn Gln
    1130                1135                1140

Gly Ser
    1145

<210> SEQ ID NO 24
<211> LENGTH: 349
<212> TYPE: PRT
<213> ORGANISM: homo sapiens

<400> SEQUENCE: 24

Met Gly Pro Ile Ser Ala Pro Ser Cys Arg Trp Arg Ile Pro Trp Gln
1               5                   10                  15

Gly Leu Leu Leu Thr Ala Ser Leu Phe Thr Phe Trp Asn Pro Pro Thr
            20                  25                  30

Thr Ala Gln Leu Thr Ile Glu Ala Val Pro Ser Asn Ala Ala Glu Gly
        35                  40                  45

Lys Glu Val Leu Leu Val His Asn Leu Pro Gln Asp Pro Arg Gly
    50                  55                  60

Tyr Asn Trp Tyr Lys Gly Glu Thr Val Asp Ala Asn Arg Arg Ile Ile
65                  70                  75                  80

Gly Tyr Val Ile Ser Asn Gln Gln Ile Thr Pro Gly Pro Ala Tyr Ser
                85                  90                  95

Asn Arg Glu Thr Ile Tyr Pro Asn Ala Ser Leu Leu Met Arg Asn Val
            100                 105                 110

Thr Arg Asn Asp Thr Gly Ser Tyr Thr Leu Gln Val Ile Lys Leu Asn
        115                 120                 125

Leu Met Ser Glu Glu Val Thr Gly Gln Phe Ser Val His Pro Glu Thr
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Val Gly Pro Tyr Glu Cys Glu Ile Gln Asn Pro Ala Ser Ala Asn
    210                 215                 220

Phe Ser Asp Pro Val Thr Leu Asn Val Leu Tyr Gly Pro Asp Ala Pro
225                 230                 235                 240

Thr Ile Ser Pro Ser Asp Thr Tyr Tyr His Ala Gly Val Asn Leu Asn
                245                 250                 255

Leu Ser Cys His Ala Ala Ser Asn Pro Pro Ser Gln Tyr Ser Trp Ser
            260                 265                 270

Val Asn Gly Thr Phe Gln Gln Tyr Thr Gln Lys Leu Phe Ile Pro Asn
        275                 280                 285

Ile Thr Thr Lys Asn Ser Gly Ser Tyr Ala Cys His Thr Thr Asn Ser
    290                 295                 300

Ala Thr Gly Arg Asn Arg Thr Thr Val Arg Met Ile Thr Val Ser Asp
305                 310                 315                 320

Ala Leu Val Gln Gly Ser Ser Pro Gly Leu Ser Ala Arg Ala Thr Val
                325                 330                 335

Ser Ile Met Ile Gly Val Leu Ala Arg Val Ala Leu Ile
            340                 345

<210> SEQ ID NO 25
<211> LENGTH: 290
<212> TYPE: PRT
<213> ORGANISM: homo sapiens

<400> SEQUENCE: 25

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Pro Thr Ala Leu Leu Leu
        35                  40                  45

Leu Val Ser Ala Gly Met Arg Thr Glu Asp Leu Pro Lys Ala Val Val
    50                  55                  60

Phe Leu Glu Pro Gln Trp Tyr Arg Val Leu Glu Lys Asp Ser Val Thr
65                  70                  75                  80

Leu Lys Cys Gln Gly Ala Tyr Ser Pro Glu Asp Asn Ser Thr Gln Trp
                85                  90                  95

Phe His Asn Glu Ser Leu Ile Ser Ser Gln Ala Ser Ser Tyr Phe Ile
            100                 105                 110

Asp Ala Ala Thr Val Asp Asp Ser Gly Glu Tyr Arg Cys Gln Thr Asn
        115                 120                 125

Leu Ser Thr Leu Ser Asp Pro Val Gln Leu Glu Val His Ile Gly Trp
130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
                180                 185                 190

Phe Tyr Ile Pro Lys Ala Thr Leu Lys Asp Ser Gly Ser Tyr Phe Cys
            195                 200                 205

Arg Gly Leu Phe Gly Ser Lys Asn Val Ser Ser Glu Thr Val Asn Ile
210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
                260                 265                 270

Thr Arg Asp Trp Lys Asp His Lys Phe Lys Trp Arg Lys Asp Pro Gln
                275                 280                 285

Asp Lys
    290

<210> SEQ ID NO 26
<211> LENGTH: 289
<212> TYPE: PRT
<213> ORGANISM: homo sapiens

<400> SEQUENCE: 26

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
                20                  25                  30

Gln Cys Gly Ile Met Trp Gln Leu Leu Pro Thr Ala Leu Leu Leu
            35                  40                  45

Leu Val Ser Ala Gly Met Arg Thr Asp Leu Pro Lys Ala Val Val Phe
50                  55                  60

Leu Glu Pro Gln Trp Tyr Arg Val Leu Glu Lys Asp Ser Val Thr Leu
65                  70                  75                  80

Lys Cys Gln Gly Ala Tyr Ser Pro Glu Asp Asn Ser Thr Gln Trp Phe
                85                  90                  95

His Asn Glu Ser Leu Ile Ser Ser Gln Ala Ser Ser Tyr Phe Ile Asp
                100                 105                 110

Ala Ala Thr Val Asp Asp Ser Gly Glu Tyr Arg Cys Gln Thr Asn Leu
            115                 120                 125

Ser Thr Leu Ser Asp Pro Val Gln Leu Glu Val His Ile Gly Trp Leu
130                 135                 140

Leu Leu Gln Ala Pro Arg Trp Val Phe Lys Glu Glu Asp Pro Ile His
145                 150                 155                 160

Leu Arg Cys His Ser Trp Lys Asn Thr Ala Leu His Lys Val Thr Tyr
                165                 170                 175

Leu Gln Asn Gly Lys Gly Arg Lys Tyr Phe His His Asn Ser Asp Phe
            180                 185                 190

Tyr Ile Pro Lys Ala Thr Leu Lys Asp Ser Gly Ser Tyr Phe Cys Arg
            195                 200                 205

```
Gly Leu Phe Gly Ser Lys Asn Val Ser Ser Glu Thr Val Asn Ile Thr
            210                 215                 220

Ile Thr Gln Gly Leu Ala Val Ser Thr Ile Ser Ser Phe Phe Pro Pro
225                 230                 235                 240

Gly Tyr Gln Val Ser Phe Cys Leu Val Met Val Leu Leu Phe Ala Val
            245                 250                 255

Asp Thr Gly Leu Tyr Phe Ser Val Lys Thr Asn Ile Arg Ser Ser Thr
            260                 265                 270

Arg Asp Trp Lys Asp His Lys Phe Lys Trp Arg Lys Asp Pro Gln Asp
            275                 280                 285

Lys
```

<210> SEQ ID NO 27
<211> LENGTH: 254
<212> TYPE: PRT
<213> ORGANISM: homo sapiens

<400> SEQUENCE: 27

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 28
<211> LENGTH: 254
<212> TYPE: PRT
<213> ORGANISM: homo sapiens

```
<400> SEQUENCE: 28

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
                115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
                195                 200                 205

Val Ser Phe Cys Leu Val Met Val Leu Leu Phe Ala Val Asp Thr Gly
                210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 29
<211> LENGTH: 253
<212> TYPE: PRT
<213> ORGANISM: homo sapiens

<400> SEQUENCE: 29

Met Trp Gln Leu Leu Leu Pro Thr Ala Leu Leu Leu Val Ser Ala
1               5                   10                  15

Gly Met Arg Thr Asp Leu Pro Lys Ala Val Val Phe Leu Glu Pro Gln
            20                  25                  30

Trp Tyr Arg Val Leu Glu Lys Asp Ser Val Thr Leu Lys Cys Gln Gly
        35                  40                  45

Ala Tyr Ser Pro Glu Asp Asn Ser Thr Gln Trp Phe His Asn Glu Ser
    50                  55                  60

Leu Ile Ser Ser Gln Ala Ser Ser Tyr Phe Ile Asp Ala Ala Thr Val
65                  70                  75                  80

Asp Asp Ser Gly Glu Tyr Arg Cys Gln Thr Asn Leu Ser Thr Leu Ser
                85                  90                  95

Asp Pro Val Gln Leu Glu Val His Ile Gly Trp Leu Leu Leu Gln Ala
                100                 105                 110
```

```
Pro Arg Trp Val Phe Lys Glu Glu Asp Pro Ile His Leu Arg Cys His
            115                 120                 125

Ser Trp Lys Asn Thr Ala Leu His Lys Val Thr Tyr Leu Gln Asn Gly
130                 135                 140

Lys Gly Arg Lys Tyr Phe His His Asn Ser Asp Phe Tyr Ile Pro Lys
145                 150                 155                 160

Ala Thr Leu Lys Asp Ser Gly Ser Tyr Phe Cys Arg Gly Leu Phe Gly
                165                 170                 175

Ser Lys Asn Val Ser Ser Glu Thr Val Asn Ile Thr Ile Thr Gln Gly
            180                 185                 190

Leu Ala Val Ser Thr Ile Ser Ser Phe Phe Pro Pro Gly Tyr Gln Val
        195                 200                 205

Ser Phe Cys Leu Val Met Val Leu Leu Phe Ala Val Asp Thr Gly Leu
    210                 215                 220

Tyr Phe Ser Val Lys Thr Asn Ile Arg Ser Ser Thr Arg Asp Trp Lys
225                 230                 235                 240

Asp His Lys Phe Lys Trp Arg Lys Asp Pro Gln Asp Lys
                245                 250

<210> SEQ ID NO 30
<211> LENGTH: 1156
<212> TYPE: PRT
<213> ORGANISM: homo sapiens

<400> SEQUENCE: 30

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240
```

-continued

```
Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
        260                 265                 270

Thr Glu Cys Ser Gly Arg Leu Glu Val Arg Phe Gln Gly Glu Trp Gly
    275                 280                 285

Thr Ile Cys Asp Asp Gly Trp Asp Ser Tyr Asp Ala Ala Val Ala Cys
290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                325                 330                 335

Gly His Glu Pro Ala Ile Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Ile Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Gly Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655
```

```
Gln His Met Gly Asp Cys Pro Val Thr Ala Leu Gly Ala Ser Leu Cys
                660                 665                 670

Pro Ser Glu Gln Val Ala Ser Val Ile Cys Ser Gly Asn Gln Ser Gln
            675                 680                 685

Thr Leu Ser Ser Cys Asn Ser Ser Ser Leu Gly Pro Thr Arg Pro Thr
        690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
        770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Thr Val Gly Lys Ser Ser Met Ser Glu Thr Thr Val Gly Val Val Cys
        850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
        915                 920                 925

Ile Arg Leu Gln Glu Gly Pro Thr Ser Cys Ser Gly Arg Val Glu Ile
        930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
        995                 1000                1005

Pro Ala Arg Arg Trp Gly His Ser Glu Cys Gly His Lys Glu Asp
        1010                1015                1020

Ala Ala Val Asn Cys Thr Asp Ile Ser Val Gln Lys Thr Pro Gln
        1025                1030                1035

Lys Ala Thr Thr Gly Arg Ser Arg Gln Ser Ser Phe Ile Ala
        1040                1045                1050

Val Gly Ile Leu Gly Val Val Leu Leu Ala Ile Phe Val Ala Leu
        1055                1060                1065
```

-continued

```
Phe Phe Leu Thr Lys Lys Arg Arg Gln Arg Gln Arg Leu Ala Val
1070                1075                1080

Ser Ser Arg Gly Glu Asn Leu Val His Gln Ile Gln Tyr Arg Glu
    1085                1090                1095

Met Asn Ser Cys Leu Asn Ala Asp Asp Leu Asp Leu Met Asn Ser
1100                1105                1110

Ser Glu Asn Ser His Glu Ser Ala Asp Phe Ser Ala Ala Glu Leu
    1115                1120                1125

Ile Ser Val Ser Lys Phe Leu Pro Ile Ser Gly Met Glu Lys Glu
1130                1135                1140

Ala Ile Leu Ser His Thr Glu Lys Glu Asn Gly Asn Leu
    1145                1150                1155

<210> SEQ ID NO 31
<211> LENGTH: 1121
<212> TYPE: PRT
<213> ORGANISM: homo sapiens

<400> SEQUENCE: 31

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
        50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285
```

-continued

```
Thr Ile Cys Asp Asp Gly Trp Asp Ser Tyr Asp Ala Val Ala Cys
    290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                325                 330                 335

Gly His Glu Pro Ala Ile Trp Gln Cys Lys His His Glu Trp Gly Lys
                340                 345                 350

His Tyr Cys Asn His Asn Glu Asp Ala Gly Val Thr Cys Ser Asp Gly
    355                 360                 365

Ser Asp Leu Glu Leu Arg Leu Arg Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
                420                 425                 430

Thr Asn Thr Trp Leu Phe Leu Ser Ser Cys Asn Gly Asn Glu Thr Ser
                435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Ile Cys Asp Ser Asp Phe Ser Leu Glu Ala Ala
                500                 505                 510

Ser Val Leu Cys Arg Glu Leu Gln Cys Gly Thr Val Val Ser Ile Leu
    515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
                580                 585                 590

Glu Gly Arg Val Glu Leu Lys Thr Leu Gly Ala Trp Gly Ser Leu Cys
                595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
                660                 665                 670

Pro Ser Glu Gln Val Ala Ser Val Ile Cys Ser Gly Asn Gln Ser Gln
                675                 680                 685

Thr Leu Ser Ser Cys Asn Ser Ser Leu Gly Pro Thr Arg Pro Thr
    690                 695                 700
```

```
Ile Pro Glu Glu Ser Ala Val Ala Cys Ile Ser Gly Gln Leu Arg
705                 710                 715                 720

Leu Val Asn Gly Gly Arg Cys Ala Gly Arg Val Glu Ile Tyr His
            725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
            755                 760                 765

Thr Gly Ser Ala His Phe Gly Glu Gly Thr Gly Pro Ile Trp Leu Asp
            770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
            805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
            835                 840                 845

Thr Val Gly Lys Ser Ser Met Ser Glu Thr Thr Val Gly Val Val Cys
850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
            885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
            915                 920                 925

Ile Arg Leu Gln Glu Gly Pro Thr Ser Cys Ser Gly Arg Val Glu Ile
            930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
            965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
            995                 1000                1005

Pro Ala Arg Arg Trp Gly His Ser Glu Cys Gly His Lys Glu Asp
        1010                1015                1020

Ala Ala Val Asn Cys Thr Asp Ile Ser Val Gln Lys Thr Pro Gln
        1025                1030                1035

Lys Ala Thr Thr Gly Arg Ser Ser Arg Gln Ser Ser Phe Ile Ala
        1040                1045                1050

Val Gly Ile Leu Gly Val Val Leu Leu Ala Ile Phe Val Ala Leu
        1055                1060                1065

Phe Phe Leu Thr Lys Lys Arg Arg Gln Arg Gln Arg Leu Ala Val
        1070                1075                1080

Ser Ser Arg Gly Glu Asn Leu Val His Gln Ile Gln Tyr Arg Glu
        1085                1090                1095
```

```
Met Asn Ser Cys Leu Asn Ala Asp Asp Leu Asp Leu Met Asn Ser
    1100                1105                1110

Ser Gly Gly His Ser Glu Pro His
    1115                1120

<210> SEQ ID NO 32
<211> LENGTH: 1456
<212> TYPE: PRT
<213> ORGANISM: homo sapiens

<400> SEQUENCE: 32

Met Arg Leu Pro Leu Leu Leu Val Phe Ala Ser Val Ile Pro Gly Ala
1               5                   10                  15

Val Leu Leu Leu Asp Thr Arg Gln Phe Leu Ile Tyr Asn Glu Asp His
            20                  25                  30

Lys Arg Cys Val Asp Ala Val Ser Pro Ser Ala Val Gln Thr Ala Ala
        35                  40                  45

Cys Asn Gln Asp Ala Glu Ser Gln Lys Phe Arg Trp Val Ser Glu Ser
    50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
    130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
    210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
    290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Thr Thr Leu Asn Ser Phe Val Ile
            340                 345                 350
```

-continued

```
Pro Ser Glu Ser Asp Val Pro Thr His Cys Pro Ser Gln Trp Trp Pro
            355                 360                 365
Tyr Ala Gly His Cys Tyr Lys Ile His Arg Asp Glu Lys Lys Ile Gln
        370                 375                 380
Arg Asp Ala Leu Thr Thr Cys Arg Lys Glu Gly Gly Asp Leu Thr Ser
385                 390                 395                 400
Ile His Thr Ile Glu Glu Leu Asp Phe Ile Ile Ser Gln Leu Gly Tyr
                405                 410                 415
Glu Pro Asn Asp Glu Leu Trp Ile Gly Leu Asn Asp Ile Lys Ile Gln
                420                 425                 430
Met Tyr Phe Glu Trp Ser Asp Gly Thr Pro Val Thr Phe Thr Lys Trp
        435                 440                 445
Leu Arg Gly Glu Pro Ser His Glu Asn Asn Arg Gln Glu Asp Cys Val
    450                 455                 460
Val Met Lys Gly Lys Asp Gly Tyr Trp Ala Asp Arg Gly Cys Glu Trp
465                 470                 475                 480
Pro Leu Gly Tyr Ile Cys Lys Met Lys Ser Arg Ser Gln Gly Pro Glu
                485                 490                 495
Ile Val Glu Val Glu Lys Gly Cys Arg Lys Gly Trp Lys Lys His His
                500                 505                 510
Phe Tyr Cys Tyr Met Ile Gly His Thr Leu Ser Thr Phe Ala Glu Ala
        515                 520                 525
Asn Gln Thr Cys Asn Asn Glu Asn Ala Tyr Leu Thr Thr Ile Glu Asp
    530                 535                 540
Arg Tyr Glu Gln Ala Phe Leu Thr Ser Phe Val Gly Leu Arg Pro Glu
545                 550                 555                 560
Lys Tyr Phe Trp Thr Gly Leu Ser Asp Ile Gln Thr Lys Gly Thr Phe
                565                 570                 575
Gln Trp Thr Ile Glu Glu Val Arg Phe Thr His Trp Asn Ser Asp
                580                 585                 590
Met Pro Gly Arg Lys Pro Gly Cys Val Ala Met Arg Thr Gly Ile Ala
        595                 600                 605
Gly Gly Leu Trp Asp Val Leu Lys Cys Asp Glu Lys Ala Lys Phe Val
    610                 615                 620
Cys Lys His Trp Ala Glu Gly Val Thr His Pro Pro Lys Pro Thr Thr
625                 630                 635                 640
Thr Pro Glu Pro Lys Cys Pro Glu Asp Trp Gly Ala Ser Ser Arg Thr
                645                 650                 655
Ser Leu Cys Phe Lys Leu Tyr Ala Lys Gly Lys His Glu Lys Lys Thr
                660                 665                 670
Trp Phe Glu Ser Arg Asp Phe Cys Arg Ala Leu Gly Gly Asp Leu Ala
        675                 680                 685
Ser Ile Asn Asn Lys Glu Glu Gln Gln Thr Ile Trp Arg Leu Ile Thr
    690                 695                 700
Ala Ser Gly Ser Tyr His Lys Leu Phe Trp Leu Gly Leu Thr Tyr Gly
705                 710                 715                 720
Ser Pro Ser Glu Gly Phe Thr Trp Ser Asp Gly Ser Pro Val Ser Tyr
                725                 730                 735
Glu Asn Trp Ala Tyr Gly Glu Pro Asn Asn Tyr Gln Asn Val Glu Tyr
                740                 745                 750
Cys Gly Glu Leu Lys Gly Asp Pro Thr Met Ser Trp Asn Asp Ile Asn
        755                 760                 765
```

Cys Glu His Leu Asn Asn Trp Ile Cys Gln Ile Gln Lys Gly Gln Thr
770                 775                 780

Pro Lys Pro Glu Pro Thr Pro Ala Pro Gln Asp Asn Pro Pro Val Thr
785                 790                 795                 800

Glu Asp Gly Trp Val Ile Tyr Lys Asp Tyr Gln Tyr Tyr Phe Ser Lys
            805                 810                 815

Glu Lys Glu Thr Met Asp Asn Ala Arg Ala Phe Cys Lys Arg Asn Phe
            820                 825                 830

Gly Asp Leu Val Ser Ile Gln Ser Glu Ser Lys Lys Phe Leu Trp
            835                 840                 845

Lys Tyr Val Asn Arg Asn Asp Ala Gln Ser Ala Tyr Phe Ile Gly Leu
850                 855                 860

Leu Ile Ser Leu Asp Lys Lys Phe Ala Trp Met Asp Gly Ser Lys Val
865                 870                 875                 880

Asp Tyr Val Ser Trp Ala Thr Gly Glu Pro Asn Phe Ala Asn Glu Asp
            885                 890                 895

Glu Asn Cys Val Thr Met Tyr Ser Asn Ser Gly Phe Trp Asn Asp Ile
            900                 905                 910

Asn Cys Gly Tyr Pro Asn Ala Phe Ile Cys Gln Arg His Asn Ser Ser
            915                 920                 925

Ile Asn Ala Thr Thr Val Met Pro Thr Met Pro Ser Val Pro Ser Gly
930                 935                 940

Cys Lys Glu Gly Trp Asn Phe Tyr Ser Asn Lys Cys Phe Lys Ile Phe
945                 950                 955                 960

Gly Phe Met Glu Glu Glu Arg Lys Asn Trp Gln Glu Ala Arg Lys Ala
            965                 970                 975

Cys Ile Gly Phe Gly Gly Asn Leu Val Ser Ile Gln Asn Glu Lys Glu
            980                 985                 990

Gln Ala Phe Leu Thr Tyr His Met Lys Asp Ser Thr Phe Ser Ala Trp
            995                 1000                1005

Thr Gly Leu Asn Asp Val Asn Ser Glu His Thr Phe Leu Trp Thr
1010                1015                1020

Asp Gly Arg Gly Val His Tyr Thr Asn Trp Gly Lys Gly Tyr Pro
1025                1030                1035

Gly Gly Arg Arg Ser Ser Leu Ser Tyr Glu Asp Ala Asp Cys Val
1040                1045                1050

Val Ile Ile Gly Gly Ala Ser Asn Glu Ala Gly Lys Trp Met Asp
1055                1060                1065

Asp Thr Cys Asp Ser Lys Arg Gly Tyr Ile Cys Gln Thr Arg Ser
1070                1075                1080

Asp Pro Ser Leu Thr Asn Pro Pro Ala Thr Ile Gln Thr Asp Gly
1085                1090                1095

Phe Val Lys Tyr Gly Lys Ser Ser Tyr Ser Leu Met Arg Gln Lys
1100                1105                1110

Phe Gln Trp His Glu Ala Glu Thr Tyr Cys Lys Leu His Asn Ser
1115                1120                1125

Leu Ile Ala Ser Ile Leu Asp Pro Tyr Ser Asn Ala Phe Ala Trp
1130                1135                1140

Leu Gln Met Glu Thr Ser Asn Glu Arg Val Trp Ile Ala Leu Asn
1145                1150                1155

Ser Asn Leu Thr Asp Asn Gln Tyr Thr Trp Thr Asp Lys Trp Arg
1160                1165                1170

Val Arg Tyr Thr Asn Trp Ala Ala Asp Glu Pro Lys Leu Lys Ser
1175                1180                1185

Ala Cys Val Tyr Leu Asp Leu Asp Gly Tyr Trp Lys Thr Ala His
1190                1195                1200

Cys Asn Glu Ser Phe Tyr Phe Leu Cys Lys Arg Ser Asp Glu Ile
1205                1210                1215

Pro Ala Thr Glu Pro Pro Gln Leu Pro Gly Arg Cys Pro Glu Ser
1220                1225                1230

Asp His Thr Ala Trp Ile Pro Phe His Gly His Cys Tyr Tyr Ile
1235                1240                1245

Glu Ser Ser Tyr Thr Arg Asn Trp Gly Gln Ala Ser Leu Glu Cys
1250                1255                1260

Leu Arg Met Gly Ser Ser Leu Val Ser Ile Glu Ser Ala Ala Glu
1265                1270                1275

Ser Ser Phe Leu Ser Tyr Arg Val Glu Pro Leu Lys Ser Lys Thr
1280                1285                1290

Asn Phe Trp Ile Gly Leu Phe Arg Asn Val Glu Gly Thr Trp Leu
1295                1300                1305

Trp Ile Asn Asn Ser Pro Val Ser Phe Val Asn Trp Asn Thr Gly
1310                1315                1320

Asp Pro Ser Gly Glu Arg Asn Asp Cys Val Ala Leu His Ala Ser
1325                1330                1335

Ser Gly Phe Trp Ser Asn Ile His Cys Ser Ser Tyr Lys Gly Tyr
1340                1345                1350

Ile Cys Lys Arg Pro Lys Ile Ile Asp Ala Lys Pro Thr His Glu
1355                1360                1365

Leu Leu Thr Thr Lys Ala Asp Thr Arg Lys Met Asp Pro Ser Lys
1370                1375                1380

Pro Ser Ser Asn Val Ala Gly Val Val Ile Ile Val Ile Leu Leu
1385                1390                1395

Ile Leu Thr Gly Ala Gly Leu Ala Ala Tyr Phe Phe Tyr Lys Lys
1400                1405                1410

Arg Arg Val His Leu Pro Gln Glu Gly Ala Phe Glu Asn Thr Leu
1415                1420                1425

Tyr Phe Asn Ser Gln Ser Ser Pro Gly Thr Ser Asp Met Lys Asp
1430                1435                1440

Leu Val Gly Asn Ile Glu Gln Asn Glu His Ser Val Ile
1445                1450                1455

<210> SEQ ID NO 33
<211> LENGTH: 235
<212> TYPE: PRT
<213> ORGANISM: homo sapiens

<400> SEQUENCE: 33

Met Ala Leu Pro Val Thr Ala Leu Leu Leu Pro Leu Ala Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
                35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

```
Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 34
<211> LENGTH: 235
<212> TYPE: PRT
<213> ORGANISM: homo sapiens

<400> SEQUENCE: 34

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205
```

```
Arg Asn Arg Arg Arg Val Cys Lys Cys Pro Arg Pro Val Val Lys Ser
    210                 215                 220
Gly Asp Lys Pro Ser Leu Ser Ala Arg Tyr Val
225                 230                 235

<210> SEQ ID NO 35
<211> LENGTH: 198
<212> TYPE: PRT
<213> ORGANISM: homo sapiens

<400> SEQUENCE: 35

Met Ala Leu Pro Val Thr Ala Leu Leu Leu Pro Leu Ala Leu Leu Leu
1               5                   10                  15
His Ala Ala Arg Pro Ser Gln Phe Arg Val Ser Pro Leu Asp Arg Thr
                20                  25                  30
Trp Asn Leu Gly Glu Thr Val Glu Leu Lys Cys Gln Val Leu Leu Ser
            35                  40                  45
Asn Pro Thr Ser Gly Cys Ser Trp Leu Phe Gln Pro Arg Gly Ala Ala
        50                  55                  60
Ala Ser Pro Thr Phe Leu Leu Tyr Leu Ser Gln Asn Lys Pro Lys Ala
65                  70                  75                  80
Ala Glu Gly Leu Asp Thr Gln Arg Phe Ser Gly Lys Arg Leu Gly Asp
                85                  90                  95
Thr Phe Val Leu Thr Leu Ser Asp Phe Arg Arg Glu Asn Glu Gly Tyr
            100                 105                 110
Tyr Phe Cys Ser Ala Leu Ser Asn Ser Ile Met Tyr Phe Ser His Phe
        115                 120                 125
Val Pro Val Phe Leu Pro Ala Lys Pro Thr Thr Thr Pro Ala Pro Arg
130                 135                 140
Pro Pro Thr Pro Ala Pro Thr Ile Ala Ser Gln Pro Leu Ser Leu Arg
145                 150                 155                 160
Pro Glu Ala Cys Arg Pro Ala Ala Gly Gly Ala Gly Asn Arg Arg Arg
                165                 170                 175
Val Cys Lys Cys Pro Arg Pro Val Val Lys Ser Gly Asp Lys Pro Ser
            180                 185                 190
Leu Ser Ala Arg Tyr Val
        195

<210> SEQ ID NO 36
<211> LENGTH: 199
<212> TYPE: PRT
<213> ORGANISM: homo sapiens

<400> SEQUENCE: 36

Met Ser Ser Glu Asn Cys Phe Val Ala Glu Asn Ser Ser Leu His Pro
1               5                   10                  15
Glu Ser Gly Gln Glu Asn Asp Ala Thr Ser Pro His Phe Ser Thr Arg
                20                  25                  30
His Glu Gly Ser Phe Gln Val Pro Val Leu Cys Ala Val Met Asn Val
            35                  40                  45
Val Phe Ile Thr Ile Leu Ile Ile Ala Leu Ile Ala Leu Ser Val Gly
        50                  55                  60
Gln Tyr Asn Cys Pro Gly Gln Tyr Thr Phe Ser Met Pro Ser Asp Ser
65                  70                  75                  80
His Val Ser Ser Cys Ser Glu Asp Trp Val Gly Tyr Gln Arg Lys Cys
                85                  90                  95
```

```
Tyr Phe Ile Ser Thr Val Lys Arg Ser Trp Thr Ala Gln Asn Ala
            100                 105                 110

Cys Ser Glu His Gly Ala Thr Leu Ala Val Ile Asp Ser Glu Lys Asp
        115                 120                 125

Met Asn Phe Leu Lys Arg Tyr Ala Gly Arg Glu Glu His Trp Val Gly
    130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
            180                 185                 190

Ile Cys Asn Lys Pro Tyr Lys
            195
```

<210> SEQ ID NO 37
<211> LENGTH: 1790
<212> TYPE: DNA
<213> ORGANISM: homo sapiens

<400> SEQUENCE: 37

```
taattacaaa aactaatgac taagagagag gtggctagag ctgaggcccc tgagtcaggc      60
tgtgggtggg atcatctcca gtacaggaag tgagactttc atttcctcct ttccaagaga     120
gggctgaggg agcagggttg agcaactggt gcagacagcc tagctggact ttgggtgagg     180
cggttcagcc atgaggctgg ctgtgctttt ctcgggggcc ctgctgggc  tactggcaga     240
gagcactgga acaaccagcc acaggactac caagagccac aaaaccacca ctcacaggac     300
aaccaccaca gcaccaccac cacggaccac ccacgactgcc actcacaacc ccaccaccac    360
cagccatgga acgtcacag  ttcatccaac aagcaatagc actgccacca gccagggacc     420
ctcaactgcc actcacagtc ctgccaccac tagtcatgga aatgcacgg  ttcatccaac     480
aagcaacagc actgccacca gcccaggatt caccagttct gcccacccag aaccacctcc     540
accctctccg agtcctagcc caacctccaa ggagaccatt ggagactaca cgtggaccaa     600
tggttcccag ccctgtgtcc acctccaagc ccagattcag attcgagtca tgtacacaac     660
ccagggtgga ggagaggcct ggggcatctc tgtactgaac cccaacaaaa ccaaggtcca     720
gggaagctgt gagggtgccc atccccacct gcttctctca ttcccctatg acacctcag     780
ctttggattc atgcaggacc tccagcagaa ggttgtctac ctgagctaca tggcggtgga     840
gtacaatgtg tccttccccc acgcagcaca gtggacattc tcggctcaga atgcatccct     900
tcgagatctc caagcacccc tggggcagag cttcagttgc agcaactcga gcatcattct     960
ttcaccagct gtccacctcg acctgctctc cctgaggctc caggctgctc agctgcccca    1020
cacagggtc tttgggcaaa gtttctcctg ccccagtgac cggtccatct tgctgcctct    1080
catcatcggc ctgatccttc ttggcctcct cgccctggtg cttattgctt tctgcatcat    1140
ccggagacgc ccatccgcct accaggccct ctgagcattt gcttcaaacc cagggcact    1200
gagggggttg gggtgtggtg gggggtacc  cttatttcct cgacacgcaa ctggctcaaa    1260
gacaatgtta ttttccttcc ctttcttgaa gaacaaaaag aaagccgggc atgacggctc    1320
atgcctgtaa tcccagcact ttgggaggct gaggcaggtg gatcactgga ggtcaggagt    1380
ttgagaccag cctggccaac atggtgaaac cctgtctcta ctaaaaatac aattagccag    1440
gtgtggcggc gtaatcccag ctggcctgta atcccagcta cttgggaggc tgaggcagaa    1500
```

| | |
|---|---|
| ctgcttgaac ccaggaggtg gaggttgcag tgagccgtca tcgcgccact aagccaagat | 1560 |
| cgcgccactg cactccagcc tgggcgacag agccagactg tctcaaataa ataaatatga | 1620 |
| gataatgcag tcgggagaag ggagggagag aattttatta aatgtgacga actgcccccc | 1680 |
| cccccccccc agcaggagag cagcaaaatt tatgcaaatc tttgacgggg ttttccttgt | 1740 |
| cctgccagga ttaaaagcca tgagtttctt gtcaaaaaaa aaaaaaaaaa | 1790 |

<210> SEQ ID NO 38
<211> LENGTH: 1872
<212> TYPE: DNA
<213> ORGANISM: homo sapiens

<400> SEQUENCE: 38

| | |
|---|---|
| ttaattacaa aaactaatga ctaagagaga ggtggctaga gctgaggccc ctgagtcagg | 60 |
| ctgtgggtgg gatcatctcc agtacaggaa gtgagacttt catttcctcc tttccaagag | 120 |
| agggctgagg gagcagggtt gagcaactgg tgcagacagc ctagctggac tttgggtgag | 180 |
| gcggttcagc catgaggctg gctgtgcttt tctcggggc cctgctgggg ctactggcag | 240 |
| cccaggggac agggaatgac tgtcctcaca aaaatcagc tactttgctg ccatccttca | 300 |
| cggtgacacc cacggttaca gagagcactg aacaaccag ccacaggact accaagagcc | 360 |
| acaaaaccac cactcacagg acaaccacca caggcaccac cagccacgga cccacgactg | 420 |
| ccactcacaa ccccaccacc accagccatg gaaacgtcac agttcatcca acaagcaata | 480 |
| gcactgccac cagccaggga ccctcaactg ccactcacag tcctgccacc actagtcatg | 540 |
| gaaatgccac ggttcatcca acaagcaaca gcactgccac cagcccagga ttcaccagtt | 600 |
| ctgcccaccc agaaccacct ccaccctctc cgagtcctag cccaacctcc aaggagacca | 660 |
| ttggagacta cacgtggacc aatggttccc agccctgtgt ccacctccaa gcccagattc | 720 |
| agattcgagt catgtacaca acccagggtg gaggagaggc ctggggcatc tctgtactga | 780 |
| accccaacaa aaccaaggtc cagggaagct gtgagggtgc ccatccccac ctgcttctct | 840 |
| cattccccta tggacacctc agctttggat tcatgcagga cctccagcag aaggttgtct | 900 |
| acctgagcta catggcggtg gagtacaatg tgtccttccc ccacgcagca cagtggacat | 960 |
| tctcggctca gaatgcatcc cttcgagatc tccaagcacc cctggggcag agcttcagtt | 1020 |
| gcagcaactc gagcatcatt ctttcaccag ctgtccacct cgacctgctc tccctgaggc | 1080 |
| tccaggctgc tcagctgccc cacacagggg tctttgggca aagtttctcc tgccccagtg | 1140 |
| accggtccat cttgctgcct ctcatcatcg gcctgatcct tcttggcctc ctcgccctgg | 1200 |
| tgcttattgc tttctgcatc atccggagac gcccatccgc ctaccaggcc ctctgagcat | 1260 |
| ttgcttcaaa ccccagggca ctgaggggt tggggtgtgg tgggggggta cccttatttc | 1320 |
| ctcgacacgc aactggctca aagacaatgt tattttcctt cccttcttg aagaacaaaa | 1380 |
| agaaagccgg gcatgacggc tcatgcctgt aatcccagca ctttgggagg ctgaggcagg | 1440 |
| tggatcactg gaggtcagga gtttgagacc agcctggcca acatggtgaa accctgtctc | 1500 |
| tactaaaaat acaattagcc aggtgtggcg gcgtaatccc agctggcctg taatcccagc | 1560 |
| tacttgggag gctgaggcag aactgcttga acccaggagg tggaggttgc agtgagccgt | 1620 |
| catcgcgcca ctaagccaag atcgcgccac tgcactccag cctgggcgac agagccagac | 1680 |
| tgtctcaaat aaataaatat gagataatgc agtcgggaga agggagggag agaattttat | 1740 |
| taaatgtgac gaactgcccc cccccccccc ccagcaggag agcagcaaaa tttatgcaaa | 1800 |

```
tctttgacgg ggttttcctt gtcctgccag gattaaaagc catgagtttc ttgtcaaaaa    1860
aaaaaaaaaa aa                                                       1872

<210> SEQ ID NO 39
<211> LENGTH: 2399
<212> TYPE: DNA
<213> ORGANISM: homo sapiens

<400> SEQUENCE: 39
agtcattgcc gaggaaggct tgcacagggt gaaagctttg cttctctgct gctgtaacag     60
ggactagcac agacacacgg atgagtgggg tcatttccag atattaggtc acagcagaag    120
cagccaaaat ggatccccag tgcactatgg gactgagtaa cattctcttt gtgatggcct    180
tcctgctctc tgctaacttc agtcaacctg aaatagtacc aatttctaat ataacagaaa    240
atgtgtacat aaatttgacc tgctcatcta tacacggtta cccagaacct aagaagatga    300
gtgttttgct aagaaccaag aattcaacta tcgagtatga tggtattatg cagaaatctc    360
aagataatgt cacagaactg tacgacgttt ccatcagctt gtctgtttca ttccctgatg    420
ttacgagcaa tatgaccatc ttctgtattc tggaaactga caagacgcgg cttttatctt    480
cacctttctc tatagagctt gaggaccctc agcctccccc agaccacatt ccttggatta    540
cagctgtact ccaacagtt attatatgtg tgatggtttt ctgtctaatt ctatggaaat    600
ggaagaagaa gaagcggcct cgcaactctt ataaatgtgg aaccaacaca atggagaggg    660
aagagagtga acagaccaag aaaagagaaa aaatccatat acctgaaaga tctgatgaag    720
cccagcgtgt ttttaaaagt tcgaagacat cttcatgcga caaaagtgat acatgttttt    780
aattaaagag taaagcccat acaagtattc attttttcta cccttttcctt tgtaagttcc    840 tgggcaacct ttttgatttc ttccagaagg caaaaagaca ttaccatgag taataagggg    900
gctccaggac tccctctaag tggaatagcc tccctgtaac tccagctctg ctccgtatgc    960
caagaggaga ctttaattct cttactgctt cttttcactt cagagcacac ttatgggcca   1020
agcccagctt aatggctcat gacctggaaa taaaatttag gaccaatacc tcctccagat   1080
cagattcttc tcttaatttc atagattgtg tttttttttt aaatagacct ctcaatttct   1140
ggaaaactgc cttttatctg cccagaattc taagctggtg ccccactgaa ttttgtgtac   1200
ctgtgactaa acaactacct cctcagtctg ggtgggactt atgtatttat gaccttatag   1260
tgttaatatc ttgaaacata gagatctatg tactgtaata gtgtgattac tatgctctag   1320
agaaaagtct acccctgcta aggagttctc atccctctgt cagggtcagt aaggaaaacg   1380
gtggcctagg gtacaggcaa caatgagcag accaacctaa atttgggaa attaggagag   1440 gcagagatag aacctggagc cacttctatc tgggctgttg ctaatattga ggaggcttgc   1500
cccacccaac aagccatagt ggagagaact gaataaacag gaaaatgcca gagcttgtga   1560
accctgtttc tcttgaagaa ctgactagtg agatggcctg gggaagctgt gaagaaccaa   1620
aaagagatca caatactcaa aagagagaga gagaaaaaa agagagatct tgatccacag   1680
aaatacatga aatgtctggt ctgtccaccc catcaacaag tcttgaaaca agcaacagat   1740
ggatagtctg tccaaatgga cataagacag acagcagttt ccctggtggt cagggagggg   1800
ttttggtgat acccaagtta ttgggatgtc atcttcctgg aagcagagct ggggagggag   1860
agccatcacc ttgataatgg gatgaatgga aggaggctta ggactttcca ctcctggctg   1920
agagaggaag agctgcaacg gaattaggaa gaccaagaca cagatcaccc ggggcttact   1980
tagcctacag atgtcctacg ggaacgtggg ctggcccagc atagggctag caaatttgag   2040
```

```
ttggatgatt gttttgctc aaggcaacca gaggaaactt gcatacagag acagatatac    2100
tgggagaaat gactttgaaa acctggctct aaggtgggat cactaaggga tggggcagtc    2160
tctgcccaaa cataaagaga actctgggga gcctgagcca caaaatgtt cctttatttt    2220 atgtaaaccc tcaagggtta tagactgcca tgctagacaa gcttgtccat gtaatattcc    2280
catgttttta ccctgcccct gccttgatta gactcctagc acctggctag tttctaacat    2340
gttttgtgca gcacagtttt taataaatgc ttgttacatt catttaaaaa aaaaaaaaa     2399
```

```
<210> SEQ ID NO 40
<211> LENGTH: 2685
<212> TYPE: DNA
<213> ORGANISM: homo sapiens

<400> SEQUENCE: 40
```

```
agtcattgcc gaggaaggct tgcacagggt gaaagctttg cttctctgct gctgtaacag      60
ggactagcac agacacacgg atgagtgggg tcatttccag atattaggtc acagcagaag     120
cagccaaaat ggatcccag tggtgctgct cctctgaaga ttcaagctta tttcaatgag     180
actgcagacc tgccatgcca atttgcaaac tctcaaaacc aaagcctgag tgagctagta    240
gtattttggc aggaccagga aaacttggtt ctgaatgagg tatacttagg caaagagaaa    300
tttgacagtg ttcattccaa gtatatgggc cgcacaagtt ttgattcgga cagttggacc    360
ctgagacttc acaatcttca gatcaaggac aagggcttgt atcaatgtat catccatcac    420
aaaaagccca caggaatgat tcgcatccac cagatgaatt ctgaactgtc agtgcttgct    480
aacttcagtc aacctgaaat agtaccaatt tctaatataa cagaaaatgt gtacataaat    540
ttgacctgct catctataca cggttaccca gaacctaaga agatgagtgt tttgctaaga    600
accaagaatt caactatcga gtatgatggt attatgcaga aatctcaaga taatgtcaca    660
gaactgtacg acgtttccat cagcttgtct gtttcattcc ctgatgttac gagcaatatg    720
accatcttct gtattctgga aactgacaag acgcggcttt atcttcacc tttctctata    780 gagcttgagg accctcagcc tccccagac cacattcctt ggattacagc tgtacttcca    840
acagttatta tatgtgtgat ggtttttctgt ctaattctat ggaaatggaa gaagaagaag    900
cggcctcgca actcttataa atgtggaacc aacacaatgg agagggaaga gagtgaacag    960
accaagaaaa gagaaaaaat ccatatacct gaaagatctg atgaagccca gcgtgttttt   1020
aaaagttcga agacatcttc atgcgacaaa agtgatacat gttttaatt aaagagtaaa    1080 gcccatacaa gtattcattt tttctaccct ttccttgta agttcctggg caaccttttt    1140
gatttcttcc agaaggcaaa aagacattac catgagtaat aaggggctc caggactccc    1200 tctaagtgga atagcctccc tgtaactcca gctctgctcc gtatgccaag aggagacttt    1260
aattctctta ctgcttcttt tcacttcaga gcacacttat gggccaagcc cagcttaatg    1320
gctcatgacc tggaaataaa atttaggacc aatacctcct ccagatcaga ttcttctctt    1380
aatttcatag attgtgtttt tttttaaat agacctctca atttctggaa aactgccttt    1440
tatctgccca gaattctaag ctggtgcccc actgaatttt gtgtacctgt gactaaacaa    1500
ctacctcctc agtctgggtg ggacttatgt atttatgacc ttatagtgtt aatatcttga    1560
aacatagaga tctatgtact gtaatagtgt gattactatg ctctagagaa aagtctaccc    1620
ctgctaagga gttctcatcc ctctgtcagg gtcagtaagg aaaacggtgg cctagggtac    1680
aggcaacaat gagcagacca acctaaattt ggggaaatta ggagaggcag agatagaacc    1740
tggagccact tctatctggg ctgttgctaa tattgaggag gcttgcccca cccaacaagc    1800
```

| | |
|---|---|
| catagtggag agaactgaat aaacaggaaa atgccagagc ttgtgaaccc tgtttctctt | 1860 |
| gaagaactga ctagtgagat ggcctgggga agctgtgaaa gaaccaaaag agatcacaat | 1920 |
| actcaaaaga gagagagaga gaaaaaagag agatcttgat ccacagaaat acatgaaatg | 1980 |
| tctggtctgt ccaccccatc aacaagtctt gaaacaagca acagatggat agtctgtcca | 2040 |
| aatggacata agacagacag cagtttccct ggtggtcagg gaggggtttt ggtgataccc | 2100 |
| aagttattgg gatgtcatct tcctggaagc agagctgggg agggagagcc atcaccttga | 2160 |
| taatgggatg aatggaagga ggcttaggac tttccactcc tggctgagag aggaagagct | 2220 |
| gcaacggaat taggaagacc aagcacagat cacccgggg cttacttagc ctacagatgt | 2280 |
| cctacgggaa cgtgggctgg cccagcatag ggctagcaaa tttgagttgg atgattgttt | 2340 |
| ttgctcaagg caaccagagg aaacttgcat acagagacag atatactggg agaaatgact | 2400 |
| ttgaaaacct ggctctaagg tgggatcact aagggatggg gcagtctctg cccaaacata | 2460 |
| aagagaactc tggggagcct gagccacaaa aatgttcctt tattttatgt aaaccctcaa | 2520 |
| gggttataga ctgccatgct agacaagctt gtccatgtaa tattcccatg ttttttaccct | 2580 |
| gccctgcct tgattagact cctagcacct ggctagtttc taacatgttt tgtgcagcac | 2640 |
| agttttaat aaatgcttgt tacattcatt taaaaaaaaa aaaaa | 2685 |

<210> SEQ ID NO 41
<211> LENGTH: 2790
<212> TYPE: DNA
<213> ORGANISM: homo sapiens

<400> SEQUENCE: 41

| | |
|---|---|
| ccctttctgt atttgagttc taccgtcagt cctggcatta tttctctctc tacaaggagc | 60 |
| cttaggaggt acggggagct cgcaaatact ccttttggtt tattcttacc accttgcttc | 120 |
| tgtgttcctt gggaatgctg ctgtgcttat gcatctggtc tcttttttgga gctacagtgg | 180 |
| acaggcattt gtgacagcac tatgggactg agtaacattc tctttgtgat ggccttcctg | 240 |
| ctctctggtg ctgctcctct gaagattcaa gcttatttca atgagactgc agacctgcca | 300 |
| tgccaatttg caaactctca aaaccaaagc ctgagtgagc tagtagtatt ttggcaggac | 360 |
| caggaaaact tggttctgaa tgaggtatac ttaggcaaag agaaatttga cagtgttcat | 420 |
| tccaagtata tgggccgcac aagttttgat tcggacagtt ggaccctgag acttcacaat | 480 |
| cttcagatca aggacaaggg cttgtatcaa tgtatcatcc atcacaaaaa gcccacagga | 540 |
| atgattcgca tccaccagat gaattctgaa ctgtcagtgc ttgctaactt cagtcaacct | 600 |
| gaaatagtac caatttctaa tataacagaa aatgtgtaca taaatttgac ctgctcatct | 660 |
| atacacggtt acccagaacc taagaagatg agtgttttgc taagaaccaa gaattcaact | 720 |
| atcgagtatg atggtattat gcagaaatct caagataatg tcacagaact gtacgacgtt | 780 |
| tccatcagct tgtctgtttc attccctgat gttacgagca atatgaccat cttctgtatt | 840 |
| ctggaaactg acaagacgcg gcttttatct tcacctttct ctatagagct tgaggaccct | 900 |
| cagcctcccc cagaccacat tccttggatt acagctgtac ttccaacagt tattatatgt | 960 |
| gtgatggttt tctgtctaat tctatggaaa tggaagaaga agaagcggcc tcgcaactct | 1020 |
| tataaatgtg gaaccaacac aatggagagg gaagagagtg aacagaccaa gaaaagagaa | 1080 |
| aaaatccata tacctgaaag atctgatgaa gcccagcgtg ttttaaaag ttcgaagaca | 1140 |
| tcttcatgcg acaaaagtga tacatgtttt taattaaaga gtaaagccca tacaagtatt | 1200 |
| catttttttct acccttttcct ttgtaagttc ctgggcaacc tttttgattt cttccagaag | 1260 |

```
gcaaaaagac attaccatga gtaataaggg ggctccagga ctccctctaa gtggaatagc    1320
ctccctgtaa ctccagctct gctccgtatg ccaagaggag actttaattc tcttactgct    1380
tctttttcact tcagagcaca cttatgggcc aagcccagct taatggctca tgacctggaa   1440
ataaaattta ggaccaatac ctcctccaga tcagattctt ctcttaattt catagattgt    1500
gtttttttttt taaatagacc tctcaatttc tggaaaactg ccttttatct gcccagaatt   1560
ctaagctggt gccccactga attttgtgta cctgtgacta acaactacc tcctcagtct     1620
gggtgggact tatgtattta tgaccttata gtgttaatat cttgaaacat agagatctat    1680
gtactgtaat agtgtgatta ctatgctcta gagaaaagtc taccctgct aaggagttct     1740
catccctctg tcagggtcag taaggaaaac ggtggcctag ggtacaggca acaatgagca    1800
gaccaaccta aatttgggga aattaggaga ggcagagata gaacctggag ccacttctat    1860
ctgggctgtt gctaatattg aggaggcttg ccccacccaa caagccatag tggagagaac    1920
tgaataaaca ggaaaatgcc agagcttgtg aaccctgttt ctcttgaaga actgactagt    1980
gagatggcct ggggaagctg tgaaagaacc aaaagagatc acaatactca aaagagagag    2040
agagagaaaa aagagagatc ttgatccaca gaaatacatg aaatgtctgg tctgtccacc    2100
ccatcaacaa gtcttgaaac aagcaacaga tggatagtct gtccaaatgg acataagaca    2160
gacagcagtt tccctggtgg tcagggaggg gttttggtga tacccaagtt attgggatgt    2220
catcttcctg gaagcagagc tggggaggga gagccatcac cttgataatg ggatgaatgg    2280
aaggaggctt aggactttcc actcctggct gagagaggaa gagctgcaac ggaattagga    2340
agaccaagac acagatcacc cggggcttac ttagcctaca gatgtcctac gggaacgtgg    2400
gctggcccag cataggcta gcaaatttga gttggatgat tgttttttgct caaggcaacc    2460
agaggaaact tgcatacaga gacagatata ctgggagaaa tgactttgaa aacctggctc    2520
taaggtggga tcactaaggg atggggcagt ctctgcccaa acataaagag aactctgggg    2580
agcctgagcc acaaaaatgt tcctttattt tatgtaaacc ctcaagggtt atagactgcc    2640
atgctagaca agcttgtcca tgtaatattc ccatgttttt accctgcccc tgccttgatt    2700
agactcctag cacctggcta gtttctaaca tgttttgtgc agcacagttt ttaataaatg    2760
cttgttacat tcatttaaaa aaaaaaaaaa                                     2790

<210> SEQ ID NO 42
<211> LENGTH: 2735
<212> TYPE: DNA
<213> ORGANISM: homo sapiens

<400> SEQUENCE: 42
agtcattgcc gaggaaggct tgcacagggt gaaagctttg cttctctgct gctgtaacag      60
ggactagcac agacacacgg atgagtgggg tcatttccag atattaggtc acagcagaag     120
cagccaaaat ggatccccag tgcactatgg gactgagtaa cattctcttt gtgatggcct     180
tcctgctctc tggtgctgct cctctgaaga ttcaagctta tttcaatgag actgcagacc     240
tgccatgcca atttgcaaac tctcaaaacc aaagcctgag tgagctagta gtattttggc     300
aggaccagga aaacttggtt ctgaatgagg tatacttagg caaagagaaa tttgacagtg     360
ttcattccaa gtatatgggc cgcacaagtt ttgattcgga cagttggacc ctgagacttc     420
acaatcttca gatcaaggac aagggcttgt atcaatgtat catccatcac aaaaagccca     480
caggaatgat tcgcatccac cagatgaatt ctgaactgtc agtgcttgct aacttcagtc     540
aacctgaaat agtaccaatt tctaatataa cagaaaatgt gtacataaat ttgacctgct     600
```

| | | |
|---|---|---|
| catctataca cggttaccca gaacctaaga agatgagtgt tttgctaaga accaagaatt | 660 | |
| caactatcga gtatgatggt attatgcaga aatctcaaga taatgtcaca gaactgtacg | 720 | |
| acgtttccat cagcttgtct gtttcattcc ctgatgttac gagcaatatg accatcttct | 780 | |
| gtattctgga aactgacaag acgcggcttt tatcttcacc tttctctata gagcttgagg | 840 | |
| accctcagcc tcccccagac cacattcctt ggattacagc tgtacttcca acagttatta | 900 | |
| tatgtgtgat ggttttctgt ctaattctat ggaaatggaa gaagaagaag cggcctcgca | 960 | |
| actcttataa atgtggaacc aacacaatgg agagggaaga gagtgaacag accaagaaaa | 1020 | |
| gagaaaaaat ccatatacct gaaagatctg atgaagccca gcgtgttttt aaaagttcga | 1080 | |
| agacatcttc atgcgacaaa agtgatacat gtttttaatt aaagagtaaa gcccatacaa | 1140 | |
| gtattcattt tttctaccct ttcctttgta agttcctggg caaccttttt gatttcttcc | 1200 | |
| agaaggcaaa aagacattac catgagtaat aaggggctc caggactccc tctaagtgga | 1260 | |
| atagcctccc tgtaactcca gctctgctcc gtatgccaag aggagacttt aattctctta | 1320 | |
| ctgcttcttt tcacttcaga gcacacttat gggccaagcc cagcttaatg gctcatgacc | 1380 | |
| tggaaataaa atttaggacc aatacctcct ccagatcaga ttcttctctt aatttcatag | 1440 | |
| attgtgtttt tttttaaat agacctctca atttctggaa aactgccttt tatctgccca | 1500 | |
| gaattctaag ctggtgcccc actgaatttt gtgtacctgt gactaaacaa ctacctcctc | 1560 | |
| agtctgggtg ggacttatgt atttatgacc ttatagtgtt aatatcttga acatagaga | 1620 | |
| tctatgtact gtaatagtgt gattactatg ctctagagaa aagtctaccc ctgctaagga | 1680 | |
| gttctcatcc ctctgtcagg gtcagtaagg aaaacggtgg cctagggtac aggcaacaat | 1740 | |
| gagcagacca acctaaatt ggggaaatta ggagaggcag agatagaacc tggagccact | 1800 | |
| tctatctggg ctgttgctaa tattgaggag gcttgcccca cccaacaagc catagtggag | 1860 | |
| agaactgaat aaacaggaaa atgccagagc ttgtgaaccc tgtttctctt gaagaactga | 1920 | |
| ctagtgagat ggcctgggga agctgtgaaa gaaccaaaag agatcacaat actcaaaaga | 1980 | |
| gagagagaga gaaaaaagag agatcttgat ccacagaaat acatgaaatg tctggtctgt | 2040 | |
| ccaccccatc aacaagtctt gaaacaagca acagatggat agtctgtcca aatggacata | 2100 | |
| agacagacag cagtttccct ggtggtcagg gaggggtttt ggtgataccc aagttattgg | 2160 | |
| gatgtcatct tcctggaagc agagctgggg agggagagcc atcaccttga taatgggatg | 2220 | |
| aatgaaagga ggcttaggac tttccactcc tggctgagag aggaagagct gcaacggaat | 2280 | |
| taggaagacc aagacacaga tcacccgggg cttacttagc ctacagatgt cctacgggaa | 2340 | |
| cgtgggctgg cccagcatag ggctagcaaa tttgagttgg atgattgttt ttgctcaagg | 2400 | |
| caaccagagg aaacttgcat acagagacag atatactggg agaaatgact ttgaaaacct | 2460 | |
| ggctctaagg tgggatcact aagggatggg gcagtctctg cccaaacata agagaactc | 2520 | |
| tggggagcct gagccacaaa aatgttcctt tattttatgt aaaccctcaa gggttataga | 2580 | |
| ctgccatgct agacaagctt gtccatgtaa tattcccatg ttttaccct gcccctgcct | 2640 | |
| tgattagact cctagcacct ggctagtttc taacatgttt tgtgcagcac agttttaat | 2700 | |
| aaatgcttgt tacattcatt taaaaaaaaaa aaaaa | 2735 | |

<210> SEQ ID NO 43
<211> LENGTH: 2646
<212> TYPE: DNA
<213> ORGANISM: homo sapiens

<400> SEQUENCE: 43

```
ccctttctgt atttgagttc taccgtcagt cctggcatta tttctctctc tacaaggagc      60
cttaggaggt acggggagct cgcaaatact ccttttggtt tattcttacc accttgcttc     120
tgtgttcctt gggaatgctg ctgtgcttat gcatctggtc tctttttgga gctacagtgg     180
acaggcattt gtgacagcac tatgggactg agtaacattc tctttgtgat ggccttcctg     240
ctctctggtg ctgctcctct gaagattcaa gcttatttca atgagactgc agacctgcca     300
tgccaatttg caaactctca aaaccaaagc ctgagtgagc tagtagtatt ttggcaggac     360
caggaaaact tggttctgaa tgaggtatac ttaggcaaag agaaatttga cagtgttcat     420
tccaagtata tgggccgcac aagttttgat tcggacagtt ggaccctgag acttcacaat     480
cttcagatca aggacaaggg cttgtatcaa tgtatcatcc atcacaaaaa gcccacagga     540
atgattcgca tccaccagat gaattctgaa ctgtcagtgc ttgctaactt cagtcaacct     600
gaaatagtac caattctaa tataacagaa aatgtgtaca taaatttgac ctgctcatct     660
atacacggtt acccagaacc taagaagatg agtgttttgc taagaaccaa gaattcaact     720
atcgagtatg atggtattat gcagaaatct caagataatg tcacagaact gtacgacgtt     780
tccatcagct tgtctgtttc attccctgat gttacgagca atatgaccat cttctgtatt     840
ctggaaactg acaagacgcg gcttttatct tcacctttct ctataggaac caacacaatg     900
gagagggaag agagtgaaca gaccaagaaa agagaaaaaa tccatatacc tgaaagatct     960
gatgaagccc agcgtgtttt taaaagttcg aagacatctt catgcgacaa aagtgataca    1020
tgttttaat taaagagtaa agcccataca agtattcatt ttttctaccc tttcctttgt    1080
aagttcctgg gcaaccttt tgatttcttc cagaaggcaa aaagacatta ccatgagtaa    1140
taaggggct ccaggactcc ctctaagtgg aatagcctcc ctgtaactcc agctctgctc    1200
cgtatgccaa gaggagactt taattctctt actgcttctt ttcacttcag agcacactta    1260
tgggccaagc ccagcttaat ggctcatgac ctggaaataa aatttaggac caatacctcc    1320
tccagatcag attcttctct taatttcata gattgtgttt tttttttaaa tagacctctc    1380
aatttctgga aaactgcctt ttatctgccc agaattctaa gctggtgccc cactgaattt    1440
tgtgtacctg tgactaaaca actacctcct cagtctgggt gggacttatg tatttatgac    1500
cttatagtgt taatatcttg aaacatagag atctatgtac tgtaatagtg tgattactat    1560
gctctagaga aaagtctacc cctgctaagg agttctcatc cctctgtcag ggtcagtaag    1620
gaaaacggtg gcctagggta caggcaacaa tgagcagacc aacctaaatt tggggaaatt    1680
aggagaggca gagatagaac ctggagccac ttctatctgg gctgttgcta atattgagga    1740
ggcttgcccc acccaacaag ccatagtgga gagaactgaa taaacaggaa atgccagag    1800
cttgtgaacc ctgtttctct tgaagaactg actagtgaga tggcctgggg aagctgtgaa    1860
agaaccaaaa gagatcacaa tactcaaaag agagagagag agaaaaaaga gagatcttga    1920
tccacagaaa tacatgaaat gtctggtctg tccaccccat caacaagtct tgaaacaagc    1980
aacagatgga tagtctgtcc aaatggacat aagacagaca gcagtttccc tggtggtcag    2040
ggagggtttt tggtgatacc caagttattg ggatgtcatc ttcctggaag cagagctggg    2100
gagggagagc catcaccttg ataatgggat gaatggaagg aggcttagga cttttccactc    2160
ctggctgaga gaggaagagc tgcaacggaa ttaggaagac caagacacag atcacccggg    2220
gcttacttag cctacagatg tcctacggga acgtgggctg gccagcata gggctagcaa    2280
atttgagttg gatgattgtt tttgctcaag gcaaccagag gaaacttgca tacagagaca    2340
```

| | |
|---|---|
| gatatactgg gagaaatgac tttgaaaacc tggctctaag gtgggatcac taagggatgg | 2400 |
| ggcagtctct gcccaaacat aaagagaact ctggggagcc tgagccacaa aaatgttcct | 2460 |
| ttattttatg taaaccctca agggttatag actgccatgc tagacaagct tgtccatgta | 2520 |
| atattcccat gtttttaccc tgcccctgcc ttgattagac tcctagcacc tggctagttt | 2580 |
| ctaacatgtt ttgtgcagca cagttttaa taaatgcttg ttacattcat ttaaaaaaaa | 2640 |
| aaaaaa | 2646 |

```
<210> SEQ ID NO 44
<211> LENGTH: 2268
<212> TYPE: DNA
<213> ORGANISM: homo sapiens

<400> SEQUENCE: 44
```

| | |
|---|---|
| aatatcttgc atgttacaga tttcactgct cccaccagct tggagacaac atgtggttct | 60 |
| tgacaactct gctcctttgg gttccagttg atgggcaagt ggacaccaca aaggcagtga | 120 |
| tcactttgca gcctccatgg gtcagcgtgt tccaagagga aaccgtaacc ttgcactgtg | 180 |
| aggtgctcca tctgcctggg agcagctcta cacagtggtt tctcaatggc acagccactc | 240 |
| agacctcgac ccccagctac agaatcacct ctgccagtgt caatgacagt ggtgaataca | 300 |
| ggtgccagag aggtctctca gggcgaagtg accccataca gctggaaatc cacagaggct | 360 |
| ggctactact gcaggtctcc agcagagtct tcacggaagg agaacctctg ccttgaggt | 420 |
| gtcatgcgtg aaggataag ctggtgtaca atgtgcttta ctatcgaaat ggcaaagcct | 480 |
| ttaagttttt ccactggaat tctaacctca ccattctgaa aaccaacata agtcacaatg | 540 |
| gcacctacca ttgctcaggc atgggaaagc atcgctacac atcagcagga atatctgtca | 600 |
| ctgtgaaaga gctatttcca gctccagtgc tgaatgcatc tgtgacatcc ccactcctgg | 660 |
| aggggaatct ggtcaccctg agctgtgaaa caaagttgct cttgcagagg cctggttgc | 720 |
| agctttactt ctccttctac atgggcagca agacccgtgcg aggcaggaac acatcctctg | 780 |
| aataccaaat actaactgct agaagagaag actctgggtt atactggtgc gaggctgcca | 840 |
| cagaggatgg aaatgtcctt aagcgcagcc ctgagttgga gcttcaagtg cttggcctcc | 900 |
| agttaccaac tcctgtctgg tttcatgtcc ttttctatct ggcagtggga ataatgtttt | 960 |
| tagtgaacac tgttctctgg gtgacaatac gtaaagaact gaaaagaaag aaaaagtggg | 1020 |
| atttagaaat ctctttggat tctggtcatg agaagaaggt aatttccagc cttcaagaag | 1080 |
| acagacattt agaagaagag ctgaaatgtc aggaacaaaa agaagaacag ctgcaggaag | 1140 |
| gggtgcaccg gaaggagccc caggggggcca cgtagcagcg gctcagtggg tggccatcga | 1200 |
| tctggaccgt cccctgccca cttgctcccc gtgagcactg cgtacaaaca tccaaaagtt | 1260 |
| caacaacacc agaactgtgt gtctcatggt atgtaactct taaagcaaat aaatgaactg | 1320 |
| acttcaactg ggatacattt ggaaatgtgg tcatcaaaga tgacttgaaa tgaggcctac | 1380 |
| tctaaagaat tcttgaaaaa cttacaagtc aagcctagcc tgataatcct attacatagt | 1440 |
| ttgaaaaata gtatttatt tctcagaaca aggtaaaaag gtgagtgggt gcatatgtac | 1500 |
| agaagattaa gacagagaaa cagacagaaa gagacacaca cacagccagg agtgggtaga | 1560 |
| tttcagggag acaagaggga atagtataga caataaggaa ggaaatagta cttacaaatg | 1620 |
| actcctaagg gactgtgaga ctgagagggc tcacgcctct gtgttcagga tacttagttc | 1680 |
| atggcttttc tctttgactt tactaaaaga gaatgtctcc atacgcgttc taggcataca | 1740 |
| aggggggtaac tcatgatgag aaatggatgt gttattcttg ccctctcttt tgaggctctc | 1800 |

```
tcataacccc tctatttcta gagacaacaa aaatgctgcc agtcctaggc ccctgccctg    1860
taggaaggca gaatgtaact gttctgtttg tttaacgatt aagtccaaat ctccaagtgc    1920
ggcactgcaa agagacgctt caagtgggga gaagcggcga taccatagag tccagatctt    1980
gcctccagag atttgcttta ccttcctgat tttctggtta ctaattagct tcaggatacg    2040
ctgctctcat acttgggctg tagtttggag acaaaatatt ttcctgccac tgtgtaacat    2100
agctgaggta aaaactgaac tatgtaaatg actctactaa aagtttaggg aaaaaaaaca    2160
ggaggagtat gacacaaaaa aaaaaaaaaa aaaaaaaaaa aaaaaaaaaa aaaaaaaaaa    2220
aaaaaaaaaa aaaaaaaaaa aaaaaaaaaa aaaaaaaaaa aaaaaaaa                 2268

<210> SEQ ID NO 45
<211> LENGTH: 1805
<212> TYPE: DNA
<213> ORGANISM: homo sapiens

<400> SEQUENCE: 45
gagacacact ctgccccaac catcctgaag ctacaggtgc tccctcctgg aatctccaat      60
ggatttcagt cgcagaagct tccacagaag cctgagctcc tccttgcagg cccctgtagt     120
cagtacagtg ggcatgcagc gcctcggac gacacccagc gtttatgggg gtgctggagg     180
ccggggcatc cgcatctcca actccagaca cacggtgaac tatgggagcg atctcacagg     240
cggcggggac ctgtttgttg gcaatgagaa aatggccatg cagaacctaa atgaccgtct     300
agcgagctac ctagaaaagg tgcggaccct ggagcagtcc aactccaaac ttgaagtgca     360
aatcaagcag tggtacgaaa ccaacgcccc gagggctggt cgcgactaca gtgcatatta     420
cagacaaatt gaagagctgc gaagtcagat taaggatgct caactgcaaa atgctcggtg     480
tgtcctgcaa attgataatg ctaaactggc tgctgaggac ttcagactga gtatgagac      540 tgagagagga atacgtctaa cagtggaagc tgatctccaa ggcctgaata aggtctttga     600
tgacctaacc ctacataaaa cagatttgga gattcaaatt gaagaactga ataaagacct     660
agctctcctc aaaaaggagc atcaggagga agtcgatggc ctacacaagc atctgggcaa     720
cactgtcaat gtggaggttg atgctgctcc aggcctgaac cttggcgtca tcatgaatga     780
aatgaggcag aagtatgaag tcatggccca gaagaacctt caagaggcca agaacagtt      840 tgagagacag actgcagttc tgcagcaaca ggtcacagtg aatactgaag aattaaaagg     900
aactgaggtt caactaacgg agctgagacg cacctcccag agccttgaga tagaactcca     960
gtcccatctc agcatgaaag agtctttgga gcacactcta gaggagacca aggcccgtta    1020
cagcagccag ttagccaacc tccagtcgct gttgagctct ctggaggccc aactgatgca    1080
gattcggagt aacatggaac gccagaacaa cgaataccat atccttcttg acataaagac    1140
tcgacttgaa caggaaattg ctacttaccg ccgccttctg gaaggagaag acgtaaaaac    1200
tacagaatat cagttaagca ccctggaaga gagagatata aagaaaacca ggaagattaa    1260
gacagtcgtg caagaagtag tggatggcaa ggtcgtgtca tctgaagtca aagaggtgga    1320
agaaaatatc taaatagcta ccagaaggag atgctgctga ggttttgaaa gaaatttggc    1380
tataatctta tctttgctcc ctgcaagaaa tcagccataa gaaagcacta ttaatactct    1440
gcagtgatta aagggggtgg ggtggcggga atcctatta tcagactctg taattgaata    1500
taaatgtttt actcagagga gctgcaaatt gcctgcaaaa atgaaatcca gtgagcacta    1560
gaatatttaa aacatcatta ctgccatctt tatcatgaag cacatcaatt acaagctgta    1620
gaccacctaa tatcaatttg taggtaatgt tcctgaaaat tgcaatacat ttcaattata    1680
```

| | |
|---|---:|
| ctaaacctca caaagtagag gaatccatgt aaattgcaaa taaaccactt tctaatttt | 1740 |
| tcctgtttct gaattgtaaa acccccttg ggagtccctg gtttcttatt gagccaattt | 1800 |
| ctggg | 1805 |

<210> SEQ ID NO 46
<211> LENGTH: 1965
<212> TYPE: DNA
<213> ORGANISM: homo sapiens

<400> SEQUENCE: 46

| | |
|---|---:|
| aggcccctgc ctgccccagc atccctgcg cgaagctggg tgccccggag agtctgacca | 60 |
| ccatgccacc tcctcgcctc ctcttcttcc tcctcttcct caccccatg gaagtcaggc | 120 |
| ccgaggaacc tctagtggtg aaggtggaag agggagataa cgctgtgctg cagtgcctca | 180 |
| aggggacctc agatggcccc actcagcagc tgacctggtc tcgggagtcc ccgcttaaac | 240 |
| ccttcttaaa actcagcctg gggctgccag gcctgggaat ccacatgagg cccctggcca | 300 |
| tctggctttt catcttcaac gtctctcaac agatgggggg cttctacctg tgccagccgg | 360 |
| ggcccccctc tgagaaggcc tggcagcctg gctggacagt caatgtggag ggcagcgggg | 420 |
| agctgttccg gtggaatgtt tcggacctag gtggcctggg ctgtggcctg aagaacaggt | 480 |
| cctcagaggg ccccagctcc ccttccggga agctcatgag ccccaagctg tatgtgtggg | 540 |
| ccaaagaccg ccctgagatc tgggaggag agcctccgtg tctcccaccg agggacagcc | 600 |
| tgaaccagag cctcagccag gacctcacca tggcccctgg ctccacactc tggctgtcct | 660 |
| gtgggggtacc ccctgactct gtgtccaggg ccccctctc ctggacccat gtgcacccca | 720 |
| aggggcctaa gtcattgctg agcctagagc tgaaggacga tcgcccggcc agagatatgt | 780 |
| gggtaatgga cgggtctg ttgttgcccc gggccacagc tcaagacgct ggaaagtatt | 840 |
| attgtcaccg tggcaacctg accatgtcat tccacctgga gatcactgct cggccagtac | 900 |
| tatggcactg gctgctgagg actggtggct ggaaggtctc agctgtgact ttggcttatc | 960 |
| tgatcttctg cctgtgttcc cttgtgggca ttcttcatct tcaaagagcc ctggtcctga | 1020 |
| ggaggaaaag aaagcgaatg actgaccca ccaggagatt cttcaaagtg acgcctcccc | 1080 |
| caggaagcgg gccccagaac cagtacggga acgtgctgtc tctccccaca cccacctcag | 1140 |
| gcctcggacg cgcccagcgt tgggccgcag gctggggggg cactgccccg tcttatggaa | 1200 |
| acccgagcag cgacgtccag gcggatggag ccttggggtc ccggagcccg ccgggagtgg | 1260 |
| gcccagaaga agaggaaggg gagggctatg aggaacctga cagtgaggag gactccgagt | 1320 |
| ctatgagaa cgactccaac cttgggcagg accagctctc ccaggatggc agcggctacg | 1380 |
| agaaccctga ggatgagccc ctgggtcctg aggatgaaga ctccttctcc aacgctgagt | 1440 |
| cttatgagaa cgaggatgaa gagctgaccc agccggtcgc caggacaatg gacttcctga | 1500 |
| gccctcatgg gtcagcctgg gaccccagcc gggaagcaac ctccctgggg tcccagtcct | 1560 |
| atgaggatat gagaggaatc ctgtatgcag cccccagct ccgctccatt cggggccagc | 1620 |
| ctggacccaa tcatgaggaa gatgcagact cttatgagaa catggataat cccgatgggc | 1680 |
| cagacccagc ctggggagga gggggccgca tgggcacctg gagcaccagg tgatcctcag | 1740 |
| gtggccagcc tggatctcct caagtcccca agattcacac ctgactctga aatctgaaga | 1800 |
| cctcgagcag atgatgccaa cctctggagc aatgttgctt aggatgtgtg catgtgtgta | 1860 |
| agtgtgtgtg tgtgtgtgtg tgtgtataca tgccagtgac acttccagtc cccttttgtat | 1920 |
| tccttaaata aactcaatga gctcttccaa tcctaaaaaa aaaaa | 1965 |

<210> SEQ ID NO 47
<211> LENGTH: 1968
<212> TYPE: DNA
<213> ORGANISM: homo sapiens

<400> SEQUENCE: 47

```
aggcccctgc ctgccccagc atccctgcg cgaagctggg tgccccggag agtctgacca      60
ccatgccacc tcctcgcctc ctcttcttcc tcctcttcct caccccatg gaagtcaggc     120
ccgaggaacc tctagtggtg aaggtggaag agggagataa cgctgtgctg cagtgcctca    180
aggggacctc agatggcccc actcagcagc tgacctggtc tcgggagtcc ccgcttaaac    240
ccttcttaaa actcagcctg gggctgccag gcctgggaat ccacatgagg cccctggcca    300
tctggctttt catcttcaac gtctctcaac agatggggg cttctacctg tgccagccgg     360
ggccccctc tgagaaggcc tggcagcctg gctggacagt caatgtggag ggcagcgggg     420
agctgttccg gtggaatgtt tcggacctag gtggcctggg ctgtggcctg aagaacaggt    480
cctcagaggg ccccagctcc ccttccggga agctcatgag ccccaagctg tatgtgtggg    540
ccaaagaccg ccctgagatc tgggagggag agcctccgtg tctcccaccg agggacagcc    600
tgaaccagag cctcagccag gacctcacca tggccctgg ctccacactc tggctgtcct    660
gtggggtacc ccctgactct gtgtccaggg gcccctctc ctggacccat gtgcacccca    720
aggggcctaa gtcattgctg agcctagagc tgaaggacga tcgccggcc agagatatgt    780
gggtaatgga gacgggtctg ttgttgcccc gggccacagc tcaagacgct ggaaagtatt    840
attgtcaccg tggcaacctg accatgtcat tccacctgga gatcactgct cggccagtac    900
tatggcactg gctgctgagg actggtggct ggaaggtctc agctgtgact ttggcttatc    960
tgatcttctg cctgtgttcc cttgtgggca ttcttcatct tcaaagagcc ctggtcctga   1020
ggaggaaaag aaagcgaatg actgaccca ccaggagatt cttcaaagtg acgcctcccc     1080
caggaagcgg gccccagaac cagtacggga acgtgctgtc tctccccaca cccacctcag   1140
gcctcggacg cgcccagcgt tgggccgcag gctgggggg cactgccccg tcttatggaa    1200
acccgagcag cgacgtccag gcggatggag ccttggggtc ccggagcccg ccgggagtgg   1260
gcccagaaga gaggaaggg gagggctatg aggaacctga cagtgaggag gactccgagt    1320
tctatgagaa cgactccaac cttgggcagg accagctctc ccaggatggc agcggctacg   1380
agaaccctga ggatgagccc ctgggtcctg aggatgaaga ctccttctcc aacgctgagt   1440
cttatgagaa cgaggatgaa gagctgaccc agccggtcgc caggacaatg gacttcctga   1500
gccctcatgg gtcagcctgg gaccccagcc gggaagcaac ctccctggca gggtcccagt   1560
cctatgagga tatgagagga atcctgtatg cagcccccca gctccgctcc attcggggcc   1620
agcctggacc caatcatgag gaagatgcag actcttatga gaacatggat aatcccgatg   1680
ggccagaccc agcctgggga ggagggggcc gcatgggcac ctggagcacc aggtgatcct   1740
caggtggcca gcctggatct cctcaagtcc ccaagattca cacctgactc tgaaatctga   1800
agacctcgag cagatgatgc caacctctgg agcaatgttg cttaggatgt gtgcatgtgt   1860
gtaagtgtgt gtgtgtgtgt gtgtgtgtat acatgccagt gacacttcca gtccccttg     1920
tattccttaa ataaactcaa tgagctcttc caatcctaaa aaaaaaa                  1968
```

<210> SEQ ID NO 48
<211> LENGTH: 7274
<212> TYPE: DNA
<213> ORGANISM: homo sapiens

```
<400> SEQUENCE: 48
cacccaccaa ggctccggat gtgttcccca tcatatcagg gtgcagacac ccaaaggata     60
acagccctgt ggtcctggca tgcttgataa ctgggtacca cccaacgtcc gtgactgtca    120
cctggtacat ggggacacag agccagcccc agagaaccct ccctgagata caaagacggg    180
acagctacta catgacaagc agccagctct ccaccccct ccagcagtgg cgccaaggcg     240
agtacaaatg cgtggtccag cacaccgcca gcaagagtaa aaggagatc ttccgctggc     300 caggtaggtc gcaccggaga tcacccagaa gggcccccca ggaccccag caccttccac     360 tcagggcctg accacaaaga cagaagcaag ggctgggctg tgaggcaacc cccacctccc    420
cctcagagca cgttcctccc ccttcaccct gtatccaccc ctccggaccc tccccatctc    480
agtccctccg ctccctctct ctgaggccca tctcccaata cccagatcac tttccttcca    540
gacccttccc tcagtgtgca cggaggcagc ttgcccagca aggtgactg tctagtgggc     600 ttcccacagc caagctccca ccccatgctg cggcccttcc cttcttcctg cttggctgcc    660 tgtgccccc acctgcctgt ccacaaccca gcctctggta catccatgcc ctctgccctc    720
agcctcacct gcactttcc ttggatttca gagtctccaa aggcacaggc ctcctcagtg    780
cccactgcac aaccccaagc agagggcagc ctcgccaagg caaccacagc cccagccacc    840
acccgtaaca caggtgagaa gccccttccc tgcacactcc acccccaccc acctgctcat    900
tcctcagccg cctcctccag gcagcccttc ataactcctt gtctgagtct ccaagtcaca    960
ctttggtaag gagagggaca ctgaacggac ctctaacaaa cacctactgc cagccagccc   1020
cagtctgggg gccagcagat gccaaacagc cagcagactc ccagagcaga cctgggccgg   1080
ctccctggcc catggaccca gctctgcctc gctgagctga ggcatgggct ctcagcgcag   1140
cctcacatag agccaccctg ccgaggcagt ccggcttgca gactcacagg tcacttgggc   1200
cgcagcagcc cctccccgtg accctcgcct cccgcccgcc ccagcctggc tctctccaag   1260
tgttggatct tggtggccag cctgcttctc accctcaccc tgcctgccac ctcagaatgg   1320
caggggaaag agggccctca ccaagaactt tatctgagga gtctgaggct tgtgactctg   1380
acctgcctga gatgtccatg tggccgggg gacgggttca gtgttcggga gaactcgggt    1440
acgtgcctga ctttctctga gtagggcagg aagctgttag gagaagcagc agtgaggtgg   1500
gctggaccaa caggcagaat gactgtccct cagccaccct ctgggatgtg ggtcaagctc   1560
tgacaaaggc atggcacagc catggtggcc cctgcttgga tgagtggcca cggtgccctc   1620
accctgggcc agaatctgcc tccactctgc aggtgcagaa acacgacatt cccgtctcta   1680
aacacaccta gctcctaggc ttggggtggg cctatcaaat gcagggagat ggacacagca   1740
caagggccag agcttccat gagaaaggtg agggcagctg ctccctgacc cgggcatctg    1800
cacttgtccc tctccaccct cctcatgggc agtggagact cagcaacaaa acaagttgag   1860
tgcattagca gccagctctg gagccaagtc actcacccca cggccttggc tgctggtgga   1920
ggggccttcc cctgggcagc ctccaagaag acggccaagt gctcttactc agaccacggc   1980
gctgcttcct ggcacctcga tttcccacaa caacatgggg tgcagacagg ctagggcccc   2040
ctgccctggg gcctggacgg catccagtta aagatgaccc ttcacgggcg gtgcctgagg   2100
tgtgctgacc tcagcagcta agccctcagg tctggtctgc actgccccac ctggaggacc   2160
caactgaccc agacacagcc agggttatgg catgaccccg tggacggtga cccacaggcc   2220
agatgcagcc aggggctgtt ttgtgtggcc tagaaatgtc tttacagttg tagtgggatg   2280
gaggaggaag aggaagagag gaggggagag aaaagcaggg aaggggaaaa agaggagttc   2340
```

-continued

```
aatgcaaccc caaaagccag aacagttttg agctgaaaga acaaggcagg aaacatccca    2400
gtacctgact tcaaaacata ctataaagca gttgtaatca aaacaggatc ataaaaacag    2460
acacacagac ccatggaaca gaaaagcgag cccagaaata aatctacatg cttgcagtcc    2520
attgattttc aacaaaggca ccaggaaaac acaatgggga gaggacagtt tcctcaataa    2580
atagtgctgg ggaaactgga tatccatgtg cagactaatg aaactacaca aaaatcaatt    2640
gaaaacagtc taggccaggc gcggtggctc atgccggtaa tcccagcact ttgggaggcc    2700
gagacaggcg gatcacctga ggtcaggagt tcgagaccag cttggccaac atggcgaaac    2760
ccggtctcca ctaaaaatac aaaaattagc acatggtggc ctacgtctgt tatcccagct    2820
tttcaggagg ctgaggcagg agaatcgctt gaatcccgga ggtgaaggtt gcagggagcc    2880
aagattgcgc cactgcattc cagcctgggc aatggagcga gactgtctca aaaaaaaaaa    2940 aaaaagaaa agaaaacagt ctaaaggttt aactgaacag ataaagctac tagaagaaaa    3000
cataggggga aaactccatg acattagtct gagcaacgat ttttggatat gatcccaaaa    3060
gctcaggcag cactagtcac aaaagccaag atacagaacc aacctaagca cccctcagca    3120
gatgcacagg taaagaaaat gtggtacgta tggggcacaa tggaatacga ttcagccttt    3180
aaaaacagtg aaattctgtc attggcaaca atgtagatga acctgaagga cacttatgct    3240
aagtgaaata agccaggcac agaaggagca atactgcatg attgcactta catctggcag    3300
gttaaaaagg caaactctta gaggcagaca gtagagaggt ggtgccaggg agcgggcact    3360
ggtggctggg gagatgttgg tcaaagggca caaaactgca gttgggagga attagttcag    3420
gacatccctt gtacatgggg acagtggtta gtaacaacgg attgtatcct tgaaaaccgc    3480
taagaaaata gttttttaagt gttcttgaca caaaaagtga cacgtatgtg agatactgca    3540
tggtcattag ctggatttag ccattccaca atgtacacat atttcaaaca ttgtgttgta    3600
tatgataaac atgtataatt tttgtcaatt aaaaattttt aggaagagga ggagaagaga    3660
agaagaagga gaaggagaaa gaggaacaag aagagagaga gacaaagaca ccaggttttt    3720
tctgacccct gggctatcaa aacacctatt gcccaataac tagttggccg ttggtgccct    3780
aaactattga agcgattgct gttatgtgga tgggcccagg acacttagaa actcgtgacc    3840
cctgaggacc cccacgagga cagtcagggt ccccccgaac tcagggagca ctgaggaagg    3900
agctcttaga ggcgtggggc ccctcaggcc cctcagaggg ctctgccaca tgggtcaggg    3960
gcaggctgag ggggagtccc aggctccatg cccagcctct gtgcctctga ccagggtgtc    4020
ccccacaccg cctcctcccc agtgccctcc actggccaca cctggccaga agctggggag    4080
aggagagcac agtggttaag tcagtccctg cagggagacg gcaccagaaa aacctggcct    4140
gtggatgagt cccggcctgg cagccacaga gcagagagct ctagaagcaa cgaaggcccg    4200
agtctgctca gggaagagcg ggcagcagcc ccagggccgg acagtgacca agagtggcac    4260
cgcccatggc tcaacgggtc tttgcccaca gatcccccag ccctggaga cagggtctgt    4320 gtgcctggcc gtgcaggcag gcaccacact caggggggagg ccactgtgga gctctgtgca    4380
gagcccgggg cggagcccta ctgctcccga aggtccggcc acagctgctc tcgtttgctc    4440 tccccctgcag agtgtccgag ccacacccag cctcttggcg tctacctgct aaccctgca    4500 gtgcaggacc tgtggctccg ggacaaagcc accttcacct gcttcgtggt gggcagtgac    4560
ctgaaggatg ctcacctgac ctgggaggtg gccgggaagg tccccacagg gggcgtggag    4620
gaagggctgc tggagcggca cagcaacggc tcccagagcc agcacagccg tctgaccctg    4680
cccaggtcct tgtggaacgc ggggacctcc gtcacctgca cactgaacca tcccagcctc    4740
```

```
ccaccccaga ggttgatggc gctgagagaa cccggtgagc ctggctccca ggtggggaga    4800
cgagggtgcc cacagcctgc tgaccsctac gcctgcccca gggccatgac ccagctgggg    4860
ccccagcagc accggtcatc ctccacagga aaggagaagg gaggcaccag caccctggcc    4920
ggccccactt ctctcccagt gccccgtgg ccagaggctg acagcctccc ccacctcccc    4980
gcagctgcgc aggcacccgt caagctttcc ctgaacctgc tggcctcgtc tgaccctccc    5040
gaggcggcct cgtggctcct gtgtgaggtg tctggcttct cgccccccaa catcctcctg    5100
atgtggctgg aggaccagcg tgaggtgaac acttctgggt ttgccccccgc acgcccccct    5160 ccacagcccg ggagcaccac gttctgggcc tggagtgtgc tgcgtgtccc agccccgccc    5220
agccctcagc cagccaccta cacgtgtgtg gtcagccacg aggactcccg gactctgctc    5280
aacgccagcc ggagcctaga agtcagctgt gagtcacccc caggcccagg gttgggacgg    5340
ggactctgag gggggccata aggagctgga atccatacta ggcaggggtg ggcactgggc    5400
aggggcgggg ctaggctgtc ctgggcacac aggccccttc tcggtgtccg gcaggagcac    5460
agacttccca gtactcctgg gccatggatg tcccagcgtc catccttgct gtccacacca    5520
cgtgctggcc caggctggct ggcacagtgt aagaggtgga tacaacccct cgccgtgccc    5580
tgaggagtgg cggtttcctc ccaagacatt ccccacgggct gggtgctggg cacaggcctt    5640
ccctggtgtg accgtgaatg tggtcaccct gaacagctgc cctctctggg gacatctgac    5700
tgtccaagac cacagtcagc acctctggga gccagagggg tctccagaga cccccagatg    5760
tcaggcttgg gctcagtgcc cagcgaaagg tcagccccac acatgcccat aatgggcgcc    5820
cacccagagt gacagccccc agcctcctgc caggcccacc cttttccgcc cccttgaggc    5880
atggcacaca gaccagtgcg cccactgccc gagcatggcc ccagtgggat gtggtggcca    5940
cgaggggctg tacacacagc aggaggctgt ccgcccctgct cagggcctgc tgcctatgcc    6000
ccagctgtcc aaccaaggga ggcatggaag ggcccctggt gtaagctgga gccaggcacc    6060
caggcccccg gccaccctgc agagccaagg aaaggaagac acccaagtca caaggggca    6120 gggctgaggg ctgtcccagg ctcttttggc ccgaggggct gccagcagcc ctgacccggc    6180
atgggccttc cccaaaagcg accctgtgag gtggcctcac agagaacccc ctctgaggac    6240
agtgtctgac cctgcctgcc tcacacagat gggccccaca gcagtgggca acctgggggg    6300
cagcagccca acctgaccct gcagggactg ccccctgcag cagcagctgc ttctcagtcc    6360
cccaacctcc ctgtccccgc cagagggtct tccccgaagc tgcagcccca acccatggct    6420
gcccacctgg aacctggact ccctgtccac tgcccctcc ccttcgggc cccatctgtg    6480 ctggggccca ggttcggcct acagattccc atcattgcca tggcctcctg accttgccta    6540
tccaccccca accaccggct ccatgctgac cctccccag gctcccacgc ccagctggcc    6600
ggccatcccc aggcacagac agtctgggat ctcacaggtt agcctggacc atccacctgg    6660
ccagacctgg gagaggctgg aagctgccct gccaccatgc tccagggccc caggttgcag    6720
tactatgggg tgagggtgtg tgtgcacacc tgtgtgtacc taggatatcc gagtgtaccc    6780
ttgtgccccc aagcacaagt ctccctccca ggcagtgagg cccagatggt gcagtggtta    6840
gagctgaggc ttatcccaca gagaaccctg gcgccttggt caaggaagcc cctatgcctt    6900
tcttgcctcg atttccccct tgtctgctg agccagcagg ggccacgtcc tgggctgctg    6960
tgaggaggaa gcaagttggt gctaggaggg gctcctgtgt gtgcatgggc gggaggggtg    7020
caggtatctg agcaccccgg tctccacttg agagagcagg gcaggagctc cctgacccac    7080
ccagactaca cacgctgtgt ccacgtgtct cccattatct gtggcagagg atccggcttc    7140
```

```
tttctcaatt tccagttctt cacaaagcaa tgcctttgta aaatgcaata agaaatacta    7200
gaaaaatgat atgaacagaa agacacgccg atttttttgtt attagatgta acagaccatg   7260
gccccatgaa atga                                                      7274

<210> SEQ ID NO 49
<211> LENGTH: 1144
<212> TYPE: DNA
<213> ORGANISM: homo sapiens

<400> SEQUENCE: 49
tccactcaca gcctgaagca tacccggcag gggctgtccc caggcccaac aagcaaaggg     60
cccagtagcg agggccactg gagcccatct ccggggggct gggcaggaag tagggtgggg    120
tttggggtag ggatctggta ccctgggact gctgcaactc aaactaacca acccactggg    180
agaagatgcc tgggggtcca ggagtcctcc aagctctgcc tgccaccatc ttcctcctct    240
tcctgctgtc tgctgtctac ctgggccctg ggtgccaggc cctgtggatg cacaaggtcc    300
cagcatcatt gatggtgagc ctgggggaag acgcccactt ccaatgcccg cacaatagca    360
gcaacaacgc caacgtcacc tggtggcgcg tcctccatgg caactacacg tggccccctg    420
agttcttggg cccgggcgag gaccccaatg agccgccccc caggcccttc ctggacatgg    480
gggagggcac caagaaccga atcatcacag ccgagggat catcctcctg ttctgcgcgg     540
tggtgcctgg gacgctgctg ctgttcagga acgatggca gaacgagaag ctcgggttgg    600
atgccgggga tgaatatgaa gatgaaaacc tttatgaagg cctgaacctg gacgactgct    660
ccatgtatga ggacatctcc cggggcctcc agggcaccta ccaggatgtg ggcagcctca    720
acataggaga tgtccagctg gagaagccgt gacacccta ctcctgccag gctgccccg     780 cctgctgtgc acccagctcc agtgtctcag ctcacttccc tgggacattc tcctttcagc    840
ccttctgggg gcttccttag tcatattccc ccagtggggg gtgggagggt aacctcactc    900
ttctccaggc caggcctcct tggactcccc tggggtgtc ccactcttct tccctctaaa     960
ctgccccacc tcctaaccta atcccccgc cccgctgcct ttcccaggct cccctcaccc    1020
cagcgggtaa tgagccctta atcgctgcct ctaggggagc tgattgtagc agcctcgtta   1080
gtgtcacccc ctcctccctg atctgtcagg gccacttagt gataataaat tcttcccaac   1140
tgca                                                                1144

<210> SEQ ID NO 50
<211> LENGTH: 1258
<212> TYPE: DNA
<213> ORGANISM: homo sapiens

<400> SEQUENCE: 50
tccactcaca gcctgaagca tacccggcag gggctgtccc caggcccaac aagcaaaggg     60
cccagtagcg agggccactg gagcccatct ccggggggct gggcaggaag tagggtgggg    120
tttggggtag ggatctggta ccctgggact gctgcaactc aaactaacca acccactggg    180
agaagatgcc tgggggtcca ggagtcctcc aagctctgcc tgccaccatc ttcctcctct    240
tcctgctgtc tgctgtctac ctgggccctg ggtgccaggc cctgtggatg cacaaggtcc    300
cagcatcatt gatggtgagc ctgggggaag acgcccactt ccaatgcccg cacaatagca    360
gcaacaacgc caacgtcacc tggtggcgcg tcctccatgg caactacacg tggccccctg    420
agttcttggg cccgggcgag gaccccaatg gtacgctgat catccagaat gtgaacaaga    480
gccatggggg catatacgtg tgccgggtcc aggagggcaa cgagtcatac cagcagtcct    540
```

| | |
|---|---|
| gcggcaccta cctccgcgtg cgccagccgc cccccaggcc cttcctggac atggggagg | 600 |
| gcaccaagaa ccgaatcatc acagccgagg ggatcatcct cctgttctgc gcggtggtgc | 660 |
| ctgggacgct gctgctgttc aggaaacgat ggcagaacga aagctcgggg ttggatgccg | 720 |
| gggatgaata tgaagatgaa aacctttatg aaggcctgaa cctggacgac tgctccatgt | 780 |
| atgaggacat ctcccggggc ctccagggca cctaccagga tgtgggcagc ctcaacatag | 840 |
| gagatgtcca gctggagaag ccgtgacacc cctactcctg ccaggctgcc cccgcctgct | 900 |
| gtgcacccag ctccagtgtc tcagctcact ccctgggac attctccttt cagcccttct | 960 |
| gggggcttcc ttagtcatat tcccccagtg ggggtgggga gggtaacctc actcttctcc | 1020 |
| aggccaggcc tccttggact ccctgggggg tgtcccactc ttcttccctc taaactgccc | 1080 |
| cacctcctaa cctaatcccc ccgcccgct gcctttccca ggctcccctc accccagcgg | 1140 |
| gtaatgagcc cttaatcgct gcctctaggg gagctgattg tagcagcctc gttagtgtca | 1200 |
| ccccctcctc cctgatctgt cagggccact tagtgataat aaattcttcc caactgca | 1258 |

```
<210> SEQ ID NO 51
<211> LENGTH: 3309
<212> TYPE: DNA
<213> ORGANISM: homo sapiens

<400> SEQUENCE: 51
```

| | |
|---|---|
| ttcagcccct ctcccgggct gcgcctccgc actccgggcc cgggcagaag ggggtgcgcc | 60 |
| tcggccccac cacccaggga gcagccgagc tgaaaggccg ggaaccgcgg cttgcgggga | 120 |
| ccacagctcc cgaaagcgac gttcggccac cggaggagcg ggagccaagc aggcggagct | 180 |
| cggcgggaga ggtgcgggcc gaatccgagc cgagcggaga ggaatccggc agtagagagc | 240 |
| ggactccagc cggcggaccc tgcagccctc gcctgggaca cgcggcgcgct gggcaggcgc | 300 |
| ccaagagagc atcgagcagc ggaacccgcg aagccggccc gcagccgcga cccgcgcagc | 360 |
| ctgccgctct cccgccgccg gtccgggcag catgaggcgc gcggcgctct ggctctggct | 420 |
| gtgcgcgctg gcgctgagcc tgcagccggc cctgccgcaa attgtggcta ctaatttgcc | 480 |
| ccctgaagat caagatggct ctggggatga ctctgacaac ttctccggct caggtgcagg | 540 |
| tgctttgcaa gatatcaccct tgtcacagca gacccctcc acttggaagg acacgcagct | 600 |
| cctgacggct attcccacgt ctccagaacc caccggcctg gaggctacag ctgcctccac | 660 |
| ctccaccctg ccggctggag aggggcccaa ggagggagag gctgtagtcc tgccagaagt | 720 |
| ggagcctggc ctcaccgccc gggagcagga ggccaccccc cgacccaggg agaccacaca | 780 |
| gctcccgacc actcatcagg cctcaacgac cacagccacc acggcccagg agcccgccac | 840 |
| ctcccacccc cacagggaca tgcagcctgg ccaccatgag acctcaaccc ctgcaggacc | 900 |
| cagccaagct gaccttcaca ctccccacac agaggatgga ggtccttctg ccaccgagag | 960 |
| ggctgctgag gatggagcct ccagtcagct cccagcagca gagggctctg ggagcagga | 1020 |
| cttcaccttt gaaacctcgg gggagaatac ggctgtagtg gccgtggagc ctgaccgccg | 1080 |
| gaaccagtcc ccagtggatc agggggccac gggggcctca cagggcctcc tggacaggaa | 1140 |
| agaggtgctg ggagggtca ttgccggagg cctcgtgggg ctcatctttg ctgtgtgcct | 1200 |
| ggtgggtttc atgctgtacc gcatgaagaa gaaggacgaa ggcagctact ccttggagga | 1260 |
| gccgaaacaa gccaacggcg gggcctacca gaagcccacc aaacaggagg aattctatgc | 1320 |
| ctgacgcggg agccatgcgc cccctccgcc ctgccactca ctaggccccc acttgcctct | 1380 |
| tccttgaaga actgcaggcc ctggcctccc ctgccaccag gccacctccc cagcattcca | 1440 |

```
gccnctctgg tcgctcctgc ccacggagtc gtggggtgtg ctgggagctc cactctgctt    1500
ctctgacttc tgcctggaga cttagggcac caggggtttc tcgcatagga cctttccacc    1560
acagccagca cctggcatcg caccattctg actcggtttc tccaaactga agcagcctct    1620
ccccaggtcc agctctggag gggaggggga tccgactgct ttggacctaa atggcctcat    1680
gtggctggaa gatcctgcgg gtggggcttg ggctcacac  acctgtagca cttactggta    1740
ggaccaagca tcttgggggg gtggccgctg agtggcaggg gacaggagtc cactttgttt    1800
cgtggggagg tctaatctag atatcgactt gttttgcac  atgtttcctc tagttctttg    1860
ttcatagccc agtagacctt gttacttctg aggtaagtta agtaagttga ttcggtatcc    1920
ccccatcttg cttccctaat ctatggtcgg gagacagcat cagggttaag aagactttt    1980 tttttttttt taaactagg  agaaccaaat ctggaagcca aaatgtaggc ttagtttgtg    2040
tgttgtctct tgagtttgtc gctcatgtgt gcaacagggt atggactatc tgtctggtgg    2100
ccccgtttct ggtggtctgt tggcaggctg ccagtccag  gctgccgtgg ggccgccgcc    2160
tctttcaagc agtcgtgcct gtgtccatgc gctcagggcc atgctgaggc ctgggccgct    2220
gccacgttgg agaagcccgt gtgagaagtg aatgctggga ctcagccttc agacagagag    2280
gactgtaggg agggcggcag gggcctggag atcctcctgc agaccacgcc cgtcctgcct    2340
gtggcgccgt ctccagggggc tgcttcctcc tggaaattga cgaggggtgt cttgggcaga    2400
gctggctctg agcgcctcca tccaaggcca ggttctccgt tagctcctgt ggccccaccc    2460
tgggccctgg gctggaatca ggaatatttt ccaagagtg  atagtctttt gcttttggca    2520
aaactctact taatccaatg gttttttccc tgtacagtag atttttccaaa tgtaataaac    2580 tttaatataa agtagtcctg tgaatgccac tgccttcgct tcttgcctct gtgctgtgtg    2640
tgacgtgacc ggacttttct gcaaacacca acatgttggg aaacttggct cgaatctctg    2700
tgccttcgtc tttcccatgg ggagggattc tggttccagg gtccctctgt gtatttgctt    2760
ttttgttttg gctgaaattc tcctggaggt cggtaggttc agccaaggtt ttataaggct    2820
gatgtcaatt tctgtgttgc caagctccaa gccccatctt ctaaatggca aggaaggtg     2880 gatggcccca gcacagcttg acctgaggct gtggtcacag cggaggtgtg gagccgaggc    2940
ctaccccgca gacaccttgg acatcctcct cccacccggc tgcagaggcc agaggccccc    3000
agcccagggc tcctgcactt acttgcttat ttgacaacgt tcagcgact  ccgttggcca    3060 ctccgagagg tgggccagtc tgtggatcag agatgcacca ccaagccaag ggaacctgtg    3120
tccggtattc gatactgcga ctttctgcct ggagtgtatg actgcacatg actcgggggt    3180
ggggaaaggg gtcggctgac catgctcatc tgctggtccg tgggacggtg cccaagccag    3240
aggctgggtt catttgtgta acgacaataa acggtacttg tcatttcggg caaaaaaaaa    3300
aaaaaaaaa                                                            3309

<210> SEQ ID NO 52
<211> LENGTH: 3217
<212> TYPE: DNA
<213> ORGANISM: homo sapiens

<400> SEQUENCE: 52
ggccgggaga cctggcggag ctggggggtgg ggggccagtt tttgcaacgg ctaaggaagg      60
gcctgtgggt ttattataag gcggagctcg gcgggagagg tgcgggccga atccgagccg     120
agcggagagg aatccggcag tagagagcgg actccagccg gcggaccctg cagccctcgc     180
ctgggacagc ggcgcgctgg gcaggcgccc aagagagcat cgagcagcgg aacccgcgaa     240
```

```
gccggcccgc agccgcgacc cgcgcagcct gccgctctcc cgccgccggt ccgggcagca    300
tgaggcgcgc ggcgctctgg ctctggctgt gcgcgctggc gctgagcctg cagccggccc    360
tgccgcaaat tgtggctact aatttgcccc ctgaagatca agatggctct ggggatgact    420
ctgacaactt ctccggctca ggtgcaggtg ctttgcaaga tatcaccttg tcacagcaga    480
cccctccac ttggaaggac acgcagctcc tgacggctat tcccacgtct ccagaaccca    540
ccggcctgga ggctacagct gcctccacct ccaccctgcc ggctgagag ggcccaagg     600
agggagaggc tgtagtcctg ccagaagtgg agcctggcct caccgcccgg gagcaggagg    660
ccacccccg acccagggag accacacagc tcccgaccac tcatcaggcc tcaacgacca    720
cagccaccac ggcccaggag cccgccacct cccacccca cagggacatg cagcctggcc    780
accatgagac ctcaacccct gcaggaccca gccaagctga ccttcacact ccccacacag    840
aggatggagg tccttctgcc accgagaggg ctgctgagga tggagcctcc agtcagctcc    900
cagcagcaga gggctctggg gagcaggact tcacctttga aacctcgggg gagaatacgg    960
ctgtagtggc cgtggagcct gaccgccgga accagtcccc agtggatcag ggggccacgg   1020
gggcctcaca gggcctcctg gacaggaaag aggtgctggg aggggtcatt gccggaggcc   1080
tcgtggggct catctttgct gtgtgcctgg tgggtttcat gctgtaccgc atgaagaaga   1140
aggacgaagg cagctactcc ttggaggagc cgaaacaagc caacggcggg gcctaccaga   1200
agcccaccaa acaggaggaa ttctatgcct gacgcgggag ccatgcgccc cctccgccct   1260
gccactcact aggcccccac ttgcctcttc cttgaagaac tgcaggccct ggcctcccct   1320
gccaccaggc cacctcccca gcattccagc ccctctggtc gctcctgccc acggagtcgt   1380
ggggtgtgct gggagctcca ctctgcttct ctgacttctg cctggagact tagggcacca   1440
ggggtttctc gcataggacc tttccaccac agccagcacc tggcatcgca ccattctgac   1500
tcggttctc caaactgaag cagcctctcc ccaggtccag ctctggaggg gaggggatc    1560
cgactgcttt ggacctaaat ggcctcatgt ggctggaaga tcctgcgggt ggggcttggg   1620
gctcacacac ctgtagcact tactggtagg accaagcatc ttggggggt ggccgctgag    1680
tggcagggga caggagtcca cttgtttcg tggggaggtc taatctagat atcgacttgt    1740
ttttgcacat gtttcctcta gttctttgtt catagcccag tagaccttgt tacttctgag   1800
gtaagttaag taagttgatt cggtatcccc ccatcttgct tccctaatct atggtcggga   1860
gacagcatca gggttaagaa gactttttt tttttttttt aaactaggag aaccaaatct    1920
ggaagccaaa atgtaggctt agtttgtgtg ttgtctcttg agtttgtcgc tcatgtgtgc   1980
aacagggtat ggactatctg tctggtggcc ccgtttctgg tggtctgttg gcaggctggc   2040
cagtccaggc tgccgtgggg ccgccgcctc tttcaagcag tcgtgcctgt gtccatgcgc   2100
tcagggccat gctgaggcct gggccgctgc cacgttggag aagcccgtgt gagaagtgaa   2160
tgctgggact cagccttcag acagagagga ctgtagggag ggcggcaggg gcctggagat   2220
cctcctgcag accacgcccg tcctgcctgt ggcgccgtct ccaggggctg cttcctcctg   2280
gaaattgacg aggggtgtct tgggcagagc tggctctgag cgcctccatc caaggccagg   2340
ttctccgtta gctcctgtgg ccccaccctg ggccctgggc tggaatcagg aatattttcc   2400
aaagagtgat agtcttttgc ttttggcaaa actctactta atccaatggg ttttcccctg   2460
tacagtagat tttccaaatg taataaactt aatataaag tagtcctgtg aatgccactg     2520
ccttcgcttc ttgcctctgt gctgtgtgtg acgtgaccgg acttttctgc aaacaccaac   2580
atgttgggaa acttggctcg aatctctgtg ccttcgtctt tcccatgggg agggattctg   2640
```

| | |
|---|---|
| gttccagggt ccctctgtgt atttgctttt ttgttttggc tgaaattctc ctggaggtcg | 2700 |
| gtaggttcag ccaaggtttt ataaggctga tgtcaatttc tgtgttgcca agctccaagc | 2760 |
| cccatcttct aaatggcaaa ggaaggtgga tggccccagc acagcttgac ctgaggctgt | 2820 |
| ggtcacagcg gaggtgtgga gccgaggcct accccgcaga caccttggac atcctcctcc | 2880 |
| cacccggctg cagaggccag aggcccccag cccagggctc ctgcacttac ttgcttattt | 2940 |
| gacaacgttt cagcgactcc gttggccact ccgagaggtg ggccagtctg tggatcagag | 3000 |
| atgcaccacc aagccaaggg aacctgtgtc cggtattcga tactgcgact ttctgcctgg | 3060 |
| agtgtatgac tgcacatgac tcggggggtgg ggaaaggggt cggctgacca tgctcatctg | 3120 |
| ctggtccgtg ggacggtgcc caagccagag gctgggttca tttgtgtaac gacaataaac | 3180 |
| ggtacttgtc atttcgggca aaaaaaaaaa aaaaaaa | 3217 |

<210> SEQ ID NO 53
<211> LENGTH: 1477
<212> TYPE: DNA
<213> ORGANISM: homo sapiens

<400> SEQUENCE: 53

| | |
|---|---|
| agaacaactt ttttgacttc ctgcaaagag gacccttaca gtattttggg agaagttagt | 60 |
| aaaaccgaat ctgacatcat cacctagcag ttcatgcagc tagcaagtgg tttgttctta | 120 |
| gggtaacaga ggaggaaatt gttcctcgtc tgataagaca acagtggaga aaggacgcat | 180 |
| gctgtttctt agggacacgg ctgacttcca gatatgacca tgtatttgtg gcttaaactc | 240 |
| ttggcatttg gctttgcctt tctggacaca gaagtatttg tgacagggca agcccaaca | 300 |
| ccttcccca ctggccatct gcaagctgag gagcaaggaa gccaatccaa gtcaccaaac | 360 |
| ctcaaaagta gggaagctga cagttcagcc ttcagttggt ggccaaaggc ccgagagccc | 420 |
| ctcacaaacc actggagtaa gtccaagagt ccaaaagctg aggaacttgg agtctgatgt | 480 |
| tcaagagcag gaagcagcca gcacgagaga agatgaaga ccagaagact cagcaagctc | 540 |
| acttctccta ccttcttgtg cctgcttttt ctagccgtgc tggcagttgc ttggatgatg | 600 |
| cccactcata ttgggtgggg gtgggggggt tggggaggtt ctgcctcccc cagtccactg | 660 |
| actcaaatgt taatctccct tggcaatacg ctcacaggca cacccaggaa caatactttg | 720 |
| catccttcaa tccaatcaag ttgacactca atattaacca tcaaatacta ttataaggag | 780 |
| aatgttgcat gattttcctt ctagtctgtt tgtaattcac atctaatgaa agagtgagag | 840 |
| tggacgataa agggaacttg ttgaaacatt tctctcaaag caaaagggat cattggaagc | 900 |
| aggcagacac cagaattggt ttaacctaaa ataacaaat taataattat caagtctata | 960 |
| atgatgacag tgacttaatg tgaatagaaa gaattctaaa ctctctcctt ccttcctccc | 1020 |
| tcccttcttt cctactttct ttccactccc tttctcccac cccctttct tttcctttct | 1080 |
| tttctcccac cctctctccc tcccttcttt ttattcaatg catagtagtt gaaaaaatct | 1140 |
| aaagttagac ctgattttac actgaagact agaggtagtt actatcctat tactgtactt | 1200 |
| agttggctat gctggcatgt cattatgggt aaaagtttga tggatttatt tgtgagttat | 1260 |
| ttggttatga aaatctagag attgaagttt ttcattagaa aataacacac ataacaagtc | 1320 |
| tatgatcatt ttgcattct gtaatcacag aatagttctg caatatttca tgtatattgg | 1380 |
| aattgaagtt caattgaatt ttatctgtat ttagtaaaaa ttaactttag ctttgatact | 1440 |
| aatgaataaa gctgggtttt ttatttaaaa aaaaaaa | 1477 |

```
<210> SEQ ID NO 54
<211> LENGTH: 5429
<212> TYPE: DNA
<213> ORGANISM: homo sapiens

<400> SEQUENCE: 54
agaacaactt ttttgacttc ctgcaaagag gacccttaca gtattttgg agaagttagt        60 aaaaccgaat ctgacatcat cacctagcag ttcatgcagc tagcaagtgg tttgttctta      120
gggtaacaga ggaggaaatt gttcctcgtc tgataagaca acagtggaga aaggacgcat      180
gctgtttctt agggacacgg ctgacttcca gatatgacca tgtatttgtg gcttaaactc      240
ttggcatttg gctttgcctt tctgacacac gaagtatttg tgacagggca aagcccaaca      300
ccttccccca ctggattgac tacagcaaag atgcccagtg ttccactttc aagtgacccc      360
ttacctactc acaccactgc attctcaccc gcaagcacct ttgaaagaga aaatgacttc      420
tcagagacca caacttctct tagtccagac aatacttcca cccaagtatc cccggactct      480
ttggataatg ctagtgcttt taataccaca ggtgtttcat cagtacagac gcctcacctt      540
cccacgcacg cagactcgca gacgccctct gctggaactg acacgcagac attcagcggc      600
tccgccgcca atgcaaaact caaccctacc ccaggcagca atgctatctc agatgtccca      660
ggagagagga gtacagccag caccttctcc acagacccag tttccccatt gacaaccacc      720
ctcagccttg cacaccacag ctctgctgcc ttacctgcac gcacctccaa caccaccatc      780
acagcgaaca cctcagatgc ctaccttaat gcctctgaaa caaccactct gagcccttct      840
ggaagcgctg tcatttcaac cacaacaata gctactactc catctaagcc aacatgtgat      900
gaaaaatatg caaacatcac tgtggattac ttatataaca aggaaactaa attatttaca      960
gcaaagctaa atgttaatga gaatgtggaa tgtggaaaca atacttgcac aaacaatgag     1020
gtgcataacc ttacagaatg taaaaatgcg tctgtttcca tatctcataa ttcatgtact     1080
gctcctgata agacattaat attagatgtg ccaccagggg ttgaaaagtt tcagttacat     1140
gattgtacac aagttgaaaa agcagatact actatttgtt taaaatggaa aaatattgaa     1200
acctttactt gtgatacaca gaatattacc tacagatttc agtgtggtaa tatgatattt     1260
gataataaag aaattaaatt agaaaacctt gaacccgaac atgagtataa gtgtgactca     1320
gaaatactct ataataacca caagtttact aacgcaagta aaattattaa aacagatttt     1380
gggagtccag gagagcctca gattattttt tgtagaagtg aagctgcaca tcaaggagta     1440
attacctgga atcccctca aagatcattt cataatttta ccctctgtta tataaaagag     1500
acagaaaaag attgcctcaa tctggataaa aacctgatca aatatgattt gcaaaattta     1560
aaaccttata cgaaatatgt tttatcatta catgcctaca tcattgcaaa agtgcaacgt     1620
aatggaagtg ctgcaatgtg tcatttcaca actaaaagtg ctcctccaag ccaggtctgg     1680
aacatgactg tctccatgac atcagataat agtatgcatg tcaagtgtag gcctccagg     1740 gaccgtaatg gcccccatga acgttaccat ttggaagttg aagctggaaa tactctggtt     1800
agaaatgagt cgcataagaa ttgcgatttc cgtgtaaaag atcttcaata ttcaacagac     1860
tacactttta aggcctattt tcacaatgga gactatcctg agaaccctt tattttacat     1920 cattcaacat cttataattc taaggcactg atagcatttc tggcatttct gattattgtg     1980
acatcaatag ccctgcttgt tgttctctac aaaatctatg atctacataa gaaaagatcc     2040
tgcaatttag atgaacagca ggagcttgtt gaaagggatg atgaaaaaca actgatgaat     2100
gtggagccaa tccatgcaga tatttgttg gaaacttata agaggaagat tgctgatgaa     2160
```

```
ggaagacttt ttctggctga atttcagagc atcccgcggg tgttcagcaa gtttcctata    2220
aaggaagctc gaaagccctt taaccagaat aaaaaccgtt atgttgacat tcttccttat    2280
gattataacc gtgttgaact ctctgagata aacggagatg cagggtcaaa ctacataaat    2340
gccagctata ttgatggttt caaagaaccc aggaaataca ttgctgcaca aggtcccagg    2400
gatgaaactg ttgatgattt ctggaggatg atttgggaac agaaagccac agttattgtc    2460
atggtcactc gatgtgaaga aggaaacagg aacaagtgtg cagaatactg gccgtcaatg    2520
gaagagggca ctcgggcttt tggagatgtt gttgtaaaga tcaaccagca caaagatgt     2580
ccagattaca tcattcagaa attgaacatt gtaaataaaa agaaaaagc aactggaaga     2640
gaggtgactc acattcagtt caccagctgg ccagaccacg gggtgcctga ggatcctcac    2700
ttgctcctca aactgagaag gagagtgaat gccttcagca atttcttcag tggtcccatt    2760
gtggtgcact gcagtgctgg tgttgggcgc acaggaacct atatcggaat tgatgccatg    2820
ctagaaggcc tggaagccga gaacaaagtg gatgtttatg gttatgttgt caagctaagg    2880
cgacagagat gcctgatggt tcaagtagag gcccagtaca tcttgatcca tcaggctttg    2940
gtggaataca atcagtttgg agaaacagaa gtgaatttgt ctgaattaca tccatatcta    3000
cataacatga agaaagggaa tccacccagt gagccgtctc cactagaggc tgaattccag    3060
agacttcctt catataggag ctggaggaca cagcacattg gaaatcaaga agaaaataaa    3120
agtaaaaaca ggaattctaa tgtcatccca tatgactata cagagtgcc acttaaacat     3180
gagctggaaa tgagtaaaga gagtgagcat gattcagatg aatcctctga tgatgacagt    3240
gattcagagg aaccaagcaa atacatcaat gcatctttta taatgagcta ctggaaacct    3300
gaagtgatga ttgctgctca gggaccactg aaggagacca ttggtgactt ttggcagatg    3360
atcttccaaa gaaaagtcaa agttattgtt atgctgacag aactgaaaca tggagaccag    3420
gaaatctgtg ctcagtactg gggagaagga agcaaacat atggagatat tgaagttgac     3480
ctgaaagaca cagacaaatc ttcaacttat acccttcgtg tctttgaact gagacattcc    3540
aagaggaaag actctcgaac tgtgtaccag taccaatata caaactggag tgtggagcag    3600
cttcctgcag aacccaagga attaatctct atgattcagg tcgtcaaaca aaaacttccc    3660
cagaagaatt cctctgaagg gaacaagcat cacaagagta cacctctact cattcactgc    3720
agggatggat ctcagcaaac gggaatattt tgtgctttgt taaatctctt agaaagtgcg    3780
gaaacagaag aggtagtgga tattttcaa gtggtaaaag ctctacgcaa agctaggcca     3840
ggcatggttt ccacattcga gcaatatcaa ttcctatatg acgtcattgc cagcacctac    3900
cctgctcaga atggacaagt aaagaaaaac aaccatcaag aagataaaat tgaatttgat    3960
aatgaagtgg acaaagtaaa gcaggatgct aattgtgtta atccacttgg tgccccagaa    4020
aagctccctg aagcaaagga acaggctgaa ggttctgaac ccacgagtgg cactgagggg    4080
ccagaacatt ctgtcaatgg tcctgcaagt ccagctttaa atcaaggttc ataggaaaag    4140
acataaatga ggaaactcca aacctcctgt tagctgttat ttctattttt gtagaagtag    4200
gaagtgaaaa taggtataca gtggattaat taaatgcagc gaaccaatat ttgtagaagg    4260
gttatatttt actactgtgg aaaaatattt aagatagttt tgccagaaca gtttgtacag    4320
acgtatgctt atttttaaaat tttatctctt attcagtaaa aaacaacttc tttgtaatcg    4380
ttatgtgtgt atatgtatgt gtgtatgggt gtgtgtttgt gtgagagaca gagaaagaga    4440
gagaattctt tcaagtgaat ctaaaagctt ttgcttttcc tttgttttta tgaagaaaaa    4500
atacatttta tattagaagt gttaacttag cttgaaggat ctgttttta aaatcataaa     4560
```

```
ctgtgtgcag actcaataaa atcatgtaca tttctgaaat gacctcaaga tgtcctcctt    4620
gttctactca tatatatcta tcttatatag tttactattt tacttctaga gatagtacat    4680
aaaggtggta tgtgtgtgta tgctactaca aaaaagttgt taactaaatt aacattggga    4740
aatcttatat tccatatatt agcatttagt ccaatgtctt tttaagctta tttaattaaa    4800
aaatttccag tgagcttatc atgctgtctt tacatggggt tttcaatttt gcatgctcga    4860
ttattccctg tacaatattt aaaatttatt gcttgatact tttgacaaca aattaggttt    4920
tgtacaattg aacttaaata aatgtcatta aaataaataa atgcaatatg tattaatatt    4980
cattgtataa aaatagaaga atacaaacat atttgttaaa tatttacata tgaaatttaa    5040
tatagctatt tttatggaat ttttcattga tatgaaaaat atgatattgc atatgcatag    5100
ttcccatgtt aaatcccatt cataactttc attaaagcat ttactttgaa tttctccaat    5160
gcttagaatg ttttttaccag gaatggatgt cgctaatcat aataaaattc aaccattatt    5220
tttttcttgt ttataataca ttgtgttata tgttcaaata tgaaatgtgt atgcacctat    5280
tgaaatatgt ttaatgcatt tattaacatt tgcaggacac ttttacaggc cccaattatc    5340
caatagtcta ataattgttt aagatctaga aaaaaaaaat caagaatagt ggtatttttc    5400
atgaagtaat aaaaactcgt tttggtgaa                                       5429
```

<210> SEQ ID NO 55
<211> LENGTH: 4946
<212> TYPE: DNA
<213> ORGANISM: homo sapiens

<400> SEQUENCE: 55

```
agaacaactt ttttgacttc ctgcaaagag gacccttaca gtattttggg agaagttagt      60
aaaaccgaat ctgacatcat cacctagcag ttcatgcagc tagcaagtgg tttgttctta     120
gggtaacaga ggaggaaatt gttcctcgtc tgataagaca acagtggaga aaggacgcat     180
gctgtttctt agggacacgg ctgacttcca gatatgacca tgtatttgtg gcttaaactc     240
ttggcatttg gctttgcctt tctggacaca gaagtatttg tgacagggca agcccaaca      300 ccttccccca ctgatgccta ccttaatgcc tctgaaacaa ccactctgag cccttctgga     360
agcgctgtca tttcaaccac aacaatagct actactccat ctaagccaac atgtgatgaa     420
aaatatgcaa acatcactgt ggattactta tataacaagg aaactaaatt atttacagca     480
aagctaaatg ttaatgagaa tgtggaatgt ggaaacaata cttgcacaaa caatgaggtg     540
cataacctta cagaatgtaa aaatgcgtct gtttccatat ctcataattc atgtactgct     600
cctgataaga cattaatatt agatgtgcca ccaggggttg aaaagtttca gttacatgat     660
tgtacacaag ttgaaaaagc agatactact atttgtttaa aatggaaaaa tattgaaacc     720
tttacttgtg atacacagaa tattacctac agatttcagt gtggtaatat gatatttgat     780
aataaagaaa ttaaattaga aaaccttgaa cccgaacatg agtataagtg tgactcagaa     840
atactctata ataaccacaa gttactaac gcaagtaaaa ttattaaaac agattttggg     900
agtccaggag agcctcagat tatttttgt agaagtgaag ctgcacatca aggagtaatt     960
acctggaatc cccctcaaag atcatttcat aattttaccc tctgttatat aaaagagaca    1020
gaaaaagatt gcctcaatct ggataaaaac ctgatcaaat atgatttgca aaatttaaaa    1080
ccttatacga aatatgtttt atcattacat gcctacatca ttgcaaaagt gcaacgtaat    1140
ggaagtgctg caatgtgtca tttcacaact aaaagtgctc ctccaagcca ggtctggaac    1200
atgactgtct ccatgacatc agataatagt atgcatgtca agtgtaggcc tcccagggac    1260
```

```
cgtaatggcc cccatgaacg ttaccatttg gaagttgaag ctggaaatac tctggttaga    1320
aatgagtcgc ataagaattg cgatttccgt gtaaaagatc ttcaatattc aacagactac    1380
acttttaagg cctatttcca caatggagac tatcctggag aacccttat tttacatcat     1440 tcaacatctt ataattctaa ggcactgata gcatttctgg catttctgat tattgtgaca    1500
tcaatagccc tgcttgttgt tctctacaaa atctatgatc tacataagaa aagatcctgc    1560
aatttagatg aacagcagga gcttgttgaa agggatgatg aaaaacaact gatgaatgtg    1620
gagccaatcc atgcagatat tttgttggaa acttataaga ggaagattgc tgatgaagga    1680 agacttttc tggctgaatt tcagagcatc ccgcgggtgt tcagcaagtt tcctataaag     1740
gaagctcgaa agccctttaa ccagaataaa aaccgttatg ttgacattct tccttatgat    1800
tataaccgtg ttgaactctc tgagataaac ggagatgcag ggtcaaacta cataaatgcc    1860
agctatattg atggtttcaa agaacccagg aaatacattg ctgcacaagg tcccagggat    1920
gaaactgttg atgatttctg gaggatgatt tgggaacaga aagccacagt tattgtcatg    1980
gtcactcgat gtgaagaagg aaacaggaac aagtgtgcag aatactggcc gtcaatggaa    2040
gagggcactc gggcttttgg agatgttgtt gtaaagatca ccagcacaa aagatgtcca    2100 gattacatca ttcagaaatt gaacattgta aataaaaaag aaaaagcaac tggaagagag    2160
gtgactcaca ttcagttcac cagctggcca gaccacgggg tgcctgagga tcctcacttg    2220
ctcctcaaac tgagaaggag agtgaatgcc ttcagcaatt tcttcagtgg tcccattgtg    2280
gtgcactgca gtgctggtgt tgggcgcaca ggaacctata tcggaattga tgccatgcta    2340
gaaggcctgg aagccgagaa caaagtggat gtttatggtt atgttgtcaa gctaaggcga    2400
cagagatgcc tgatggttca gtagaggcc cagtacatct tgatccatca ggctttggtg      2460
gaatacaatc agtttggaga aacagaagtg aatttgtctg aattacatcc atatctacat    2520
aacatgaaga aagggatcc acccagtgag ccgtctccac tagaggctga attccagaga     2580
cttccttcat ataggagctg gaggacacag cacattggaa atcaagaaga aaataaaagt    2640
aaaaacagga attctaatgt catcccatat gactataaca gagtgccact taaacatgag    2700
ctggaaatga gtaaagagag tgagcatgat tcagatgaat cctctgatga tgacagtgat    2760
tcagaggaac caagcaaata catcaatgca tcttttataa tgagctactg gaaacctgaa    2820
gtgatgattg ctgctcaggg accactgaag gagaccattg gtgacttttg gcagatgatc    2880
ttccaaagaa aagtcaaagt tattgttatg ctgacagaac tgaaacatgg agaccaggaa    2940
atctgtgctc agtactgggg agaaggaaag caaacatatg gagatattga agttgacctg    3000
aaagacacag acaaatcttc aacttatacc cttcgtgtct ttgaactgag acattccaag    3060
aggaaagact ctcgaactgt gtaccagtac caatatacaa actggagtgt ggagcagctt    3120
cctgcagaac ccaaggaatt aatctctatg attcaggtcg tcaaacaaaa acttccccag    3180
aagaattcct ctgaagggaa caagcatcac aagagtacac ctctactcat tcactgcagg    3240
gatggatctc agcaaacggg aatatttgt gctttgttaa atctcttaga aagtgcggaa    3300
acagaagagg tagtggatat ttttcaagtg gtaaagctc tacgcaaagc taggccaggc    3360
atggtttcca cattcgagca atatcaattc ctatatgacg tcattgccag cacctaccct    3420
gctcagaatg gacaagtaaa gaaaaacaac catcaagaag ataaattga atttgataat    3480 gaagtggaca agtaaagca ggatgctaat tgtgttaatc cacttggtgc cccagaaaag    3540
ctccctgaag caaaggaaca ggctgaaggt tctgaaccca cgagtggcac tgaggggcca    3600
gaacattctg tcaatggtcc tgcaagtcca gctttaaatc aaggttcata ggaaaagaca    3660
```

```
taaatgagga aactccaaac ctcctgttag ctgttatttc tattttttgta gaagtaggaa    3720 gtgaaaatag gtatacagtg gattaattaa atgcagcgaa ccaatatttg tagaagggtt    3780
atattttact actgtggaaa aatatttaag atagttttgc cagaacagtt tgtacagacg    3840
tatgcttatt ttaaaatttt atctcttatt cagtaaaaaa caacttcttt gtaatcgtta    3900
tgtgtgtata tgtatgtgtg tatgggtgtg tgtttgtgtg agagacagag aaagagagag    3960
aattctttca agtgaatcta aaagcttttg ctttttccttt gttttatga agaaaaaata    4020 cattttatat tagaagtgtt aacttagctt gaaggatctg tttttaaaaa tcataaactg    4080
tgtgcagact caataaaatc atgtacattt ctgaaatgac ctcaagatgt cctccttgtt    4140
ctactcatat atatctatct tatatagttt actatttttac ttctagagat agtacataaa    4200
ggtggtatgt gtgtgtatgc tactacaaaa aagttgttaa ctaaattaac attgggaaat    4260
cttatattcc atatattagc atttagtcca atgtcttttt aagcttattt aattaaaaaa    4320
tttccagtga gcttatcatg ctgtctttac atggggtttt caattttgca tgctcgatta    4380
ttccctgtac aatatttaaa atttattgct tgatactttt gacaacaaat taggttttgt    4440
acaattgaac ttaaataaat gtcattaaaa taaataaatg caatatgtat taatattcat    4500
tgtataaaaa tagaagaata caaacatatt tgttaaatat ttacatatga aatttaatat    4560
agctattttt atggaatttt tcattgatat gaaaaatatg atattgcata tgcatagttc    4620
ccatgttaaa tcccattcat aactttcatt aaagcattta ctttgaattt ctccaatgct    4680
tagaatgttt ttaccaggaa tggatgtcgc taatcataat aaaattcaac cattattttt    4740
ttcttgttta taatacattg tgttatatgt tcaaatatga aatgtgtatg cacctattga    4800
aatatgttta atgcatttat taacatttgc aggacacttt tacaggcccc aattatccaa    4860
tagtctaata attgtttaag atctagaaaa aaaaaatcaa gaatagtggt attttttcatg    4920 aagtaataaa aactcgtttt ggtgaa                                         4946
```

<210> SEQ ID NO 56
<211> LENGTH: 2333
<212> TYPE: DNA
<213> ORGANISM: homo sapiens

<400> SEQUENCE: 56

```
agcacaaaag gaggaaggac agcacagctg acagccgtgc tcagaaagtt tctggatccc      60
aggctcatct ccacagagga gaacacgcag gcagcagaga ccatggggcc catctcagcc     120
ccttcctgca gatggcgcat cccctggcag gggctcctgc tcacagcctc acttttcacc     180
ttctggaacc cgcccaccac tgctcagctc actattgaag ctgtgccatc caatgctgca     240 gagggggaagg aggttcttct acttgtccac aatctgcccc aggaccctcg tggctacaac     300
tggtacaaag gggaaacagt ggatgccaac cgtcgaatta aggatatgt aatatcaaat      360 caacagatta ccccagggcc tgcatacagc aatcgagaga caatataccc caatgcatcc     420
ctgctgatgc ggaacgtcac cagaaatgac acaggatcct acaccctaca agtcataaag     480
ctaaatctta tgagtgaaga agtaactggc cagttcagcg tacatccgga gactcccaag     540
ccctccatct ccagcaacaa ctccaacccc gtggaggaca aggatgctgt ggccttcacc     600
tgtgaacctg agactcagaa cacaacctac ctgtggtggg taaatggtca gagtctcccg     660
gtcagtccca ggctgcagct gtccaatggc aacaggaccc tcactctact cagtgtcaca     720
aggaatgacg taggacccta tgaatgtgaa atacagaacc cagcgagtgc aaacttcagt     780
gacccagtca ccctgaatgt cctctatggc ccagatgccc ccaccatttc cccttcagac     840
```

| | | |
|---|---|---|
| acctattacc atgcagggt aaatctcaac ctctcctgcc atgcggcctc taatccaccc | 900 | |
| tcacagtatt cttggtctgt caatggcaca ttccagcaat acacacaaaa gctctttatc | 960 | |
| cccaacatca ctacaaagaa cagcggatcc tatgcctgcc acaccactaa ctcagccact | 1020 | |
| ggccgcaaca ggaccacagt caggatgatc acagtctctg atgctttagt caaggaagt | 1080 | |
| tctcctggcc tctcagctag agccactgtc agcatcatga ttggagtact ggccagggtg | 1140 | |
| gctctgatat agtagcctg gtgtagtttc tgcatttcaa gaagactggc agacagttgt | 1200 | |
| ttttattctt cctcaaagca tttgcaatca gctaccattc aaaattgctt cttcttcaag | 1260 | |
| atttatggaa aatactctga cgagtactct tgaacacaag ttcctgataa ctttaagatc | 1320 | |
| acgccactgg actgtctatg aacttgcaaa caggctgata cctttgtgaa gttgcccacc | 1380 | |
| aaaacacaga aggaaaaaaa catgaatttc attgaactaa ataataatga ggataatgtt | 1440 | |
| tttaagattt tttttttttt tttttgaga tggaatctcg ctctgtcgcc caggctggag | 1500 | |
| tgcagtggca cgatctcaac tcactgcaag ctccgcctcc tgggttcaca ccattctcct | 1560 | |
| gcctcagcct cctgagtagc tgggactaca ggcgcctgcc acaacgcccg ctaattttt | 1620 | |
| tgtatttta gtagagacgg ggtttcactg tggtctcaat ctcctgactt catggtccgc | 1680 | |
| ctgcctcagc ctcccaaagt tctgggatta caggtgtgag ccaccgcgcc cagcccgttt | 1740 | |
| ttaagatttt ttatttgaaa aattgccaat tctttaagtg ttttctttt cagatttatg | 1800 | |
| aatttcttta tcttttaagc tatctatacc ttactgcaat ttggtaaagc agactttgt | 1860 | |
| gaacaaaaat tataacattt acttttgctc cctacctgac tgccacagaa ctgggcaact | 1920 | |
| attcatgagt attcatatgt ttatggtaat tcagttattt gcacaagttc agtgagaatc | 1980 | |
| tgctgtcttt ataatgggat atagtttaaa acattggtta tattaccaag gctttgattg | 2040 | |
| ggatgttata tttgagaaaa tacagagaat gatagattaa cggagtgtct aatctatcgt | 2100 | |
| gtcaaccca aattttttacg tatgagatcc tttagtccac ccaatggctg acagtaacag | 2160 | |
| catctttaac acaactcttt gttcaaatgt actatggtct cttttagagt cagactccta | 2220 | |
| gactcacttg ttctcactgt ctgttttaat ttaacccagg catgcaatgc tagataataa | 2280 | |
| aattgctccc tattggctga tcaaaaaaaa aaaaaaaaa aaaaaaaaaa aaa | 2333 | |

```
<210> SEQ ID NO 57
<211> LENGTH: 2406
<212> TYPE: DNA
<213> ORGANISM: homo sapiens

<400> SEQUENCE: 57
```

| | | |
|---|---|---|
| gattctgtgt gtgtcctcag atgctcagcc acagaccttt gagggagtaa aggggcaga | 60 | |
| cccacccacc ttgcctccag gctctttcct tcctggtcct gttctatggt ggggctccct | 120 | |
| tgccagactt cagactgaga agtcagatga agtttcaaga aaaggaaatt ggtgggtgac | 180 | |
| agagatgggt ggaggggctg gggaaaggct gtttacttcc tcctgtctag tcggtttggt | 240 | |
| cccttaggg ctccggatat ctttggtgac ttgtccactc cagtgtggca tcatgtggca | 300 | |
| gctgctcctc ccaactgctc tgctacttct agtttcagct ggcatgcgga ctgaagatct | 360 | |
| cccaaaggct gtggtgttcc tggagcctca atggtacagg gtgctcgaga aggacagtgt | 420 | |
| gactctgaag tgccagggag cctactcccc tgaggacaat tccacacagt ggtttcacaa | 480 | |
| tgagagcctc atctcaagcc aggcctcgag ctacttcatt gacgctgcca cagtcgacga | 540 | |
| cagtggagag tacaggtgcc agacaaacct ctccaccctc agtgaccgg tgcagctaga | 600 | |
| agtccatatc ggctggctgt tgctccaggc ccctcggtgg gtgttcaagg aggaagaccc | 660 | |

| | |
|---|---|
| tattcacctg aggtgtcaca gctggaagaa cactgctctg cataaggtca catatttaca | 720 |
| gaatggcaaa ggcaggaagt attttcatca taattctgac ttctacattc caaaagccac | 780 |
| actcaaagac agcggctcct acttctgcag ggggcttttt gggagtaaaa atgtgtcttc | 840 |
| agagactgtg aacatcacca tcactcaagg tttggcagtg tcaaccatct catcattctt | 900 |
| tccacctggg taccaagtct cttctgctt ggtgatggta ctccttttg cagtggacac | 960 |
| aggactatat ttctctgtga agacaaacat tcgaagctca acaagagact ggaaggacca | 1020 |
| taaatttaaa tggagaaagg accctcaaga caaatgaccc ccatcccatg ggggtaataa | 1080 |
| gagcagtagc agcagcatct ctgaacattt ctctggattt gcaaccccat catcctcagg | 1140 |
| cctctctaca agcagcagga aacatagaac tcagagccag atcccttatc caactctcga | 1200 |
| cttttccttg gtctccagtg aagggaaaa gcccatgatc ttcaagcagg aagccccag | 1260 |
| tgagtagctg cattcctaga aattgaagtt tcagagctac acaaacactt tttctgtccc | 1320 |
| aaccgttccc tcacagcaaa gcaacaatac aggctaggga tggtaatcct ttaaacatac | 1380 |
| aaaaattgct cgtgttataa attcccagt ttagagggga aaaaaaaca attattccta | 1440 |
| aataaatgga taagtagaat taatggttga ggcaggacca tacagagtgt gggaactgct | 1500 |
| ggggatctag ggaattcagt gggaccaatg aaagcatggc tgaaaatag caggtagtcc | 1560 |
| aggatagtct aagggaggtg ttcccatctg agcccagaga taagggtgtc ttcctagaac | 1620 |
| attagccgta gtggaattaa caggaaatca tgagggtgac gtagaattga gtcttccagg | 1680 |
| ggactctatc agaactggac catctccaag tatataacga tgagtcctct taatgctagg | 1740 |
| agtagaaaat ggtcctagga aggggactga ggattgcggt gggggggtggg gtggaaagaa | 1800 |
| aagtacagaa caaaccctgt gtcactgtcc caagttgcta agtgaacaga actatctcag | 1860 |
| catcagaatg agaaagcctg agaagaaaga accaaccaca agcacacagg aaggaaagcg | 1920 |
| caggaggtga aaatgctttc ttggccaggg tagtaagaat tagaggttaa tgcagggact | 1980 |
| gtaaaaccac cttttctgct tcaatatcta attcctgtgt agctttgttc attgcattta | 2040 |
| ttaaacaaat gttgtataac caatactaaa tgtactactg agcttcgctg agttaagtta | 2100 |
| tgaaactttc aaatccttca tcatgtcagt tccaatgagg tggggatgga gaagacaatt | 2160 |
| gttgcttatg aaagaaagct ttagctgtct ctgttttgta agctttaagc gcaacatttc | 2220 |
| ttggttccaa taaagcattt tacaagatct tgcatgctac tcttagatag aagatgggaa | 2280 |
| aaccatggta ataaaatatg aatgataaaa aaaaaaaaa aaaaaaaaa aaaaaaaaa | 2340 |
| aaaaaaaaa aaaaaaaaa aaaaaaaaa aaaaaaaaa aaaaaaaaa aaaaaaaaa | 2400 |
| aaaaaa | 2406 |

```
<210> SEQ ID NO 58
<211> LENGTH: 2338
<212> TYPE: DNA
<213> ORGANISM: homo sapiens

<400> SEQUENCE: 58
```

| | |
|---|---|
| gattctgtgt gtgtcctcag atgctcagcc acagaccttt gagggagtaa aggggggcaga | 60 |
| cccacccacc ttgcctccag gctctttcct tcctggtcct gttctatggt ggggctccct | 120 |
| tgccagactt cagactgaga agtcagatga agtttcaaga aaaggaaatt ggtgggtgac | 180 |
| agagatgggt ggaggggctg gggaaaggct gtttacttcc tcctgtctag tcggtttggt | 240 |
| cccttaggg ctccggatat cttttggtgac ttgtccactc cagtgtggca tcatgtggca | 300 |
| gctgctcctc ccaactgctc tgctacttct agtttcagct ggcatgcgga ctgatctccc | 360 |

| | |
|---|---|
| aaaggctgtg gtgttcctgg agcctcaatg gtacagggtg ctcgagaagg acagtgtgac | 420 |
| tctgaagtgc cagggagcct actcccctga ggacaattcc acacagtggt ttcacaatga | 480 |
| gagcctcatc tcaagccagg cctcgagcta cttcattgac gctgccacag tcgacgacag | 540 |
| tggagagtac aggtgccaga caaacctctc caccctcagt gacccggtgc agctagaagt | 600 |
| ccatatcggc tggctgttgc tccaggcccc tcggtgggtg ttcaaggagg aagaccctat | 660 |
| tcacctgagg tgtcacagct ggaagaacac tgctctgcat aaggtcacat atttacagaa | 720 |
| tggcaaaggc aggaagtatt ttcatcataa ttctgacttc tacattccaa aagccacact | 780 |
| caaagacagc ggctcctact tctgcagggg gcttttttggg agtaaaaatg tgtcttcaga | 840 |
| gactgtgaac atcaccatca ctcaaggttt ggcagtgtca accatctcat cattctttcc | 900 |
| acctgggtac caagtctctt tctgcttggt gatggtactc cttttttgcag tggacacagg | 960 |
| actatatttc tctgtgaaga caaacattcg aagctcaaca agagactgga aggaccataa | 1020 |
| atttaaatgg agaaaggacc ctcaagacaa atgaccccca tcccatgggg gtaataagag | 1080 |
| cagtagcagc agcatctctg aacatttctc tggatttgca accccatcat cctcaggcct | 1140 |
| ctctacaagc agcaggaaac atagaactca gagccagatc ccttatccaa ctctcgactt | 1200 |
| ttccttggtc tccagtggaa gggaaaagcc catgatcttc aagcagggaa gccccagtga | 1260 |
| gtagctgcat tcctagaaat tgaagtttca gagctacaca aacactttttt ctgtcccaac | 1320 |
| cgttccctca cagcaaagca acaatacagg ctagggatgg taatccttta aacatacaaa | 1380 |
| aattgctcgt gttataaatt acccagttta gaggggaaaa aaaacaatt attcctaaat | 1440 |
| aaatggataa gtagaattaa tggttgaggc aggaccatac agagtgtggg aactgctggg | 1500 |
| gatctaggga attcagtggg accaatgaaa gcatggctga gaaatagcag gtagtccagg | 1560 |
| atagtctaag ggaggtgttc ccatctgagc ccagagataa gggtgtcttc ctagaacatt | 1620 |
| agccgtagtg gaattaacag gaaatcatga gggtgacgta gaattgagtc ttccagggga | 1680 |
| ctctatcaga actggaccat ctccaagtat ataacgatga gtcctcttaa tgctaggagt | 1740 |
| agaaaatggt cctaggaagg ggactgagga ttgcggtggg gggtggggtg gaaaagaaag | 1800 |
| tacagaacaa accctgtgtc actgtcccaa gttgctaagt gaacagaact atctcagcat | 1860 |
| cagaatgaga aagcctgaga agaaagaacc aaccacaagc acacaggaag gaaagcgcag | 1920 |
| gaggtgaaaa tgctttcttg gccagggtag taagaattag aggttaatgc agggactgta | 1980 |
| aaaccacctt ttctgcttca atatctaatt cctgtgtagc tttgttcatt gcatttatta | 2040 |
| aacaaatgtt gtataaccaa tactaaatgt actactgagc ttcgctgagt taagttatga | 2100 |
| aactttcaaa tccttcatca tgtcagttcc aatgaggtgg ggatggagaa gacaattgtt | 2160 |
| gcttatgaaa gaaagcttta gctgtctctg ttttgtaagc tttaagcgca acatttcttg | 2220 |
| gttccaataa agcattttac aagatcttgc atgctactct tagatagaag atgggaaaac | 2280 |
| catggtaata aatatgaat gataaaaaaa aaaaaaaaa aaaaaaaaa aaaaaaa | 2338 |

<210> SEQ ID NO 59
<211> LENGTH: 2204
<212> TYPE: DNA
<213> ORGANISM: homo sapiens

<400> SEQUENCE: 59

| | |
|---|---|
| ggagccccgg ctcctaggct gacagaccag cccagatcca gtggcccgga ggggcctgag | 60 |
| ctaaatccgc aggacctggg taacacgagg aagtcggttt ggtccctta gggctccgga | 120 |
| tatctttggt gacttgtcca ctccagtgtg gcatcatgtg gcagctgctc ctcccaactg | 180 |

```
ctctgctact tctagtttca gctggcatgc ggactgaaga tctcccaaag gctgtggtgt    240
tcctggagcc tcaatggtac agggtgctcg agaaggacag tgtgactctg aagtgccagg    300
gagcctactc ccctgaggac aattccacac agtggtttca caatgagagc ctcatctcaa    360
gccaggcctc gagctacttc attgacgctg ccacagtcga cgacagtgga gagtacaggt    420
gccagacaaa cctctccacc ctcagtgacc cggtgcagct agaagtccat atcggctggc    480
tgttgctcca ggcccctcgg tgggtgttca aggaggaaga cccctattcac ctgaggtgtc    540 acagctggaa gaacactgct ctgcataagg tcacatattt acagaatggc aaaggcagga    600
agtattttca tcataattct gacttctaca ttccaaaagc cacactcaaa gacagcggct    660
cctacttctg caggggggctt tttgggagta aaaatgtgtc ttcagagact gtgaacatca    720
ccatcactca aggtttggca gtgtcaacca tctcatcatt ctttccacct gggtaccaag    780
tctctttctg cttggtgatg gtactccttt tgcagtggga cacaggacta tatttctctg    840
tgaagacaaa cattcgaagc tcaacaagag actggaagga ccataaattt aaatggagaa    900
aggaccctca agacaaatga cccccatccc atggggggtaa taagagcagt agcagcagca    960
tctctgaaca tttctctgga tttgcaaccc catcatcctc aggcctctct acaagcagca   1020
ggaaacatag aactcagagc cagatccctt atccaactct cgacttttcc ttggtctcca   1080
gtggaaggga aaagcccatg atcttcaagc agggaagccc cagtgagtag ctgcattcct   1140
agaaattgaa gtttcagagc tacacaaaca ctttttctgt cccaaccgtt ccctcacagc   1200
aaagcaacaa tacaggctag ggatggtaat ccttttaaaca tacaaaaatt gctcgtgtta   1260
taaattaccc agtttagagg ggaaaaaaaa acaattattc ctaaataaat ggataagtag   1320
aattaatggt tgaggcagga ccatacagag tgtgggaact gctgggggatc tagggaattc   1380 agtgggacca atgaaagcat ggctgagaaa tagcaggtag tccaggatag tctaagggag   1440
gtgttcccat ctgagcccag ataagggt gtcttcctag aacattagcc gtagtggaat   1500
taacaggaaa tcatgagggt gacgtagaat tgagtcttcc aggggactct atcagaactg   1560
gaccatctcc aagtatataa cgatgagtcc tcttaatgct aggagtagaa aatggtccta   1620 ggaagggac tgaggattgc ggtgggggt ggggtggaaa agaaagtaca gaacaaaccc   1680
tgtgtcactg tcccaagttg ctaagtgaac agaactatct cagcatcaga atgagaaagc   1740
ctgagaagaa agaaccaacc acaagcacac aggaaggaaa gcgcaggagg tgaaaatgct   1800
ttcttggcca gggtagtaag aattagaggt taatgcaggg actgtaaaac caccttttct   1860
gcttcaatat ctaattcctg tgtagctttg ttcattgcat ttattaaaca aatgttgtat   1920
aaccaatact aaatgtacta ctgagcttcg ctgagttaag ttatgaaact ttcaaatcct   1980
tcatcatgtc agttccaatg aggtggggat ggagaagaca attgttgctt atgaaagaaa   2040
gctttagctg tctctgtttt gtaagcttta agcgcaacat ttcttggttc caataaagca   2100
ttttacaaga tcttgcatgc tactcttaga tagaagatgg gaaaaccatg gtaataaaat   2160
atgaatgata aaaaaaaaaa aaaaaaaaa aaaaaaaaa aaaa                      2204
```

<210> SEQ ID NO 60
<211> LENGTH: 2186
<212> TYPE: DNA
<213> ORGANISM: homo sapiens

<400> SEQUENCE: 60

```
ggagccccgg ctcctaggct gacagaccag cccagatcca gtggcccgga ggggcctgag     60
ctaaatccgc aggacctggg taacacgagg aagggctccg gatatctttg gtgacttgtc    120
```

```
cactccagtg tggcatcatg tggcagctgc tcctcccaac tgctctgcta cttctagttt        180
cagctggcat gcggactgaa gatctcccaa aggctgtggt gttcctggag cctcaatggt        240
acagggtgct cgagaaggac agtgtgactc tgaagtgcca gggagcctac tcccctgagg        300
acaattccac acagtggttt cacaatgaga gcctcatctc aagccaggcc tcgagctact        360
tcattgacgc tgccacagtc gacgacagtg gagagtacag gtgccagaca aacctctcca        420
ccctcagtga cccggtgcag ctagaagtcc atatcggctg gctgttgctc caggcccctc        480
ggtgggtgtt caaggaggaa gaccctattc acctgaggtg tcacagctgg aagaacactg        540
ctctgcataa ggtcacatat ttacagaatg gcaaaggcag gaagtatttt catcataatt        600
ctgacttcta cattccaaaa gccacactca agacagcgg ctcctacttc tgcaggggc         660 tttttgggag taaaaatgtg tcttcagaga ctgtgaacat caccatcact caaggtttgg        720
cagtgtcaac catctcatca ttctttccac ctgggtacca agtctctttc tgcttggtga        780
tggtactcct ttttgcagtg gacacaggac tatatttctc tgtgaagaca acattcgaa         840 gctcaacaag agactggaag gaccataaat ttaaatggag aaaggaccct caagacaaat        900
gacccccatc ccatgggggt aataagagca gtagcagcag catctctgaa catttctctg        960
gatttgcaac cccatcatcc tcaggcctct ctacaagcag caggaaacat agaactcaga       1020
gccagatccc ttatccaact ctcgactttt ccttggtctc cagtggaagg gaaaagccca       1080
tgatcttcaa gcagggaagc cccagtgagt agctgcattc ctagaaattg aagtttcaga       1140
gctacacaaa cacttttttct gtcccaaccg ttccctcaca gcaaagcaac aatacaggct       1200
agggatggta atcctttaaa catacaaaaa ttgctcgtgt tataaattac ccagtttaga       1260
ggggaaaaaa aaacaattat tcctaaataa atggataagt agaattaatg gttgaggcag       1320
gaccatacag agtgtgggaa ctgctgggga tctagggaat tcagtgggac caatgaaagc       1380
atggctgaga aatagcaggt agtccaggat agtctaaggg aggtgttccc atctgagccc       1440
agagataagg gtgtcttcct agaacattag ccgtagtgga attaacagga aatcatgagg       1500
gtgacgtaga attgagtctt ccaggggact ctatcagaac tggaccatct ccaagtatat       1560
aacgatgagt cctcttaatg ctaggagtag aaaatggtcc taggaagggg actgaggatt       1620
gcggtggggg gtgggtgga aagaaagta cagaacaaac cctgtgtcac tgtcccaagt        1680
tgctaagtga acagaactat ctcagcatca gaatgagaaa gcctgagaag aaagaaccaa       1740
ccacaagcac acaggaagga aagcgcagga ggtgaaaatg ctttcttggc cagggtagta       1800
agaattagag gttaatgcag ggactgtaaa accacctttt ctgcttcaat atctaattcc       1860
tgtgtagctt tgttcattgc atttattaaa caaatgttgt ataaccaata ctaaatgtac       1920
tactgagctt cgctgagtta agttatgaaa ctttcaaatc cttcatcatg tcagttccaa       1980
tgaggtgggg atggagaaga caattgttgc ttatgaaaga aagctttagc tgtctctgtt       2040
ttgtaagctt taagcgcaac atttcttggt tccaataaag cattttacaa gatcttgcat       2100
gctactctta gatagaagat gggaaaacca tggtaataaa atatgaatga taaaaaaaaa       2160
aaaaaaaaaa aaaaaaaaa aaaaaa                                            2186

<210> SEQ ID NO 61
<211> LENGTH: 2183
<212> TYPE: DNA
<213> ORGANISM: homo sapiens
```

<400> SEQUENCE: 61

```
ggagccccgg ctcctaggct gacagaccag cccagatcca gtggcccgga ggggcctgag      60
ctaaatccgc aggacctggg taacacgagg aagggctccg gatatctttg gtgacttgtc     120
cactccagtg tggcatcatg tggcagctgc tcctcccaac tgctctgcta cttctagttt     180
cagctggcat gcggactgat ctcccaaagg ctgtggtgtt cctggagcct caatggtaca     240
gggtgctcga gaaggacagt gtgactctga agtgccaggg agcctactcc cctgaggaca     300
attccacaca gtggtttcac aatgagagcc tcatctcaag ccaggcctcg agctacttca     360
ttgacgctgc cacagtcgac gacagtggag agtacaggtg ccagacaaac ctctccaccc     420
tcagtgaccc ggtgcagcta gaagtccata tcggctggct gttgctccag gcccctcggt     480
gggtgttcaa ggaggaagac cctattcacc tgaggtgtca cagctggaag aacactgctc     540
tgcataaggt cacatattta cagaatggca aggcaggaa gtattttcat cataattctg     600
acttctacat tccaaaagcc acactcaaag acagcggctc ctacttctgc agggggcttt     660
ttgggagtaa aaatgtgtct tcagagactg tgaacatcac catcactcaa ggtttggcag     720
tgtcaaccat ctcatcattc tttccacctg gtaccaagt ctctttctgc ttggtgatgg      780
tactcctttt tgcagtggac acaggactat atttctctgt gaagacaaac attcgaagct     840
caacaagaga ctggaaggac cataaattta atggagaaa ggaccctcaa gacaaatgac      900
ccccatccca tggggtaat aagagcagta gcagcagcat ctctgaacat ttctctggat      960
ttgcaacccc atcatcctca ggcctctcta caagcagcag gaaacataga actcagagcc    1020
agatcccta tccaactctc gacttttcct tggtctccag tggaagggaa aagcccatga    1080
tcttcaagca gggaagcccc agtgagtagc tgcattccta gaaattgaag tttcagagct    1140
acacaaacac tttttctgtc ccaaccgttc cctcacagca aagcaacaat acaggctagg    1200
gatggtaatc ctttaaacat acaaaaattg ctcgtgttat aaattaccca gtttagaggg    1260
gaaaaaaaaa caattattcc taaataaatg gataagtaga attaatggtt gaggcaggac    1320
catacagagt gtgggaactg ctggggatct agggaattca gtgggaccaa tgaaagcatg    1380
gctgagaaat agcaggtagt ccaggatagt ctaagggagg tgttcccatc tgagcccaga    1440
gataagggtg tcttcctaga acattagccg tagtggaatt aacaggaaat catgagggtg    1500
acgtagaatt gagtcttcca ggggactcta tcagaactgg accatctcca agtatataac    1560
gatgagtcct cttaatgcta ggagtagaaa atggtcctag gaaggggact gaggattgcg    1620
gtggggggtg gggtggaaaa gaaagtacag aacaaaccct gtgtcactgt cccaagttgc    1680
taagtgaaca gaactatctc agcatcagaa tgagaaagcc tgagaagaaa gaaccaacca    1740
caagcacaca ggaaggaaag cgcaggaggt gaaaatgctt tcttggccag ggtagtaaga    1800
attagaggtt aatgcaggga ctgtaaaacc acctttctg cttcaatatc taattcctgt     1860
gtagctttgt tcattgcatt tattaaacaa atgttgtata accaatacta aatgtactac    1920
tgagcttcgc tgagttaagt tatgaaactt tcaaatcctt catcatgtca gttccaatga    1980
ggtggggatg gagaagacaa ttgttgctta tgaaagaaag ctttagctgt ctctgttttg    2040
taagctttaa gcgcaacatt tcttggttcc aataaagcat tttacaagat cttgcatgct    2100
actcttagat agaagatggg aaaaccatgg taataaaata tgaatgataa aaaaaaaaaa    2160
aaaaaaaaaa aaaaaaaaaa aaa                                            2183
```

```
<210> SEQ ID NO 62
<211> LENGTH: 4190
<212> TYPE: DNA
<213> ORGANISM: homo sapiens

<400> SEQUENCE: 62
```

| | | | | | |
|---|---|---|---|---|---|
| atatgtagcc | ttttcattt | catgaaagtg | aagtgatttt | tagaattctt | agttgttttc | 60 |
| tttagaagaa | catttctagg | gaataataca | agaagattta | ggaatcattg | aagttataaa | 120 |
| tctttggaat | gagcaaactc | agaatggtgc | tacttgaaga | ctctggatct | gctgacttca | 180 |
| gaagacattt | tgtcaacttg | agtcccttca | ccattactgt | ggtcttactt | ctcagtgcct | 240 |
| gttttgtcac | cagttctctt | ggaggaacag | acaaggagct | gaggctagtg | gatggtgaaa | 300 |
| acaagtgtag | cgggagagtg | gaagtgaaag | tccaggagga | gtggggaacg | gtgtgtaata | 360 |
| atggctggag | catggaagcg | gtctctgtga | tttgtaacca | gctgggatgt | ccaactgcta | 420 |
| tcaaagcccc | tggatgggct | aattccagtg | caggttctgg | acgcatttgg | atggatcatg | 480 |
| tttcttgtcg | tgggaatgag | tcagctcttt | gggattgcaa | acatgatgga | tggggaaagc | 540 |
| atagtaactg | tactcaccaa | caagatgctg | gagtgacctg | ctcagatgga | tccaatttgg | 600 |
| aaatgaggct | gacgcgtgga | gggaatatgt | gttctggaag | aatagagatc | aaattccaag | 660 |
| gacggtgggg | aacagtgtgt | gatgataact | tcaacataga | tcatgcatct | gtcatttgta | 720 |
| gacaacttga | atgtgaagt | gctgtcagtt | tctctggttc | atctaattt | ggagaaggct | 780 |
| ctggaccaat | ctggtttgat | gatcttatat | gcaacggaaa | tgagtcagct | ctctggaact | 840 |
| gcaaacatca | aggatgggga | aagcataact | gtgatcatgc | tgaggatgct | ggagtgattt | 900 |
| gctcaaaggg | agcagatctg | agcctgagac | tggtagatgg | agtcactgaa | tgttcaggaa | 960 |
| gattagaagt | gagattccaa | ggagaatggg | ggacaatatg | tgatgacggc | tgggacagtt | 1020 |
| acgatgctgc | tgtggcatgc | aagcaactgg | gatgtccaac | tgccgtcaca | gccattggtc | 1080 |
| gagttaacgc | cagtaaggga | tttgacaca | tctggcttga | cagcgtttct | gccagggac | 1140 |
| atgaacctgc | tatctggcaa | tgtaaacacc | atgaatgggg | aaagcattat | tgcaatcaca | 1200 |
| atgaagatgc | tggcgtgaca | tgttctgatg | gatcagatct | ggagctaaga | cttagaggtg | 1260 |
| gaggcagccg | ctgtgctggg | acagttgagg | tggagattca | gagactgtta | gggaaggtgt | 1320 |
| gtgacagagg | ctggggactg | aaagaagctg | atgtggtttg | caggcagctg | ggatgtggat | 1380 |
| ctgcactcaa | aacatcttat | caagtgtact | ccaaaatcca | ggcaacaaac | acatggctgt | 1440 |
| ttctaagtag | ctgtaacgga | aatgaaactt | ctctttggga | ctgcaagaac | tggcaatggg | 1500 |
| gtggacttac | ctgtgatcac | tatgaagaag | ccaaaattac | ctgctcagcc | cacagggaac | 1560 |
| ccagactggt | tggagggac | attccctgtt | ctggacgtgt | tgaagtgaag | catggtgaca | 1620 |
| cgtgggggctc | catctgtgat | tcggacttct | ctctggaagc | tgccagcgtt | ctatgcaggg | 1680 |
| aattacagtg | tggcacagtt | gtctctatcc | tggggggagc | tcactttgga | gagggaaatg | 1740 |
| gacagatctg | ggctgaagaa | ttccagtgtg | agggacatga | gtcccatctt | tcactctgcc | 1800 |
| cagtagcacc | ccgcccagaa | ggaacttgta | gccacagcag | ggatgttgga | gtagtctgct | 1860 |
| caagatacac | agaaattcgc | ttggtgaatg | gcaagacccc | gtgtgagggc | agagtggagc | 1920 |
| tcaaaacgct | tggtgcctgg | ggatccctct | gtaactctca | ctgggacata | aagatgcccc | 1980 |
| atgttctttg | ccagcagctt | aaatgtggag | ttgcccttc | taccccagga | ggagcacgtt | 2040 |
| ttggaaaagg | aaatggtcag | atctggaggc | atatgtttca | ctgcactggg | actgagcagc | 2100 |
| acatgggaga | ttgtcctgta | actgctctag | gtgcttcatt | atgtccttca | gagcaagtgg | 2160 |

```
cctctgtaat ctgctcagga aaccagtccc aaacactgtc ctcgtgcaat tcatcgtctt    2220
tgggcccaac aaggcctacc attccagaag aaagtgctgt ggcctgcata gagagtggtc    2280
aacttcgcct ggtaaatgga ggaggtcgct gtgctgggag agtagagatc tatcatgagg    2340
gctcctgggg caccatctgt gatgacagct gggacctgag tgatgcccac gtggtttgca    2400
gacagctggg ctgtggagag gccattaatg ccactggttc tgctcatttt ggggaaggaa    2460
cagggcccat ctggctggat gagatgaaat gcaatggaaa agaatcccgc atttggcagt    2520
gccattcaca cggctggggg cagcaaaatt gcaggcacaa ggaggatgcg ggagttatct    2580
gctcagaatt catgtctctg agactgacca gtgaagccag cagagaggcc tgtgcagggc    2640
gtctggaagt tttttacaat ggagcttggg gcactgttgg caagagtagc atgtctgaaa    2700
ccactgtggg tgtggtgtgc aggcagctgg gctgtgcaga caaagggaaa atcaaccctg    2760
catctttaga caaggccatg tccattccca tgtgggtgga caatgttcag tgtccaaaag    2820
gacctgacac gctgtggcag tgcccatcat ctccatggga gaagagactg gccagcccct    2880
cggaggagac ctggatcaca tgtgacaaca agataagact tcaggaagga cccacttcct    2940
gttctggacg tgtggagatc tggcatggag gttcctgggg gacagtgtgt gatgactctt    3000
gggacttgga cgatgctcag gtggtgtgtc aacaacttgg ctgtggtcca gctttgaaag    3060
cattcaaaga agcagagttt ggtcagggga ctggaccgat atggctcaat gaagtgaagt    3120
gcaaagggaa tgagtcttcc ttgtgggatt gtcctgccag acgctgggc catagtgagt    3180 gtgggcacaa ggaagacgct gcagtgaatt gcacagatat ttcagtgcag aaaaccccac    3240
aaaaagccac aacaggtcgc tcatcccgtc agtcatcctt tattgcagtc gggatccttg    3300
gggttgttct gttggccatt ttcgtcgcat tattcttctt gactaaaaag cgaagacaga    3360
gacagcggct tgcagtttcc tcaagaggag agaacttagt ccaccaaatt caataccggg    3420
agatgaattc ttgcctgaat gcagatgatc tggacctaat gaattcctca gaaaattccc    3480
atgagtcagc tgatttcagt gctgctgaac taatttctgt gtctaaattt cttcctattt    3540
ctggaatgga aaaggaggcc attctgagcc acactgaaaa ggaaaatggg aatttataac    3600
ccagtgagtt cagcctttaa gataccttga tgaagacctg gactattgaa tggagcagaa    3660
attcacctct ctcactgact attacagttg catttttatg gagttcttct tctcctagga    3720
ttcctaagac tgctgctgaa tttataaaaa ttaagtttgt gaatgtgact acttagtggt    3780
gtatatgaga ctttcaaggg aattaaataa ataaataaga atgttattga tttgagtttg    3840 cttttaattac ttgtccttaa ttctattaat ttctaaatgg gcttcctaat tttttgtaga    3900
gtttcctaga tgtattataa tgtgtttat ttgacagtgt ttcaatttgc atatacagta    3960
ctgtatattt tttcttattt ggtttgaata attttcctat taccaaataa aaataaattt    4020
atttttactt tagttttttct aagacaggaa aagtaatga tattgaaggg tctgtaaata    4080
atatatggct aacttataa ggcatgactc acaacgattc tttaactgct ttttgttact    4140
gtaattctgt tcactagaat aaaatgcaga gccacacctg gtgagggcac                4190

<210> SEQ ID NO 63
<211> LENGTH: 4107
<212> TYPE: DNA
<213> ORGANISM: homo sapiens

<400> SEQUENCE: 63
atatgtagcc ttttcatttt catgaaagtg aagtgatttt tagaattctt agttgttttc      60
tttagaagaa catttctagg gaataataca agaagattta ggaatcattg aagttataaa     120
```

```
tctttggaat gagcaaactc agaatggtgc tacttgaaga ctctggatct gctgacttca    180
gaagacattt tgtcaacttg agtcccttca ccattactgt ggtcttactt ctcagtgcct    240
gttttgtcac cagttctctt ggaggaacag acaaggagct gaggctagtg gatggtgaaa    300
acaagtgtag cggagagtg gaagtgaaag tccaggagga gtggggaacg gtgtgtaata    360
atggctggag catggaagcg gtctctgtga tttgtaacca gctgggatgt ccaactgcta    420
tcaaagcccc tggatgggct aattccagtg caggttctgg acgcatttgg atggatcatg    480
tttcttgtcg tgggaatgag tcagctcttt gggattgcaa acatgatgga tggggaaagc    540
atagtaactg tactcaccaa caagatgctg gagtgacctg ctcagatgga tccaatttgg    600
aaatgaggct gacgcgtgga gggaatatgt gttctggaag aatagagatc aaattccaag    660
gacggtgggg aacagtgtgt gatgataact caacataga tcatgcatct gtcatttgta    720
gacaacttga atgtggaagt gctgtcagtt tctctggttc atctaatttt ggagaaggct    780
ctggaccaat ctggtttgat gatcttatat gcaacgaaaa tgagtcagct ctctggaact    840
gcaaacatca aggatgggga aagcataact gtgatcatgc tgaggatgct ggagtgattt    900
gctcaaaggg agcagatctg agcctgagac tggtagatgg agtcactgaa tgttcaggaa    960
gattagaagt gagattccaa ggagaatggg ggacaatatg tgatgacggc tgggacagtt   1020
acgatgctgc tgtggcatgc aagcaactgg gatgtccaac tgccgtcaca gccattggtc   1080
gagttaacgc cagtaaggga tttggacaca tctggcttga cagcgtttct gccagggac    1140 atgaacctgc tatctggcaa tgtaaacacc atgaatgggg aaagcattat tgcaatcaca   1200
atgaagatgc tggcgtgaca tgttctgatg gatcagatct ggagctaaga cttagaggtg   1260
gaggcagccg ctgtgctggg acagttgagg tggagattca gagactgtta gggaaggtgt   1320
gtgacagagg ctggggactg aaagaagctg atgtggttg caggcagctg ggatgtggat   1380
ctgcactcaa acatcttat caagtgtact ccaaaatcca ggcaacaaac acatggctgt   1440
ttctaagtag ctgtaacgga aatgaaactt ctctttggga ctgcaagaac tggcaatggg   1500
gtggacttac ctgtgatcac tatgaagaag ccaaaattac ctgctcagcc cacagggaac   1560
ccagactggt tggaggggac attccctgtt ctggacgtgt tgaagtgaag catggtgaca   1620 cgtgggctc catctgtgat tcggacttct ctctggaagc tgccagcgtt ctatgcaggg   1680
aattacagtg tggcacagtt gtctctatcc tgggggagc tcactttgga gagggaaatg   1740
gacagatctg ggctgaagaa ttccagtgtg agggacatga gtcccatctt tcactctgcc   1800
cagtagcacc ccgcccagaa ggaacttgta gccacagcag ggatgttgga gtagtctgct   1860
caagatacac agaaattcgc ttggtgaatg gcaagacccc gtgtgagggc agagtggagc   1920
tcaaaacgct tggtgcctgg ggatccctct gtaactctca ctgggacata aagatgccc    1980 atgttctttg ccagcagctt aaatgtggag ttgccctttc taccccagga ggagcacgtt   2040
ttggaaaagg aaatggtcag atctggaggc atatgtttca ctgcactggg actgagcagc   2100
acatgggaga ttgtcctgta actgctctag gtgcttcatt atgtccttca gagcaagtgg   2160
cctctgtaat ctgctcagga aaccagtccc aaacactgtc ctcgtgcaat tcatcgtctt   2220
tgggcccaac aaggcctacc attccagaag aaagtgctgt ggcctgcata gagagtggtc   2280
aacttcgcct ggtaaatgga ggaggtcgct gtgctgggag agtagagatc tatcatgagg   2340
gctcctgggg caccatctgt gatgacagct gggacctgag tgatgccac gtggtttgca   2400 gacagctggg ctgtggagag gccattaatg ccactggttc tgctcatttt ggggaaggaa   2460
cagggcccat ctggctggat gagatgaaat gcaatggaaa agaatcccgc atttggcagt   2520
```

```
gccattcaca cggctggggg cagcaaaatt gcaggcacaa ggaggatgcg ggagttatct 2580
gctcagaatt catgtctctg agactgacca gtgaagccag cagagaggcc tgtgcagggc 2640
gtctggaagt tttttacaat ggagcttggg gcactgttgg caagagtagc atgtctgaaa 2700
ccactgtggg tgtggtgtgc aggcagctgg gctgtgcaga caaagggaaa atcaaccctg 2760
catctttaga caaggccatg tccattccca tgtgggtgga caatgttcag tgtccaaaag 2820
gacctgacac gctgtggcag tgcccatcat ctccatggga gaagagactg gccagcccct 2880
```

```
cggaggagac ctggatcaca tgtgacaaca agataagact tcaggaagga cccacttcct 2940
gttctggacg tgtggagatc tggcatggag gttcctgggg gacagtgtgt gatgactctt 3000
gggacttgga cgatgctcag gtggtgtgtc aacaacttgg ctgtggtcca gctttgaaag 3060
cattcaaaga agcagagttt ggtcagggga ctggaccgat atggctcaat gaagtgaagt 3120
gcaaagggaa tgagtcttcc ttgtgggatt gtcctgccag acgctggggc catagtgagt 3180
gtgggcacaa ggaagacgct gcagtgaatt gcacagatat ttcagtgcag aaaaccccac 3240
aaaaagccac aacaggtcgc tcatcccgtc agtcatcctt tattgcagtc gggatccttg 3300
gggttgttct gttggccatt ttcgtcgcat tattcttctt gactaaaaag cgaagacaga 3360
gacagcggct tgcagtttcc tcaagaggag agaacttagt ccaccaaatt caataccggg 3420
agatgaattc ttgcctgaat gcagatgatc tggacctaat gaattcctca ggaggccatt 3480
ctgagccaca ctgaaaagga aaatgggaat ttataaccca gtgagttcag cctttaagat 3540
accttgatga agacctggac tattgaatgg agcagaaatt cacctctctc actgactatt 3600
acagttgcat ttttatggag ttcttcttct cctaggattc ctaagactgc tgctgaattt 3660
ataaaaatta agtttgtgaa tgtgactact tagtggtgta tatgagactt tcaagggaat 3720
taaataaata aataagaatg ttattgattt gagtttgctt taattacttg tccttaattc 3780
tattaatttc taaatgggct tcctaatttt ttgtagagtt tcctagatgt attataatgt 3840
gttttatttg acagtgtttc aatttgcata tacagtactg tatatttttt cttatttggt 3900
ttgaataatt ttcctattac caaataaaaa taaatttatt tttactttag tttttctaag 3960
acaggaaaag ttaatgatat tgaagggtct gtaaataata tatggctaac tttataaggc 4020
atgactcaca acgattcttt aactgctttt tgttactgta attctgttca ctagaataaa 4080
atgcagagcc acacctggtg agggcac 4107

<210> SEQ ID NO 64
<211> LENGTH: 5205
<212> TYPE: DNA
<213> ORGANISM: homo sapiens
<400> SEQUENCE: 64
cttttcagct gggcagctct gggaacttgg attaggtgga gaggcagttg gggggcctcg 60
ttgttttgcg tcttagttcc gccctcctgt ccatcaggag aaggaaagga taaaccctgg 120
gccatgaggc taccccctgct cctggttttt gcctctgtca ttccgggtgc tgttctccta 180
ctggacacca ggcaattttt aatctataat gaagatcaca agcgctgcgt ggatgcagtg 240
agtcccagtg ccgtccaaac cgcagcttgc aaccaggatg ccgaatcaca gaaattccga 300
tgggtgtccg aatctcagat tatgagtgtt gcatttaaat tatgcctggg agtgccatca 360
aaaacggact gggttgctat cactctctat gcctgtgact caaaaagtga atttcagaaa 420
tgggagtgca aaaatgacac acttttgggg atcaaaggag aagatttatt ttttaactac 480
ggcaacagac aagaaaagaa tattatgctc tacaagggat cgggtttatg gagcaggtgg 540
```

```
aagatctatg gaaccacaga caatctgtgc tccagaggtt atgaagccat gtatacgcta      600
ctaggcaatg ccaatggagc aacctgtgca ttcccgttca gtttgaaaaa caagtggtac      660
gcagattgca cgagtgctgg gcggtcggat ggatggctct ggtgcggaac cactactgac      720
tatgacacag acaagctatt tggatattgt ccattgaaat ttgagggcag tgaaagctta      780
tggaataaag acccgctgac cagcgtttcc taccagataa actccaaatc cgctttaacg      840
tggcaccagg cgaggaaaag ctgccaacaa cagaacgctg agctcctgag catcacagag      900
attcatgagc aaacatacct gacaggatta accagttcct tgacctcagg actctggatt      960
ggacttaaca gtctgagctt caacagcggt tggcagtgga gtgaccgcag tcctttccga     1020
tatttgaact ggttaccagg aagtccatca gctgaacctg aaaaagctg tgtgtcacta      1080 aatcctggaa aaaatgctaa atgggaaaat ctggaatgtg ttcagaaact gggctatatt     1140
tgcaaaaagg caacaccac tttaaattct tttgttattc cctcagaaag tgatgtgcct      1200
actcactgtc ctagtcagtg gtggccgtat gccggtcact gttacaagat tcacagagat     1260
gagaaaaaaa tccagaggga tgctctgacc acctgcagga aggaaggcgg tgacctcaca     1320
agtatccaca ccatcgagga attggacttt attatctccc agctaggata tgagccaaat     1380
gacgaattgt ggatcggctt aaatgacatt aagattcaaa tgtactttga gtggagtgat     1440
gggacccctg taacgtttac caaatggctt cgtggagaac caagccatga aacaacaga     1500 caggaggatt gtgtggtgat gaaaggcaag gatgggtact gggcagatcg gggctgtgag     1560
tggcctcttg gctacatctg caagatgaaa tcacgaagcc aaggtccaga aatagtggaa     1620
gtcgaaaaag gctgcaggaa aggctggaaa aaacatcact tttactgcta tatgattgga     1680
catacgcttt caacatttgc agaagcaaac caaacctgta ataatgagaa tgcttattta     1740
acaactattg aagacagata tgaacaagcc ttcctgacta gtttcgttgg cttaaggcct     1800
gaaaaatatt tctggacagg acttttcagat atacaaacca aagggacttt tcagtggacc     1860
atcgaggaag aggttcggtt cacccactgg aattcagata tgccagggcg aaagccaggg     1920
tgtgttgcca tgagaaccgg gattgcaggg gcttatggga tgttttgaa atgtgatgaa      1980 aaggcaaaat ttgtgtgcaa gcactgggca gaaggagtaa cccacccacc gaagcccacg     2040
acgactcccg aacccaaatg tccggaggat tggggcgcca gcagtagaac aagcttgtgt     2100
ttcaagctgt atgcaaaagg aaaacatgag aagaaaacgt ggtttgaatc tcgagatttt     2160
tgtcgagctc tgggtggaga cttagctagc atcaataaca aagaggaaca gcaaacaata     2220
tggcgattaa taacagctag tggaagctac cacaaactgt tttggttggg attgacatat     2280 ggaagcccctt cagaaggttt tacttggagt gatggttctc ctgtttcata tgaaaactgg     2340
gcttatggag aacctaataa ttatcaaaat gttgaatact gtggtgagct gaaaggtgac     2400
cctactatgt cttggaatga tattaattgt gaacaccta acaactggat tgccagata      2460 caaaaaggac aaaacaccaaa acctgagcca caccagctc ctcaagacaa tccaccagtt     2520
actgaagatg ggtgggttat ttacaaagac taccagtatt atttcagcaa agagaaggaa     2580
accatggaca atgcgcgagc gttttgcaag aggaattttg gtgatcttgt ttctattcaa     2640
agtgaaagtg aaaagaagtt tctatggaaa tatgtaaaca gaaatgatgc acagtctgca     2700
tattttattg gtttattgat cagcttggat aaaaagtttg cttggatgga tggaagcaaa     2760
gtggattacg tgtcttgggc cacaggtgaa cccaattttg caaatgaaga tgaaaactgt     2820
gtgaccatgt attcaaattc agggttttgg aatgacatta actgtggcta tccaaacgcc     2880
ttcatttgcc agcgacataa cagtagtatc aatgctacca cagttatgcc taccatgccc     2940
```

```
tcggtcccat cagggtgcaa ggaaggttgg aatttctaca gcaacaagtg tttcaaaatc    3000
tttggattta tggaagaaga aagaaaaaat tggcaagagg cacgaaaagc ttgtataggc    3060
tttggaggga atctggtctc catacaaaat gaaaagagc aagcatttct tacctatcac     3120
atgaaggact ccactttcag tgcctggact gggctgaatg atgtcaattc agaacacacg    3180
ttcctttgga cggatggacg aggagtccat tacacaaact gggggaaagg ttaccctggt    3240
ggaagaagaa gcagtctttc ttatgaagat gctgactgtg ttgttattat tggaggtgca    3300
tcaaatgaag caggaaaatg gatggatgat acctgcgaca gtaaacgagg ctacatatgc    3360
cagacacgat ccgacccttc cttgactaat cctccagcaa cgattcaaac agatggcttt    3420
gttaaatatg gcaaaagcag ctattcactc atgagacaaa atttcaatg gcatgaagcg     3480 gagacatact gcaagcttca caattccctt atagccagca ttctggatcc ctacagtaat    3540
gcatttgcgt ggctgcagat ggaaacatct aatgaacgtg tgtggatcgc cctgaacagt    3600
aacttgactg ataatcaata cacttggact gataagtgga gggtgaggta cactaactgg    3660
gctgctgatg agcccaaatt gaaatcagca tgtgtttatc tggatcttga tggctactgg    3720
aagacagcac attgcaatga aagttttac tttctctgta aaagatcaga tgaaatccct     3780
gctactgaac ccccacaact gcctggcaga tgcccggagt cagatcacac agcatggatt    3840
cctttccatg gtcactgtta ctatattgag tcctcatata caagaaactg gggccaagct    3900
tctctggaat gtcttcgaat gggttcctct ctggtttcca ttgaaagtgc tgcagaatcc    3960
agttttctgt catatcgggt tgagccactt aaaagtaaaa ccaattttg ataggattg      4020 ttcagaaatg ttgaagggac gtggctgtgg ataataaca gtccggtctc ctttgtcaac    4080
tggaacacag gagatccctc tggtgaacgg aatgattgtg tagctttaca tgcgtcttct   4140
gggttttgga gtaatattca ctgttcatcc tacaaaggat atatttgtaa aagaccaaaa   4200
attattgatg ctaaacctac tcatgaatta cttacaacaa agctgacac aaggaagatg     4260 gaccctcta aaccgtcttc caacgtggcc ggagtagtca tcattgtgat cctcctgatt     4320
ttaacgggtg ctggccttgc cgcctatttc ttttataaga aaagacgtgt gcacctacct    4380
caagagggcg cctttgaaaa cactctgtat tttaacagtc agtcaagccc aggaactagt    4440
gatatgaaag atctcgtggg caatattgaa cagaatgaac actcggtcat ctagtacctc    4500
aatgcgattc tgagatattt gaatttcata aaattgtaac tgaaatttaa attttttagt    4560
tcaatgtgat tgttttcttt aaaatgagta ctgaattgta ctggtctgtc cttttttcct   4620
ttgcctaatt gaagaaataa ttgcttgttt tctagcctgg caagatattt tcataaaaga   4680
gggataacaa tgctgattac tacctttaa aatatttag ataaatgcac agcaccacag      4740
caccacatct aagcattagt gatgggtagc tgatgtcagc ttcatgtgga ttttaagcac    4800
tctagaaaca atgaagcttc ttggcatatt ttaaggagct cccaaaatgt gttacctatt    4860
aaattgtaac tcagcaagta gaagaccatt tgaaagtca ggtacaaatt tcctcaagtg     4920
gcataaaaat gtagtcagtt ttctcttta ccagttttta tttccactcc aattattag      4980 aactttattt gtacatgtgc agaagaataa ggcagctgag aatcttgttt cccccaagag    5040
agttttacag gctgagtgtt gcaaatgtgt tctttgtcct gttatatgta tatcaggaat    5100
acaaggatgt gaaataaaac tgtaaatttg cataactgga tgtacttaga aatgtgaaa    5160 taaacattaa agacaaggtc tatttttaat aaaaaaaaaa aaaaa                    5205
```

<210> SEQ ID NO 65
<211> LENGTH: 3177
<212> TYPE: DNA
<213> ORGANISM: Homo sapiens

<400> SEQUENCE: 65

| | | | | | |
|---|---|---|---|---|---|
| ctctgtaaaa | taaatgcgct | gggccggatc | ttttctgagt | tctcttctcc | cctacgaatt | 60 |
| ctagatccct | cctctgtcct | ccctgcgcca | gggaccttcg | ggcgacccctt | ccctgtaccc | 120 |
| ccaccccacc | ctctctggac | cccgtttctg | cctcagtacg | cgcgcgctgag | ctctgccccc | 180 |
| tgcccaggcc | ctgaccccct | caggagccgc | ggtttcctgg | ggtaacagtg | ggaaacgtgt | 240 |
| cggccgtctc | cgctcaggcg | cttgctgtgt | acagaaaggc | tgattcaggc | acaccggctc | 300 |
| tcgtcgcctt | ggtggccctc | cccagccctc | ctccgcgcct | gctccgggtg | gcgctccgct | 360 |
| gggctcctcg | tgcgcctgtc | cgcgaccgca | cccacctcat | cctggcaccc | catcgtggc | 420 |
| atcacgtgtt | ccctcatctg | tcctcatggc | tggcgtgccc | ctctgcggtg | agacctgcag | 480 |
| aacaggaatt | ggtgccgggt | cagcagccgg | cgatgaagcc | ggacgaagcc | tgcaaacccc | 540 |
| acccatacgc | cagcttcaca | tagctcctat | ccattgcaca | gcagcgtggg | gaagcaccgt | 600 |
| tctctaccct | ccaaacaaaa | gcatgaacca | ggtgcagtgg | ctcacgtctg | taatcccagc | 660 |
| attttggagg | ccaaggtgga | tggatggatt | ccttgagtcc | aggagttcaa | gaccagcctg | 720 |
| ggcaacatgg | tgaaccccca | tctctacaaa | aatttagcca | gttttcagct | gcccccagtt | 780 |
| gcctggccag | gctgcctcga | cggccctatt | cacgggcccc | agcctcctcg | ccgggctgga | 840 |
| aggcgacaac | cgcgaaaagg | agggtgactc | tcctcggcgg | gggcttcggg | tgacatcaca | 900 |
| tcctccaaat | gcgaaatcag | gctccgggcc | ggccgaaggg | cgcaactttc | cccctcggc | 960 |
| gccccaccgg | ctcccgcgcg | cctccccctcg | cgcccgagct | tcgagccaag | cagcgtcctg | 1020 |
| gggagcgcgt | catggcctta | ccagtgaccg | ccttgctcct | gccgctggcc | ttgctgctcc | 1080 |
| acgccgccag | gccgagccag | ttccgggtgt | cgccgctgga | tcggacctgg | aacctgggcg | 1140 |
| agacagtgga | gctgaagtgc | caggtgctgc | tgtccaaccc | gacgtcgggc | tgctcgtggc | 1200 |
| tcttccagcc | gcgcggcgcc | gccgccagtc | ccaccttcct | cctataccctc | tcccaaaaca | 1260 |
| agcccaaggc | ggccgagggg | ctggacaccc | agcggttctc | gggcaagagg | ttggggaca | 1320 |
| ccttcgtcct | caccctgagc | gacttccgcc | gagagaacga | gggctactat | ttctgctcgg | 1380 |
| ccctgagcaa | ctcatcatg | tacttcagcc | acttcgtgcc | ggtcttcctg | ccagcgaagc | 1440 |
| ccaccacgac | gccagcgccg | cgaccaccaa | caccggcgcc | caccatcgcg | tcgcagcccc | 1500 |
| tgtccctgcg | cccagaggcg | tgccggccag | cggcgggggg | cgcagtgcac | acgagggggc | 1560 |
| tggacttcgc | ctgtgatatc | tacatctggg | cgccccttggc | cgggacttgt | ggggtccttc | 1620 |
| tcctgtcact | ggttatcacc | ctttactgca | accacaggaa | ccgaagacgt | gtttgcaaat | 1680 |
| gtccccggcc | tgtggtcaaa | tcgggagaca | agcccagcct | tcggcgagca | tacgtctaac | 1740 |
| cctgtgcaac | agccactaca | ttacttcaaa | ctgagatcct | tcctttgag | ggagcaagtc | 1800 |
| cttcccttc | attttttcca | gtcttcctcc | ctgtgtattc | attctcatga | ttattatttt | 1860 |
| agtggggcg | ggtgggaaa | gattactttt | tctttatgtg | tttgacggga | aacaaaacta | 1920 |
| ggtaaaatct | acagtacacc | acaagggtca | caatactgtt | gtgcgcacat | cgcggtaggg | 1980 |
| cgtggaaagg | ggcaggccag | agctaccgc | agagttctca | gaatcatgct | gagagagctg | 2040 |
| gaggcaccca | tgccatctca | acctcttccc | cgcccgtttt | acaagggggg | aggctaaagc | 2100 |
| ccagagacag | cttgatcaaa | ggcacacagc | aagtcagggt | tggagcagta | gctggaggga | 2160 |

| | | | | |
|---|---|---|---|---|
| ccttgtctcc | cagctcaggg | ctctttcctc | cacaccattc | aggtctttct | ttccgaggcc | 2220 |
| cctgtctcag | ggtgaggtgc | ttgagtctcc | aacggcaagg | gaacaagtac | ttcttgatac | 2280 |
| ctgggatact | gtgcccagag | cctcgaggag | gtaatgaatt | aaagaagaga | actgcctttg | 2340 |
| gcagagttct | ataatgtaaa | caatatcaga | cttttttttt | ttataatcaa | gcctaaaatt | 2400 |
| gtatagacct | aaaataaaat | gaagtggtga | gcttaacccct | ggaaaatgaa | tccctctatc | 2460 |
| tctaaagaaa | atctctgtga | aaccccctatg | tggaggcgga | attgctctcc | cagcccttgc | 2520 |
| attgcagagg | ggcccatgaa | agaggacagg | ctaccccttt | acaaatagaa | tttgagcatc | 2580 |
| agtgaggtta | aactaaggcc | ctcttgaatc | tctgaatttg | agatacaaac | atgttcctgg | 2640 |
| gatcactgat | gacttttttat | actttgtaaa | gacaattgtt | ggagagcccc | tcacacagcc | 2700 |
| ctggcctctg | ctcaactagc | agatacaggg | atgaggcaga | cctgactctc | ttaaggaggc | 2760 |
| tgagagccca | aactgctgtc | ccaaacatgc | acttccttgc | ttaaggtatg | gtacaagcaa | 2820 |
| tgcctgccca | ttggagagaa | aaacttaag | tagataagga | aataagaacc | actcataatt | 2880 |
| cttcacctta | ggaataatct | cctgttaata | tggtgtacat | tcttcctgat | tattttctac | 2940 |
| acatacatgt | aaaatatgtc | tttctttttt | aaatagggtt | gtactatgct | gttatgagtg | 3000 |
| gctttaatga | ataaacattt | gtagcatcct | ctttaatggg | taaacagcat | ccgaaaaaaa | 3060 |
| aaaaaaaaaa | aaaaaaaaaa | aaaaaaaaaa | aaaaaaaaaa | aaaaaaaaaa | aaaaaaaaaa | 3120 |
| aaaaaaaaaa | aaaaaaaaaa | aaaaaaaaaa | aaaaaaaaaa | aaaaaaaaaa | aaaaaaa | 3177 |

<210> SEQ ID NO 66
<211> LENGTH: 3035
<212> TYPE: DNA
<213> ORGANISM: Homo sapiens

<400> SEQUENCE: 66

| | | | | |
|---|---|---|---|---|
| agcacccaag | ggctggtcaa | ccaagctggg | ggttgaattt | ccatccagca | atgcaggcca | 60 |
| tgggaggctg | cagcagtgac | gctgtcagat | cccctttgtg | agaataataa | ttttttataac | 120 |
| aacgtggctg | gaggactgat | caggagagag | actggtgtga | attgaaggct | gttgcaatgg | 180 |
| ctccaagaag | agatgaggct | gtgtggtgag | tttagccgct | ggatgaaagg | ccggaagaat | 240 |
| gaggtcagca | gcgcactgac | accgacaccc | aaagcttcgg | ctgctgccgc | tctcatggaa | 300 |
| atctcctggg | ggaagggaga | gggtccttcc | tcggtgaaaa | ctggggctgc | tctagcgagt | 360 |
| tcctcagaag | cggggcaggtc | gctagttcct | cttccttttc | agccctcagt | gcccattttg | 420 |
| ccaataaaaa | gtcccaaggt | gacagtacaa | gagacgcctt | tagtgaaggc | aaaggaaggg | 480 |
| acactcccct | cctttgctgc | ctactctcgc | cctcacttct | tgaaatcttt | ggtctccctt | 540 |
| cacccactct | gtcactctca | caagacaacc | atttccaagg | actatttcca | agccctttttc | 600 |
| ctcatcccca | aacccgcagt | tttcagctgc | ccccagttgc | ctggccaggc | tgcctcgacg | 660 |
| gccctattca | cgggcccccag | cctcctcgcc | gggctggaag | gcgacaaccg | cgaaaaggag | 720 |
| ggtgactctc | ctcggcgggg | gcttcgggtg | acatcacatc | ctccaaatgc | gaaatcaggc | 780 |
| tccgggccgg | ccgaagggcg | caactttccc | ccctcggcgc | ccaccggct | cccgcgcgcc | 840 |
| tccccctcgcg | cccgagcttc | gagccaagca | gcgtcctggg | gagcgcgtca | tggccttacc | 900 |
| agtgaccgcc | ttgctcctgc | cgctggcctt | gctgctccac | gccgccaggc | cgagccagtt | 960 |
| ccgggtgtcg | ccgctggatc | ggacctggaa | cctgggcgag | acagtggagc | tgaagtgcca | 1020 |
| ggtgctgctg | tccaacccga | cgtcgggctg | ctcgtggctc | ttccagccgc | gcggcgccgc | 1080 |
| cgccagtccc | accttcctcc | tatacctctc | ccaaaacaag | cccaaggcgg | ccgagggct | 1140 |

```
ggacacccag cggttctcgg gcaagaggtt gggggacacc ttcgtcctca ccctgagcga   1200
cttccgccga gagaacgagg gctactattt ctgctcggcc ctgagcaact ccatcatgta   1260
cttcagccac ttcgtgccgg tcttcctgcc agcgaagccc accacgacgc cagcgccgcg   1320
accaccaaca ccggcgccca ccatcgcgtc gcagcccctg tccctgcgcc cagaggcgtg   1380
ccggccagcg gcgggggggcg cagtgcacac gaggggggctg gacttcgcct gtgatatcta   1440
catctgggcg cccttggccg ggacttgtgg ggtccttctc ctgtcactgg ttatcacccct  1500 ttactgcaac cacaggaacc gaagacgtgt ttgcaaatgt ccccggcctg tggtcaaatc   1560
gggagacaag cccagccttt cggcgagata cgtctaaccc tgtgcaacag ccactacatt   1620
acttcaaact gagatccttc cttttgaggg agcaagtcct tccctttcat ttttttccagt  1680 cttcctccct gtgtattcat tctcatgatt attattttag tggggcggg gtgggaaaga   1740 ttacttttc tttatgtgtt tgacgggaaa caaaactagg taaaatctac agtacaccac   1800
aagggtcaca atactgttgt gcgcacatcg cggtagggcg tggaaagggg caggccagag   1860
ctacccgcag agttctcaga atcatgctga gagagctgga ggcacccatg ccatctcaac   1920
ctcttccccg cccgttttac aaaggggggag gctaaagccc agagacagct tgatcaaagg   1980
cacacagcaa gtcagggttg gagcagtagc tggagggacc ttgtctccca gctcagggct   2040 cttcctcca caccattcag gtctttcttt ccgaggcccc tgtctcaggg tgaggtgctt   2100
gagtctccaa cggcaaggga acaagtactt cttgatacct gggatactgt gcccagagcc   2160
tcgaggaggt aatgaattaa agaagagaac tgcctttggc agagttctat aatgtaaaca   2220
atatcagact tttttttttt ataatcaagc ctaaaattgt atagacctaa aataaaatga   2280
agtggtgagc ttaaccctgg aaaatgaatc cctctatctc taaagaaaat ctctgtgaaa   2340
cccctatgtg gaggcggaat tgctctccca gcccttgcat tgcagagggg cccatgaaag   2400
aggacaggct accccttttac aaatagaatt tgagcatcag tgaggttaaa ctaaggccct   2460
cttgaatctc tgaatttgag atacaaacat gttcctggga tcactgatga cttttttatac  2520 tttgtaaaga caattgttgg agagcccctc acacagccct ggcctctgct caactagcag   2580
atacagggat gaggcagacc tgactctctt aaggaggctg agagcccaaa ctgctgtccc   2640
aaacatgcac ttccttgctt aaggtatggt acaagcaatg cctgcccatt ggagagaaaa   2700
aacttaagta gataaggaaa taagaaccac tcataattct tcaccttagg aataatctcc   2760
tgttaatatg gtgtacattc ttcctgatta ttttctacac atacatgtaa aatatgtctt   2820
tcttttttaa atagggttgt actatgctgt tatgagtggc tttaatgaat aaacatttgt   2880
agcatcctct ttaatgggta aacagcatcc gaaaaaaaaa aaaaaaaaa aaaaaaaaa    2940 aaaaaaaaa aaaaaaaaa aaaaaaaaa aaaaaaaaa aaaaaaaaa aaaaaaaaa        3000 aaaaaaaaa aaaaaaaaa aaaaaaaaa aaaaa                                3035
```

<210> SEQ ID NO 67
<211> LENGTH: 2924
<212> TYPE: DNA
<213> ORGANISM: Homo sapiens

<400> SEQUENCE: 67

```
agcacccaag ggctggtcaa ccaagctggg ggttgaattt ccatccagca atgcaggcca     60
tgggaggctg cagcagtgac gctgtcagat cccctttgtg agaataataa ttttttataac   120 aacgtggctg gaggactgat caggagagag actggtgtga attgaaggct gttgcaatgg    180
ctccaagaag agatgaggct gtgtggtgag tttagccgct ggatgaaagg ccggaagaat    240
```

```
gaggtcagca gcgcactgac accgacaccc aaagcttcgg ctgctgccgc tctcatggaa    300
atctcctggg ggaagggaga gggtccttcc tcggtgaaaa ctggggctgc tctagcgagt    360
tcctcagaag cgggcaggtc gctagttcct cttccttttc agccctcagt gcccattttg    420
ccaataaaaa gtcccaaggt gacagtacaa gagacgcctt tagtgaaggc aaaggaaggg    480
acactcccct cctttgctgc ctactctcgc cctcacttct tgaaatcttt ggtctccctt    540
cacccactct gtcactctca caagacaacc atttccaagg actatttcca agccttttc     600 ctcatcccca aacccgcagt tttcagctgc ccccagttgc ctggccaggc tgcctcgacg    660
gccctattca cgggcccccag cctcctcgcc gggctggaag cgacaaccg cgaaaaggag     720 ggtgactctc ctcggcgggg gcttcgggtg acatcacatc ctccaaatgc gaaatcaggc    780
tccgggccgg ccgaagggcg caactttccc ccctcggcgc cccaccggct cccgcgcgcc    840
tcccctcgcg cccgagcttc gagccaagca gcgtcctggg gagcgcgtca tggccttacc    900
agtgaccgcc ttgctcctgc cgctggcctt gctgctccac gccgccaggc cgagccagtt    960
ccgggtgtcg ccgctggatc ggacctggaa cctgggcgac acagtggagc tgaagtgcca   1020
ggtgctgctg tccaacccga cgtcgggctg ctcgtggctc ttccagccgc gcggcgccgc   1080
cgccagtccc accttcctcc tatacctctc ccaaaacaag cccaaggcgg ccgaggggct   1140
ggacacccag cggttctcgg gcaagaggtt gggggacacc ttcgtcctca ccctgagcga   1200
cttccgccga gagaacgagg gctactattt ctgctcggcc ctgagcaact ccatcatgta   1260
cttcagccac ttcgtgccgg tcttcctgcc agcgaagccc accacgacgc cagcgccgcg   1320
accaccaaca ccggcgccca ccatcgcgtc gcagccctg ccctgcgcc cagaggcgtg     1380 ccggccagcg gcggggggcg cagggaaccg aagacgtgtt tgcaaatgtc cccggcctgt   1440
ggtcaaatcg ggagacaagc ccagcctttc ggcgagatac gtctaaccct gtgcaacagc   1500
cactacatta cttcaaactg agatccttcc ttttgaggga gcaagtcctt cccttttcatt   1560 tttccagtc ttcctcctg tgtattcatt ctcatgatta ttattttagt gggggcgggg    1620
tgggaaagat actttttct ttatgtgttt gacgggaaac aaaactaggt aaaatctaca     1680
gtacaccaca agggtcacaa tactgttgtg cgcacatcgc ggtagggcgt ggaaaggggc   1740
aggccagagc tacccgcaga gttctcagaa tcatgctgag agagctggag gcacccatgc   1800
catctcaacc tcttccccgc ccgttttaca aaggggagg ctaaagccca gagacagctt     1860
gatcaaaggc acacagcaag tcagggttgg agcagtagct ggagggacct tgtctcccag   1920
ctcagggctc tttcctccac accattcagg tctttctttc cgaggcccct gtctcagggt   1980
gaggtgcttg agtctccaac ggcaagggaa caagtacttc ttgatacctg ggatactgtg   2040
cccagagcct cgaggaggta atgaattaaa gaagagaact gcctttggca gagttctata   2100
atgtaaacaa tatcagactt ttttttttta taatcaagcc taaaattgta tagacctaaa   2160
ataaaatgaa gtggtgagct taaccctgga aaatgaatcc ctctatctct aaagaaaatc   2220
tctgtgaaac cccatgtgg aggcggaatt gctctcccag cccttgcatt gcagagggc      2280 ccatgaaaga ggacaggcta ccccttaca aatagaattt gagcatcagt gaggttaaac     2340
taaggccctc ttgaatctct gaatttgaga tacaaacatg ttcctgggat cactgatgac   2400 ttttatact ttgtaaagac aattgttgga gagcccctca cacagccctg gcctctgctc    2460
aactagcaga tacagggatg aggcagacct gactctctta aggaggctga gagcccaaac   2520
tgctgtccca acatgcact tccttgctta aggtatggta caagcaatgc ctgcccattg     2580
gagagaaaaa acttaagtag ataaggaaat aagaaccact cataattctt caccttagga   2640
```

```
ataatctcct gttaatatgg tgtacattct tcctgattat tttctacaca tacatgtaaa    2700
atatgtcttt cttttttaaa tagggttgta ctatgctgtt atgagtggct ttaatgaata    2760
aacatttgta gcatcctctt taatgggtaa acagcatccg aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaa                     2924

<210> SEQ ID NO 68
<211> LENGTH: 1676
<212> TYPE: DNA
<213> ORGANISM: Homo sapiens

<400> SEQUENCE: 68
agactcaaca agagctccag caaagacttt cactgtagct tgacttgacc tgagattaac      60
tagggaatct tgagaataaa gatgagctct gaaaattgtt tcgtagcaga gaacagctct     120
ttgcatccgg agagtggaca agaaaatgat gccaccagtc cccatttctc aacacgtcat     180
gaagggtcct tccaagttcc tgtcctgtgt gctgtaatga atgtggtctt catcaccatt     240
ttaatcatag ctctcattgc cttatcagtg ggccaataca attgtccagg ccaatacaca     300
ttctcaatgc catcagacag ccatgtttct tcatgctctg aggactgggt tggctaccag     360
aggaaatgct actttatttc tactgtgaag aggagctgga cttcagccca aaatgcttgt     420
tctgaacatg gtgctactct tgctgtcatt gattctgaaa aggacatgaa cttctaaaa      480 cgatacgcag gtagagagga acactgggtt ggactgaaaa aggaacctgg tcacccatgg     540
aagtggtcaa atgcaaagaa atttaacaac tggttcaacg ttacagggtc tgacaagtgt     600 gttttctga aaaacacaga ggtcagcagc atggaatgtg agaagaattt atactggata      660
tgtaacaaac cttacaaata taaggaaac atgttcactt attgactatt atagaatgga      720
actcaaggaa atctgtgtca gtggatgctg ctctgtggtc cgaagtcttc catagagact     780
ttgtgaaaaa aaatttttata gtgtcttggg aattttcttc caaacagaac tatgaaaaaa     840
aaggaagaaa ttccaggaaa atctgcactg tgggctttta ttgccatgag ctagaagcat     900
cacaggttga ccaataacca tgcccaagaa tgagaagaat gactatgcaa cctttggatg     960
cactttatat tattttgaat ccagaaataa tgaataact aggcgtggac ttactattta     1020
ttgctgaatg actaccaaca gtgagagccc ttcatgcatt tgcactattg aaggagtta     1080 gatgttggta ctagatactg aatgtaaaca aaggaattat ggctggtaac ataggttttt     1140
agtctaattg aatcccttaa actcagggag catttataaa tggacaaatg cttatgaaac     1200
taagatttgt aatatttctc tcttttttaga gaaatttgcc aatttacttt gttattttc     1260 cccaaaaaga atgggatgat catgtattta ttttttttact tcctcagctg tagacaggtc     1320
cttttcgatg gtacatattt ctttgccttt ataatctttt atacagtgtc ttacagagaa     1380 aagcataag caaagactat gaggaatatt tgcaagacat agaatagtgt tggaaaatgt      1440
gcaatatgtg atgtggcaaa tctctattag gaaatattct gtaatcttca gacctagaat     1500
aatactagtc ttataatagg tttgtgactt tcctaaatca attctattac gtgcaatact     1560
tcaatacttc atttaaaata tttttatgtg caataaaatg tatttgtttg tattttgtgt     1620
tcagtacaat tataagctgt ttttatatat gtgaaataaa agtagaataa acacaa         1676

<210> SEQ ID NO 69
<211> LENGTH: 238
<212> TYPE: PRT
<213> ORGANISM: Artificial sequence
```

<220> FEATURE:
<223> OTHER INFORMATION: Green Fluorescent protein amino acid sequence

<400> SEQUENCE: 69

```
Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
50                  55                  60

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Leu Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235
```

<210> SEQ ID NO 70
<211> LENGTH: 489
<212> TYPE: PRT
<213> ORGANISM: Artificial sequence
<220> FEATURE:
<223> OTHER INFORMATION: Alkaline phosphatase amino acid sequence

<400> SEQUENCE: 70

```
Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Leu Gln Gly Thr Ala
            20                  25                  30

Val Asp Gly Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg
    50                  55                  60

Leu Thr Gly Asp Gln Thr Ala Ala Leu Arg Asp Ser Leu Ser Asp Lys
65                  70                  75                  80

Pro Ala Lys Asn Ile Ile Leu Leu Ile Gly Asp Gly Met Gly Asp Ser
                85                  90                  95
```

```
Glu Ile Thr Ala Ala Arg Asn Tyr Ala Glu Gly Ala Gly Gly Phe Phe
            100                 105                 110

Lys Gly Ile Asp Ala Leu Pro Leu Thr Gly Gln Tyr Thr His Tyr Ala
        115                 120                 125

Leu Asn Lys Lys Thr Gly Lys Pro Asp Tyr Val Thr Asp Ser Ala Ala
    130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
            180                 185                 190

Asp Ala Thr Pro Ala Ala Leu Val Ala His Val Thr Ser Arg Lys Cys
        195                 200                 205

Tyr Gly Pro Ser Ala Thr Ser Glu Lys Cys Pro Gly Asn Ala Leu Glu
    210                 215                 220

Lys Gly Lys Gly Ser Ile Thr Glu Gln Leu Leu Asn Ala Arg Ala
225                 230                 235                 240

Asp Val Thr Leu Gly Gly Ala Lys Thr Phe Ala Glu Thr Ala Thr
                245                 250                 255

Ala Gly Glu Trp Gln Gly Lys Thr Leu Arg Glu Gln Ala Gln Ala Arg
            260                 265                 270

Gly Tyr Gln Leu Val Ser Asp Ala Ala Ser Leu Asn Ser Val Thr Glu
        275                 280                 285

Ala Asn Gln Gln Lys Pro Leu Leu Gly Leu Phe Ala Asp Gly Asn Met
    290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                325                 330                 335

Pro Thr Leu Ala Gln Met Thr Asp Lys Ala Ile Glu Leu Leu Ser Lys
            340                 345                 350

Asn Glu Lys Gly Phe Phe Leu Gln Val Glu Gly Ala Ser Ile Asp Lys
        355                 360                 365

Gln Asp His Ala Ala Asn Pro Cys Gly Gln Ile Gly Glu Thr Val Asp
    370                 375                 380

Leu Asp Glu Ala Val Gln Arg Ala Leu Glu Phe Ala Lys Lys Glu Gly
385                 390                 395                 400

Asn Thr Leu Val Ile Val Thr Ala Asp His Ala His Ala Ser Gln Ile
                405                 410                 415

Val Ala Pro Asp Thr Lys Ala Pro Gly Leu Thr Gln Ala Leu Asn Thr
            420                 425                 430

Lys Asp Gly Ala Val Met Val Met Ser Tyr Gly Asn Ser Glu Glu Asp
        435                 440                 445

Ser Gln Glu His Thr Gly Ser Gln Leu Arg Ile Ala Ala Tyr Gly Pro
    450                 455                 460

His Ala Ala Asn Val Val Gly Leu Thr Asp Gln Thr Asp Leu Phe Tyr
465                 470                 475                 480

Thr Met Lys Ala Ala Leu Gly Leu Lys
            485
```

-continued

```
<210> SEQ ID NO 71
<211> LENGTH: 309
<212> TYPE: PRT
<213> ORGANISM: Artificial sequence
<220> FEATURE:
<223> OTHER INFORMATION: Peroxidase amino acid sequence

<400> SEQUENCE: 71

Met Gln Leu Thr Pro Thr Phe Tyr Asp Asn Ser Cys Pro Asn Val Ser
1               5                   10                  15

Asn Ile Val Arg Asp Thr Ile Val Asn Glu Leu Arg Ser Asp Pro Arg
            20                  25                  30

Ile Ala Ala Ser Ile Leu Arg Leu His Phe His Asp Cys Phe Val Asn
        35                  40                  45

Gly Cys Asp Ala Ser Ile Leu Leu Asp Asn Thr Thr Ser Phe Arg Thr
    50                  55                  60

Glu Lys Asp Ala Phe Gly Asn Ala Asn Ser Ala Arg Gly Phe Pro Val
65                  70                  75                  80

Ile Asp Arg Met Lys Ala Ala Val Glu Ser Ala Cys Pro Arg Thr Val
                85                  90                  95

Ser Cys Ala Asp Leu Leu Thr Ile Ala Ala Gln Gln Ser Val Thr Leu
            100                 105                 110

Ala Gly Gly Pro Ser Trp Arg Val Pro Leu Gly Arg Arg Asp Ser Leu
        115                 120                 125

Gln Ala Phe Leu Asp Leu Ala Asn Ala Asn Leu Pro Ala Pro Phe Phe
    130                 135                 140

Thr Leu Pro Gln Leu Lys Asp Ser Phe Arg Asn Val Gly Leu Asn Arg
145                 150                 155                 160

Ser Ser Asp Leu Val Ala Leu Ser Gly Gly His Thr Phe Gly Lys Asn
                165                 170                 175

Gln Cys Arg Phe Ile Met Asp Arg Leu Tyr Asn Phe Ser Asn Thr Gly
            180                 185                 190

Leu Pro Asp Pro Thr Leu Asn Thr Thr Tyr Leu Gln Thr Leu Arg Gly
        195                 200                 205

Leu Cys Pro Leu Asn Gly Asn Leu Ser Ala Leu Val Asp Phe Asp Leu
    210                 215                 220

Arg Thr Pro Thr Ile Phe Asp Asn Lys Tyr Tyr Val Asn Leu Glu Glu
225                 230                 235                 240

Gln Lys Gly Leu Ile Gln Ser Asp Gln Glu Leu Phe Ser Ser Pro Asn
                245                 250                 255

Ala Thr Asp Thr Ile Pro Leu Val Arg Ser Phe Ala Asn Ser Thr Gln
            260                 265                 270

Thr Phe Phe Asn Ala Phe Val Glu Ala Met Asp Arg Met Gly Asn Ile
        275                 280                 285

Thr Pro Leu Thr Gly Thr Gln Gly Gln Ile Arg Leu Asn Cys Arg Val
    290                 295                 300

Val Asn Ser Asn Ser
305

<210> SEQ ID NO 72
<211> LENGTH: 6
<212> TYPE: PRT
<213> ORGANISM: Artificial sequence
<220> FEATURE:
<223> OTHER INFORMATION: Histidine tag amino acid sequence
```

```
<400> SEQUENCE: 72

His His His His His His
1               5

<210> SEQ ID NO 73
<211> LENGTH: 11
<212> TYPE: PRT
<213> ORGANISM: Artificial sequence
<220> FEATURE:
<223> OTHER INFORMATION: Myc tag amino acid sequence

<400> SEQUENCE: 73

Glu Gln Lys Leu Ile Ser Glu Glu Asp Leu Asn
1               5                   10

<210> SEQ ID NO 74
<211> LENGTH: 15
<212> TYPE: PRT
<213> ORGANISM: Artificial sequence
<220> FEATURE:
<223> OTHER INFORMATION: Biotin lygase tag amino acid sequence

<400> SEQUENCE: 74

Leu His His Ile Leu Asp Ala Gln Lys Met Val Trp Asn His Arg
1               5                   10                  15

<210> SEQ ID NO 75
<211> LENGTH: 238
<212> TYPE: PRT
<213> ORGANISM: Artificial sequence
<220> FEATURE:
<223> OTHER INFORMATION: orange fluorescent protein amino acid sequence

<400> SEQUENCE: 75

Met Ser Lys Gly Glu Glu Leu Phe Thr Gly Val Val Pro Ile Leu Val
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Gly Tyr Gly Ile Leu Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Tyr Gln Thr Ala Ile Ser
        195                 200                 205
```

```
Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235

<210> SEQ ID NO 76
<211> LENGTH: 1019
<212> TYPE: PRT
<213> ORGANISM: Artificial sequence
<220> FEATURE:
<223> OTHER INFORMATION: Beta galactosidase amino acid sequence

<400> SEQUENCE: 76

Met Ala Asp Pro Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

Ser Leu Asn Gly Glu Trp Arg Phe Ala Trp Phe Pro Ala Pro Glu Ala
    50                  55                  60

Val Pro Glu Ser Trp Leu Glu Cys Asp Leu Pro Glu Ala Asp Thr Val
65                  70                  75                  80

Val Val Pro Ser Asn Trp Gln Met His Gly Tyr Asp Ala Pro Ile Tyr
                85                  90                  95

Thr Asn Val Thr Tyr Pro Ile Thr Val Asn Pro Pro Phe Val Pro Thr
            100                 105                 110

Glu Asn Pro Thr Gly Cys Tyr Ser Leu Thr Phe Asn Val Asp Glu Ser
        115                 120                 125

Trp Leu Gln Glu Gly Gln Thr Arg Ile Ile Phe Asp Gly Val Asn Ser
    130                 135                 140

Ala Phe His Leu Trp Cys Asn Gly Arg Trp Val Gly Tyr Gly Gln Asp
145                 150                 155                 160

Ser Arg Leu Pro Ser Glu Phe Asp Leu Ser Ala Phe Leu Arg Ala Gly
                165                 170                 175

Glu Asn Arg Leu Ala Val Met Val Leu Arg Trp Ser Asp Gly Ser Tyr
            180                 185                 190

Leu Glu Asp Gln Asp Met Trp Arg Met Ser Gly Ile Phe Arg Asp Val
        195                 200                 205

Ser Leu Leu His Lys Pro Thr Thr Gln Ile Ser Asp Phe His Val Ala
    210                 215                 220

Thr Arg Phe Asn Asp Asp Phe Ser Arg Ala Val Leu Glu Ala Glu Val
225                 230                 235                 240

Gln Met Cys Gly Glu Leu Arg Asp Tyr Leu Arg Val Thr Val Ser Leu
                245                 250                 255

Trp Gln Gly Glu Thr Gln Val Ala Ser Gly Thr Ala Pro Phe Gly Gly
            260                 265                 270

Glu Ile Ile Asp Glu Arg Gly Gly Tyr Ala Asp Arg Val Thr Leu Arg
        275                 280                 285

Leu Asn Val Glu Asn Pro Lys Leu Trp Ser Ala Glu Ile Pro Asn Leu
    290                 295                 300

Tyr Arg Ala Val Val Glu Leu His Thr Ala Asp Gly Thr Leu Ile Glu
305                 310                 315                 320

Ala Glu Ala Cys Asp Val Gly Phe Arg Glu Val Arg Ile Glu Asn Gly
                325                 330                 335
```

-continued

| | | | | | | | | | | | | | |
|---|---|---|---|---|---|---|---|---|---|---|---|---|---|
|Leu|Leu|Leu|Leu|Asn|Gly|Lys|Pro|Leu|Ile|Arg|Gly|Val|Asn|Arg|
| | | |340| | | |345| | | |350| | |

His Glu His His Pro Leu His Gly Gln Val Met Asp Glu Gln Thr Met
           355             360             365

Val Gln Asp Ile Leu Leu Met Lys Gln Asn Asn Phe Asn Ala Val Arg
        370             375             380

Cys Ser His Tyr Pro Asn His Pro Leu Trp Tyr Thr Leu Cys Asp Arg
385             390             395             400

Tyr Gly Leu Tyr Val Asp Glu Ala Asn Ile Glu Thr His Gly Met
               405             410             415

Val Pro Met Asn Arg Leu Thr Asp Asp Pro Arg Trp Leu Pro Ala Met
           420             425             430

Ser Glu Arg Val Thr Arg Met Val Gln Arg Asp Arg Asn His Pro Ser
           435             440             445

Val Ile Ile Trp Ser Leu Gly Asn Glu Ser Gly His Gly Ala Asn His
           450             455             460

Asp Ala Leu Tyr Arg Trp Ile Lys Ser Val Asp Pro Ser Arg Pro Val
465             470             475             480

Gln Tyr Glu Gly Gly Gly Ala Asp Thr Thr Ala Thr Asp Ile Ile Cys
               485             490             495

Pro Met Tyr Ala Arg Val Asp Glu Asp Gln Pro Phe Pro Ala Val Pro
           500             505             510

Lys Trp Ser Ile Lys Lys Trp Leu Ser Leu Pro Gly Glu Thr Arg Pro
           515             520             525

Leu Ile Leu Cys Glu Tyr Ala His Ala Met Gly Asn Ser Leu Gly Gly
           530             535             540

Phe Ala Lys Tyr Trp Gln Ala Phe Arg Gln Tyr Pro Arg Leu Gln Gly
545             550             555             560

Gly Phe Val Trp Asp Trp Val Asp Gln Ser Leu Ile Lys Tyr Asp Glu
               565             570             575

Asn Gly Asn Pro Trp Ser Ala Tyr Gly Gly Asp Phe Gly Asp Thr Pro
           580             585             590

Asn Asp Arg Gln Phe Cys Met Asn Gly Leu Val Phe Ala Asp Arg Thr
           595             600             605

Pro His Pro Ala Leu Thr Glu Ala Lys His Gln Gln Gln Phe Phe Gln
           610             615             620

Phe Arg Leu Ser Gly Gln Thr Ile Glu Val Thr Ser Glu Tyr Leu Phe
625             630             635             640

Arg His Ser Asp Asn Glu Leu Leu His Trp Met Val Ala Leu Asp Gly
               645             650             655

Lys Pro Leu Ala Ser Gly Glu Val Pro Leu Asp Val Ala Pro Gln Gly
           660             665             670

Lys Gln Leu Ile Glu Leu Pro Glu Leu Pro Gln Pro Glu Ser Ala Gly
           675             680             685

Gln Leu Trp Leu Thr Val Arg Val Val Gln Pro Asn Ala Thr Ala Trp
           690             695             700

Ser Glu Ala Gly His Ile Ser Ala Trp Gln Gln Trp Arg Leu Ala Glu
705             710             715             720

Asn Leu Ser Val Thr Leu Pro Ala Ala Ser His Ala Ile Pro His Leu
               725             730             735

Thr Thr Ser Glu Met Asp Phe Cys Ile Glu Leu Gly Asn Lys Arg Trp
           740             745             750

```
Gln Phe Asn Arg Gln Ser Gly Phe Leu Ser Gln Met Trp Ile Gly Asp
            755                 760                 765

Lys Lys Gln Leu Leu Thr Pro Leu Arg Asp Gln Phe Thr Arg Ala Pro
770                 775                 780

Leu Asp Asn Asp Ile Gly Val Ser Glu Ala Thr Arg Ile Asp Pro Asn
785                 790                 795                 800

Ala Trp Val Glu Arg Trp Lys Ala Ala Gly His Tyr Gln Ala Glu Ala
            805                 810                 815

Ala Leu Leu Gln Cys Thr Ala Asp Thr Leu Ala Asp Ala Val Leu Ile
                820                 825                 830

Thr Thr Ala His Ala Trp Gln His Gln Gly Lys Thr Leu Phe Ile Ser
            835                 840                 845

Arg Lys Thr Tyr Arg Ile Asp Gly Ser Gly Gln Met Ala Ile Thr Val
850                 855                 860

Asp Val Glu Val Ala Ser Asp Thr Pro His Pro Ala Arg Ile Gly Leu
865                 870                 875                 880

Asn Cys Gln Leu Ala Gln Val Ala Glu Arg Val Asn Trp Leu Gly Leu
                885                 890                 895

Gly Pro Gln Glu Asn Tyr Pro Asp Arg Leu Thr Ala Ala Cys Phe Asp
            900                 905                 910

Arg Trp Asp Leu Pro Leu Ser Asp Met Tyr Thr Pro Tyr Val Phe Pro
            915                 920                 925

Ser Glu Asn Gly Leu Arg Cys Gly Thr Arg Glu Leu Asn Tyr Gly Pro
            930                 935                 940

His Gln Trp Arg Gly Asp Phe Gln Phe Asn Ile Ser Arg Tyr Ser Gln
945                 950                 955                 960

Gln Gln Leu Met Glu Thr Ser His Arg His Leu Leu His Ala Glu Glu
                965                 970                 975

Gly Thr Trp Leu Asn Ile Asp Gly Phe His Met Gly Ile Gly Gly Asp
            980                 985                 990

Asp Ser Trp Ser Pro Ser Val Ser Ala Asp Phe Gln Leu Ser Ala Gly
            995                1000                1005

Arg Tyr His Tyr Gln Leu Val Trp Cys Gln Lys
        1010                1015

<210> SEQ ID NO 77
<211> LENGTH: 159
<212> TYPE: PRT
<213> ORGANISM: Artificial sequence
<220> FEATURE:
<223> OTHER INFORMATION: Streptavidin amino acid sequence

<400> SEQUENCE: 77

Asp Pro Ser Lys Asp Ser Lys Ala Gln Val Ser Ala Ala Glu Ala Gly
1               5                  10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95
```

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 78
<211> LENGTH: 717
<212> TYPE: DNA
<213> ORGANISM: Artificial sequence
<220> FEATURE:
<223> OTHER INFORMATION: Green Fluorescent protein nucleic acid sequence

<400> SEQUENCE: 78

| | | |
|---|---|---|
| atgagtaaag gagaagaact tttcactggg attgtcccag ttctcattga gttagacggt | 60 |
| gatgtccatg gacataaatt ctctgtcaga ggagaagggg aaggcgatgc agattatgga | 120 |
| aaacttgaaa tcaaattcat ttgcactact ggaaagctac cagttccatg ccaacactt | 180 |
| gttactacac tgggctacgg catccaatgt ttcgcaagat acccagaaca catgaaaatg | 240 |
| aatgacttct tcaagagtgc catgcctgag ggttacattc aagaaagaac catcttttc | 300 |
| caagatgatg gaaaatacaa gacacgtggt gaagtcaagt tgaaggtga tactcttgtt | 360 |
| aacagaattg agctcaaagg tatggacttt aagaagatg gcaatatcct tggacacaag | 420 |
| ttggagtaca attttaattc acataatgta tacattatgc cggacaaagc caataatgga | 480 |
| ctcaaagtca atttcaaaat tagacacaat atcgaaggtg gtggtgtcca acttgctgat | 540 |
| cattaccaaa caaatgttcc ccttggagac ggtcctgtcc ttataccaat caatcactac | 600 |
| ctatccttgc aaacagccat ttcaaagat cgaaatgaga cgagagatca tatggtgttt | 660 |
| ctggaatttt tctcagcttg tggacataca catggcatgg atgaactata caaataa | 717 |

<210> SEQ ID NO 79
<211> LENGTH: 7151
<212> TYPE: DNA
<213> ORGANISM: Artificial sequence
<220> FEATURE:
<223> OTHER INFORMATION: Alkaline phosphatase nucleic acid sequence

<400> SEQUENCE: 79

| | | |
|---|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa agttggccc agggcttccc | 360 |
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg tccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |

```
actgactcgc tacgctcggt cgttcgactg cggcgagcgg aaatggctta cgaacggggc   780
ggagatttcc tggaagatgc caggaagata cttaacaggg aagtgagagg ccgcggcaa    840
agccgttttt ccataggctc cgccccctg acaagcatca cgaaatctga cgctcaaatc    900
agtggtggcg aaacccgaca ggactataaa gataccaggc gtttccccct ggcggctccc   960
tcgtgcgctc tcctgttcct gcctttcggt ttaccggtgt cattccgctg ttatggccgc  1020
gtttgtctca ttccacgcct gacactcagt tccgggtagg cagttcgctc caagctggac  1080
tgtatgcacg aaccccccgt tcagtccgac cgctgcgcct tatccggtaa ctatcgtctt  1140
gagtccaacc cggaaagaca tgcaaaagca ccactggcag cagccactgg taattgattt  1200
agaggagtta gtcttgaagt catgcgccgg ttaaggctaa actgaaagga caagttttgg  1260
tgactgcgct cctccaagcc agttacctcg gttcaaagag ttggtagctc agagaacctt  1320
cgaaaaaccg ccctgcaagg cggttttttc gttttcagag caagagatta cgcgcagacc  1380
aaaacgatct caagaagatc atcttattaa tcagataaaa tatttctaga tttcagtgca  1440
atttatctct tcaaatgtag cacctgaagt cagccccata cgatataagt tgtaattctc  1500
atgtttgaca gcttatcatc gataagcttt tttcgccagg cgcagacttg ctgttcttca  1560
ggcaatcact catgtaggtc ttacgagcat ccccttttcaa cgcctgcgcc gtcgcctgct  1620
gattacagga ggtcatacgc tgttgttgtg gggttaaagt tctctcggca gcgccgacgg  1680
tggttaaaaa aaccagaccg aaaagcaagg taaccagtaa tgttattttc atagcaccat  1740
ccctcttcat gttttaacca tgagcgtatg cgcccgtgat ctgccattaa gtctggttgc  1800
taacagcaaa aaaaccaccc ggcagcgaaa attcactgcc gggcgcggtt ttatttcagc  1860
cccagagcgg ctttcatggt gtagaagaga tcggtctggt cggtcagtcc aacaacattg  1920
gcggcatgcg ggccatacgc cgcaatacgc aactgactgc cggtatgttc ttgtgaatcc  1980
tcttcggagt tcccgtaact catcaccatc actgcgccat cttggtatt tagcgcctgg  2040
gtgaggcccg gagctttggt atccggcgca caatctggc tggcgtgggc gtgatcagcg  2100
gtgactatga ccagcgtgtt accctccttt ttagcgaatt ccagcgcccg ttgtacggct  2160
tcatcgagat cgaccgtctc gccaatttgc ccacaaggat tcgcagcatg atcctgttta  2220
tcgattgacg caccttcaac ttgcaggaaa aagcctttct cattttttact caacaattca  2280
atggctttgt cggtcatctg cgccagggtt ggtacactgt cattacgttg cggatttggc  2340
gtacaggtga ctgcgggctt atcgatattg ccatggtacg ttgctttcgg tcctagccag  2400
cgcactggca tattgccgtc agcaaacagg ccaagcaggg gttttgctg attcgcttcc  2460
gtcaccgaat tcagtgaggc agcatcgctc accaactgat aaccacgcgc ctgtgcctgt  2520
tcacgcagcg ttttccctg ccattcacca gcggttgccg tttcagcaaa ggttttgcg   2580
ccgccgccaa gcgtaacgtc ggcacgagcg ttaagcagct gttcggtaat cgatcctttt  2640
ccgccttttt ccagagcgtt acccggacat ttttcactgg tcgcgctcgg accgtagcat  2700
ttgcgcgagg tcacatgtgc caccagcgca gcgggcgtgg catcctgcaa ctctgcggta  2760
gaaacgttac cggtcgccag acctgcggct tttgccattt ccagaatcgt tgggtgatct  2820
ttttcgtgaa tatcgacgcc cagcgcgccg ttataggttt tgacaccggt tgaccaggcg  2880
gttgctgatg cagccgagtc ggtgacgtag tccggtttgc cggttttttt attcagcgca  2940
tagtgagtgt attgcccggt aagcggtaag gcatctatac cttttaaaaa gccgcccgca  3000
ccttcggcat aattacgtgc ggcagtaatt tccgagtccc ccatcccatc gccaatcagc  3060
aaaataatat ttttttgcagg tttatcgcta agagaatcac gcagagcggc agtctgatca  3120
```

```
cccgttaaac ggcgagcacc gccgggtgca gtaatatcgc cctgagcagc ccggttttcc    3180
agaacctcga ggctagcatg catagaaccg ccaccaccgt cgacagcggt accctgcaga    3240
ggcatttctg gtgtccgggc ttttgtcaca ggggtaaaca gtaacggtaa gagtgccagt    3300
gcaatagtgc tttgtttcac tttattttct ccatgtcgcg tcttatcagg ggaattctg    3360
tttcctgtgt gaaattgtta ccgctcaca attccacaca ttatacgagc cgatgattaa    3420
ttgtcaacag ctcatttcag aatatttgcc agaaccgtta tgatgtcggc gcaaaaaaca    3480
ttatctagag gggaattgtt atccgctcac aattcccta tagtgagtcg tattaatttc    3540
gcgggatcga gatctcgatc ctctacgccg gacgcatcgt ggccggcatc accgcgcca    3600
caggtgcggt tgctggcgcc tatatcgccg acatcaccga tggggaagat cgggctcgcc    3660
acttcgggct catgagcgct tgtttcggcg tgggtatggt ggcaggcccc gtggccgggg    3720
gactgttggg cgccatctcc ttgcatgcac cattccttgc ggcggcggtg ctcaacggcc    3780
tcaacctact actgggctgc ttcctaatgc aggagtcgca taaggagag cgtcgagatc    3840
ccggacacca tcgaatggcg caaaaccttt cgcggtatgg catgatagcg cccggaagag    3900
agtcaattca gggtggtgaa tgtgaaacca gtaacgttat acgatgtcgc agagtatgcc    3960
ggtgtctctt atcagaccgt ttcccgcgtg gtgaaccagg ccagccacgt ttctgcgaaa    4020
acgcgggaaa aagtggaagc ggcgatggcg gagctgaatt acattcccaa ccgcgtggca    4080
caacaactgg cggcaaaca gtcgttgctg attggcgttg ccacctccag tctggccctg    4140
cacgcgccgt cgcaaattgt cgcggcgatt aaatctcgcg ccgatcaact gggtgccagc    4200
gtggtggtgt cgatggtaga acgaagcggc gtcgaagcct gtaaagcggc ggtgcacaat    4260
cttctcgcgc aacgcgtcag tgggctgatc attaactatc cgctggatga ccaggatgcc    4320
attgctgtgt aagctgcctg cactaatgtt ccggcgttat ttcttgatgt ctctgaccag    4380
acacccatca acagtattat tttctcccat gaagacggta cgcgactggg cgtggagcat    4440
ctggtcgcat tgggtcacca gcaaatcgcg ctgttagcgg gcccattaag ttctgtctcg    4500
gcgcgtctgc gtctggctgg ctggcataaa tatctcactc gcaatcaaat tcagccgata    4560
gcggaacggg aaggcgactg gagtgccatg tccggttttc aacaaaccat gcaaatgctg    4620
aatgagggca tcgttcccac tgcgatgctg gttgccaacg atcagatggc gctgggcgca    4680
atgcgcgcca ttaccgagtc cgggctgcgc gttggtgcgg atatctcggt agtgggatac    4740
gacgataccg aagacagctc atgttatatc ccgccgttaa ccaccatcaa acaggatttt    4800
cgcctgctgg ggcaaaccag cgtggaccgc ttgctgcaac tctctcaggg ccaggcggtg    4860
aagggcaatc agctgttgcc cgtctcactg gtgaaaagaa aaaccaccct ggcgcccaat    4920
acgcaaaccg cctctccccg cgcgttggcc gattcattaa tgcagctggc acgacaggtt    4980
tcccgactgg aaagcgggca gtgagcgcaa cgcaattaat gtaagttagc tcactcatta    5040
ggcaccggga tctcgaccga tgcccttgag agccttcaac ccagtcagct ccttccggtg    5100
ggcgcggggc atgactatcg tcgccgcact tatgactgtc ttctttatca tgcaactcgt    5160
aggacaggtg ccggcagcgc tctgggtcat tttcggcgag gaccgctttc gctggagcgc    5220
gacgatgatc ggcctgtcgc ttgcggtatt cggaatcttg cacgccctcg ctcaagcctt    5280
cgtcactggt cccgccacca aacgtttcgg cgagaagcag gccattatcg ccggcatggc    5340
ggccgacgcg ctgggctacg tcttgctggc gttcgcgacg cgaggctgga tggccttccc    5400
cattatgatt cttctcgctt ccggcggcat cgggatgccc gcgttgcagg ccatgctgtc    5460
caggcaggta gatgacgacc atcagggaca gcttcaagga tcgctcgcgg ctcttaccag    5520
```

```
cctaacttcg atcactggac cgctgatcgt cacggcgatt tatgccgcct cggcgagcac      5580
atggaacggg ttggcatgga ttgtaggcgc cgccctatac cttgtctgcc tccccgcgtt      5640
gcgtcgcggt gcatggagcc gggccacctc gacctgaatg gaagccggcg gcacctcgct      5700
aacggattca ccactccaag aattggagcc aatcaattct tgcggagaac tgtgaatgcg      5760
caaaccaacc cttggcagaa catatccatc gcgtccgcca tctccagcag ccgcacgcgg      5820
cgcatctcgg gcagcgttgg gtcctggcca cgggtgcgca tgatcgtgct cctgtcgttg      5880
aggacccggc taggctggcg gggttgcctt actggttagc agaatgaatc accgatacgc      5940
gagcgaacgt gaagcgactg ctgctgcaaa acgtctgcga cctgagcaac aacatgaatg      6000
gtcttcggtt tccgtgtttc gtaaagtctg gaaacgcgga agtcccctac gtgctgctga      6060
agttgcccgc aacagagagt ggaaccaacc ggtgatacca cgatactatg actgagagtc      6120
aacgccatga gcggcctcat ttcttattct gagttacaac agtccgcacc gctgtccggt      6180
agctccttcc ggtgggcgcg gggcatgact atcgtcgccg cactatgac tgtcttcttt      6240 atcatgcaac tcgtaggaca ggtgccggca gcgcccaaca gtcccccggc cacggggcct      6300
gccaccatac ccacgccgaa acaagcgccc tgcaccatta tgttccggat ctgcatcgca      6360
ggatgctgct ggctaccctg tggaacacct acatctgtat taacgaagcg ctaaccgttt      6420
ttatcaggct ctgggaggca gaataaatga tcatatcgtc aattattacc tccacgggga      6480
gagcctgagc aaactggcct caggcatttg agaagcacac ggtcacactg cttccggtag      6540
tcaataaacc ggtaaaccag caatagacat aagcggctat ttaacgaccc tgccctgaac      6600
cgacgaccgg gtcgaatttg ctttcgaatt tctgccattc atccgcttat tatcacttat      6660
tcaggcgtag caccaggcgt ttaagggcac caataactgc cttaaaaaaa ttacgccccg      6720
ccctgccact catcgcagta ctgttgtaat tcattaagca ttctgccgac atggaagcca      6780
tcacagacgg catgatgaac ctgaatcgcc agcggcatca gcaccttgtc gccttgcgta      6840
taatatttgc ccatggtgaa aacgggggcg aagaagttgt ccatattggc cacgtttaaa      6900
tcaaaactgg tgaaactcac ccagggattg gctgagacga aaacatatt ctcaataaac       6960 cctttaggga aataggccag gttttcaccg taacacgcca catcttgcga atatatgtgt      7020
agaaactgcc ggaaatcgtc gtggtattca ctccagagcg atgaaaacgt ttcagtttgc      7080
tcatggaaaa cggtgtaaca agggtgaaca ctatccata tcaccagctc accgtctttc      7140
attgccatac g                                                          7151
```

<210> SEQ ID NO 80
<211> LENGTH: 955
<212> TYPE: DNA
<213> ORGANISM: Artificial sequence
<220> FEATURE:
<223> OTHER INFORMATION: Peroxidase nucleic acid sequence

<400> SEQUENCE: 80

```
aagcttaacc atgcagttaa ccccctacatt ctacgacaat agctgtccca acgtgtccaa       60
catcgttcgc gacacaatcg tcaacgagct cagatccgat cccaggatcg ctgcttcaat      120
attacgtctg cacttccatg actgcttcgt gaatggttgc gacgctagca tattactgga      180
caacaccacc agtttccgca ctgaaaagga tgcattcggg aacgctaaca gcgccagggg      240
ctttccagtg atcgatcgca tgaaggctgc cgttgagtca gcatgccac gaacagtcag      300 ttgtgcagac ctgctgacta tagctgcgca acagagcgtg actcttgcag gcggaccgtc      360
ctggagagtg ccgctcggtc gacgtgactc cctacaggca ttcctagatc tggccaacgc      420
```

| | |
|---|---|
| caacttgcct gctccattct tcaccctgcc ccagctgaag gatagcttta gaaacgtggg | 480 |
| tctgaatcgc tcgagtgacc ttgtggctct gtccggagga cacacatttg gaaagaacca | 540 |
| gtgtaggttc atcatggata ggctctacaa tttcagcaac actgggttac ctgaccccac | 600 |
| gctgaacact acgtatctcc agacactgag aggcttgtgc ccactgaatg caacctcag | 660 |
| tgcactagtg gactttgatc tgcggacccc aaccatcttc gataacaagt actatgtgaa | 720 |
| tctagaggag cagaaaggcc tgatacagag tgatcaagaa ctgtttagca gtccaaacgc | 780 |
| cactgacacc atcccactgg tgagaagttt tgctaactct actcaaacct tctttaacgc | 840 |
| cttcgtggaa gccatggacc gtatgggtaa cattacccct ctgacgggta cccaaggcca | 900 |
| gattcgtctg aactgcagag tggtcaacag caactcttaa taaggatccg aattc | 955 |

<210> SEQ ID NO 81
<211> LENGTH: 18
<212> TYPE: DNA
<213> ORGANISM: Artificial sequence
<220> FEATURE:
<223> OTHER INFORMATION: Histidine tag nucleic acid sequence

<400> SEQUENCE: 81

| | |
|---|---|
| catcatcatc accatcac | 18 |

<210> SEQ ID NO 82
<211> LENGTH: 861
<212> TYPE: DNA
<213> ORGANISM: Artificial sequence
<220> FEATURE:
<223> OTHER INFORMATION: Myc tag nucleic acid sequence

<400> SEQUENCE: 82

| | |
|---|---|
| cagtctgtgt tgacgcagcc gccctcagtg tctgggtctc ctggacagtc gatcaccatc | 60 |
| tcctgcactg gaaccagcag tgatattggg acttataaaa ttgtctcctg gtaccaacag | 120 |
| cacccctggc aagcccccaa actcatgatt tatgacgtca atcagcggcc ctcaggggtt | 180 |
| tctgatcgct tctctggctc caagtctggc aacacggcct ccctgacaat ctctgggctc | 240 |
| caggctgagg acgaggctga ttattactgc agctcatata caagcggcag cactctggta | 300 |
| ttcggcgggg ggaccaagct gaccgtccta ggctcgagtg gtggaggcgg ttcaggcgga | 360 |
| ggtggctctg gcggtagtgc acttcaggta cagctgcagc agtcaggagc agaggtgaaa | 420 |
| aagcccgggg agtctctgaa gatctcctgt aagggttctg gatacagctt taccagctac | 480 |
| tggatcggct gggtgcgcca gatgcccggg aaaggcctgg agtggatggg gatcatctat | 540 |
| cctggtgact ctgataccag atacagcccg tccttccaag gccaggtcac catctcagcc | 600 |
| gacaagtcca tcagcaccgc ctacctgcag tggagcagcc tgaaggcctc ggacaccgcc | 660 |
| atgtattact gtgcgagaca tcgggccgct agtgggagcc cggacgcgtg tgactactgg | 720 |
| ggccagggaa ccctggtcac cgtctcctca gggagtgcat ccgccccaac cctttttccc | 780 |
| gcggccgcac atcatcatca ccatcacggg gccgcagaac aaaaactcat ctcagaagag | 840 |
| gatctgaatg gggccgcata g | 861 |

<210> SEQ ID NO 83
<211> LENGTH: 717
<212> TYPE: DNA
<213> ORGANISM: Artificial sequence
<220> FEATURE:
<223> OTHER INFORMATION: orange fluorescent protein nucleic acid sequence

<400> SEQUENCE: 83

```
atgagtaaag gagaagaact tttcactgga gttgtcccaa ttcttgttga attagatggt    60
gatgtccatg gacataaatt ctctgtcaga ggagaagggg aaggcgatgc agattatgga   120
aaacttgaaa tcaaattcat ttgcactact ggaaagctac cagttccatg gccaacactt   180
gttactacac tgggctatgg catcctatgt ttcgcaagat acccagaaca catgaaaatg   240
aatgacttct tcaagagtgc catgcctgag ggttacattc aagaaagaac catctttttc   300
caagatgatg aaaatacaa gacacgtggt gaagtcaagt ttgaaggtga tactcttgtt   360
aacagaattg agctcaaagg tatggacttt aagaagatg gcaatatcct tggacacaag   420
ttggagtaca attttaactc acataatgta tacattatgc cggacaaagc caataatgga   480
ctcaaagtca atttcaaaat tagacacaat atcgaaggtg gtggtgtcca actcgctgat   540
cattaccaaa caaatgttcc ccttggagac ggtcctgtcc ttataccaat caatcactac   600
ctatcctatc aaacagccat ttcaaaagat cgaaatgaga cgagagatca tatggtgttt   660
ctggaatttt tctcagcttg tggacataca catggcatgg atgaactata caaataa    717
```

<210> SEQ ID NO 84
<211> LENGTH: 8388
<212> TYPE: DNA
<213> ORGANISM: Artificial sequence
<220> FEATURE:
<223> OTHER INFORMATION: Beta galactosidase Nucleic acid sequence

<400> SEQUENCE: 84

```
acgttaaggg attttggtca tggacggcca gcaggtaggc cgacaggctc atgccggccg    60
ccgccgcctt ttcctcaatc gctcttcgtt cgtctggaag gcagtacacc ttgataggtg   120
ggctgccctt cctggttggc ttggtttcat cagccatccg cttgccctca tctgttacgc   180
cggcggtagc cggccagcct cgcagagcag gattcccgtt gagcaccgcc aggtgcgaat   240
aagggacagt gaagaaggaa cacccgctcg cgggtgggcc tacttcacct atcctgcccg   300
gctgacgccg ttggatacac caaggaaagt ctacacgaac cctttggcaa atcctgtat   360
atcgtgcgaa aaaggatgga tataccgaaa aaatcgctat aatgacccg aagcagggtt   420
atgcagcgga aaagcgctgc ttccctgctg ttttgtggaa tatctaccga ctggaaacag   480
gcaaatgcag gaaattactg aactgagggg acaggcgaga gacgatgcca agagctaca   540
ccgacgagct ggccgagtgg gttgaatccc gcgcggccaa gaagcgccgg cgtgatgagg   600
ctgcggttgc gttcctggcg gtgagggcgg atgtcgatat gcgtaaggag aaaataccgc   660
atcaggcgca tatttgaatg tatttagaaa aataaacaaa aagagtttgt agaaacgcaa   720
aaaggccatc cgtcaggatg gccttctgct taatttgatg cctggcagtt tatggcgggc   780
gtcctgcccg ccaccctccg ggccgttgct tcgcaacgtt caaatccgct cccggcggat   840
ttgtcctact caggagagcg ttcaccgaca acaacagat aaaacgaaag cccagtctt   900
tcgactgagc cttttcgtttt atttgatgcc tggcagttcc ctactctcgc atggggagac   960
cccacactac catcggcgct acggcgtttc acttctgagt tcggcatggg gtcaggtggg  1020
accaccgcgc tactgccgcc aggcaaattc tgttttatca gaccgcttct gcgttctgat  1080
ttaatctgta tcaggctgaa aattaaggaa tcccccagga cccaacgctg cccgagtttg  1140
tcagaaagca gaccaaacag cggttggaat aatagcgaga acagagaaat agcggcaaaa  1200
ataatacccg tatcactttt gctgatatgg ttgatgtcat gtagccaaat cgggaaaaac  1260
gggaagtagg ctcccatgat aaaaaagtaa agaaaaaga ataaaccgaa catccaaaag  1320
```

-continued

```
tttgtgtttt ttaaatagta cataatggat ttccttacgc gaaatacggg cagacatggc    1380
ctgcccggtt attattattt ttgacaccag accaactggt aatggtagcg accggcgctc    1440
agctggaaat ccgccgatac tgacgggctc caggagtcgt cgccaccaat ccccatatgg    1500
aaaccgtcga tattcagcca tgtgccttct tccgcgtgca gcagatggcg atggctggtt    1560
tccatcagtt gctgttgact gtagcggctg atgttgaact ggaagtcgcc gcgccactgg    1620
tgtgggccat aattcaattc gcgcgtcccg cagcgcagac cgttttcgct cgggaagacg    1680
tacggggtat acatgtctga caatggcaga tcccagcggt caaaacaggc ggcagtaagg    1740
cggtcgggat agttttcttg cggccctaat ccgagccagt ttacccgctc tgctacctgc    1800
gccagctggc agttcaggcc aatccgcgcc ggatgcggtg tatcgctcgc cacttcaaca    1860
tcaacggtaa tcgccatttg accactacca tcaatccggt aggttttccg gctgataaat    1920
aaggttttcc cctgatgctg ccacgcgtga gcggtcgtaa tcagcaccgc atcagcaagt    1980
gtatctgccg tgcactgcaa caacgctgct tcggcctggt aatggcccgc cgccttccag    2040
cgttcgaccc aggcgttagg gtcaatgcgg gtcgcttcac ttacgccaat gtcgttatcc    2100
agcggtgcac gggtgaactg atcgcgcagc ggcgtcagca gttgtttttt atcgccaatc    2160
cacatctgtg aaagaaagcc tgactggcgg ttaaattgcc aacgcttatt acccagctcg    2220
atgcaaaaat ccatttcgct ggtggtcaga tgcgggatgg cgtgggacgc ggcggggagc    2280
gtcacactga ggttttccgc cagacgccac tgctgccagg cgctgatgtg cccggcttct    2340
gaccatgcgg tcgcgttcgg ttgcactacg cgtactgtga gccagagttg cccggcgctc    2400
tccggctgcg gtagttcagg cagttcaatc aactgtttac cttgtggagc gacatccaga    2460
ggcacttcac cgcttgccag cggcttacca tccagcgcca ccatccagtg caggagctcg    2520
ttatcgctat gacggaacag gtattcgctg gtcacttcga tggtttgccc ggataaacgg    2580
aactggaaaa actgctgctg gtgttttgct tccgtcagcg ctggatgcgg cgtgcggtcg    2640
gcaaagacca gaccgttcat acagaactgg cgatcgttcg gcgtatcgcc aaaatcaccg    2700
ccgtaagccg accacgggtt gccgtttttca tcatatttaa tcagcgactg atccacccag    2760
tcccagacga agccgccctg taaacgggga tactgacgaa acgcctgcca gtatttagcg    2820
aaaccgccaa gactgttacc catcgcgtgg gcgtattcgc aaaggatcag cgggcgcgtc    2880
tctccaggta gcgaaagcca ttttttgatg gaccatttcg gcacagccgg gaagggctgg    2940
tcttcatcca cgcgcgcgta catcgggcaa ataatatcgg tggccgtggt gtcggctccg    3000
ccgccttcat actgcaccgg gcgggaagga tcgacagatt tgatccagcg atacagcgcg    3060
tcgtgattag cgccgtggcc tgattcattc cccagcgacc agatgatcac actcgggtga    3120
ttacgatcgc gctgcaccat tcgcgttacg cgttcgctca tcgccggtag ccagcgcgga    3180
tcatcggtca gacgattcat tggcaccatg ccgtgggttt caatattggc ttcatccacc    3240
acatacaggc cgtagcggtc gcacagcgtg taccacagcg gatggttcgg ataatgcgaa    3300
cagcgcacgg cgttaaagtt gttctgcttc atcagcagga tatcctgcac catcgtctgc    3360
tcatccatga cctgaccatg cagaggatga tgctcgtgac ggttaacgcc tcgaatcagc    3420
aacggcttgc cgttcagcag cagcagacca ttttcaatcc gcacctcgcg gaaaccgaca    3480
tcgcaggctt ctgcttcaat cagcgtgccg tcggcggtgt gcagttcaac caccgcacga    3540
tagagattcg ggatttcggc gctccacagt ttcgggtttt cgacgttcag acgtagtgtg    3600
acgcgatcgg cataaccacc acgctcatcg ataatttcac cgccgaaagg cgcggtgccg    3660
ctggcgacct gcgtttcacc ctgccataaa gaaactgtta cccgtaggta gtcacgcaac    3720
```

```
tcgccgcaca tctgaacttc agcctccagt acagcgcggc tgaaatcatc attaaagcga    3780
gtggcaacat ggaaatcgct gatttgtgta gtcggtttat gcagcaacga acgtcacgg    3840 aaaatgccgc tcatccgcca catatcctga tcttccagat aactgccgtc actccaacgc    3900
agcaccatca ccgcgaggcg gttttctccg gcgcgtaaaa atgcgctcag gtcaaattca    3960
gacggcaaac gactgtcctg gccgtaaccg acccagcgcc cgttgcacca cagatgaaac    4020
gccgagttaa cgccatcaaa aataattcgc gtctggcctt cctgtagcca gctttcatca    4080
acattaaatg tgagcgagta acaacccgtc ggattctccg tgggaacaaa cggcggattg    4140
accgtaatgg gataggttac gttggtgtag atgggcgcat cgtaaccgtg catctgccag    4200
tttgagggga cgacgacagt atcggcctca ggaagatcgc actccagcca gctttccggc    4260
accgcttctg gtgccggaaa ccaggcaaag cgccattcgc cattcaggct gcgcaactgt    4320
tgggaagggc gatcggtgcg ggcctcttcg ctattacgcc agctggcgaa aggggatgt    4380 gctgcaaggc gattaagttg gtaacgcca gggttttccc agtcacgacg ttgtaaaacg    4440
acgggatcag ccattttttt ctccttactt acttaggatc cccgggtacc gagctcgaat    4500
tggggatctt gaagttccta ttccgaagtt cctattctct agaaagtata ggaacttcag    4560
agcgcttttg aagctaattc gagctcggta cccggggatc ccccgggctc gactgcatta    4620
atgaatcggc caacgcgcgg ggagaggcgg tttgcgtatt gggcgctctt ccgctcgaat    4680
tgacataagc ctgttcggtt cgtaaactgt aatgcaagta gcgtatgcgc tcacgcaact    4740
ggtccagaac cttgaccgaa cgcagcggtg gtaacggcgc agtggcggtt ttcatggctt    4800
gttatgactg ttttttttgta ctcgagcaga aagtcaaaag cctccgaccg gaggcttttg    4860
acttgagggg gatcgatccc ttatggctct gcacccggct ccatcaccaa caggtcgcgc    4920
acgcgcttca ctcggttgcg gatcgacact gccagcccaa caaagccggt tgccgccgcc    4980
gccaggatcg cgccgatgat gccggccaca ccggccatcg cccaccaggt cgccgccttc    5040
cggttccatt cctgctggta ctgcttcgca atgctggacc tcggctcacc ataggctgac    5100
cgctcgatgg cgtatgccgc ttctcccctt ggcgtaaaac ccagcgccgc aggcggcatt    5160
gccatgctgc ccgccgcttt cccgaccacg acgcgcgcac caggcttgcg gtccagacct    5220
tcggccacgg cgagctgcgc aaggacataa tcagccgccg acttggctcc acgcgcctcg    5280
atcagctctt gcactcgcgc gaaatccttg gcctccacgg ccgccatgaa tcgcgcacgc    5340
ggcgaaggct ccgcagggcc ggcgtcgtga tcgccgccga gaatgcccCtt caccaagttc    5400 gacgacacga aaatcatgct gacggctatc accatcatgc agacggatcg cacgaacccg    5460
cagaactcac ccccgaacac gagcacggca cccgcgacca ctatgccaag aatgcccaag    5520
gtaaaaattg ccggccccgc catgaagtcc gtgaatgccc cgacggccga agtgaagggc    5580
aggccgccac ccaggccgcc gccctcactg cccggcacct ggtcgctgaa tgtcgatgcc    5640
agcacctgcg gcacgtcaat gcttccgggc gtcgcgctcg ggctgatcgc ccatcccgtt    5700
actgccccga tcccggcaat ggcaaggact gccagcgccg cgatgaggaa gcgggtgccc    5760
cgcttcttca tcttcgcgcc tcgggcctcc aggccgccta cctgggcgaa acatcggtg    5820 tttgtggcat tcatacggac tcctgttggg ccagctcgcg cacgggctgg cgggtcagct    5880
tggcttgaag atcgccacgc attgcggcga tctgcttctc ggcatccttg cgcttctgca    5940
cgccttcctg ctggatgcga ataacgtcct cgacggtctt gatgagcgtc gtctgaacct    6000
gcttgagcgt gtccacgtcg atcaccaggc gttggttctc cttcgccgtc tcgacggacg    6060
tgcgatgcag cagggccgca ttgcgcttca tcaggtcgtt ggtggtgtcg tcgatggccg    6120
```

-continued

```
tggccagttc gacggcgttc ttctgctcgt tgaggctcaa ggccagcatg aattgccgct    6180
tccacgccgg cacggtgatt tcgcggatgg tgtggaattt atcgaccagc atctggttgt    6240
tggcctggat catgcggatg gtcggcaggc tctgcatggc cgaatgttgc aaggcgatca    6300
ggtcgccgat gcgcttgtcc aggttggcaa ccatcgcatc gaggtcggcc agctcctgca    6360
cgcggccagg gtcgttcccg acattgccgc gcagaccctc ggcctgctcg cgcagctcgg    6420
caaggcggac cttgccggcc gcgatgtgga cgccaagaag gcggtgttcc tcgcgcacgg    6480
ctgcgaacat ttcgtcgagc gaggcattgc gctgcgcgat gccttgctgg gtggtctgca    6540
cttcgctgac caggtgttcg atctgctcgc gggtcgtgtc gaagcgcgcc atgaagcccg    6600
tcgaacggac gcggaagcgg tcgatcagcg ggccaatcag gggcaggcgg aacggttgt    6660
cggacaaagg gccgacgttc agggaacggg ccttggcgac aacctgggtc agtttctcgc    6720
ctgcttcgtc caggtcgctg ttgcgcacct ggtccagcag gctatcggcg tagcgggacg    6780
tgtgctcggc cacgtcgcgg ccgaactcgg caacggtctg cggactgccg acctcgatcc    6840
gctgcgcgac cgcatggact tccggcacgt cgctttcctg caagcccagc tcgcgcaggg    6900
ttgccggggt catgtcgaag gcgacgatag gggccttggc gtcgtgcgtc gttttcagtg    6960
cgttcatagg gttctcccgc cgtgttattg gttgatgcct tccaggctct gcgaaaggct    7020
ccgcatgagc gcctggtgag cttggccgc ctcggcgacc attgccggat tcatgttctt    7080
ggtggtgatg agcgcgaggg tgtgctgacg ccagacgggc accaggacgg atgccgtttc    7140
agagaagcgg tccagcatgt ccacggcctg cgcccgcgtg agcttcatct gagtgacgct    7200
catttcatgg gacgccatga gggttgccag gttggcgagc ttgcgcgcga agcgttcgcg    7260
cggcttgtcg aactcgatca cgccggcctt ggccgcgccg gcctcggggt tctcgtccag    7320
gaactcgcgc ccggcttgaa tgtaggctct gagccggtct acctcggcct catgcgtatt    7380
gagcatgtca tccaaggcgc gcaacgtgtc ccgcacgcgc tgcgctacgc cctcggcttc    7440
gtccagcaac tggtcgagcg tcttgcgggc gacctgatac ctcacctggc gttcaacctc    7500
acggccaagc atcttctcga accaggtagg cttttccgcg atcttgcggg ggtccgcgtc    7560
ggccagcttc gccacgatct ggctgatttt gtcggccagc gcggcaactg cgccgtgctc    7620
catcagattc gacagctcgt tgagggaatc cgccccgtcg atgccggccc cgtactcgcc    7680
aatcgtcgcc ggcgacgcga agagggcggg caaaacctcc cccttcaatc gcgccatgtt    7740
cacgctttgt tcttccatgg tatatctcct tcttaaagtt aaacaaaatt attcggaacc    7800
cagcatgata ttccggaaat accaactaag tcaacggctg atggccaatt cggcttcctc    7860
gctcactgac tcgctgcgct cggtcgttcg gctgcggcga gcggtatcag ctcactcaaa    7920
ggcggtaata cggttatcca cagaatcagg ggataacgca ggaaagaaca tgtgagatcg    7980
atcagcagtt caacctgttg atagtacgta ctaagctctc atgtttcacg tactaagctc    8040
tcatgtttaa cgtactaagc tctcatgttt aacgaactaa accctcatgg ctaacgtact    8100
aagctctcat ggctaacgta ctaagctctc atgtttcacg tactaagctc tcatgtttga    8160
acaataaaat taatataaat cagcaactta atagcctct aaggttttaa gttttataag    8220
aaaaaaaaga atatataagg cttttaaagc tagcttttaa ggtttaacgg ttgtggacaa    8280
caagccaggt atgtaacgca ctgagaagcc cttagagcct ctcaaagcaa ttttcagtga    8340
cacaggaaca cttaacggct gacatgacgc tcagtggaac gaaaactc                 8388
```